United States Patent
Doudna et al.

(10) Patent No.: US 9,745,610 B2
(45) Date of Patent: Aug. 29, 2017

(54) METHODS AND COMPOSITIONS FOR CONTROLLING GENE EXPRESSION BY RNA PROCESSING

(71) Applicant: The Regents of the University of California, Oakland, CA (US)

(72) Inventors: Jennifer A. Doudna, Berkeley, CA (US); Lei S. Qi, El Cerrito, CA (US); Rachel E. Haurwitz, Kensington, CA (US); Adam P. Arkin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/248,980

(22) Filed: Apr. 9, 2014

(65) Prior Publication Data

US 2014/0302563 A1    Oct. 9, 2014

Related U.S. Application Data

(63) Continuation of application No. PCT/US2013/053287, filed on Aug. 1, 2013.

(60) Provisional application No. 61/679,397, filed on Aug. 3, 2012.

(51) Int. Cl.
*C12P 19/34* (2006.01)
*C12N 15/85* (2006.01)

(52) U.S. Cl.
CPC .............. *C12P 19/34* (2013.01); *C12N 15/85* (2013.01); *C12N 2830/50* (2013.01)

(58) Field of Classification Search
CPC .................................. C12P 19/34; C12N 15/85
See application file for complete search history.

(56) References Cited

U.S. PATENT DOCUMENTS

| | | |
|---|---|---|
| 2010/0093026 A1 | 4/2010 | Shimada et al. |
| 2011/0189776 A1 | 8/2011 | Terns et al. |
| 2011/0217739 A1 | 9/2011 | Terns et al. |

FOREIGN PATENT DOCUMENTS

WO    WO 2011/143124    11/2011

OTHER PUBLICATIONS

Beloglazova et al (The Journal of Biological Chemistry. 2008; 283(29): 20361-20371).*
Yen et al (Nature. 2004; 431: 472-476).*
Weidenheft et al (PNAS. Jun. 21, 2011; 108(25): 10092-10097 and PNAS. Sep. 6, 2011, 108(36): 15010 and Supporting Information, pp. 1-9).*
Rachel Haurwitz. PhD Dissertation, Spring 2012. "The CRISPR endoribonuclease Cys4 utilizes unusual sequence- and structure-specific mechanisms to recognize and process crRNAs" UC Berkeley. Permalink: https://escholarship.org/uc/item/0rh5940p.*
Haurwitz et al., "Sequence- and Structure-Specific RNA Processing by a CRISPR Endonuclease", Science, 2010, 329(5997): 1355-1358.
Janssen et al., "Kinetics of Paused Ribosome Recycling in *Escherichia coli*", J. Mol. Biol., 2009, 394(2): 251-267.
Kumar et al., "Plasmid pT181 Replication is Regulated by Two Countertranscripts", Proc. Nati. Acad. Sci. USA, 1985, 82:638-642.
Lucks et al., "Versatile RNA-sensing Transcriptional Regulators for Engineering Genetic Networks", Proc. Nati. Acad. Sci. USA, 2011, 108(21):8617-8622.
Marakova et al., "Evolution and Classification of the CRISPR—Cas Systems", Nature Reviews Microbiology, 2011, 9(6): 467-477.
Mutalik et al., "Rationally Designed Families of Orthogonal RNA Regulators of Translation", Nature Chemical Biology, 2012, 8:447-454.
Wek et al., "Rho-Dependent Transcriptional Polarity in the ilvGMEDA Operon of Wild-Type *Escherichia coli* K12*", J. Biol. Chem., 1987, 262(31):15256-15261.

* cited by examiner

*Primary Examiner* — Scott Long
(74) *Attorney, Agent, or Firm* — Bozicevic Field & Francis, LLP; Paula A. Borden

(57) ABSTRACT

The present disclosure provides nucleic acids encoding an RNA recognition sequence positioned proximal to an insertion site for the insertion of a sequence of interest; and host cells genetically modified with the nucleic acids. The present disclosure also provides methods of modifying the activity of a target RNA, and kits and compositions for carrying out the methods.

18 Claims, 55 Drawing Sheets

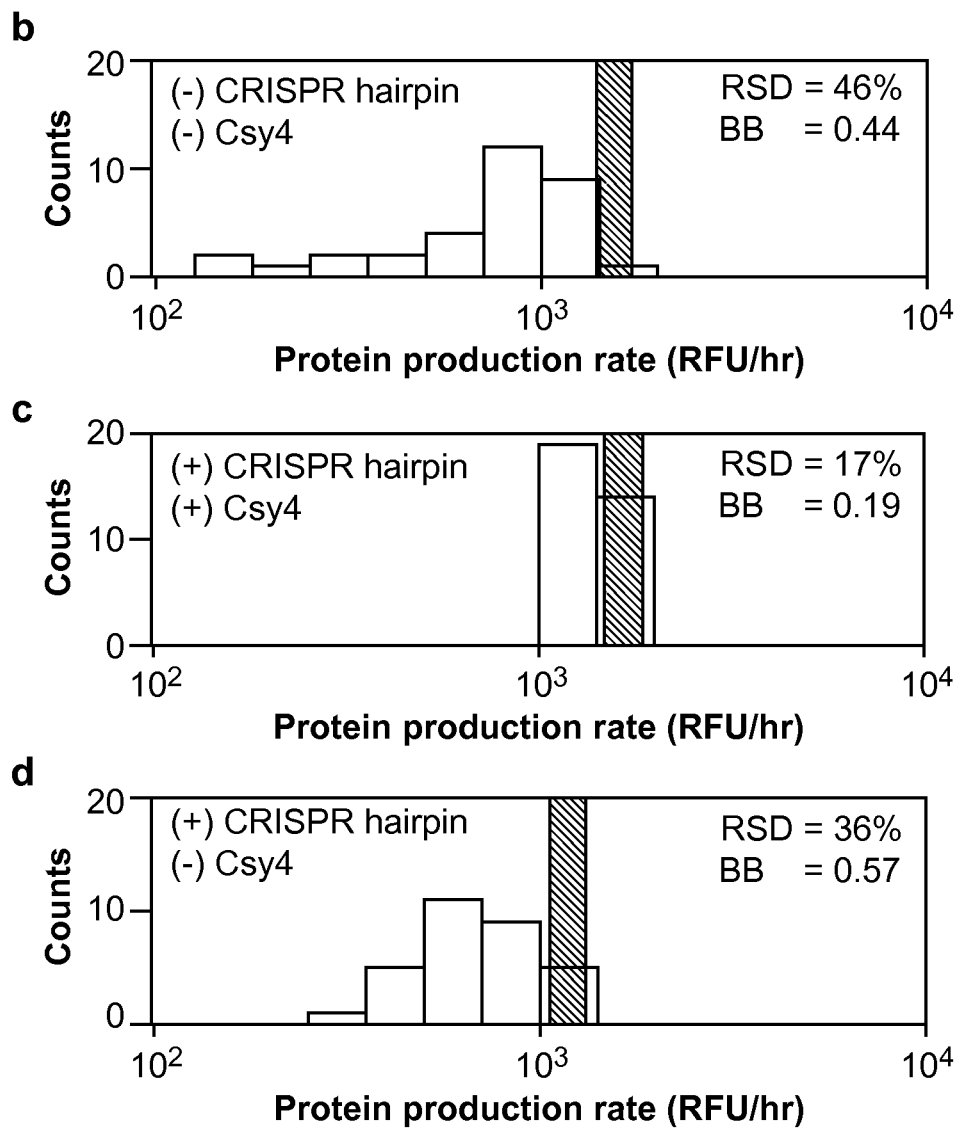
FIG. 3 (Cont. 1)

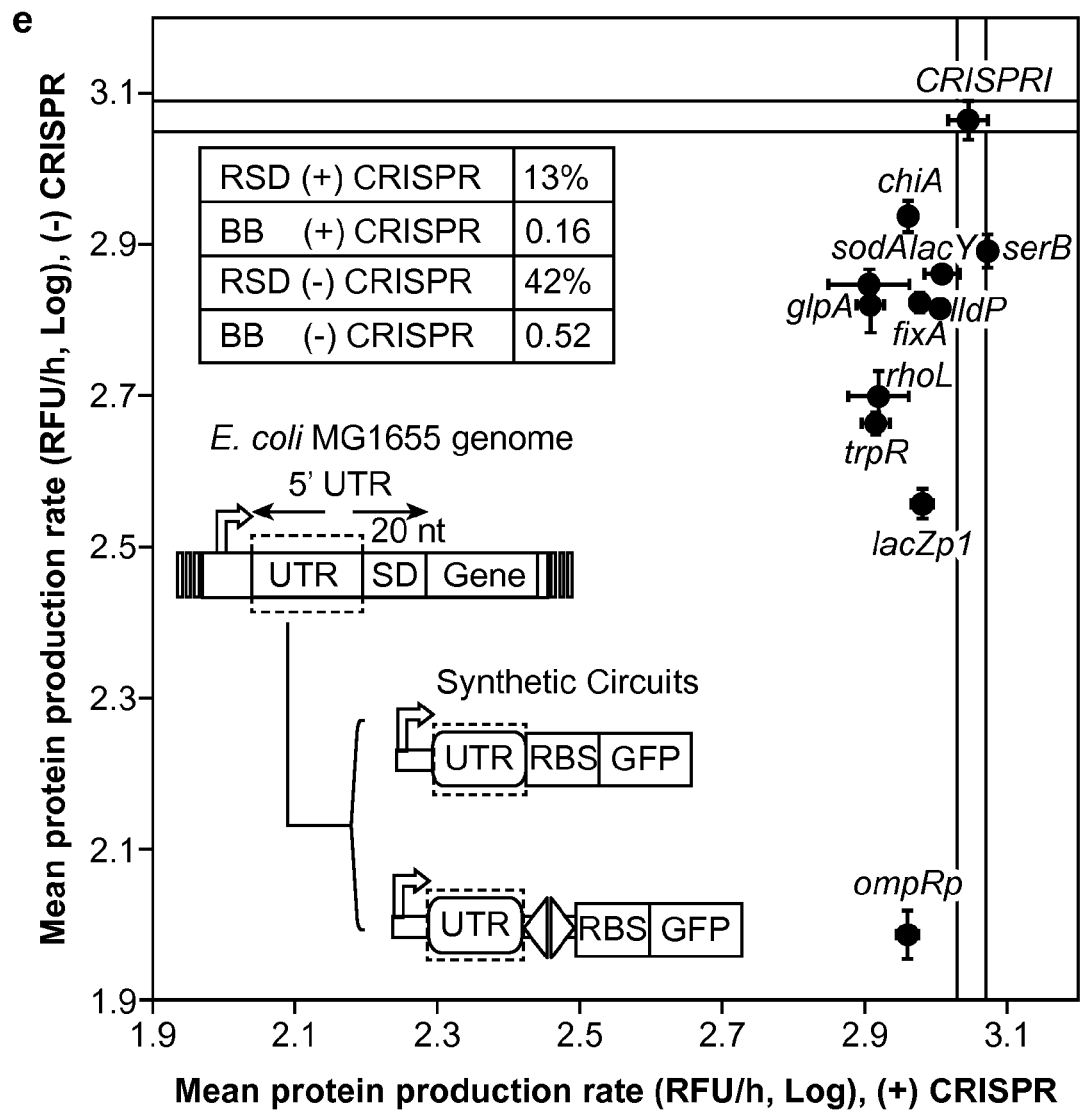
FIG. 3 (Cont. 2)

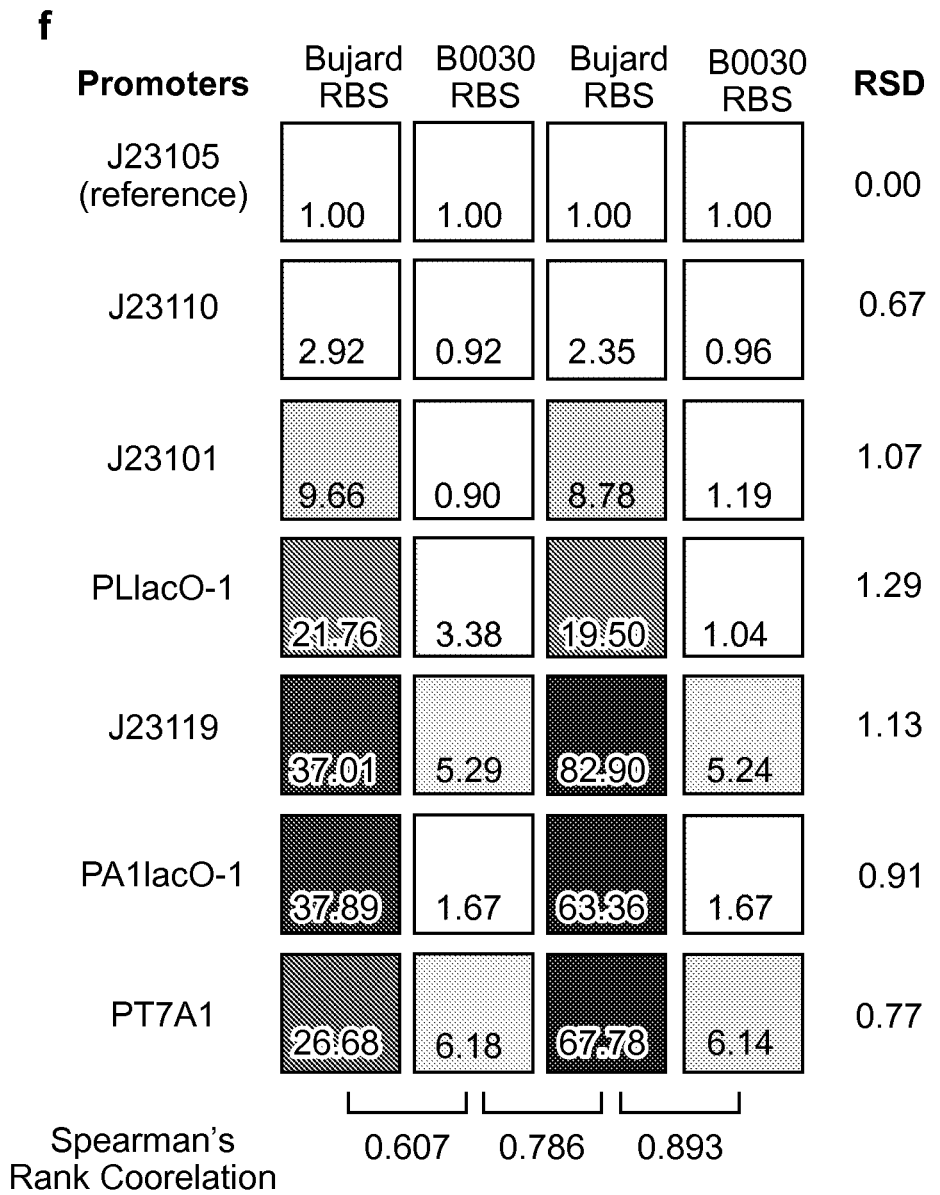
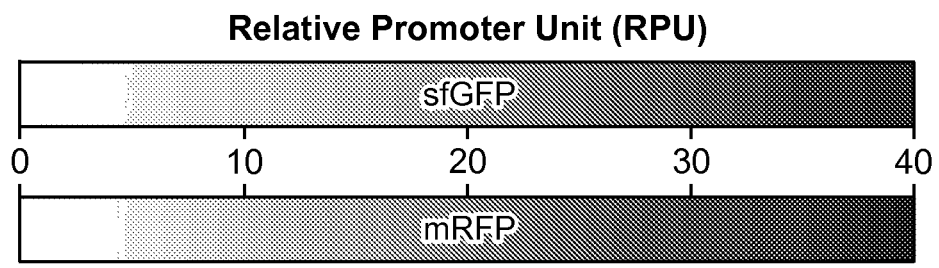
FIG. 3 (Cont. 3)

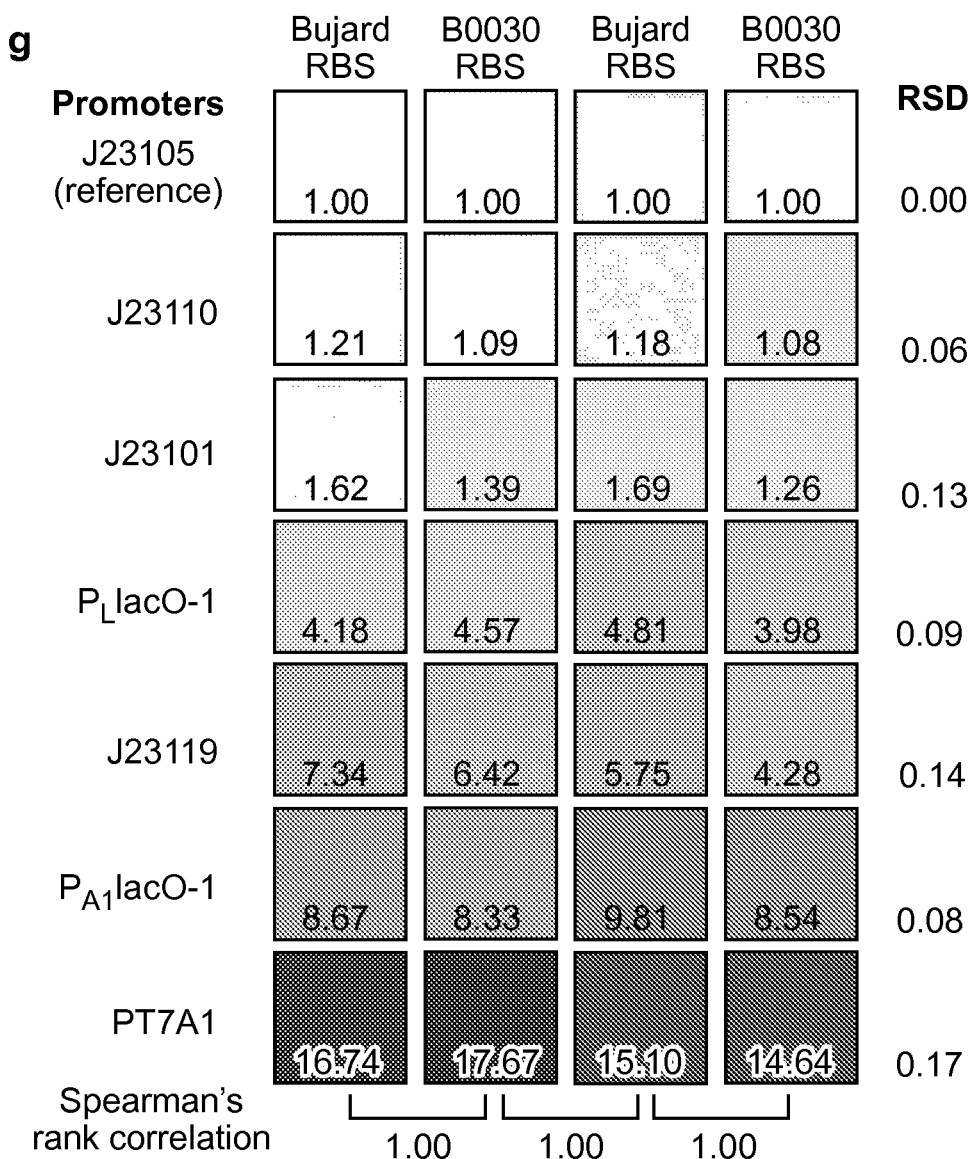
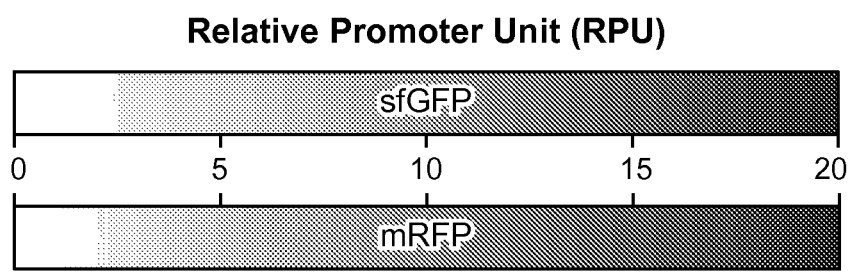
FIG. 3 (Cont. 4)

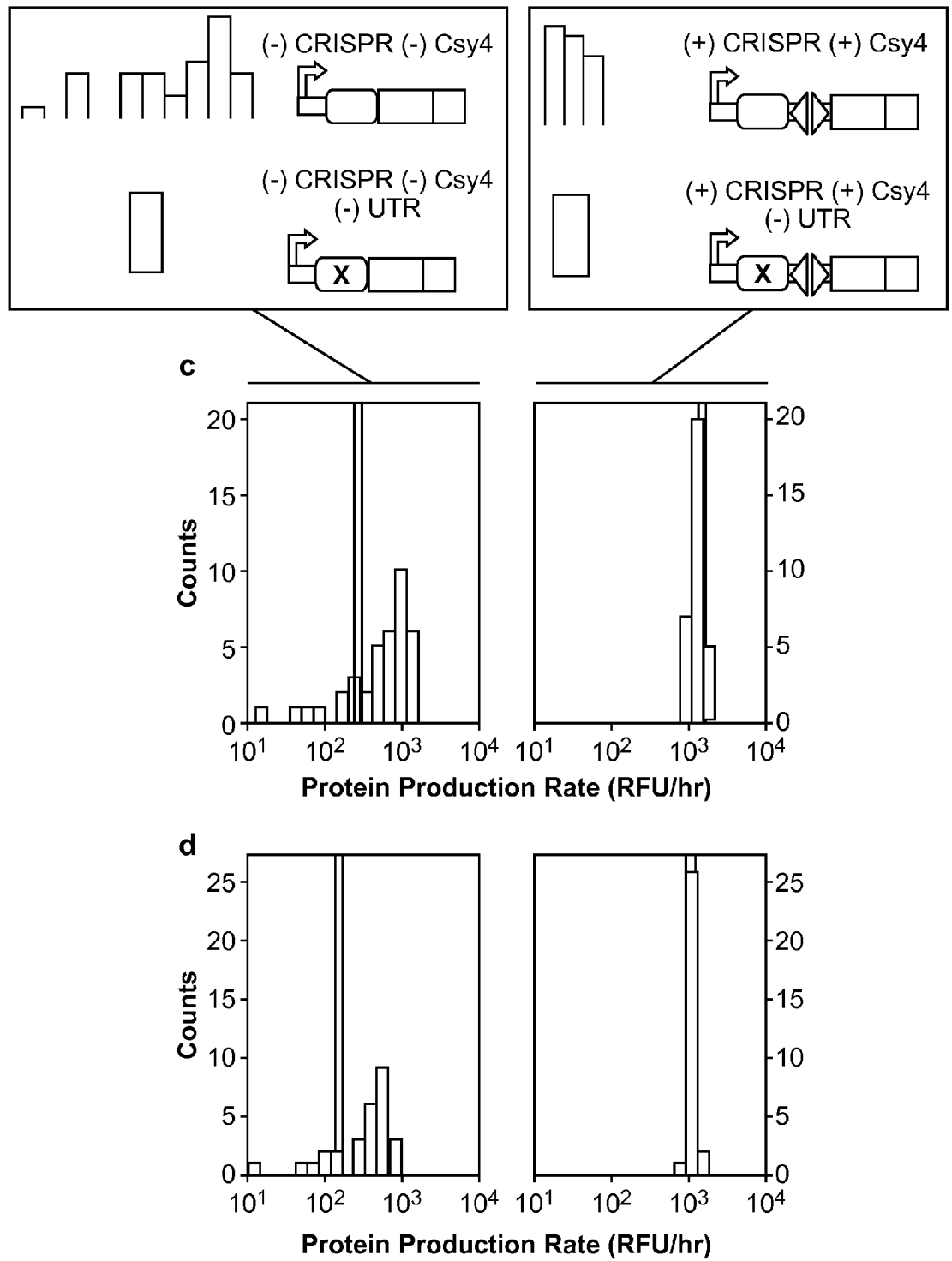
FIG. 5 (Cont. 1)

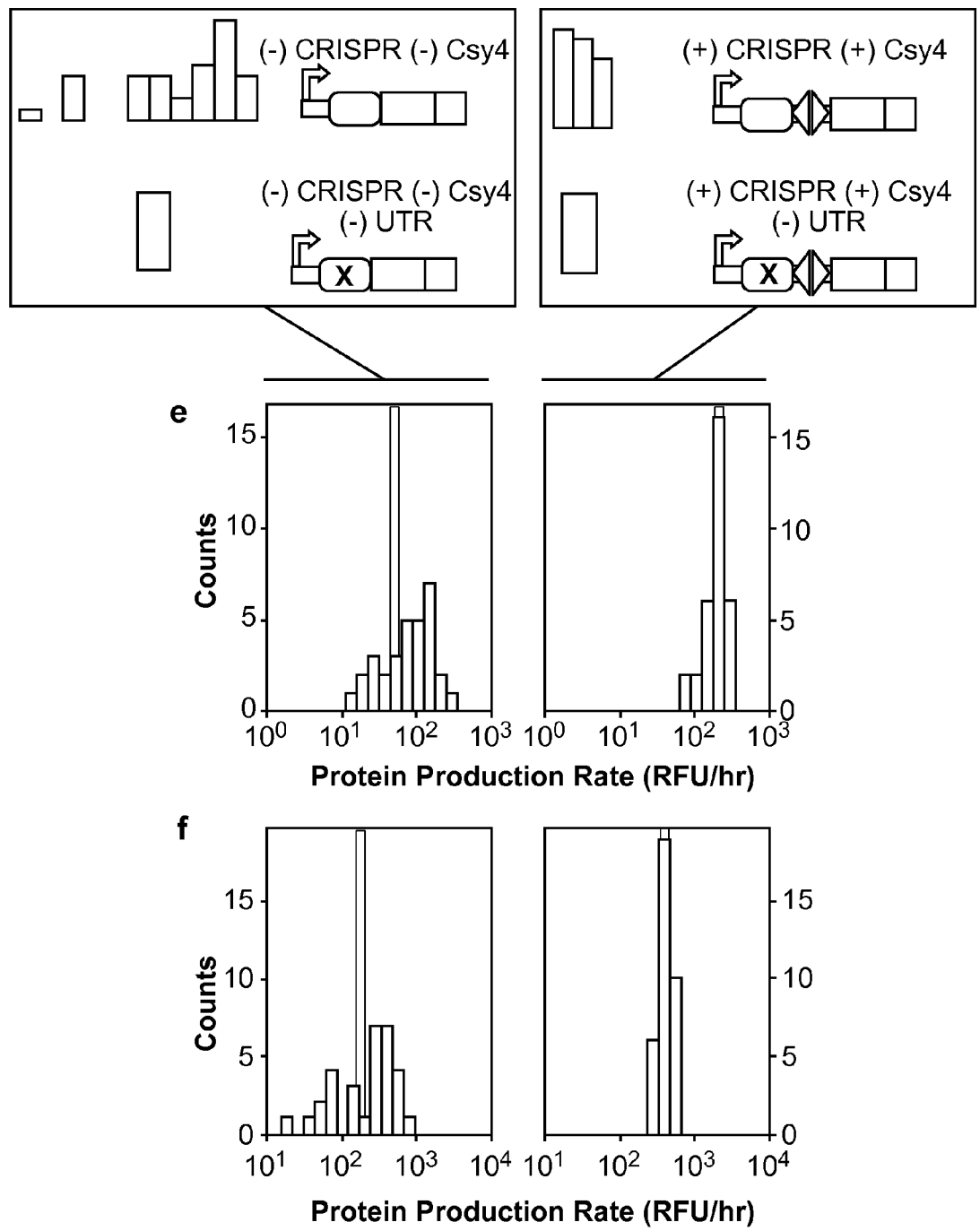
FIG. 5 (Cont. 2)

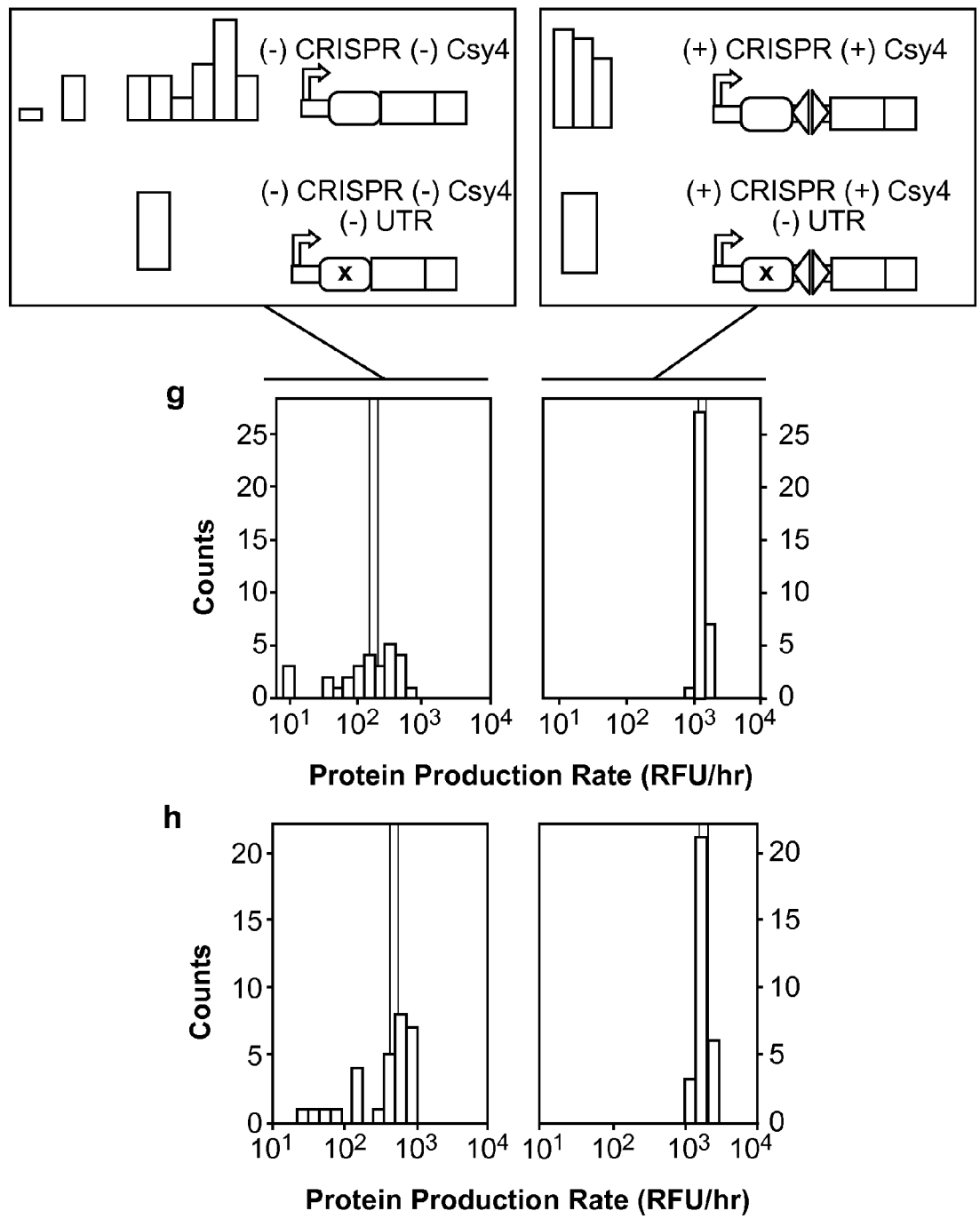
FIG. 5 (Cont. 3)

i

| # | RBS | Reporter | (±) CRISPR | BB | RSD (%) |
|---|---|---|---|---|---|
| a | Bujard | sfGFP | (-) | 0.56 | 46% |
| | | | (+) | 0.74 | 19% |
| b | B0030 | sfGFP | (-) | 2.21 | 60% |
| | | | (+) | 0.73 | 13% |
| c | Anderson | sfGFP | (-) | 1.88 | 68% |
| | | | (+) | 0.81 | 27% |
| d | Weiss | sfGFP | (-) | 1.77 | 67% |
| | | | (+) | 0.97 | 22% |
| e | Bujard | mRFP | (-) | 0.55 | 32% |
| | | | (+) | 0.70 | 15% |
| f | B0030 | mRFP | (-) | 2.35 | 61% |
| | | | (+) | 0.88 | 11% |
| g | Anderson | mRFP | (-) | 1.39 | 80% |
| | | | (+) | 0.79 | 13% |
| h | Weiss | mRFP | (-) | 0.94 | 62% |
| | | | (+) | 0.80 | 12% |

FIG. 5 (Cont. 4)

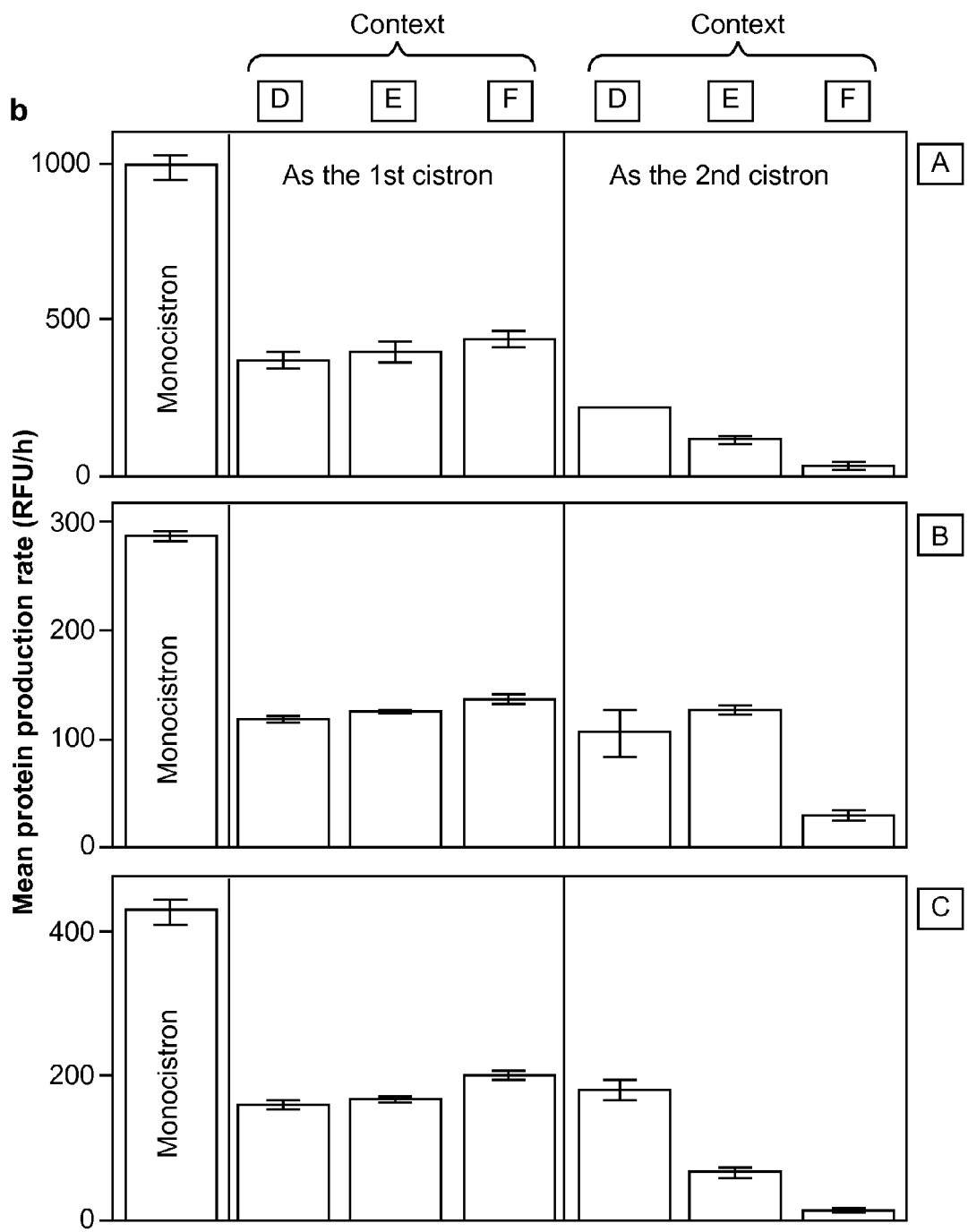
FIG. 6 (Cont. 1)

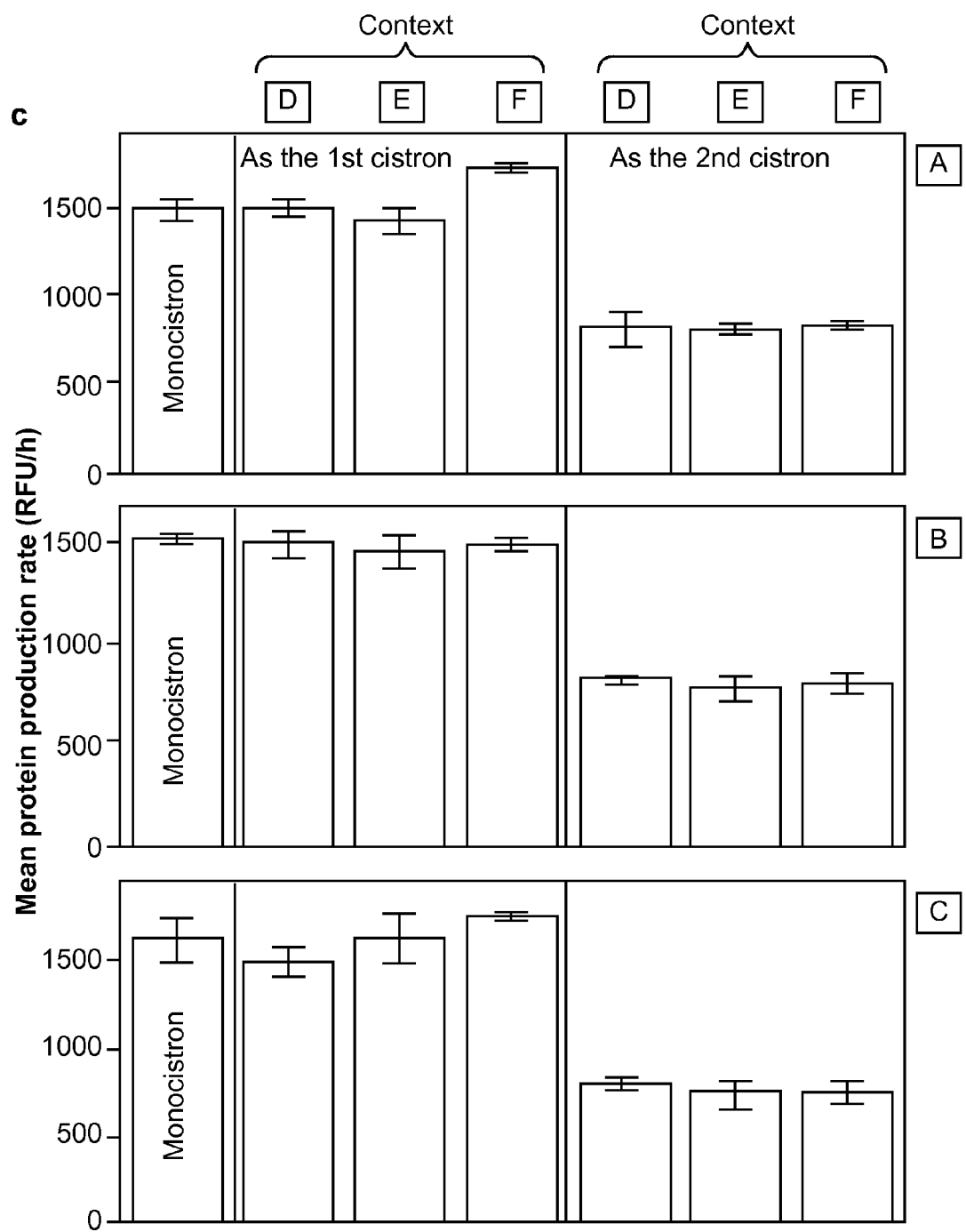
FIG. 6 (Cont. 2)

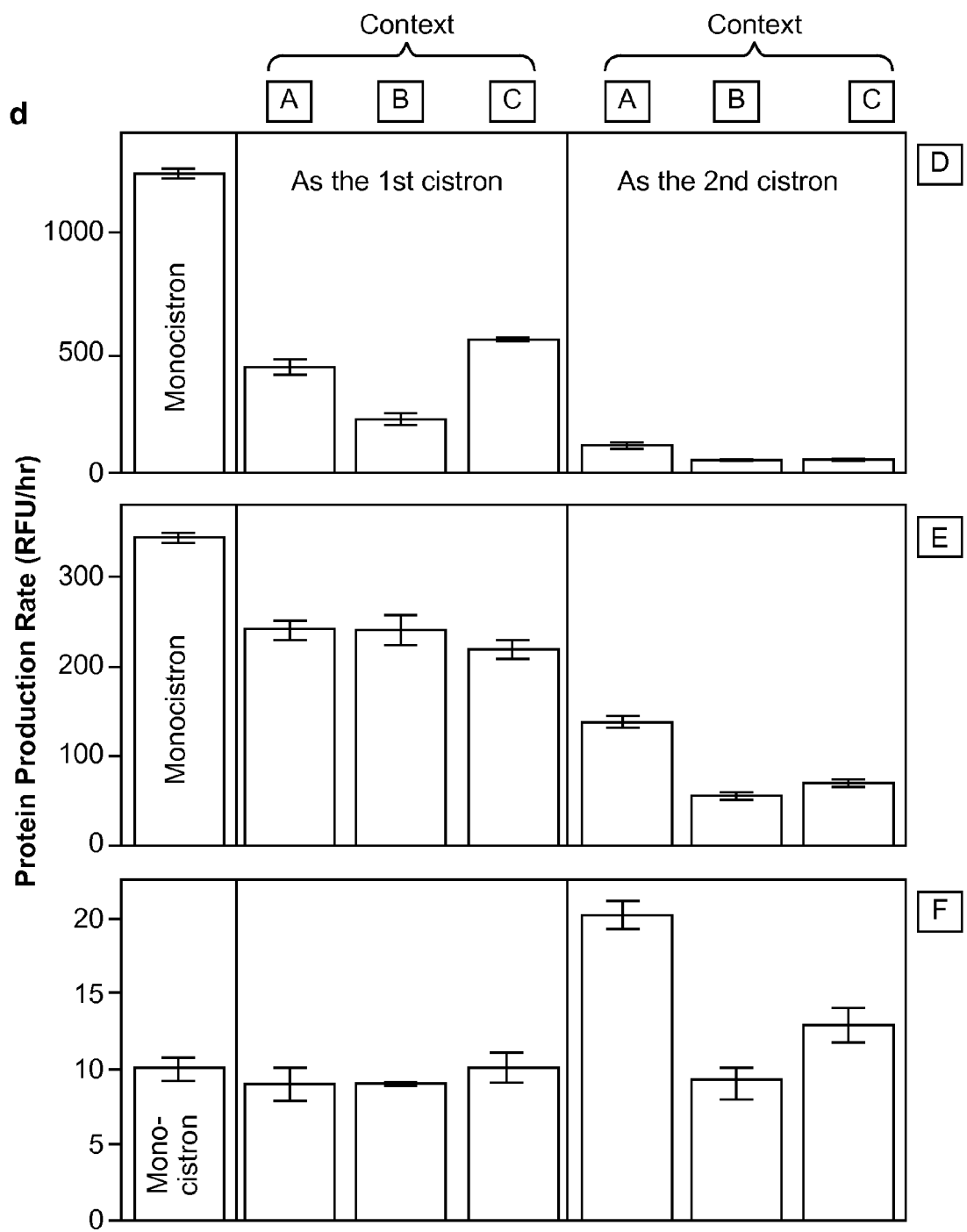
FIG. 6 (Cont. 3)

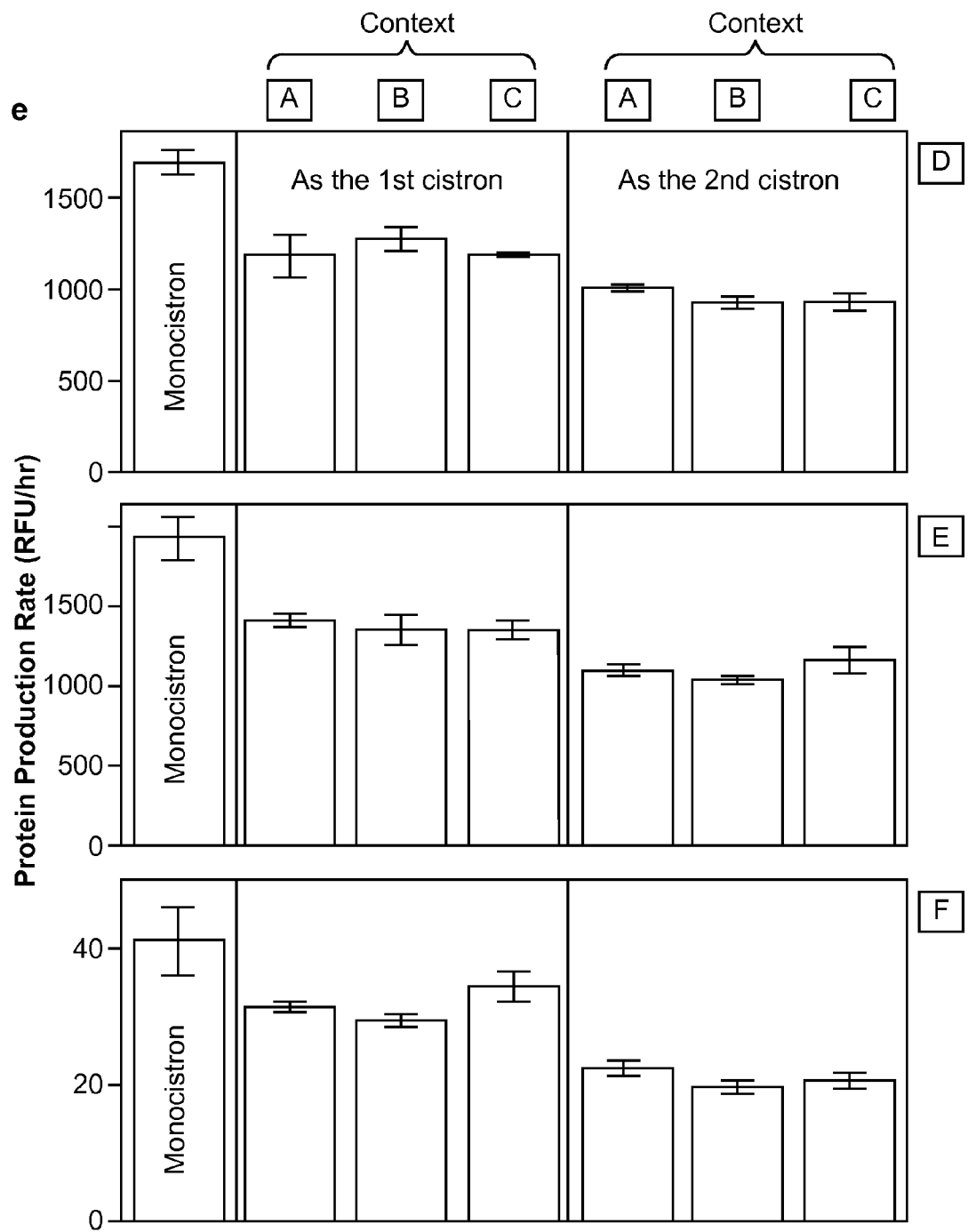
FIG. 6 (Cont. 4)

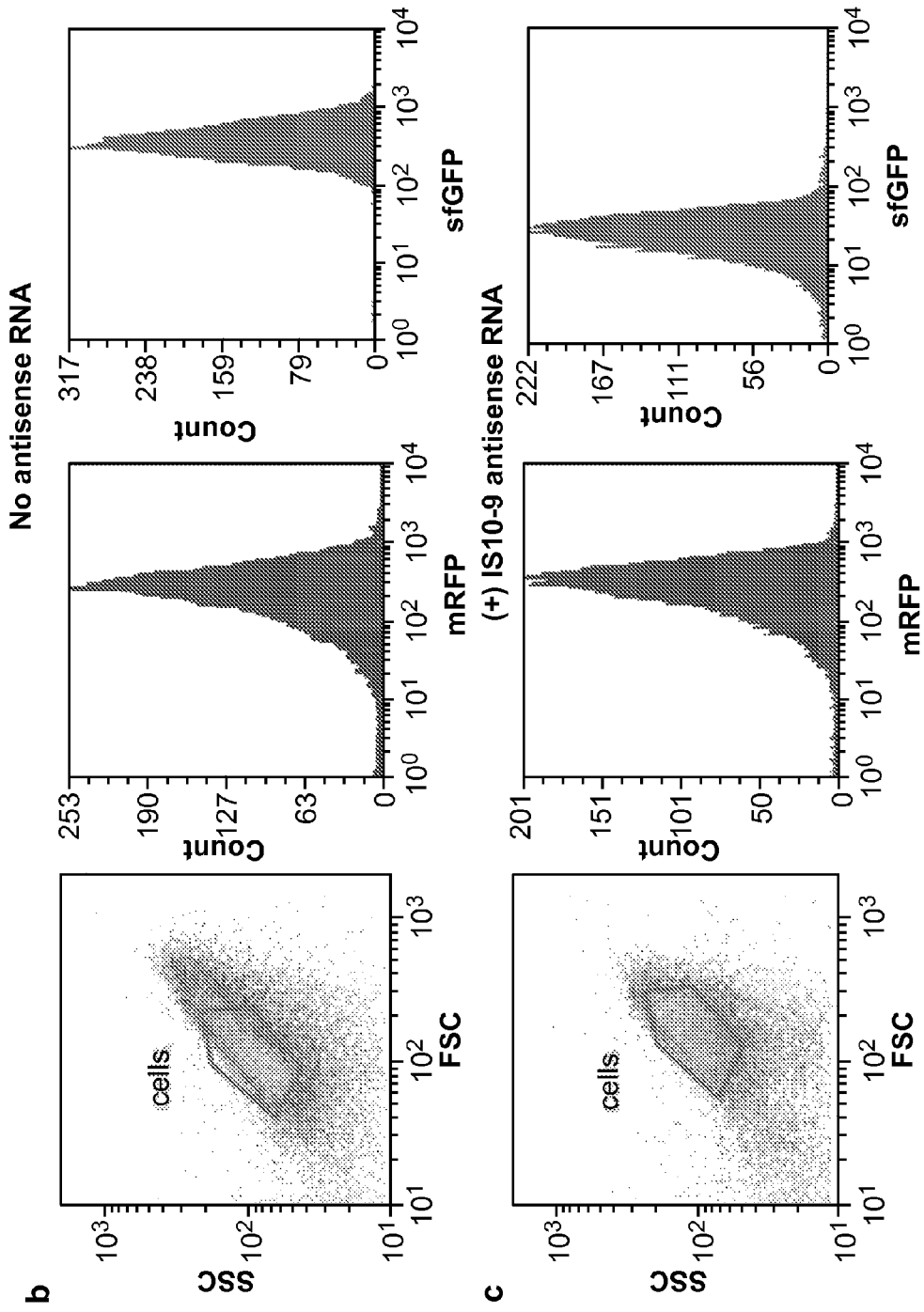
FIG. 8 (Cont. 1)

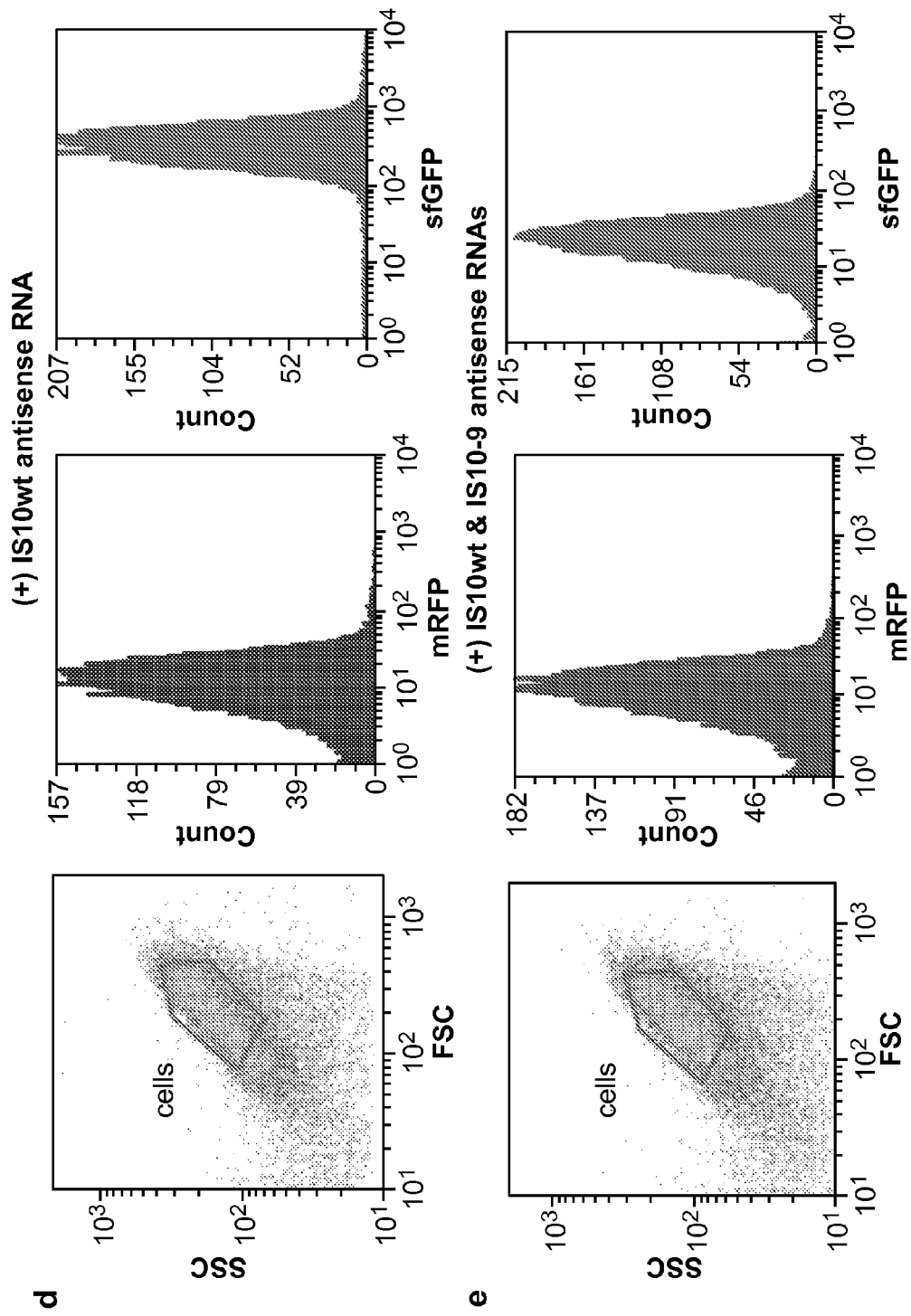
FIG. 8 (Cont. 2)

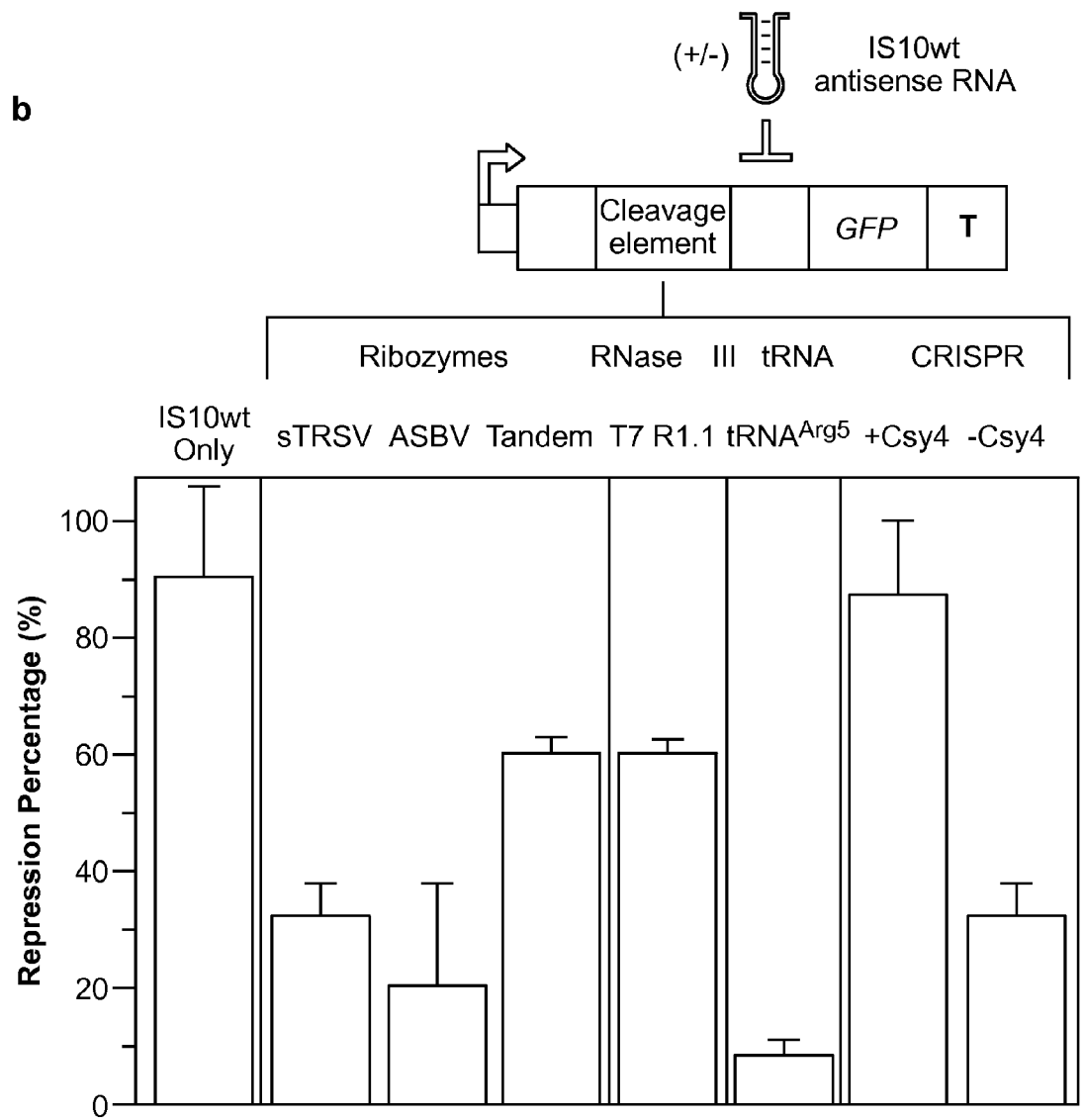
FIG. 9 (Cont. 1)

C
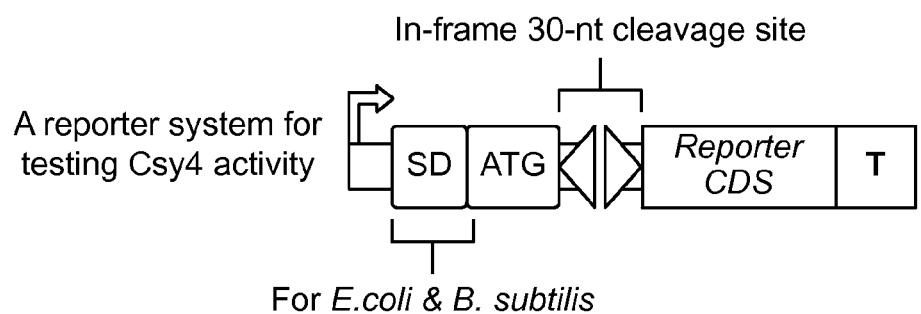
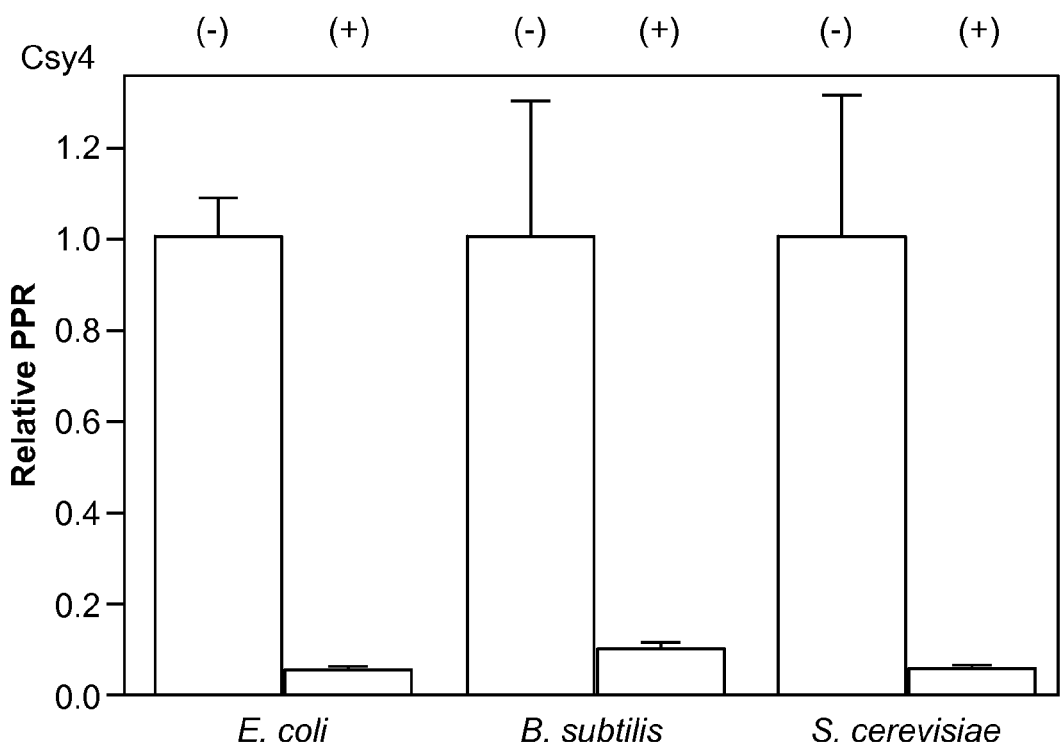
FIG. 9 (Cont. 2)

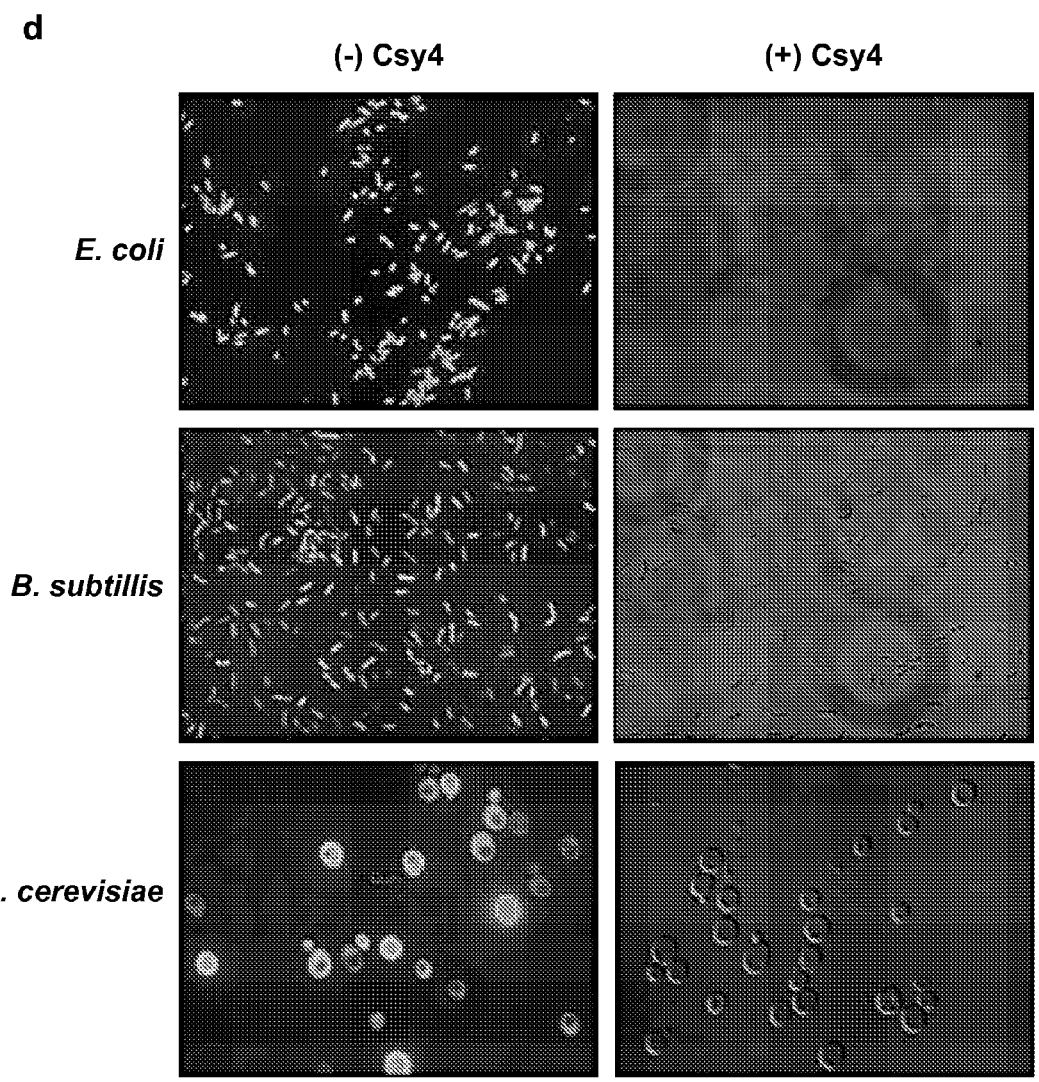
FIG. 9 (Cont. 3)

Csy4 sequence
>gi|116050369|ref|YP_790814.1| hypothetical protein PA14_33300 [Pseudomonas aeruginosa UCBPP-PA14]
MSVLFGKLHQALVAQGGDRIGVSFPDLDESRSRLGERLRIHASADDLRALLARPWLEGLRDHLQFGEPAVVPHPTPYRQVSRVQAKSNPERLRRRLMRRHDLSEEEARKRIPDTVARALDLPFVTLRSQSTGQHFRLFIRHGPLQVTAEEGGFTCYGLSKGGFVPWF (SEQ ID NO:1)

RNA recognition sequence
GUUCACUGCCGUAUAGGCAGCUAAGAAA (SEQ ID NO:56)

FIG. 10A

Csy4 sequence
>gi|107101871|ref|ZP_01365789.1| hypothetical protein PaerPA_01002916 [Pseudomonas aeruginosa PACS2]
MDHYLDIRLRPDPEFPPAQLMSVLFGKLHQALVAQGGDRIGVSFPDLDESRSRLGERLRIHASADDLRALLARPWLEGLRDHLQFGEPAVVPHPTPYRQVSRVQVKSNPERLRRRLMRRHDLSEEEARKRIPDTVARALDLPFVTLRSQSTGQHFRLFIRHGPLQVTAEEGGFTCYGLSKGGFVPWF (SEQ ID NO: 2)

RNA recognition sequences
GUUCACUGCCGUGUAGGCAGCUAAGAAA (SEQ ID NO:57)
GUUCACUGCCGUAUAGGCAGCUAAGAAA (SEQ ID NO:58)

FIG. 10B

>gi|254235433|ref|ZP_04928756.1| hypothetical protein PACG_01340 [Pseudomonas aeruginosa C3719]
MDHYLDIRLRPDPEFPPAQLMSVLFGKLHQALVAQGGDRIGVSFPDLDESRSRLGERLRIHASADDLRALLARPWLEGLRDHLQFGEPAVVPHPTPYRQVSRVQAKSNPERLRRRLMRRHDLSEEEARKRIPDTVARTLDLPFVTLRSQSTGQHFRLFIRHGPLQATAEEGGFTCYGLSKGGFVPWF (SEQ ID NO: 3)

RNA recognition sequences
GUUCACUGCCGUGUAGGCAGCUAAGAAA (SEQ ID NO: 59)
GUUCACUGCCGUAUAGGCAGCUAAGAAA (SEQ ID NO: 60)

FIG. 10C

>gi|254240857|ref|ZP_04934179.1| hypothetical protein PA2G_01531 [Pseudomonas aeruginosa 2192]
MDHYLDIRLRPDPEFPPAQLMSVLFGKLHQALVAQGGDRIGVSFPDLDESRSRLGERLRIHASADDLHAL
LARPWLEGLRDHLQFGEAAVVPHPTPYRQVSRVQAKSNPERLRRLMRRHDLSEEEARKRIPDTVARTLD
LPFVTLRSQSTGQHFRLFIRHGPLQATAEEGGFTCYGLSKGGFVPWF (SEQ ID NO: 4)

RNA recognition sequences
GUUCACUGCCGUGUAGGCAGCUAAGAAA (SEQ ID NO: 61)
GUUCACUGCCGUAUAGGCAGCUAAGAAA (SEQ ID NO: 62)

FIG. 10D

>gi|242238181|ref|YP_002986362.1| CRISPR-associated protein, Csy4 family [Dickeya dadantii Ech703]
MDHYIEIRVLPDLEFSAVQLLSALFAKLHRALGQRATGAIGVSFPDVDKTLGERLRLHGSVQELAALEQT
GWLKGLRDYTAITEPLPVPAGAKHRTVRRVQVKSSAERLRRAVSKGRMTEDEAATRIPYAVEKRSSLPY
LPLRSLSSGQTFLLFVEHGPLQDKPVAGAFSSYGLSATTTIPWF (SEQ ID NO: 5)

RNA recognition sequences
GUUCACUGCCGCGUAGGCAGCUUAGAAA (SEQ ID NO: 63)
GUUCACUGCCGAGUAGGCAGCUUAGAAA (SEQ ID NO: 64)

FIG. 10E

>gi|261822890|ref|YP_003260996.1| CRISPR-associated protein, Csy4 family [Pectobacterium wasabiae WPP163]
MDHYIDIRVQPDPEFTAPQLLNALFAKLHRALGQLADGKIGISFPEVGKTLGECLRLHGTADALSTLEKT
SWLKGLRDYTQVSECKAVPNNVKFRTVRRVQLKTSAERLRRRSVNKGWLTEAEAAARIPDAVEKRSTLPF
VQIKSLSNGQMFFVFVEHGPLQNAPATGRFSSYGLSAEATVPWF (SEQ ID NO: 6)

RNA recognition sequence
GUUCACUGCCGUAUAGGCAGCUUAGAAA (SEQ ID NO: 65)

FIG. 10F

>gi|253990195|ref|YP_003041551.1| hypothetical protein PAU_02718 [Photorhabdus asymbiotica subsp. asymbiotica ATCC 43949]
MDYYFEILVLPDPEFSKQSLMEALFAKLHRALGQVGNGRIGVSFPCARKTLGDKLRIHGASEALNDLQAL
PWLKGLRDYTEIMDIQPVPQDTQYRRVSRVQVKSSAERLRRSIKKGWLTEEQARQRIPISKEQRTHLPF
LLVKSLSSRQTFPLFIEQGPIEDKPTPGVFSSYGLSASATIPWF (SEQ ID NO: 7)

RNA recognition sequences
GUUCACUGCGUACAGGCAGCUUAGAAAA (SEQ ID NO: 66)
GUGCACUGCCGUACAGGCAGCUUAGAAA (SEQ ID NO: 67)
ACUGCCGUACAGGCAGUUUAGAAA (SEQ ID NO: 68)
GUUCACUGCCGCACAGGCAGCUUAGAAA (SEQ ID NO: 69)
GUGUACUGCCGUACAGGCAGCUUAGAAA (SEQ ID NO: 70)
GUUCACUGCCGUACAGGCAGCUUAGAAA (SEQ ID NO: 71)

FIG. 10G

>gi|307132482|ref|YP_003884498.1| hypothetical protein Dda3937_03453 [Dickeya dadantii 3937]
MDHYIEIRVLPDPEFSGVQLLSALFAKLHRALGQRATGAIGVSFPDAGKTLGERLRLHGSVQELAALEQT
GWLRGLRDYTAITEPLPVPAGVKHRTVRRVQVKSSAERLRRRAVNKGRMTVDEADARIPYTVEKRTSLPY
LPLRSLSNGQTFLLFVEHGPLQDKPVAGAFSSYGLSAVATIPWF (SEQ ID NO: 8)

RNA recognition sequences
GUUCACUGCCGUGUAGGCAGCUUAGAAA (SEQ ID NO: 72)
GUUCACUGCCGAGUAGGCAGCUUAGAAA (SEQ ID NO: 73)

FIG. 10H

>gi|285019813|ref|YP_003377524.1| CRISPR-associated protein, csy4 family [Xanthomonas albilineans GPE PC73]
MQHYLDLHLRPDPELAPYQLLGALYARLHRSLVTLNTTRIGVSFPGHDNRVPTLGTHLRLHGDDSTLHHL
MATTWLHGVRDHVTITSIGAVPSEAVHRQVTRVQAKSSPERLRRRAMRRHGISEDLAVQRIPDSAAEQLR
LPFVVLGSRSTGQTAFPVFVRHGPVQQEPVPGDFSSYGLSRGATVPWF (SEQ ID NO: 9)

RNA recognition sequences
GUUCACUGCCGUGUAGGCAGCUCAGAAA (SEQ ID NO: 74)
UUCACUGCCGUGUAGGCAGCUCAGAAA (SEQ ID NO: 75)
GUUCACUGCCGUAUAGGCAGCUCAGAAA (SEQ ID NO: 76)

FIG. 10I

>gi|50122605|ref|YP_051772.1| hypothetical protein ECA3684 [Pectobacterium atrosepticum SCRI1043]
MDHYIDIRVQPDPEFTASQLLNALFAKLHRVLGQLANGKIGISFPEVGKTLGECLRLHGTEDALSTLEKT
SWLKGLRDYTQVSECKVVPNGVKFRTVRRVQLKSSAERLRRRSVSKGWLTAAEAAARIPDAVEKRSALPF
VQIKSLSNGQMFFVFVEHGPLQNAPTAGRFSSYGLSTEATVPWF (SEQ ID NO: 10)

RNA recognition sequence
GUUCACUGCCGUACAGGCAGCUUAGAAA (SEQ ID NO: 77)

FIG. 10J

>gi|37525730|ref|NP_929074.1| hypothetical protein plu1796 [Photorhabdus luminescens subsp. laumondii TTO1]
MDYYLEIRVLPDLEFSQQSLFEALFAKLHRALGQLSNGQVGVSFPCARKTLGDTLRIHGSSEALNDLQAL
PWLKGLRDYTEVIDIQPIPQETKYRCVSRVQVKSSAERLRRRAIKKGWLTGEQARQRIPISKEQRTHLPF
LFLKSLSSGQSFLLFVKQGPIQDKPTSGIFSSYGLSSSATIPWF (SEQ ID NO: 11)

RNA recognition sequences
GUGCACUGCCGUACAGGCAGCUUAGAAA (SEQ ID NO: 78)
GUUCACUGCCGUACAGGCAGCUUAGAAA (SEQ ID NO: 79)

FIG. 10K

>gi|297569494|ref|YP_003690838.1| CRISPR-associated protein, Csy4 family [Desulfurivibrio alkaliphilus AHT2]
MVMAMDCYVEISLLPDPEFPDSILMNALFAKLHRALAENGKQEIGVSFPEFGKKLNSKLRIHGSEESLKR
LMDLNWIQGMKDYTRVSGIAKVPDSCQYRTVKRVQAKSSVDRLYRRSVKKGWLSEENAEQQKERAREGRL
KLPFVQLKSQTTGQQFRLFIQHGSLQEKPVTGRFSSYGLSNEATVPWF (SEQ ID NO: 12)

RNA recognition sequence
GUUCACUGCCCGCACAGGCAGCUCAGAAA (SEQ ID NO: 80)

FIG. 10L

>gi|251788340|ref|YP_003003061.1| Csy4 family CRISPR-associated protein [Dickeya zeae Ech1591]
MDHYIEIRVLPDLEFSAVQLLSALFAKLHRALGQOATGAIGVSFPDVGKTLGERLRLHGSEQALTALEQT
GWRTGLRDYSTITDVLTVPTGAQYRTVRRVQVKSSAERLRRRAVSKGWLTADEAAARIPYAVEKRTSLPY
LPLRSLSSGQPFLLFVEHGPLQDKPVAGTFSSYGLSATATIPWF (SEQ ID NO: 13)

RNA recognition sequences
GUUCACUGCCGUGUAGGCAGCUUAGAAA (SEQ ID NO: 81)
GUGCACUGCCGUAUAGGCAGCUUAGAAA (SEQ ID NO: 82)

FIG. 10M

>gi|22125621|ref|NP_669044.1| hypothetical protein y1727 [Yersinia pestis KIM 10]
MDHYLDIRVLPDPEFSAQTLLEALFAKLHRALVATIPGRVGVSFPTAGKTLGSQLRLHGSRGDLLELQSA
GWLKGLQDYCECSEILPVPADVKHRTIRRVQVKSSAQRLRRRSVSKGWLTEEQARLRIPDSHDKRCDLPF
LRLKSRSSEQYFLLFIEQGTLQASATTGEFSAYGLSVNATIPWF (SEQ ID NO: 14)

RNA recognition sequences
GUUCACUGCCGCACAGGCAGCAGGCUUAGAAA (SEQ ID NO: 83)
UGUUCACUGCCGCACAGGCAGCAGGCUUAGAAAA (SEQ ID NO: 84)

FIG. 10N

>gi|271501952|ref|YP_003334978.1| Csy4 family CRISPR-associated protein [Dickeya dadantii Ech586]
MDHYIEIRVLPDPEFSAVQLLSALFAKLHRALGQRATGDIGVSFPDAGKTLGERLRLHGSVQALAALEQT
GWLKGLRDYSTITDVLTVPTGAQYRTVRRVQVKSSAERLRRRAVSKGRMTADEAAARIPYAAEKRTSLPY
LPLRSLSSGQTFLLFVEHGPLQEKPVAGVFSSYGLSAIATIPWF (SEQ ID NO: 15)

RNA recognition sequences
GUGAACUGCCGCAUAGGCAGCUUAGAAA (SEQ ID NO: 85)
GUUCACUGCCGAGUAGGCAGCUUAGAAA (SEQ ID NO: 86)

FIG. 10O

>gi|117623067|ref|YP_851980.1| hypothetical protein APECO1_1206 [Escherichia coli APEC O1]
MAVSLVRNRNKELPMDHYLEIRVLPDPEFSSEMLMAALFAKLHRVLGARGQGDIGVSFPDVNVMPGARLR
LHGSAQALQALEASTWRKGLTDYCQCSPVTPVPEIKGWRVVSRVQVKSNPQRLLRRSVKKGWLTEEQAIE
RLATQAEQRTDLPFLNMKSLSSQQLFKLFIRHGDLLKEPVKGEFSSYGLSATATIPWF (SEQ ID NO: 16)

RNA recognition sequence
GUUCACUGCCGUACAGGCAGCUUAGAAA (SEQ ID NO: 87)

FIG. 10P

>gi|91209927|ref|YP_539913.1| hypothetical protein UTI89_C0896 [Escherichia coli UTI89]
MDHYLEIRVLPDPEFSSEMLMAALFAKLHRVLGARGQGDIGVSFPDVNVMPGARLRLHGSAQALQALEAS
TWRKGLTDYCQCSPVTPVPEIKGWRVVSRVQVKSNPQRLLRRSVKKGWLTEEQAIERLATQAEQRTDLPF
LNMKSLSSQQLFKLFIRHGDLLKEPVKGEFSSYGLSATATIPWF (SEQ ID NO: 17)

RNA recognition sequence
GUUCACUGCCGUACAGGCAGCUUAGAAA (SEQ ID NO: 88)

FIG. 10Q

>gi|237808124|ref|YP_002892564.1| CRISPR-associated protein, Csy4 family [Tolumonas auensis DSM 9187]
MDHYLDIRLLPEEPEVSESFLLNALFAKLHVRLGQQAQGRVGVSFPDHHKRLGDLLRLHGQRTDLQALMA
DDWLQGLKGYTQCSEVLPIPATVSYRAVKRVQAKSAHNKRQRSIAKGWLTESEAQIRIPDTQQKELHLPF
VQLKSRSNGQMMRVYVEHGPVLAVPVSGYFNAYGLSSIATIPWF (SEQ ID NO: 18)

RNA recognition sequence
CUUCACUGCCGCACAGGCAGCUUAGAAA (SEQ ID NO: 89)

FIG. 10R

>gi|259907505|ref|YP_002647861.1| CRISPR-associated protein Csy4 [Erwinia pyrifoliae Ep1/96]
MDHYQDIRVRVDEENGEAVLLAQVFMHLHQVLMRAANGRIGISFPNVKRTLGDRIRLHGTLDDLSALQQS
GWNKCLRDYIACSDIAPVPKGAAWRTVRRVQVKSSAERLRRRSVNKGWLSEQEAAERISVLNEQRSNLPF
LQIKSGSNGQAWRLFIEHGSLVSAPSDGSFSSYGLSAAATIPWF (SEQ ID NO: 19)

RNA recognition sequences
GUUCACUGCCGCACAGGCAGCUUAGAAA (SEQ ID NO: 90)
UUCACUGCCGUACAGGCAGCUUAGAAAA (SEQ ID NO: 91)

FIG. 10S

>gi|218688670|ref|YP_002396882.1| hypothetical protein ECED1_0855 [Escherichia coli ED1a]
MAVSLVRNRNKELPMDHYLEIRVLPDPEFSSEMLMAALFAKLHRVLGARGQGDIGVSFPDVNVMPGTHLR
LHGSAQALQELEASTWRKGLTDYCQCSPVTPVPEIKGWRVVSRVQVKSNPQRLLRRSVKKGWLTEEQAIE
RLATQAEQRTDLPFLNMKSLSSQQQFKLFIRHGDLLKEPVKGEFSSYGLSATATIPWF (SEQ ID NO: 20)

RNA recognition sequence
GUUCACUGCCGUACAGGCAGCUUAGAAA (SEQ ID NO: 92)

FIG. 10T

>gi|121608426|ref|YP_996233.1| CRISPR-associated Csy4 family protein [Verminephrobacter eiseniae EF01-2]
MSTHYIDITLRPDPEFSPAHLLNALHAQLHLALVQLGTGDVGVSFPGFILRGEHSHLGTTLRLHGATSAL
QRLQALSWLRGMRDHVKTSEVAPVPTHTQHRVRRVQAKSSPERSRRRLMRRLEIDEAQALQRIPDQEGR
RLALPYLRLQSASKGQVFRLFIEHGPLLDTPSPGSFGTYGLSTQATIPWF (SEQ ID NO: 21)

RNA recognition sequences
GUUCACUGCCGGAUAGGCAGCUCAGAAA (SEQ ID NO: 93)

FIG. 10U

>gi|34497206|ref|NP_901421.1| hypothetical protein CV_1751 [Chromobacterium violaceum ATCC 12472]
MDHYLDIRLLPDADFGPPVLMNALYAKLHRALAAQQRQDIGVSFPGYDPAPSSHDGKPLPPTLGLTLRLH
GSAAALDGLMARRWLSGFADHAIVGDIRPVPAGASAVSVRRRQAKSSPARARDRLMRRQGISAEEARRRI
PDETAQRLNLPYLTVDSASTGQCFRLFVEQQAAPSIAAGSFNAYGLSAAAALPAW (SEQ ID NO: 22)

RNA recognition sequence
GUUCACUGCCGGAUAGGCAGCUUAGAAA (SEQ ID NO: 94)

FIG. 10V

>gi|188532992|ref|YP_001906789.1| hypothetical protein ETA_08450 [Erwinia tasmaniensis Et1/99]
MDRYQDIRVRVDAEMTAPVLLAQVFMRLHQVLMRAANGRIGISFPDVKLTLGDRIRLHGTLDDLSSLQQS
GWDKGLTDYIACSAIDPVPPGAAWRTVRRVQVKSSAERLRRRSVNKGWLNEAEAAERINVLSEQRSDLPY
LQIKSGSNGHAWRLFIEHGPLVSVPVNGGFSSYGLSATATVPWF (SEQ ID NO: 23)

RNA recognition sequences
GUUCACUGCCGCACAGGCAGCAGCUUAGAAA (SEQ ID NO: 95)
GUUCACUGCCGUACAGGCAGCAGCUUAGAAG (SEQ ID NO: 96)

FIG. 10W

>gi|160896663|ref|YP_001562245.1| CRISPR-associated Csy4 family protein [Delftia acidovorans SPH-1]
MAMTSHYIDTTLLPDPEFSHAHLLGALVAKLHRALVQLGSTDIGISFPGYSLRPRTLGTILRLHGSEAAL
RGLMEQPWLQGMRDHVHCTPPALVPEGAVPCLVQRRQFKTSPDRLRRRMRRKGETAEQAAAAIPDSVER
TPDLPYVQLRSASTGQPFCLFVEQKAVQGTAGQEGFNTYGLSLGTAVPWF (SEQ ID NO: 24)

RNA recognition sequence
GUUCGCUGCCGCGUAGGCAGCUCAGAAA (SEQ ID NO: 97)

FIG. 10X

>gi|146311064|ref|YP_001176138.1| CRISPR-associated Csy4 family protein [Enterobacter sp. 638]
MDHYLEIRVLSDPEFSEETLMAALFAKLHRALGARGQGDIGVSFPRYSLKPGDTLRLHGSAQSLDELEKM
AWRKGLSDYCLCKGVLPAPDVNAWRCVSRVQVKSSPQRLMRRSVKKGWLTEEEAQQRLLNLQEARTDLPW
LNLQSLSTGQSFRLFIRHGDIVDMPMCGEFSSYGLSATATIPWF (SEQ ID NO: 25)

RNA recognition sequence
GUUCACUGCCGUACAGGCAGCUUAGAAA (SEQ ID NO: 98)

FIG. 10Y

>gi|289209612|ref|YP_003461678.1| CRISPR-associated protein, Csy4 family [Thioalkalivibrio sp. K90mix]
MDHYLDLRVMPDPEFKETTLLGALVSKLHRRLVSMSADDIGISLPDHEQEPPLGRRLRVHGTQGRLNLLM
QDEWLGGMQSLVDATPVQPVPDQVTYRPVRRRQYKTNAERLRRRMRRHGESYEEARQHIPDTVERRVNT
PFLSVQSASTGQRFSLFIEHGPPQQHASPGRFNTYGLSQDATVPWF (SEQ ID NO: 26)

RNA recognition sequence
GUUAGCUGCCGCACAGGCAGCUCAGAAA (SEQ ID NO: 99)

FIG. 10Z

>gi|283856310|ref|YP_162420.2| Csy4 family CRISPR-associated protein [Zymomonas mobilis subsp. mobilis ZM4]
MLANPVDSYQDYILPNQEIAPHIIMEKLFSLLHLELVRLGSQHIGISFPEHDNNKPCLGSRLRLHGTGA
DLHELALSGWITRLDDYLYCEDIKSVPEIRQYCVVSRVQAKSSPARLRRRAIRRHGFHDEEAKKVIPDTA
FERLELPFIMTGSCSTKQPRFPVFISHKIIQNKLMNGNFNSYGLSLGASVPWF  (SEQ ID NO: 27)

RNA recognition sequence
GUUCACUGCCGCACAGGCAGCUUAGAAA (SEQ ID NO: 100)

FIG. 10AA

>gi|260752821|ref|YP_003225714.1| CRISPR-associated protein, Csy4 family [Zymomonas mobilis subsp. mobilis NCIMB 11163]
MLANPVDSYQDYILPNQEIAPHIIMEKLFSLLHLELVRLGSQHIGISFPEHDNNKPCLGSRLRLHGAGA
DLHELALSGWITRLDDYLYCEDIKSVPEIRQYCVVSRVQAKSSPARLRRRAIRRHGFHDEEAKKVIPDTA
FERLELPFIMTGSCSTKQPRFPVFISHKIIQDKLMNGNFNSYGLSLGASVPWF  (SEQ ID NO:28)

RNA recognition sequence
GUUCACUGCCGCACAGGCAGCUUAGAAA (SEQ ID NO:101)

FIG. 10AB

>gi|121592915|ref|YP_984811.1| CRISPR-associated Csy4 family protein [Acidovorax sp. JS42]
MTTHYINTLLPDPEFSHAHLLGALVAKLHRALVQGHTTDIGVSYPQHVSQPLTKRTLGAVLRLHGTPEA
LQRLMEEDWLKGMRDHTQVGELLPVPANAQHRTVRRRQFKTNADRLRRRRMQRKGETAEQAAAAIPDTVE
RRPDLPFVQLRSSSTGQSFCLCVEHGPLQPLPVAGAFNAYGLGHDATVPWF  (SEQ ID NO: 29)

RNA recognition sequences
GUUCACUGCCGCAUAGGCAGCUCAGAAA (SEQ ID NO: 102)

FIG. 10AC

>gi|317051103|ref|YP_004112219.1| Csy4 family CRISPR-associated protein [Desulfurispirillum indicum S5]
MDSYIEIRILPDQEFEATTLMSTVFAKLHRALVESGRSDIGVSFPEAGKTPGALLRLHGSLAALESIMTL
SWLTGLQDYTQTSGILQVPAQAAYVQVARVQSKMTASRIRRALKRGSLSEERALELLQSRDQLNQPFFRL
LSASTAQKFPLFIEQRNAEKAGKQSVYSAYGLSVGGSTVPWF (SEQ ID NO: 30)

RNA recognition sequence
GUUCACUGCCGCAUAGGGCAGCUCAGAAA (SEQ ID NO: 103)

FIG. 10AD

>gi|543036463|ref|YP_133636.1| hypothetical protein PBPRB1991 [Photobacterium profundum SS9]
MMDSYVDIQLKPDAEMREAELSSKVFTKFHKALATLNTNKIGISFPQMNLKLGRLFRIHGNASLLKDLQG
IKWLGALAGYCQVGEITVPDQVQYRVISVKRSNLSKAKLKRLIARGSIDKDGEKRYKVKMLSQGFDNPY
LDLFSSSTGQVYRKFFEFGDIQATSVSDEFDSYGLSNTATIPWF (SEQ ID NO: 31)

RNA recognition sequence
GUUCACUGCCGCACAGGGCAGCUUAGAAA (SEQ ID NO: 104)

FIG. 10AE

>gi|54292953|ref|YP_122340.1| hypothetical protein plpl0047 [Legionella pneumophila str. Lens]
MDHYLDISILPDSEFTTPVLMNAIYTNLHKALHTLASTNIGVSFPKYSSTLGNLLRIHGKKEALQELQNL
NWIGGMIGYCEASLIKTVPADTKFRTVSRKQPTMSQSKLRLIKRNSLTEDEIRQYKAKMFSKGLDNPYI
ELVSVSNGQRHRRYIEFGELFNEPIPGLFDQFGLSNSATVPWFD (SEQ ID NO: 32)

RNA recognition sequences
GUUCACUGCCGCUACAGGCAGCUUAGAAA (SEQ ID NO: 105)
GUUCACUGCCGCACAGGCAGCUUAGAAA (SEQ ID NO: 106)

FIG. 10AF

\>gi|54295752|ref|YP_128167.1| hypothetical protein lpl2842 [Legionella pneumophila str. Lens]
MDHYLEISILPDSEFTTPVLMNAIYTNLHKALHTLASTSIGVSFPKYSSTLGNILRIHGKKEVLQDLQNL
NWIGGMIGYCEASLIKTVPADTKFRTVSRKQPTMSQSKLRRLIKRNTLTEDEIRQYKAKMFSKGLDNPYI
ELVSVSNGQRHRRYIEFGELFNEPSPGLFDQFGLSNSATVPWFD (SEQ ID NO: 33)

RNA recognition sequences
GUUCACUGCCGUACAGGCAGCUUAGAAA (SEQ ID NO: 107)
GUUCACUGCCGCACAGGCAGCUUAGAAA (SEQ ID NO: 108)

FIG. 10AG

>gi|146292921|ref|YP_001183345.1| CRISPR-associated Csy4 family protein [Shewanella putrefaciens CN-32]
MNSYIDIRLKPDAEMREAELSSKVFTKFHKALVTLNSHKIGISFPQMKLSLGQLFRIHGDASLLHDLQGL
DWLGPLAGYCQVTAVSAVPDHVQYRIVSVKRSNLSKAKLKRLIARGSIDKDGEKRYKVKMLGQGFDNPYL
DLFSSSTGQVYRKFFEFSDIQAHPLDGEFDSYGLSKTATVPWF (SEQ ID NO: 34)

RNA recognition sequence
GUUCACCGCCGCACAGGCGGCUUAGAAA (SEQ ID NO: 109)

FIG. 10AH

>gi|296106567|ref|YP_003618267.1| hypothetical protein lpa_01476 [Legionella pneumophila 2300/99 Alcoy]
MDYYVDILIKPDSEKSLNFLLSTLYTKLHKVLHDMASTNIGVSFPKYNITLGNILRIHSKKVVLDELLGM
NFLSGINNYYEVSPIKSVPADSKFRIISRKQTTMSQSKMRRLFKRGSMTVGDIRQYKAKMFAKSIDNPYL
ELVSGSNGYRYRRYIEFGELLDQPVYGEFDRFGLSKTATVPWFD (SEQ ID NO: 35)

RNA recognition sequence
GUUAACUGCCGCACAGGCAGCUUAGAAG (SEQ ID NO: 110)

FIG. 10AI

\>gi|260772736|ref|ZP_05881652.1| hypothetical protein VIB_001192 [Vibrio metschnikovii CIP 69.14]
MDSYIEIRLQPDAEMPEAELSSKVFTKFHKALVILHSNQIGISFPEVNVKLGRLFRLHGEASFLHDLQGL
NWLGPLSGYCQVSEILAIPEQVQYRVISVKRSNLSQAKLRRLIARGSIDKEGEKRYKVKMLSQGFDNPYL
DLFSSSTKQVHRKFFEFGEIQPLPVSGKFDSYGLSHTTTVPWF (SEQ ID NO: 36)

RNA recognition sequences
GUUCACUGCCGCACAGGCAGCUUAGAAA (SEQ ID NO: 111)
GUUCACUGCCGCAUAGGCAGCUUAGAAA (SEQ ID NO: 112)

FIG. 10AJ

>gi|157146437|ref|YP_001453756.1| hypothetical protein CKO_02197 [Citrobacter koseri ATCC BAA-895]
MAITPVPAVKGWRTVSRVQVKSSPQRLLRRSVRKGWLTEEQAQLRLVESTEQHSDLPYLNVKSLSNQQQF
RVFIRHSELRSEPVSGTFTSYGLSSTATIPWF (SEQ ID NO: 37)

RNA recognition sequence
UGUUCACUGCCGUACAGGCAGCUUAGAAA (SEQ ID NO: 113)

FIG. 10AK

>gi|262402803|ref|ZP_06079364.1| hypothetical protein VOA_000785 [Vibrio sp. RC586]
MDAYIDIRLMPDAEMREAELSSKVFIKFHKALVKLRSNKIGISFPEANIKLGRLFRLHGEMSALHDLQGL
NWLGPLAGYCKITTVTHVPDQVQYRIISVKRSNLSKAKLTRLIARGSIDKDGEKRYKVKMLSQGFDNPYL
DLSSSSTGQVYRKFFEFSDIQADPVDGEFDSYGLSKTATVPWF (SEQ ID NO: 38)

RNA recognition sequences
GUUCACUGCCGCACAGGCAGCUUAGAAA (SEQ ID NO: 114)
AGUGUUCUGCCGAAUAGGCAGCUAAGAA (SEQ ID NO: 115)

FIG. 10AL

\>gi|229523353|ref|ZP_04412760.1| hypothetical protein VIF_000211 [Vibrio cholerae TM 11079-80]
MMDAYIDIRLMPDAEMREAELSSKVFIKFHKALVKLQSNKIGISFPEANIKLGRLFRLHGEVSALHDLQG
LNWLGPLAGYCKITTVTHVPDQVEYRIISVKRSNLSKAKLARLIARGSIDKDGEKRYKVKMLRQGFDNPY
LDLSSSSTGQVYRKFFEFSDIQAEPVDGEFDSYGLSKTATVPWF (SEQ ID NO: 39)

RNA recognition sequence
GUUCACUGCCGCACAGGCAGCUUAGAAAU (SEQ ID NO: 116)

FIG. 10AM

>gi|237748015|ref|ZP_04578495.1| crispr-associated protein [Oxalobacter formigenes OXCC13]
MKHYIEITLTGSPDFPLYHLWSKLYTQLHLALVENRDASDQVNIGVSFPEYYFNEEKGMGFLGTKLRLFA
EDETSLQKIDIQKWFVRLNDCIHITPVCRVPLNEITGYATFSRKHIKSNAERLARRQMKRHKDLSFHETV
QRYQKNLAKSPLPFIQLESLTNSHPFKLFIEKKPAINASLKVFTTYGLSAESTIPEF (SEQ ID NO: 40)

RNA recognition sequence
GUUCACUGCCGUAUAGGCAGCUUAGAAG (SEQ ID NO: 117)

FIG. 10AN

>gi|119945137|ref|YP_942817.1| CRISPR-associated Csy4 family protein [Psychromonas ingrahamii 37]
MKYYLDITLLPDIEIPLGFIWQKVFQQVHIALADNKVGENESDIALSLPNYGDKAFPLGNKLRLFSVSEQ
ALERLAITKWLKRFTDHTHITSVKAVPESANEYACFTRKQFNTNISRLARRRAKRHMETFEKALQYYDNF
AEEQTKLPFMNIKSLTNNAQFRIFIERSITKIPKQGTFNCYGLSQAIATVPWF (SEQ ID NO: 41)

RNA recognition sequence
GUGUUCCCCGUGCCCACGGGGAUGAACCG (SEQ ID NO: 118)

FIG. 10AO

>gi|146328647|ref|YP_001209099.1| hypothetical protein DNO_0170 [Dichelobacter nodosus VCS1703A]
MNFYQEITLLPDAEVSLYFLWSKVYGQLHIALADVRNRYGIDTIGVNFPHYYEEQNHKVVAARLGDQLR
IFALAENDLEKLQINQWLERLSDYVHIKRISKIEPNKVTGYVVKRYRYPSLDKVALRFAQFRKINFEEA
RKHCTKYKHQAKNYPFIMLKSQSNQEYYKLSIRQENAQESVSGRFNVYGINSATGIVTVPNW (SEQ ID NO: 42)

RNA recognition sequence
GUUCACCGCCGCACAGGCGGGCUUAGAAA (SEQ ID NO: 119)

FIG. 10AP

>gi|160876478|ref|YP_001555794.1| CRISPR-associated Csy4 family protein [Shewanella baltica OS195]
MNHYLDITLLPNEEVGHYFLWEKLYHQVFLALVEHKNRVGQFEIAAAFPQFNEMDNSLGSKLRLLATQPQ
HLEDLKVSNWLRHFTDYLHISSIRPVPEKIEVYYAYSRPAIRANKAREIARRMKRHNETLEQATAHFEGF
KPKKTKAPFVYMQSYTKDSRFPLFIQQTHSAVVKEGSVSFDSYGLSSRGYLPKF (SEQ ID NO: 43)

RNA recognition sequence
GUUCACCGCCGCACAGGCGGGCUUAGAAA (SEQ ID NO: 120)

FIG. 10AQ

>gi|153001745|ref|YP_001367426.1| CRISPR-associated Csy4 family protein [Shewanella baltica OS185]
MNHYLDITLLPNEEVGHYFLWEKLYHQMHLALVEHKNRVGQFEIAAAFPQFNEMDNNLGSKLRLLATQPQ
HLEDLKVSNWLRHFTDYLHISSIRPVPDKIEVYYAYSRPAIRANKAREIARRMKRHNETLVQATAHFEGF
KPKKTKAPFVYMQSYTKDSRFPLFIQQTHSAVVKEGNVSFDSYGLSSRGYLPKF (SEQ ID NO: 44)

RNA recognition sequence
GUUCACCGCCGCACAGGCGGGCUUAGAAA (SEQ ID NO: 121)

FIG. 10AR

>gi|169795154|ref|YP_001712947.1| hypothetical protein ABAYE1000 [Acinetobacter baumannii AYE]
MMNWYQEITLIDQDEISLYFIWSKVYTQLHIAFAEHSNEQGRISFGVSFPQYRINEQKKIGFLGTKIRVF
ASSENDLQQLNLGKWLERFIDYVHITQPREVPRAKITGYAHYYRVNHRMSVEERIVHQAQRRNISLDQAR
QHFKQYVEQPVVEPYVSLKSLSAKREENVDRPYRLYIGKSLVDEARDGMFGTYGLSRMTTVPEF (SEQ ID NO: 45)

RNA recognition sequence
GUUCAUGGCGGCAUACGCCAUUUAGAAA (SEQ ID NO: 122)

FIG. 10AS

>gi|213158184|ref|YP_002320235.1| crispr-associated protein, Csy4 family [Acinetobacter baumannii AB0057]
MNWYQEITLIDQDEISLYFIWSKVYTQLHIAFAEHSNEQGRISFGVSFPQYRINEQKKIGFLGTKIRVFA
SSENDLQQLNLGKWLERFIDYVHITQPREVPRAKITGYAHYYRVNHRMSVEERIVHQAQRRNISLDQARQ
HFKQYVEQPVVEPYVSLKSLSAKREENVDRPYRLYIGKSLVDEARDGMFGTYGLSRMTTVPEF (SEQ ID NO: 46)

RNA recognition sequence
GUUCAUGGCGGCAUACGCCAUUUAGAAA (SEQ ID NO: 123)

FIG. 10AT

>gi|15602173|ref|NP_245245.1| hypothetical protein PM0308 [Pasteurella multocida subsp. multocida str. Pm70]
MTTHYIELKAIPQMDMLQSEVIGHCMQILHQFLPHFEGRVGVAFPAYGLGRTLGGIVRLFANQEDCNQLH
QQLLRSGLSDYALISEVSKTPLPTEHRSYSRVHRKGQSAIRRTEKRLKSQGRWDESIRADMQQRQQNVAF
FPHCHLKSASTGQRFILAVKENRMPQSCVGVFNAYGLSNSATVPHF (SEQ ID NO: 47)

RNA recognition sequences
GUUCACCAUCGUGUAGAUGGCUUAGAAA (SEQ ID NO: 124)
GUUAACUGCCGUAUAGGCAGCUUAGAAA (SEQ ID NO: 125)

FIG. 10AU

>gi|293390434|ref|ZP_06634768.1| Csy4 family CRISPR-associated protein [Aggregatibacter actinomycetemcomitans D7S-1]
MTVQTHYIEIKAIPQVDMLQTEVIGFCLQKLHQILPHFEGRIGLAFPAYGNDKTLGGIIRLFGTENDCGF
IHFKLQSLRDYALISEVMPIPEKVRSRYRIYQRIQPKGQSSIRRAEKRLTAQGKWNEEVLQNMLQKQATQR
IYPHAHLKSSSTKQQFILAIKSVHQTKAVEGVFSAYGLSQTTTVPHF (SEQ ID NO:48)

RNA recognition sequence
CUUCACUGCCGAAUAGGCAGCUUAGAAA (SEQ ID NO:126)

FIG. 10AV

>gi|152996699|ref|YP_001341534.1| CRISPR-associated Csy4 family protein [Marinomonas sp. MWYL1]
MKHYIDITLLPSDDIGVHFLWSKLMMQVHLALVEIQNEQKQVPVAVSFPKYQPRENEKLGFVGNKLRLFA
NDKTDLERLNFGKWLHRLEDYVHIKSIADVPNDVISYESFNRRSKSGSPDKHIKRRMQRHNETWEQAAAF
FKGYSMEKADKDLPFIRMKSLHSDNEFCMSIIRKEAAPSNKHIMFNTYGLSAEGVLPKF (SEQ ID NO:49)

RNA recognition sequence
GUUCGCCGCCGAGCACGCGGCUUAGAAA (SEQ ID NO:127)

FIG. 10AW

>gi|258645690|ref|ZP_05733159.1| CRISPR-associated protein, Csy4 family [Dialister invisus DSM 15470]
MEYYQEITLLPCAEVSLAFLWTKVFTQLHIAFADEKNKSGHNLYAVSFPEYRETGLGEKIRVFAEAQELE
RLNLSKVLGRLLDYVHCTSIRKVPERKLRGYAVYSRYQPEGSIWKARRYAKRHPGVTIEEAARLLQGKR
KSVRLPYIQMKSLSRGGTFSLFIKKRVEKESALTECGTYGLSNNRTVPEF (SEQ ID NO:50)

RNA recognition sequences
GUUAACUGCCGCAUAGGUAGUUUAGAAA (SEQ ID NO:128)
GUUAUCUGCCGUAUAGGCAGUUUAGAAA (SEQ ID NO:129)

FIG. 10AX

>gi|165975671|ref|YP_001651264.1| hypothetical protein APJL_0216 [Actinobacillus pleuropneumoniae serovar 3 str. JL03]
MSELTHYIELKAIPQVDILQTDVIAHGLQILHKFLPLYQGEIGLSFPAYGLGRTLGGIIRVFGNEQHCTQ
IKTQLIGEGLQDYVLITSVTPVPEEIVEYHRYQRVHRKGQSAIRRTEQFLVQQGKWTEEIRQEMLIHQQN
QKVFPYVKLKSGSTKQHFVLAIRQLRLAEPASGLFNAYGLSQAATVPHF (SEQ ID NO: 51)

RNA recognition sequence
CUUCACUGCCGUAUAGGCAGCUUAGAAA (SEQ ID NO: 130)

FIG. 10AY

>gi|190149486|ref|YP_001968011.1| hypothetical protein APP7_0217 [Actinobacillus pleuropneumoniae serovar 7 str. AP76]
MSELTHYIELKAIPQVDILQTDVIAHGLQILHKFLPLYQGEIGLSFPAYGLGRTLGGIIRVFGNEQHCTQ
IKTQLIGEGLQDYVLITSVTPVPEEIVEYHRYQRVHRKGQSAIRRTEQFLVQQGKWTEEIRQEMLIHQQN
QKVFPYVKLKSGSTKQHFVLAIRQLRLAEPVSGLFNAYGLSKIATVPHF (SEQ ID NO: 52)

RNA recognition sequence
CUUCACUGCCGUAUAGGCAGCUUAGAAA (SEQ ID NO: 131)

FIG. 10AZ

>gi|303253029|ref|ZP_07339182.1| hypothetical protein APP2_1978 [Actinobacillus pleuropneumoniae serovar 2 str. 4226]
MSELTHYIELKAIPQVDILQTDVIAHGLQILHKFLPLYQGEIGLSFPAYGLGRTLGGIIRVFGNEQHCTQ
IKTQLIGEGLQDYVLITSVTPVPEEIVEYHRYQRVHRKGQSAIRRTEQFLVQQGKWTEEIRQEMLIHQQN
QKVFPHVKLKSGSTKQHFVLAIRQLRLAEPSFGLFNTYGLSKIATVPHF (SEQ ID NO:53)

FIG. 10BA

>gi|303251662|ref|ZP_07337835.1| hypothetical protein APP6_0866 [Actinobacillus pleuropneumoniae serovar 6 str. Femø]
MSELTHYIELKAIPQVDILQTDVIAHGLQILHKFLPLYQGEIGLSFPAYGLGRTLGGIIRVLGNEQHCTQ
IKTQLIGEGLQDYVLITSVTPVPEEIVEYHRYQRVHRKGQSAIRRTEQFLVQQGKWTEEIRQEMLIHQQN
QKVFPHVKLKSGSTKQHFVLAIRQLRLAEPSFGLFNTYGLSKIATVPHF (SEQ ID NO: 54)

FIG. 10BB

>gi|116627507|ref|YP_820126.1| dephospho-CoA kinase [Streptococcus thermophilus LMD-9]
MSKTMIIGLTGGIASGKSTVVEIIKDAGYKVIDADQLVHDMQVKGGRLYQALLDWLGDGILLPNGELNRP
KLGQLIFSSEEMRYQSAEIQGKIIREELAAKRDCLAKEEDVFFMDIPLLFENDYQDWFDQIWLVAVSPQV
QGQRLMKRNHLSAEEAGMRIASQMPLAEKLPYASLVIDNNGNIDDLKKKVKGAIKDLANLV (SEQ ID NO:55)

FIG. 10BC

His29 Ala

```
  1 mdhyldirlr pdpefppaql msvlfgklaq alvagggdri gvsfpdldes rsrlgerlri
 61 hasaddlral larpwleglr dhlqfgepav vphptpyrqv srvqvksnpe rlrrrlmrrh
121 dlseeearkr ipdtvarald lpfvtlrsqs tgghfrlfir hgplqataee ggftcyglsk
181 ggfvpwf
```

His29 Ala/Ser50Cys

```
  1 mdhyldirlr pdpefppaql msvlfgklaq alvagggdri gvsfpdldec rsrlgerlri
 61 hasaddlral larpwleglr dhlqfgepav vphptpyrqv srvqvksnpe rlrrrlmrrh
121 dlseeearkr ipdtvarald lpfvtlrsqs tgghfrlfir hgplqataee ggftcyglsk
181 ggfvpwf
```

FIG. 12

>gi|16130663|ref|NP_417236.1| CRISPR RNA precursor cleavage enzyme; CRISP RNA (crRNA) containing Cascade antiviral complex protein [Escherichia coli str. K-12 substr. MG1655]
MYLSKVIIARAWSRDLYQLHQGLWHLFPNRPDAARDFLFHVEKRNTPEGCHVLLQSAQMPVSTAVATVI KTKQVEFQLQVGVPLYFRLRANPIKTILDNQKRLDSKGNIKRCRVPLIKEAEQIAWLQRKLGNAARVEDV HPISERPQYFSGDGKSGKIQTVCFEGVLTINDAPALIDLVQQGIGPAKSMGCGLLSLAPL (SEQ ID NO: 134)

FIG. 13A

>gi|309786155|ref|ZP_07680783.1| CRISPR associated family protein [Shigella dysenteriae 1617]
MYLSKVIIARAWSRDLYQLHQGLWHLFPNRPDAARDFLFHVEKRNTPEGCHVLLQSAQMPVSTAVATVI KTKQVEFQLQVGVPLYFRLRANPIKTILDNQKRLDSKGNIKRCRVPLIKEAEQIAWLQRKLGNAARVEDV HPISERPQYFSGEGKNGKIQTVCFEGVLTINDAPALIDLLQQGIGPAKSMGCGLLSLAPL (SEQ ID NO: 135)

FIG. 13B

>gi|157162205|ref|YP_001459523.1| CRISPR-associated Cse3 family protein [Escherichia coli HS]
MYLSKIIIARAWSRDLYQLHQELWHLFPNRPDAARDFLFHVEKRNTPEGCHVLLQSAQMPVSTAVATVIK TKQVEFQLQVGVPLYFRLRANPIKTILDNQKRLDSKGNIKRCRVPLIKEAEQIAWLQRKLGNAARVEDVH PISERPQYFSGEGKNGKIQTVCFEGVLTINDAPALIDLLQQGIGPAKSMGCGLLSLAPL (SEQ ID NO: 136)

FIG. 13C

>gi|292898488|ref|YP_003537857.1| CRISPR-associated protein [Erwinia amylovora ATCC 49946]
MIYLSQIAVPWSWAKDPYQLHRALWQLFPDRPSDRRDFLFRVETRHARAGQVVLLQSLQAPQNCAAA
QVLASKVTQFALSPGQRLHFRLRANPVKNIKDNRGRVNSRGEVKSCRVPLIDDNQLMQWLVRKLQDAA
VLHSASVSKEPALCFNKQAVAGKIQPVCFEGILQVTSETHFYQCLVNGIGPAKSMGCGMLSIARA (SEQ ID NO: 137)

FIG. 13D

>gi|298505493|gb|ADI84216.1| CRISPR processing complex protein CasE [Geobacter sulfurreducens KN400]
MYLSKVLINGTACRNPYEIHRVLWKLFPEDADAERDFLFRVERSGQQSVEVLLQSRREPTMAASREVLL
MGSKPYLLSLQQDQQLRFMLVANPIKTINDESARLNSANEIKKCRVPLIREEDLRAWLKRKLEGVAVIEAV
EVEKRPAMNFRKAREKRVGKVQAVSFHGVLSVTDPVGLISLINTGIGPAKAFGCGLLSLART (SEQ ID NO: 138)

FIG. 13E

>gi|207858199|ref|YP_002244850.1| hypothetical protein SEN2778 [Salmonella enterica subsp. enterica serovar Enteritidis str. P125109]
MYLSRITLHTSELSPAQLLHLVERGEYVMHQWLWDLFPGGKERQFLYRREELQGAFRFFVLSQEQPAA
STIFDVQTRPFAPMLSAGQTLRFNLRANPTICKNGKRHDLLMEAKRQRKTQGDSQDIWSYQQQAALEW
LARQGEQNGFTLREASVDAYRQQQIRREKSRQMIQFSSVDYTGVLVINEPALFLQRLAQGYGKSRAFG
CGMMMIKPGDDA (SEQ ID NO: 139)

FIG. 13F

>gi|18893208|gb|AAL81255.1| hypothetical protein PF1131 [Pyrococcus furiosus DSM 3638]
MRFLIRLVPEDKDRAFKVPYNHQYYLQGLIYNAIKSSNPKLATYLHEVKGPKLFTYSLFMAEKREHPKGL
PYFLGYKKGFFYFSTCVPEIAEALVNGLLMNPEVRLWDERFYLHEIKVLREPKKFNGSTFVTLSPIAVTVV
RKGKSYDVPPMEKEFYSIIKDDLQDKYVMAYGDKPPSEFEMEVLIAKPKRFRIKPGIYQTAWHLVFRAYG
NDDLLKVGYEVGFGEKNSLGFGMVKVEGNKTTKEAEEQEKITFNSREELKTGV (SEQ ID NO: 140)

FIG. 14A

>gi|14521345|ref|NP_126821.1| hypothetical protein PAB1613 [Pyrococcus abyssi GE5]
MRFLIRVRPEERKFKVPYNHQYYLQGLIYNRIKMVNPRLSTFLHETRGPKMFTYSLFMTEKRKHPKGLPY
FLGFKRGFFYFSTCIPEIAEAFITGLFREPEIVLWGERFYLEEVKTLREPTKFSGSTFITLSPVAVTMVKEG
KRYDVSPLEEEFYTLIKENLKDKYVMIKGEKPPDDFEMEVIVAKPKRFEVKPGIYQMAWHLVFKAYGDDE
LIKVGYVVGFGEKNSLGFGMVKVENNREEKGMGVQERMLFKNEDGLKTGP (SEQ ID NO: 141)

FIG. 14B

>gi|315230235|ref|YP_004070671.1| CRISPR repeat RNA endoribonuclease Cas6-like protein [Thermococcus barophilus MP]
MRFLIRLRNENLEFKVPYNHLYYLQGLVYRRIQRVNPELSLSLHRPKVPKLFTFSLFMTKERHRMSGNNK
YFIGRKEAFFYFSTAVPEIAEAFIGGLLQEPEVKLWGERFYVETVKALPEPISFSGKIYSTLSPIAVTTVKM
QFGKPRHYDLGPDEPEFYENLKENLKQKYLLIYGKKPPEDFEIEVLSAKPKRFEVKPGIFQRAWHLIFRA
YGDDELIRAGYLAGFGEKNSLGFGMVKVDE (SEQ ID NO: 142)

FIG. 14C

>gi|297619092|ref|YP_003707197.1| CRISPR-associated protein Cas6 [Methanococcus voltae A3]
MRISINLKCEKNTTIPFNYQYQLSTALYNCMYDNNKEFAENLHKSKDFKFFTHSWLFMPNSKVGKNGIIC
KDGNAFFKVSSPNDELMTHLLQGLFKVGYMQINNTKLDVVGVLNEKGYNSNIKKMKTISPVLLRTKKER
NGIDNTEGLKIYDILPQENSEKFHENLKNNLKRKYSLFYDKDYENCDLDFDINISEAKSKRVKIKDSFQRC
SNLKFEISGDEDLIKFAYECGLGELNSMGFGMIDKYSYKC (SEQ ID NO: 143)

FIG. 14D

>gi|260688338|ref|YP_003219472.1| CRISPR-associated protein cas6 [Clostridium difficile R20291]
MHLVRRHLILTVDNEVVLDYNYQYELMKRIYEAIEINDKRKALSLHNEGYKVDKKVFKLFNYTIMFENAKY
LKEGIHLNPQTKIKLILSGYDDILNNIIKGFIKCKVFKLNNIEFKVSDIEEDSKKNFNNITLYKVRSPIVASLYD
LKSRKQVYLNPMQEEFYKALHDNLGNKYKLIHNKEYTGELYFDIEDVLAVKKYITNIKGKGFIIGYTDFEI
FVQANKDMQEVIYYCGLGEKNSIGMGLLTYITSRRA (SEQ ID NO: 144)

FIG. 14E

Figure 15
>gi|16131572|ref|NP_418159.1| protein C5 component of RNase P [Escherichia coli str. K-12 substr. MG1655]
MVKLAFPRELRLLTPSQFTFVFQQPQRAGTPQITILGRLNSLGHPRIGLTVAKKNVRRAHERNRIKRLTR
ESFRLRQHELPAMDFVVVAKKGVADLDNRALSEALEKLWRRHCRLARGS (SEQ ID NO: 145)

SEQUENCE LISTING

<160> NUMBER OF SEQ ID NOS: 193

<210> SEQ ID NO 1
<211> LENGTH: 167
<212> TYPE: PRT
<213> ORGANISM: Pseudomonas aeruginosa

<400> SEQUENCE: 1

```
Met Ser Val Leu Phe Gly Lys Leu His Gln Ala Leu Val Ala Gln Gly
1               5                   10                  15

Gly Asp Arg Ile Gly Val Ser Phe Pro Asp Leu Asp Glu Ser Arg Ser
                20                  25                  30

Arg Leu Gly Glu Arg Leu Arg Ile His Ala Ser Ala Asp Asp Leu Arg
            35                  40                  45

Ala Leu Leu Ala Arg Pro Trp Leu Glu Gly Leu Arg Asp His Leu Gln
        50                  55                  60

Phe Gly Glu Pro Ala Val Val Pro His Pro Thr Pro Tyr Arg Gln Val
65                  70                  75                  80

Ser Arg Val Gln Ala Lys Ser Asn Pro Glu Arg Leu Arg Arg Arg Leu
                85                  90                  95

Met Arg Arg His Asp Leu Ser Glu Glu Glu Ala Arg Lys Arg Ile Pro
                100                 105                 110
```

Asp Thr Val Ala Arg Ala Leu Asp Leu Pro Phe Val Thr Leu Arg Ser
                115                 120                 125

Gln Ser Thr Gly Gln His Phe Arg Leu Phe Ile Arg His Gly Pro Leu
            130                 135                 140

Gln Val Thr Ala Glu Glu Gly Phe Thr Cys Tyr Gly Leu Ser Lys
145                 150                 155                 160

Gly Gly Phe Val Pro Trp Phe
                165

<210> SEQ ID NO 2
<211> LENGTH: 187
<212> TYPE: PRT
<213> ORGANISM: Pseudomonas aeruginosa

<400> SEQUENCE: 2

Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
                20                  25                  30

Val Ala Gln Gly Gly Asp Arg Ile Gly Val Ser Phe Pro Asp Leu Asp
            35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Pro His Pro Thr Pro
                85                  90                  95

Tyr Arg Gln Val Ser Arg Val Gln Val Lys Ser Asn Pro Glu Arg Leu
                100                 105                 110

Arg Arg Arg Leu Met Arg Arg His Asp Leu Ser Glu Glu Ala Arg
            115                 120                 125

Lys Arg Ile Pro Asp Thr Val Ala Arg Ala Leu Asp Leu Pro Phe Val
    130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Phe Thr Cys Tyr
                165                 170                 175

Gly Leu Ser Lys Gly Gly Phe Val Pro Trp Phe
            180                 185

<210> SEQ ID NO 3
<211> LENGTH: 187
<212> TYPE: PRT
<213> ORGANISM: Pseudomonas aeruginosa

<400> SEQUENCE: 3

Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
                20                  25                  30

Val Ala Gln Gly Gly Asp Arg Ile Gly Val Ser Phe Pro Asp Leu Asp
            35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Ala Arg
            115                 120             125

Lys Arg Ile Pro Asp Thr Val Ala Arg Thr Leu Asp Leu Pro Phe Val
130                 135                 140

Thr Leu Arg Ser Gln Ser Thr Gly Gln His Phe Arg Leu Phe Ile Arg
145                 150                 155                 160

His Gly Pro Leu Gln Ala Thr Ala Glu Glu Gly Gly Phe Thr Cys Tyr
                165                 170                 175

Gly Leu Ser Lys Gly Gly Phe Val Pro Trp Phe
            180                 185

<210> SEQ ID NO 4
<211> LENGTH: 187
<212> TYPE: PRT
<213> ORGANISM: Pseudomonas aeruginosa

<400> SEQUENCE: 4

Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
                20                  25                  30

Val Ala Gln Gly Gly Asp Arg Ile Gly Val Ser Phe Pro Asp Leu Asp
            35                  40                  45

Glu Ser Arg Ser Arg Leu Gly Glu Arg Leu Arg Ile His Ala Ser Ala
50                  55                  60

Asp Asp Leu His Ala Leu Leu Ala Arg Pro Trp Leu Glu Gly Leu Arg
65                  70                  75                  80

Asp His Leu Gln Phe Gly Glu Ala Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Ala Arg
            115                 120             125

Lys Arg Ile Pro Asp Thr Val Ala Arg Thr Leu Asp Leu Pro Phe Val
130                 135                 140

Thr Leu Arg Ser Gln Ser Thr Gly Gln His Phe Arg Leu Phe Ile Arg
145                 150                 155                 160

His Gly Pro Leu Gln Ala Thr Ala Glu Glu Gly Gly Phe Thr Cys Tyr
                165                 170                 175

Gly Leu Ser Lys Gly Gly Phe Val Pro Trp Phe
            180                 185

<210> SEQ ID NO 5
<211> LENGTH: 184
<212> TYPE: PRT
<213> ORGANISM: Dickeya dadantii

<400> SEQUENCE: 5

Met Asp His Tyr Ile Glu Ile Arg Val Leu Pro Asp Leu Glu Phe Ser
1               5                   10                  15

Ala Val Gln Leu Leu Ser Ala Leu Phe Ala Lys Leu His Arg Ala Leu
                20                  25                  30

```
Gly Gln Arg Ala Thr Gly Ala Ile Gly Val Ser Phe Pro Asp Val Asp
            35                  40                  45

Lys Thr Leu Gly Glu Arg Leu Arg Leu His Gly Ser Val Gln Glu Leu
 50                  55                  60

Ala Ala Leu Glu Gln Thr Gly Trp Leu Lys Gly Leu Arg Asp Tyr Thr
 65                  70                  75                  80

Ala Ile Thr Glu Pro Leu Pro Val Pro Ala Gly Ala Lys His Arg Thr
                 85                  90                  95

Val Arg Arg Val Gln Val Lys Ser Ser Ala Glu Arg Leu Arg Arg Arg
            100                 105                 110

Ala Val Ser Lys Gly Arg Met Thr Glu Asp Glu Ala Ala Thr Arg Ile
            115                 120                 125

Pro Tyr Ala Val Glu Lys Arg Ser Ser Leu Pro Tyr Leu Pro Leu Arg
            130                 135                 140

Ser Leu Ser Ser Gly Gln Thr Phe Leu Leu Phe Val Glu His Gly Pro
145                 150                 155                 160

Leu Gln Asp Lys Pro Val Ala Gly Ala Phe Ser Ser Tyr Gly Leu Ser
                165                 170                 175

Ala Thr Thr Thr Ile Pro Trp Phe
            180

<210> SEQ ID NO 6
<211> LENGTH: 184
<212> TYPE: PRT
<213> ORGANISM: Pectobacterium wasabiae

<400> SEQUENCE: 6

Met Asp His Tyr Ile Asp Ile Arg Val Gln Pro Asp Pro Glu Phe Thr
  1               5                  10                  15

Ala Pro Gln Leu Leu Asn Ala Leu Phe Ala Lys Leu His Arg Ala Leu
                 20                  25                  30

Gly Gln Leu Ala Asp Gly Lys Ile Gly Ile Ser Phe Pro Glu Val Gly
            35                  40                  45

Lys Thr Leu Gly Glu Cys Leu Arg Leu His Gly Thr Ala Asp Ala Leu
 50                  55                  60

Ser Thr Leu Glu Lys Thr Ser Trp Leu Lys Gly Leu Arg Asp Tyr Thr
 65                  70                  75                  80

Gln Val Ser Glu Cys Lys Ala Val Pro Asn Asn Val Lys Phe Arg Thr
                 85                  90                  95

Val Arg Arg Val Gln Leu Lys Thr Ser Ala Glu Arg Leu Arg Arg Arg
            100                 105                 110

Ser Val Asn Lys Gly Trp Leu Thr Glu Ala Glu Ala Ala Arg Ile
            115                 120                 125

Pro Asp Ala Val Glu Lys Arg Ser Thr Leu Pro Phe Val Gln Ile Lys
            130                 135                 140

Ser Leu Ser Asn Gly Gln Met Phe Phe Val Phe Val Glu His Gly Pro
145                 150                 155                 160

Leu Gln Asn Ala Pro Ala Thr Gly Arg Phe Ser Ser Tyr Gly Leu Ser
                165                 170                 175

Ala Glu Ala Thr Val Pro Trp Phe
            180

<210> SEQ ID NO 7
<211> LENGTH: 184
<212> TYPE: PRT
<213> ORGANISM: Photorhabdus asymbiotica
```

<400> SEQUENCE: 7

```
Met Asp Tyr Tyr Phe Glu Ile Leu Val Leu Pro Asp Pro Glu Phe Ser
1               5                   10                  15

Lys Gln Ser Leu Met Glu Ala Leu Phe Ala Lys Leu His Arg Ala Leu
            20                  25                  30

Gly Gln Val Gly Asn Gly Arg Ile Gly Val Ser Phe Pro Cys Ala Arg
        35                  40                  45

Lys Thr Leu Gly Asp Lys Leu Arg Ile His Gly Ala Ser Glu Ala Leu
    50                  55                  60

Asn Asp Leu Gln Ala Leu Pro Trp Leu Lys Gly Leu Arg Asp Tyr Thr
65                  70                  75                  80

Glu Ile Met Asp Ile Gln Pro Val Pro Gln Asp Thr Gln Tyr Arg Arg
                85                  90                  95

Val Ser Arg Val Gln Val Lys Ser Ser Ala Glu Arg Leu Arg Arg Arg
            100                 105                 110

Ser Ile Lys Lys Gly Trp Leu Thr Glu Gln Ala Arg Gln Arg Ile
        115                 120                 125

Pro Ile Ser Lys Glu Gln Arg Thr His Leu Pro Phe Leu Leu Val Lys
    130                 135                 140

Ser Leu Ser Ser Arg Gln Thr Phe Pro Leu Phe Ile Glu Gln Gly Pro
145                 150                 155                 160

Ile Glu Asp Lys Pro Thr Pro Gly Val Phe Ser Ser Tyr Gly Leu Ser
                165                 170                 175

Ala Ser Ala Thr Ile Pro Trp Phe
            180
```

<210> SEQ ID NO 8
<211> LENGTH: 184
<212> TYPE: PRT
<213> ORGANISM: Dickeya dadantii

<400> SEQUENCE: 8

```
Met Asp His Tyr Ile Glu Ile Arg Val Leu Pro Asp Pro Glu Phe Ser
1               5                   10                  15

Gly Val Gln Leu Leu Ser Ala Leu Phe Ala Lys Leu His Arg Ala Leu
            20                  25                  30

Gly Gln Arg Ala Thr Gly Ala Ile Gly Val Ser Phe Pro Asp Ala Gly
        35                  40                  45

Lys Thr Leu Gly Glu Arg Leu Arg Leu His Gly Ser Val Gln Glu Leu
    50                  55                  60

Ala Ala Leu Glu Gln Thr Gly Trp Leu Arg Gly Leu Arg Asp Tyr Thr
65                  70                  75                  80

Ala Ile Thr Glu Pro Leu Pro Val Pro Ala Gly Val Lys His Arg Thr
                85                  90                  95

Val Arg Arg Val Gln Val Lys Ser Ser Ala Glu Arg Leu Arg Arg Arg
            100                 105                 110

Ala Val Asn Lys Gly Arg Met Thr Val Asp Glu Ala Asp Ala Arg Ile
        115                 120                 125

Pro Tyr Thr Val Glu Lys Arg Thr Ser Leu Pro Tyr Leu Pro Leu Arg
    130                 135                 140

Ser Leu Ser Asn Gly Gln Thr Phe Leu Leu Phe Val Glu His Gly Pro
145                 150                 155                 160

Leu Gln Asp Lys Pro Val Ala Gly Ala Phe Ser Ser Tyr Gly Leu Ser
                165                 170                 175
```

Ala Val Ala Thr Ile Pro Trp Phe
            180

<210> SEQ ID NO 9
<211> LENGTH: 188
<212> TYPE: PRT
<213> ORGANISM: Xanthomonas albilineans

<400> SEQUENCE: 9

Met Gln His Tyr Leu Asp Leu His Leu Arg Pro Asp Pro Glu Leu Ala
1               5                   10                  15

Pro Tyr Gln Leu Leu Gly Ala Leu Tyr Ala Arg Leu His Arg Ser Leu
            20                  25                  30

Val Thr Leu Asn Thr Thr Arg Ile Gly Val Ser Phe Pro Gly His Asp
        35                  40                  45

Asn Arg Val Pro Thr Leu Gly Thr His Leu Arg Leu His Gly Asp Asp
    50                  55                  60

Ser Thr Leu His His Leu Met Ala Thr Thr Trp Leu His Gly Val Arg
65                  70                  75                  80

Asp His Val Thr Ile Thr Ser Ile Gly Ala Val Pro Ser Glu Ala Val
                85                  90                  95

His Arg Gln Val Thr Arg Val Gln Ala Lys Ser Ser Pro Glu Arg Leu
            100                 105                 110

Arg Arg Arg Ala Met Arg Arg His Gly Ile Ser Glu Asp Leu Ala Val
        115                 120                 125

Gln Arg Ile Pro Asp Ser Ala Ala Glu Gln Leu Arg Leu Pro Phe Val
    130                 135                 140

Val Leu Gly Ser Arg Ser Thr Gly Gln Thr Ala Phe Pro Val Phe Val
145                 150                 155                 160

Arg His Gly Pro Val Gln Gln Glu Pro Val Pro Gly Asp Phe Ser Ser
                165                 170                 175

Tyr Gly Leu Ser Arg Gly Ala Thr Val Pro Trp Phe
            180                 185

<210> SEQ ID NO 10
<211> LENGTH: 184
<212> TYPE: PRT
<213> ORGANISM: Pectobacterium atrosepticum

<400> SEQUENCE: 10

Met Asp His Tyr Ile Asp Ile Arg Val Gln Pro Asp Pro Glu Phe Thr
1               5                   10                  15

Ala Ser Gln Leu Leu Asn Ala Leu Phe Ala Lys Leu His Arg Val Leu
            20                  25                  30

Gly Gln Leu Ala Asn Gly Lys Ile Gly Ile Ser Phe Pro Glu Val Gly
        35                  40                  45

Lys Thr Leu Gly Glu Cys Leu Arg Leu His Gly Thr Glu Asp Ala Leu
    50                  55                  60

Ser Thr Leu Glu Lys Thr Ser Trp Leu Lys Gly Leu Arg Asp Tyr Thr
65                  70                  75                  80

Gln Val Ser Glu Cys Lys Val Val Pro Asn Gly Val Lys Phe Arg Thr
                85                  90                  95

Val Arg Arg Val Gln Leu Lys Ser Ser Ala Glu Arg Leu Arg Arg Arg
            100                 105                 110

Ser Val Ser Lys Gly Trp Leu Thr Ala Ala Glu Ala Ala Ala Arg Ile
        115                 120                 125

```
Pro Asp Ala Val Glu Lys Arg Ser Ala Leu Pro Phe Val Gln Ile Lys
        130                 135                 140

Ser Leu Ser Asn Gly Gln Met Phe Phe Val Phe Val Glu His Gly Pro
145                 150                 155                 160

Leu Gln Asn Ala Pro Thr Ala Gly Arg Phe Ser Ser Tyr Gly Leu Ser
                165                 170                 175

Thr Glu Ala Thr Val Pro Trp Phe
            180

<210> SEQ ID NO 11
<211> LENGTH: 184
<212> TYPE: PRT
<213> ORGANISM: Photorhabdus luminescens

<400> SEQUENCE: 11

Met Asp Tyr Tyr Leu Glu Ile Arg Val Leu Pro Asp Leu Glu Phe Ser
1               5                   10                  15

Gln Gln Ser Leu Phe Glu Ala Leu Phe Ala Lys Leu His Arg Ala Leu
            20                  25                  30

Gly Gln Leu Ser Asn Gly Gln Val Gly Val Ser Phe Pro Cys Ala Arg
        35                  40                  45

Lys Thr Leu Gly Asp Thr Leu Arg Ile His Gly Ser Ser Glu Ala Leu
50                  55                  60

Asn Asp Leu Gln Ala Leu Pro Trp Leu Lys Gly Leu Arg Asp Tyr Thr
65                  70                  75                  80

Glu Val Ile Asp Ile Gln Pro Ile Pro Gln Glu Thr Lys Tyr Arg Cys
                85                  90                  95

Val Ser Arg Val Gln Val Lys Ser Ser Ala Glu Arg Leu Arg Arg Arg
            100                 105                 110

Ala Ile Lys Lys Gly Trp Leu Thr Gly Glu Gln Ala Arg Gln Arg Ile
        115                 120                 125

Pro Ile Ser Lys Glu Gln Arg Thr His Leu Pro Phe Leu Phe Leu Lys
    130                 135                 140

Ser Leu Ser Ser Gly Gln Ser Phe Leu Leu Phe Val Lys Gln Gly Pro
145                 150                 155                 160

Ile Gln Asp Lys Pro Thr Ser Gly Ile Phe Ser Ser Tyr Gly Leu Ser
                165                 170                 175

Ser Ser Ala Thr Ile Pro Trp Phe
            180

<210> SEQ ID NO 12
<211> LENGTH: 188
<212> TYPE: PRT
<213> ORGANISM: Desulfurivibrio alkaliphilus

<400> SEQUENCE: 12

Met Val Met Ala Met Asp Cys Tyr Val Glu Ile Ser Leu Leu Pro Asp
1               5                   10                  15

Pro Glu Phe Pro Asp Ser Ile Leu Met Asn Ala Leu Phe Ala Lys Leu
            20                  25                  30

His Arg Ala Leu Ala Glu Asn Gly Lys Gln Glu Ile Gly Val Ser Phe
        35                  40                  45

Pro Glu Phe Gly Lys Lys Leu Asn Ser Lys Leu Arg Ile His Gly Ser
    50                  55                  60

Glu Glu Ser Leu Lys Arg Leu Met Asp Leu Asn Trp Ile Gln Gly Met
65                  70                  75                  80
```

Lys Asp Tyr Thr Arg Val Ser Gly Ile Ala Lys Val Pro Asp Ser Cys
85 90 95

Gln Tyr Arg Thr Val Lys Arg Val Gln Ala Lys Ser Ser Val Asp Arg
100 105 110

Leu Tyr Arg Arg Ser Val Lys Lys Gly Trp Leu Ser Glu Glu Asn Ala
115 120 125

Glu Gln Gln Lys Glu Arg Ala Arg Glu Gly Arg Leu Lys Leu Pro Phe
130 135 140

Val Gln Leu Lys Ser Gln Thr Thr Gly Gln Gln Phe Arg Leu Phe Ile
145 150 155 160

Gln His Gly Ser Leu Gln Glu Lys Pro Val Thr Gly Arg Phe Ser Ser
165 170 175

Tyr Gly Leu Ser Asn Glu Ala Thr Val Pro Trp Phe
180 185

<210> SEQ ID NO 13
<211> LENGTH: 184
<212> TYPE: PRT
<213> ORGANISM: Dickeya zeae

<400> SEQUENCE: 13

Met Asp His Tyr Ile Glu Ile Arg Val Leu Pro Asp Leu Glu Phe Ser
1 5 10 15

Ala Val Gln Leu Leu Ser Ala Leu Phe Ala Lys Leu His Arg Ala Leu
20 25 30

Gly Gln Gln Ala Thr Gly Ala Ile Gly Val Ser Phe Pro Asp Val Gly
35 40 45

Lys Thr Leu Gly Glu Arg Leu Arg Leu His Gly Ser Glu Gln Ala Leu
50 55 60

Thr Ala Leu Glu Gln Thr Gly Trp Arg Thr Gly Leu Arg Asp Tyr Ser
65 70 75 80

Thr Ile Thr Asp Val Leu Thr Val Pro Thr Gly Ala Gln Tyr Arg Thr
85 90 95

Val Arg Arg Val Gln Val Lys Ser Ser Ala Glu Arg Leu Arg Arg Arg
100 105 110

Ala Val Ser Lys Gly Trp Leu Thr Ala Asp Glu Ala Ala Ala Arg Ile
115 120 125

Pro Tyr Ala Val Glu Lys Arg Thr Ser Leu Pro Tyr Leu Pro Leu Arg
130 135 140

Ser Leu Ser Ser Gly Gln Pro Phe Leu Leu Phe Val Glu His Gly Pro
145 150 155 160

Leu Gln Asp Lys Pro Val Ala Gly Thr Phe Ser Ser Tyr Gly Leu Ser
165 170 175

Ala Thr Ala Thr Ile Pro Trp Phe
180

<210> SEQ ID NO 14
<211> LENGTH: 184
<212> TYPE: PRT
<213> ORGANISM: Yersinia pestis

<400> SEQUENCE: 14

Met Asp His Tyr Leu Asp Ile Arg Val Leu Pro Asp Pro Glu Phe Ser
1 5 10 15

Ala Gln Thr Leu Leu Glu Ala Leu Phe Ala Lys Leu His Arg Ala Leu
20 25 30

Val Ala Thr Ile Pro Gly Arg Val Gly Val Ser Phe Pro Thr Ala Gly
         35                  40                  45

Lys Thr Leu Gly Ser Gln Leu Arg Leu His Gly Ser Arg Gly Asp Leu
 50                  55                  60

Leu Glu Leu Gln Ser Ala Gly Trp Leu Lys Gly Leu Gln Asp Tyr Cys
 65                  70                  75                  80

Glu Cys Ser Glu Ile Leu Pro Val Pro Ala Asp Val Lys His Arg Thr
                 85                  90                  95

Ile Arg Arg Val Gln Val Lys Ser Ser Ala Gln Arg Leu Arg Arg Arg
                100                 105                 110

Ser Val Ser Lys Gly Trp Leu Thr Glu Glu Gln Ala Arg Leu Arg Ile
                115                 120                 125

Pro Asp Ser His Asp Lys Arg Cys Asp Leu Pro Phe Leu Arg Leu Lys
    130                 135                 140

Ser Arg Ser Ser Glu Gln Tyr Phe Leu Leu Phe Ile Glu Gln Gly Thr
145                 150                 155                 160

Leu Gln Ala Ser Ala Thr Thr Gly Glu Phe Ser Ala Tyr Gly Leu Ser
                165                 170                 175

Val Asn Ala Thr Ile Pro Trp Phe
            180

<210> SEQ ID NO 15
<211> LENGTH: 184
<212> TYPE: PRT
<213> ORGANISM: Dickeya dadantii

<400> SEQUENCE: 15

Met Asp His Tyr Ile Glu Ile Arg Val Leu Pro Asp Pro Glu Phe Ser
1               5                  10                  15

Ala Val Gln Leu Leu Ser Ala Leu Phe Ala Lys Leu His Arg Ala Leu
             20                  25                  30

Gly Gln Arg Ala Thr Gly Asp Ile Gly Val Ser Phe Pro Asp Ala Gly
         35                  40                  45

Lys Thr Leu Gly Glu Arg Leu Arg Leu His Gly Ser Val Gln Ala Leu
 50                  55                  60

Ala Ala Leu Glu Gln Thr Gly Trp Leu Lys Gly Leu Arg Asp Tyr Ser
 65                  70                  75                  80

Thr Ile Thr Asp Val Leu Thr Val Pro Thr Gly Ala Gln Tyr Arg Thr
                 85                  90                  95

Val Arg Arg Val Gln Val Lys Ser Ser Ala Glu Arg Leu Arg Arg Arg
                100                 105                 110

Ala Val Ser Lys Gly Arg Met Thr Ala Asp Glu Ala Ala Arg Ile
                115                 120                 125

Pro Tyr Ala Ala Glu Lys Arg Thr Ser Leu Pro Tyr Leu Pro Leu Arg
    130                 135                 140

Ser Leu Ser Ser Gly Gln Thr Phe Leu Leu Phe Val Glu His Gly Pro
145                 150                 155                 160

Leu Gln Glu Lys Pro Val Ala Gly Val Phe Ser Ser Tyr Gly Leu Ser
                165                 170                 175

Ala Ile Ala Thr Ile Pro Trp Phe
            180

<210> SEQ ID NO 16
<211> LENGTH: 198
<212> TYPE: PRT

<213> ORGANISM: Escherichia coli

<400> SEQUENCE: 16

```
Met Ala Val Ser Leu Val Arg Asn Arg Asn Lys Glu Leu Pro Met Asp
 1               5                  10                  15

His Tyr Leu Glu Ile Arg Val Leu Pro Asp Pro Glu Phe Ser Ser Glu
            20                  25                  30

Met Leu Met Ala Ala Leu Phe Ala Lys Leu His Arg Val Leu Gly Ala
        35                  40                  45

Arg Gly Gln Gly Asp Ile Gly Val Ser Phe Pro Asp Val Asn Val Met
 50                  55                  60

Pro Gly Ala Arg Leu Arg Leu His Gly Ser Ala Gln Ala Leu Gln Ala
 65                  70                  75                  80

Leu Glu Ala Ser Thr Trp Arg Lys Gly Leu Thr Asp Tyr Cys Gln Cys
                85                  90                  95

Ser Pro Val Thr Pro Val Pro Glu Ile Lys Gly Trp Arg Val Val Ser
            100                 105                 110

Arg Val Gln Val Lys Ser Asn Pro Gln Arg Leu Leu Arg Arg Ser Val
            115                 120                 125

Lys Lys Gly Trp Leu Thr Glu Glu Gln Ala Ile Glu Arg Leu Ala Thr
130                 135                 140

Gln Ala Glu Gln Arg Thr Asp Leu Pro Phe Leu Asn Met Lys Ser Leu
145                 150                 155                 160

Ser Ser Gln Gln Leu Phe Lys Leu Phe Ile Arg His Gly Asp Leu Leu
                165                 170                 175

Lys Glu Pro Val Lys Gly Glu Phe Ser Ser Tyr Gly Leu Ser Ala Thr
            180                 185                 190

Ala Thr Ile Pro Trp Phe
            195
```

<210> SEQ ID NO 17
<211> LENGTH: 184
<212> TYPE: PRT
<213> ORGANISM: Escherichia coli

<400> SEQUENCE: 17

```
Met Asp His Tyr Leu Glu Ile Arg Val Leu Pro Asp Pro Glu Phe Ser
 1               5                  10                  15

Ser Glu Met Leu Met Ala Ala Leu Phe Ala Lys Leu His Arg Val Leu
            20                  25                  30

Gly Ala Arg Gly Gln Gly Asp Ile Gly Val Ser Phe Pro Asp Val Asn
        35                  40                  45

Val Met Pro Gly Ala Arg Leu Arg Leu His Gly Ser Ala Gln Ala Leu
 50                  55                  60

Gln Ala Leu Glu Ala Ser Thr Trp Arg Lys Gly Leu Thr Asp Tyr Cys
 65                  70                  75                  80

Gln Cys Ser Pro Val Thr Pro Val Pro Glu Ile Lys Gly Trp Arg Val
                85                  90                  95

Val Ser Arg Val Gln Val Lys Ser Asn Pro Gln Arg Leu Leu Arg Arg
            100                 105                 110

Ser Val Lys Lys Gly Trp Leu Thr Glu Glu Gln Ala Ile Glu Arg Leu
            115                 120                 125

Ala Thr Gln Ala Glu Gln Arg Thr Asp Leu Pro Phe Leu Asn Met Lys
130                 135                 140

Ser Leu Ser Ser Gln Gln Leu Phe Lys Leu Phe Ile Arg His Gly Asp
```

```
                145                 150                 155                 160
Leu Leu Lys Glu Pro Val Lys Gly Glu Phe Ser Ser Tyr Gly Leu Ser
                    165                 170                 175

Ala Thr Ala Thr Ile Pro Trp Phe
            180

<210> SEQ ID NO 18
<211> LENGTH: 184
<212> TYPE: PRT
<213> ORGANISM: Tolumonas auensis

<400> SEQUENCE: 18

Met Asp His Tyr Leu Asp Ile Arg Leu Leu Pro Glu Glu Pro Glu Val
1               5                   10                  15

Ser Glu Ser Phe Leu Leu Asn Ala Leu Phe Ala Lys Leu His Val Arg
            20                  25                  30

Leu Gly Gln Gln Ala Gln Gly Arg Val Gly Val Ser Phe Pro Asp His
        35                  40                  45

His Lys Arg Leu Gly Asp Leu Leu Arg Leu His Gly Gln Arg Thr Asp
    50                  55                  60

Leu Gln Ala Leu Met Ala Asp Asp Trp Leu Gln Gly Leu Lys Gly Tyr
65                  70                  75                  80

Thr Gln Cys Ser Glu Val Leu Pro Ile Pro Ala Thr Val Ser Tyr Arg
                85                  90                  95

Ala Val Lys Arg Val Gln Ala Lys Ser Ala His Asn Lys Arg Gln Arg
            100                 105                 110

Ser Ile Ala Lys Gly Trp Leu Thr Glu Ser Glu Ala Gln Ile Arg Ile
        115                 120                 125

Pro Asp Thr Gln Gln Lys Glu Leu His Leu Pro Phe Val Gln Leu Lys
    130                 135                 140

Ser Arg Ser Asn Gly Gln Met Met Arg Val Tyr Val Glu His Gly Pro
145                 150                 155                 160

Val Leu Ala Val Pro Val Ser Gly Tyr Phe Asn Ala Tyr Gly Leu Ser
                165                 170                 175

Ser Ile Ala Thr Ile Pro Trp Phe
            180

<210> SEQ ID NO 19
<211> LENGTH: 184
<212> TYPE: PRT
<213> ORGANISM: Erwinia pyrifoliae

<400> SEQUENCE: 19

Met Asp His Tyr Gln Asp Ile Arg Val Arg Val Asp Glu Glu Asn Gly
1               5                   10                  15

Glu Ala Val Leu Leu Ala Gln Val Phe Met His Leu His Gln Val Leu
            20                  25                  30

Met Arg Ala Ala Asn Gly Arg Ile Gly Ile Ser Phe Pro Asn Val Lys
        35                  40                  45

Arg Thr Leu Gly Asp Arg Ile Arg Leu His Gly Thr Leu Asp Asp Leu
    50                  55                  60

Ser Ala Leu Gln Gln Ser Gly Trp Asn Lys Cys Leu Arg Asp Tyr Ile
65                  70                  75                  80

Ala Cys Ser Asp Ile Ala Pro Val Pro Lys Gly Ala Ala Trp Arg Thr
                85                  90                  95

Val Arg Arg Val Gln Val Lys Ser Ser Ala Glu Arg Leu Arg Arg Arg
```

```
            100                 105                 110
Ser Val Asn Lys Gly Trp Leu Ser Glu Gln Glu Ala Ala Glu Arg Ile
        115                 120                 125

Ser Val Leu Asn Glu Gln Arg Ser Asn Leu Pro Phe Leu Gln Ile Lys
    130                 135                 140

Ser Gly Ser Asn Gly Gln Ala Trp Arg Leu Phe Ile Glu His Gly Ser
145                 150                 155                 160

Leu Val Ser Ala Pro Ser Asp Gly Ser Phe Ser Ser Tyr Gly Leu Ser
                165                 170                 175

Ala Ala Ala Thr Ile Pro Trp Phe
            180

<210> SEQ ID NO 20
<211> LENGTH: 198
<212> TYPE: PRT
<213> ORGANISM: Escherichia coli

<400> SEQUENCE: 20

Met Ala Val Ser Leu Val Arg Asn Arg Asn Lys Glu Leu Pro Met Asp
1               5                   10                  15

His Tyr Leu Glu Ile Arg Val Leu Pro Asp Pro Glu Phe Ser Ser Glu
            20                  25                  30

Met Leu Met Ala Ala Leu Phe Ala Lys Leu His Arg Val Leu Gly Ala
        35                  40                  45

Arg Gly Gln Gly Asp Ile Gly Val Ser Phe Pro Asp Val Asn Val Met
    50                  55                  60

Pro Gly Thr His Leu Arg Leu His Gly Ser Ala Gln Ala Leu Gln Glu
65                  70                  75                  80

Leu Glu Ala Ser Thr Trp Arg Lys Gly Leu Thr Asp Tyr Cys Gln Cys
                85                  90                  95

Ser Pro Val Thr Pro Val Pro Glu Ile Lys Gly Trp Arg Val Val Ser
            100                 105                 110

Arg Val Gln Val Lys Ser Asn Pro Gln Arg Leu Leu Arg Arg Ser Val
        115                 120                 125

Lys Lys Gly Trp Leu Thr Glu Glu Gln Ala Ile Glu Arg Leu Ala Thr
    130                 135                 140

Gln Ala Glu Gln Arg Thr Asp Leu Pro Phe Leu Asn Met Lys Ser Leu
145                 150                 155                 160

Ser Ser Gln Gln Gln Phe Lys Leu Phe Ile Arg His Gly Asp Leu Leu
                165                 170                 175

Lys Glu Pro Val Lys Gly Glu Phe Ser Ser Tyr Gly Leu Ser Ala Thr
            180                 185                 190

Ala Thr Ile Pro Trp Phe
        195

<210> SEQ ID NO 21
<211> LENGTH: 190
<212> TYPE: PRT
<213> ORGANISM: Verminephrobacter eiseniae

<400> SEQUENCE: 21

Met Ser Thr His Tyr Ile Asp Ile Thr Leu Arg Pro Asp Pro Glu Phe
1               5                   10                  15

Ser Pro Ala His Leu Leu Asn Ala Leu His Ala Gln Leu His Leu Ala
            20                  25                  30

Leu Val Gln Leu Gly Thr Gly Asp Val Gly Val Ser Phe Pro Gly Phe
```

```
                35                  40                  45
Ile Leu Arg Gly Glu His Ser His Leu Gly Thr Thr Leu Arg Leu His
 50                  55                  60

Gly Ala Thr Ser Ala Leu Gln Arg Leu Gln Ala Leu Ser Trp Leu Arg
 65                  70                  75                  80

Gly Met Arg Asp His Val Lys Thr Ser Glu Val Ala Pro Val Pro Thr
                 85                  90                  95

His Thr Gln His Arg Val Val Arg Val Gln Ala Lys Ser Ser Pro
                100                 105                 110

Glu Arg Ser Arg Arg Arg Leu Met Arg Arg Leu Glu Ile Asp Glu Ala
            115                 120                 125

Gln Ala Leu Gln Arg Ile Pro Asp Gln Glu Gly Arg Arg Leu Ala Leu
        130                 135                 140

Pro Tyr Leu Arg Leu Gln Ser Ala Ser Lys Gly Gln Val Phe Arg Leu
145                 150                 155                 160

Phe Ile Glu His Gly Pro Leu Leu Asp Thr Pro Ser Pro Gly Ser Phe
                165                 170                 175

Gly Thr Tyr Gly Leu Ser Thr Gln Ala Thr Ile Pro Trp Phe
            180                 185                 190
```

```
<210> SEQ ID NO 22
<211> LENGTH: 195
<212> TYPE: PRT
<213> ORGANISM: Chromobacterium violaceum

<400> SEQUENCE: 22

Met Asp His Tyr Leu Asp Ile Arg Leu Leu Pro Asp Ala Asp Phe Gly
 1               5                  10                  15

Pro Pro Val Leu Met Asn Ala Leu Tyr Ala Lys Leu His Arg Ala Leu
                 20                  25                  30

Ala Ala Gln Gln Arg Gln Asp Ile Gly Val Ser Phe Pro Gly Tyr Asp
             35                  40                  45

Pro Ala Pro Ser Ser His Asp Gly Lys Pro Leu Pro Pro Thr Leu Gly
         50                  55                  60

Leu Thr Leu Arg Leu His Gly Ser Ala Ala Leu Asp Gly Leu Met
 65                  70                  75                  80

Ala Arg Arg Trp Leu Ser Gly Phe Ala Asp His Ala Ile Val Gly Asp
                 85                  90                  95

Ile Arg Pro Val Pro Ala Gly Ala Ser Ala Val Ser Val Arg Arg Arg
                100                 105                 110

Gln Ala Lys Ser Ser Pro Ala Arg Ala Arg Asp Arg Leu Met Arg Arg
            115                 120                 125

Gln Gly Ile Ser Ala Glu Glu Ala Arg Arg Ile Pro Asp Glu Thr
        130                 135                 140

Ala Gln Arg Leu Asn Leu Pro Tyr Leu Thr Val Asp Ser Ala Ser Thr
145                 150                 155                 160

Gly Gln Cys Phe Arg Leu Phe Val Glu Gln Gln Ala Ala Pro Ser Ile
                165                 170                 175

Ala Ala Gly Ser Phe Asn Ala Tyr Gly Leu Ser Ala Ala Ala Ala Leu
            180                 185                 190

Pro Ala Trp
        195

<210> SEQ ID NO 23
<211> LENGTH: 184
```

<212> TYPE: PRT
<213> ORGANISM: Erwinia tasmaniensis

<400> SEQUENCE: 23

```
Met Asp Arg Tyr Gln Asp Ile Arg Val Arg Val Asp Ala Glu Met Thr
1               5                   10                  15

Ala Pro Val Leu Leu Ala Gln Val Phe Met Arg Leu His Gln Val Leu
            20                  25                  30

Met Arg Ala Ala Asn Gly Arg Ile Gly Ile Ser Phe Pro Asp Val Lys
        35                  40                  45

Leu Thr Leu Gly Asp Arg Ile Arg Leu His Gly Thr Leu Asp Asp Leu
    50                  55                  60

Ser Ser Leu Gln Gln Ser Gly Trp Asp Lys Gly Leu Thr Asp Tyr Ile
65                  70                  75                  80

Ala Cys Ser Ala Ile Asp Pro Val Pro Gly Ala Ala Trp Arg Thr
                85                  90                  95

Val Arg Arg Val Gln Val Lys Ser Ser Ala Glu Arg Leu Arg Arg Arg
            100                 105                 110

Ser Val Asn Lys Gly Trp Leu Asn Glu Ala Glu Ala Glu Arg Ile
        115                 120                 125

Asn Val Leu Ser Glu Gln Arg Ser Asp Leu Pro Tyr Leu Gln Ile Lys
    130                 135                 140

Ser Gly Ser Asn Gly His Ala Trp Arg Leu Phe Ile Glu His Gly Pro
145                 150                 155                 160

Leu Val Ser Val Pro Val Asn Gly Gly Phe Ser Ser Tyr Gly Leu Ser
                165                 170                 175

Ala Thr Ala Thr Val Pro Trp Phe
            180
```

<210> SEQ ID NO 24
<211> LENGTH: 190
<212> TYPE: PRT
<213> ORGANISM: Delftia acidovorans

<400> SEQUENCE: 24

```
Met Ala Met Thr Ser His Tyr Ile Asp Thr Thr Leu Leu Pro Asp Pro
1               5                   10                  15

Glu Phe Ser His Ala His Leu Leu Gly Ala Leu Val Ala Lys Leu His
            20                  25                  30

Arg Ala Leu Val Gln Leu Gly Ser Thr Asp Ile Gly Ile Ser Phe Pro
        35                  40                  45

Gly Tyr Ser Leu Arg Pro Arg Thr Leu Gly Thr Ile Leu Arg Leu His
    50                  55                  60

Gly Ser Glu Ala Ala Leu Arg Gly Leu Met Glu Gln Pro Trp Leu Gln
65                  70                  75                  80

Gly Met Arg Asp His Val His Cys Thr Pro Pro Ala Leu Val Pro Glu
                85                  90                  95

Gly Ala Val Pro Cys Leu Val Gln Arg Gln Phe Lys Thr Ser Pro
            100                 105                 110

Asp Arg Leu Arg Arg Arg Met Arg Lys Gly Glu Thr Ala Glu
        115                 120                 125

Gln Ala Ala Ala Ile Pro Asp Ser Val Glu Arg Thr Pro Asp Leu
    130                 135                 140

Pro Tyr Val Gln Leu Arg Ser Ala Ser Thr Gly Gln Pro Phe Cys Leu
145                 150                 155                 160
```

```
Phe Val Glu Gln Lys Ala Val Gln Gly Thr Ala Gly Gln Glu Gly Phe
            165                 170                 175

Asn Thr Tyr Gly Leu Ser Leu Gly Thr Ala Val Pro Trp Phe
            180                 185                 190

<210> SEQ ID NO 25
<211> LENGTH: 184
<212> TYPE: PRT
<213> ORGANISM: Unknown
<220> FEATURE:
<223> OTHER INFORMATION: Enterobacter sp. 638

<400> SEQUENCE: 25

Met Asp His Tyr Leu Glu Ile Arg Val Leu Ser Asp Pro Glu Phe Ser
1               5                   10                  15

Glu Glu Thr Leu Met Ala Ala Leu Phe Ala Lys Leu His Arg Ala Leu
            20                  25                  30

Gly Ala Arg Gly Gln Gly Asp Ile Gly Val Ser Phe Pro Arg Tyr Ser
        35                  40                  45

Leu Lys Pro Gly Asp Thr Leu Arg Leu His Gly Ser Ala Gln Ser Leu
    50                  55                  60

Asp Glu Leu Glu Lys Met Ala Trp Arg Lys Gly Leu Ser Asp Tyr Cys
65                  70                  75                  80

Leu Cys Lys Gly Val Leu Pro Ala Pro Asp Val Asn Ala Trp Arg Cys
                85                  90                  95

Val Ser Arg Val Gln Val Lys Ser Ser Pro Gln Arg Leu Met Arg Arg
            100                 105                 110

Ser Val Lys Lys Gly Trp Leu Thr Glu Glu Ala Gln Gln Arg Leu
        115                 120                 125

Leu Asn Leu Gln Glu Ala Arg Thr Asp Leu Pro Trp Leu Asn Leu Gln
    130                 135                 140

Ser Leu Ser Thr Gly Gln Ser Phe Arg Leu Phe Ile Arg His Gly Asp
145                 150                 155                 160

Ile Val Asp Met Pro Met Cys Gly Glu Phe Ser Ser Tyr Gly Leu Ser
                165                 170                 175

Ala Thr Ala Thr Ile Pro Trp Phe
            180

<210> SEQ ID NO 26
<211> LENGTH: 186
<212> TYPE: PRT
<213> ORGANISM: Unknown
<220> FEATURE:
<223> OTHER INFORMATION: Thioalkalivibrio sp. K90mix

<400> SEQUENCE: 26

Met Asp His Tyr Leu Asp Leu Arg Val Met Pro Asp Pro Glu Phe Lys
1               5                   10                  15

Glu Thr Thr Leu Leu Gly Ala Leu Val Ser Lys Leu His Arg Arg Leu
            20                  25                  30

Val Ser Met Ser Ala Asp Asp Ile Gly Ile Ser Leu Pro Asp His Glu
        35                  40                  45

Gln Glu Pro Pro Leu Gly Arg Arg Leu Arg Val His Gly Thr Gln Gly
    50                  55                  60

Arg Leu Asn Leu Leu Met Gln Asp Glu Trp Leu Gly Gly Met Gln Ser
65                  70                  75                  80

Leu Val Asp Ala Thr Pro Val Gln Pro Val Pro Asp Gln Val Thr Tyr
                85                  90                  95
```

```
Arg Pro Val Arg Arg Gln Tyr Lys Thr Asn Ala Glu Arg Leu Arg
            100                 105                 110

Arg Arg Arg Met Arg Arg His Gly Glu Ser Tyr Glu Glu Ala Arg Gln
        115                 120                 125

His Ile Pro Asp Thr Val Glu Arg Arg Val Asn Thr Pro Phe Leu Ser
    130                 135                 140

Val Gln Ser Ala Ser Thr Gly Gln Arg Phe Ser Leu Phe Ile Glu His
145                 150                 155                 160

Gly Pro Pro Gln Gln His Ala Ser Pro Gly Arg Phe Asn Thr Tyr Gly
                165                 170                 175

Leu Ser Gln Asp Ala Thr Val Pro Trp Phe
            180                 185
```

<210> SEQ ID NO 27
<211> LENGTH: 193
<212> TYPE: PRT
<213> ORGANISM: Zymomonas mobilis

<400> SEQUENCE: 27

```
Met Leu Ala Asn Pro Val Asp Ser Tyr Gln Asp Ile Tyr Ile Leu Pro
1               5                   10                  15

Asn Gln Glu Ile Ala Pro His Ile Ile Met Glu Lys Leu Phe Ser Leu
            20                  25                  30

Leu His Leu Glu Leu Val Arg Leu Gly Ser Gln His Ile Gly Ile Ser
        35                  40                  45

Phe Pro Glu His Asp Asn Asn Lys Pro Cys Leu Gly Ser Arg Leu Arg
    50                  55                  60

Leu His Gly Thr Gly Ala Asp Leu His Glu Leu Ala Leu Ser Gly Trp
65                  70                  75                  80

Ile Thr Arg Leu Asp Asp Tyr Leu Tyr Cys Glu Asp Ile Lys Ser Val
                85                  90                  95

Pro Glu Ile Arg Gln Tyr Cys Val Val Ser Arg Val Gln Ala Lys Ser
            100                 105                 110

Ser Pro Ala Arg Leu Arg Arg Arg Ala Ile Arg Arg His Gly Phe His
        115                 120                 125

Asp Glu Glu Ala Lys Lys Val Ile Pro Asp Thr Ala Phe Glu Arg Leu
    130                 135                 140

Glu Leu Pro Phe Ile Met Thr Gly Ser Cys Ser Thr Lys Gln Pro Arg
145                 150                 155                 160

Phe Pro Val Phe Ile Ser His Lys Ile Ile Gln Asn Lys Leu Met Asn
                165                 170                 175

Gly Asn Phe Asn Ser Tyr Gly Leu Ser Leu Gly Ala Ser Val Pro Trp
            180                 185                 190

Phe
```

<210> SEQ ID NO 28
<211> LENGTH: 193
<212> TYPE: PRT
<213> ORGANISM: Zymomonas mobilis

<400> SEQUENCE: 28

```
Met Leu Ala Asn Pro Val Asp Ser Tyr Gln Asp Ile Tyr Ile Leu Pro
1               5                   10                  15

Asn Gln Glu Ile Ala Pro His Ile Ile Met Glu Lys Leu Phe Ser Leu
            20                  25                  30
```

Leu His Leu Glu Leu Val Arg Leu Gly Ser Gln His Ile Gly Ile Ser
 35                  40                  45

Phe Pro Glu His Asp Asn Asn Lys Pro Cys Leu Gly Ser Arg Leu Arg
 50                  55                  60

Leu His Gly Ala Gly Ala Asp Leu His Glu Leu Ala Leu Ser Gly Trp
65                  70                  75                  80

Ile Thr Arg Leu Asp Asp Tyr Leu Tyr Cys Glu Asp Ile Lys Ser Val
                 85                  90                  95

Pro Glu Ile Arg Gln Tyr Cys Val Val Ser Arg Val Gln Ala Lys Ser
            100                 105                 110

Ser Pro Ala Arg Leu Arg Arg Ala Ile Arg His Gly Phe His
        115                 120                 125

Asp Glu Glu Ala Lys Lys Val Ile Pro Asp Thr Ala Phe Glu Arg Leu
130                 135                 140

Glu Leu Pro Phe Ile Met Thr Gly Ser Cys Ser Thr Lys Gln Pro Arg
145                 150                 155                 160

Phe Pro Val Phe Ile Ser His Lys Ile Ile Gln Asp Lys Leu Met Asn
                165                 170                 175

Gly Asn Phe Asn Ser Tyr Gly Leu Ser Leu Gly Ala Ser Val Pro Trp
            180                 185                 190

Phe

<210> SEQ ID NO 29
<211> LENGTH: 191
<212> TYPE: PRT
<213> ORGANISM: Unknown
<220> FEATURE:
<223> OTHER INFORMATION: Acidovorax sp. JS42

<400> SEQUENCE: 29

Met Thr Thr His Tyr Ile Asn Ile Thr Leu Leu Pro Asp Pro Glu Phe
1               5                   10                  15

Ser His Ala His Leu Leu Gly Ala Leu Val Ala Lys Leu His Arg Ala
                20                  25                  30

Leu Val Gln Gly His Thr Thr Asp Ile Gly Val Ser Tyr Pro Gln His
        35                  40                  45

Val Ser Gln Pro Leu Thr Lys Arg Thr Leu Gly Ala Val Leu Arg Leu
50                  55                  60

His Gly Thr Pro Glu Ala Leu Gln Arg Leu Met Glu Glu Asp Trp Leu
65                  70                  75                  80

Lys Gly Met Arg Asp His Thr Gln Val Gly Glu Leu Leu Pro Val Pro
                85                  90                  95

Ala Asn Ala Gln His Arg Thr Val Arg Arg Gln Phe Lys Thr Asn
            100                 105                 110

Ala Asp Arg Leu Arg Arg Arg Met Gln Arg Lys Gly Glu Thr Ala
        115                 120                 125

Glu Gln Ala Ala Ala Ile Pro Asp Thr Val Glu Arg Arg Pro Asp
130                 135                 140

Leu Pro Phe Val Gln Leu Arg Ser Ser Thr Gly Gln Ser Phe Cys
145                 150                 155                 160

Leu Cys Val Glu His Gly Pro Leu Gln Pro Leu Pro Val Ala Gly Ala
                165                 170                 175

Phe Asn Ala Tyr Gly Leu Gly His Asp Ala Thr Val Pro Trp Phe
            180                 185                 190

```
<210> SEQ ID NO 30
<211> LENGTH: 182
<212> TYPE: PRT
<213> ORGANISM: Desulfurispirillum indicum

<400> SEQUENCE: 30

Met Asp Ser Tyr Ile Glu Ile Arg Ile Leu Pro Asp Gln Glu Phe Glu
1               5                   10                  15

Ala Thr Thr Leu Met Ser Thr Val Phe Ala Lys Leu His Arg Ala Leu
            20                  25                  30

Val Glu Ser Gly Arg Ser Asp Ile Gly Val Ser Phe Pro Glu Ala Gly
        35                  40                  45

Lys Thr Pro Gly Ala Leu Leu Arg Leu His Gly Ser Leu Ala Ala Leu
    50                  55                  60

Glu Ser Ile Met Thr Leu Ser Trp Leu Thr Gly Leu Gln Asp Tyr Thr
65                  70                  75                  80

Gln Thr Ser Gly Ile Leu Gln Val Pro Ala Gln Ala Ala Tyr Val Gln
                85                  90                  95

Val Ala Arg Val Gln Ser Lys Met Thr Ala Ser Arg Ile Arg Arg Ala
            100                 105                 110

Leu Lys Arg Gly Ser Leu Ser Glu Glu Arg Ala Leu Glu Leu Leu Gln
        115                 120                 125

Ser Arg Asp Gln Leu Asn Gln Pro Phe Phe Arg Leu Leu Ser Ala Ser
    130                 135                 140

Thr Ala Gln Lys Phe Pro Leu Phe Ile Glu Gln Arg Asn Ala Glu Lys
145                 150                 155                 160

Ala Gly Lys Gln Ser Val Tyr Ser Ala Tyr Gly Leu Ser Val Gly Gly
                165                 170                 175

Ser Thr Val Pro Trp Phe
            180

<210> SEQ ID NO 31
<211> LENGTH: 184
<212> TYPE: PRT
<213> ORGANISM: Photobacterium profundum

<400> SEQUENCE: 31

Met Met Asp Ser Tyr Val Asp Ile Gln Leu Lys Pro Asp Ala Glu Met
1               5                   10                  15

Arg Glu Ala Glu Leu Ser Ser Lys Val Phe Thr Lys Phe His Lys Ala
            20                  25                  30

Leu Ala Thr Leu Asn Thr Asn Lys Ile Gly Ile Ser Phe Pro Gln Met
        35                  40                  45

Asn Leu Lys Leu Gly Arg Leu Phe Arg Ile His Gly Asn Ala Ser Leu
    50                  55                  60

Leu Lys Asp Leu Gln Gly Ile Lys Trp Leu Gly Ala Leu Ala Gly Tyr
65                  70                  75                  80

Cys Gln Val Gly Glu Ile Thr Val Val Pro Asp Gln Val Gln Tyr Arg
                85                  90                  95

Val Ile Ser Val Lys Arg Ser Asn Leu Ser Lys Ala Lys Leu Lys Arg
            100                 105                 110

Leu Ile Ala Arg Gly Ser Ile Asp Lys Asp Gly Glu Lys Arg Tyr Lys
        115                 120                 125

Val Lys Met Leu Ser Gln Gly Phe Asp Asn Pro Tyr Leu Asp Leu Phe
    130                 135                 140

Ser Ser Ser Thr Gly Gln Val Tyr Arg Lys Phe Phe Glu Phe Gly Asp
```

```
145                 150                 155                 160
Ile Gln Ala Thr Ser Val Ser Asp Glu Phe Asp Ser Tyr Gly Leu Ser
                165                 170                 175
Asn Thr Ala Thr Ile Pro Trp Phe
            180

<210> SEQ ID NO 32
<211> LENGTH: 184
<212> TYPE: PRT
<213> ORGANISM: Legionella pneumophila

<400> SEQUENCE: 32

Met Asp His Tyr Leu Asp Ile Ser Ile Leu Pro Asp Ser Glu Phe Thr
1               5                   10                  15

Thr Pro Val Leu Met Asn Ala Ile Tyr Thr Asn Leu His Lys Ala Leu
            20                  25                  30

His Thr Leu Ala Ser Thr Asn Ile Gly Val Ser Phe Pro Lys Tyr Ser
        35                  40                  45

Ser Thr Leu Gly Asn Leu Leu Arg Ile His Gly Lys Lys Glu Ala Leu
    50                  55                  60

Gln Glu Leu Gln Asn Leu Asn Trp Ile Gly Gly Met Ile Gly Tyr Cys
65                  70                  75                  80

Glu Ala Ser Leu Ile Lys Thr Val Pro Ala Asp Thr Lys Phe Arg Thr
                85                  90                  95

Val Ser Arg Lys Gln Pro Thr Met Ser Gln Ser Lys Leu Arg Arg Leu
            100                 105                 110

Ile Lys Arg Asn Ser Leu Thr Glu Asp Glu Ile Arg Gln Tyr Lys Ala
        115                 120                 125

Lys Met Phe Ser Lys Gly Leu Asp Asn Pro Tyr Ile Glu Leu Val Ser
    130                 135                 140

Val Ser Asn Gly Gln Arg His Arg Arg Tyr Ile Glu Phe Gly Glu Leu
145                 150                 155                 160

Phe Asn Glu Pro Ile Pro Gly Leu Phe Asp Gln Phe Gly Leu Ser Asn
                165                 170                 175

Ser Ala Thr Val Pro Trp Phe Asp
            180

<210> SEQ ID NO 33
<211> LENGTH: 184
<212> TYPE: PRT
<213> ORGANISM: Legionella pneumophila

<400> SEQUENCE: 33

Met Asp His Tyr Leu Glu Ile Ser Ile Leu Pro Asp Ser Glu Phe Thr
1               5                   10                  15

Thr Pro Val Leu Met Asn Ala Ile Tyr Thr Asn Leu His Lys Ala Leu
            20                  25                  30

His Thr Leu Ala Ser Thr Ser Ile Gly Val Ser Phe Pro Lys Tyr Ser
        35                  40                  45

Ser Thr Leu Gly Asn Ile Leu Arg Ile His Gly Lys Lys Glu Val Leu
    50                  55                  60

Gln Asp Leu Gln Asn Leu Asn Trp Ile Gly Gly Met Ile Gly Tyr Cys
65                  70                  75                  80

Glu Ala Ser Leu Ile Lys Thr Val Pro Ala Asp Thr Lys Phe Arg Thr
                85                  90                  95

Val Ser Arg Lys Gln Pro Thr Met Ser Gln Ser Lys Leu Arg Arg Leu
```

```
            100                 105                 110
Ile Lys Arg Asn Thr Leu Thr Glu Asp Glu Ile Arg Gln Tyr Lys Ala
            115                 120                 125

Lys Met Phe Ser Lys Gly Leu Asp Asn Pro Tyr Ile Glu Leu Val Ser
            130                 135                 140

Val Ser Asn Gly Gln Arg His Arg Arg Tyr Ile Glu Phe Gly Glu Leu
145                 150                 155                 160

Phe Asn Glu Pro Ser Pro Gly Leu Phe Asp Gln Phe Gly Leu Ser Asn
                    165                 170                 175

Ser Ala Thr Val Pro Trp Phe Asp
            180

<210> SEQ ID NO 34
<211> LENGTH: 183
<212> TYPE: PRT
<213> ORGANISM: Shewanella putrefaciens

<400> SEQUENCE: 34

Met Asn Ser Tyr Ile Asp Ile Arg Leu Lys Pro Asp Ala Glu Met Arg
1               5                   10                  15

Glu Ala Glu Leu Ser Ser Lys Val Phe Thr Lys Phe His Lys Ala Leu
            20                  25                  30

Val Thr Leu Asn Ser His Lys Ile Gly Ile Ser Phe Pro Gln Met Lys
        35                  40                  45

Leu Ser Leu Gly Gln Leu Phe Arg Ile His Gly Asp Ala Ser Leu Leu
    50                  55                  60

His Asp Leu Gln Gly Leu Asp Trp Leu Gly Pro Leu Ala Gly Tyr Cys
65                  70                  75                  80

Gln Val Thr Ala Val Ser Ala Val Pro Asp His Val Gln Tyr Arg Ile
                85                  90                  95

Val Ser Val Lys Arg Ser Asn Leu Ser Lys Ala Lys Leu Lys Arg Leu
            100                 105                 110

Ile Ala Arg Gly Ser Ile Asp Lys Asp Gly Glu Lys Arg Tyr Lys Val
        115                 120                 125

Lys Met Leu Gly Gln Gly Phe Asp Asn Pro Tyr Leu Asp Leu Phe Ser
    130                 135                 140

Ser Ser Thr Gly Gln Val Tyr Arg Lys Phe Phe Glu Phe Ser Asp Ile
145                 150                 155                 160

Gln Ala His Pro Leu Asp Gly Glu Phe Asp Ser Tyr Gly Leu Ser Lys
                165                 170                 175

Thr Ala Thr Val Pro Trp Phe
            180

<210> SEQ ID NO 35
<211> LENGTH: 184
<212> TYPE: PRT
<213> ORGANISM: Legionella pneumophila

<400> SEQUENCE: 35

Met Asp Tyr Tyr Val Asp Ile Leu Ile Lys Pro Asp Ser Glu Lys Ser
1               5                   10                  15

Leu Asn Phe Leu Leu Ser Thr Leu Tyr Thr Lys Leu His Lys Val Leu
            20                  25                  30

His Asp Met Ala Ser Thr Asn Ile Gly Val Ser Phe Pro Lys Tyr Asn
        35                  40                  45

Ile Thr Leu Gly Asn Ile Leu Arg Ile His Ser Lys Lys Val Val Leu
```

```
            50                  55                  60
Asp Glu Leu Leu Gly Met Asn Phe Leu Ser Gly Ile Asn Asn Tyr Tyr
 65                  70                  75                  80

Glu Val Ser Pro Ile Lys Ser Val Pro Ala Asp Ser Lys Phe Arg Ile
                 85                  90                  95

Ile Ser Arg Lys Gln Thr Thr Met Ser Gln Ser Lys Met Arg Arg Leu
                100                 105                 110

Phe Lys Arg Gly Ser Met Thr Val Gly Asp Ile Arg Gln Tyr Lys Ala
                115                 120                 125

Lys Met Phe Ala Lys Ser Ile Asp Asn Pro Tyr Leu Glu Leu Val Ser
130                 135                 140

Gly Ser Asn Gly Tyr Arg Tyr Arg Arg Tyr Ile Glu Phe Gly Glu Leu
145                 150                 155                 160

Leu Asp Gln Pro Val Tyr Gly Glu Phe Asp Arg Phe Gly Leu Ser Lys
                165                 170                 175

Thr Ala Thr Val Pro Trp Phe Asp
                180
```

<210> SEQ ID NO 36
<211> LENGTH: 183
<212> TYPE: PRT
<213> ORGANISM: Vibrio metschnikovii

<400> SEQUENCE: 36

```
Met Asp Ser Tyr Ile Glu Ile Arg Leu Gln Pro Asp Ala Glu Met Pro
 1               5                  10                  15

Glu Ala Glu Leu Ser Ser Lys Val Phe Thr Lys Phe His Lys Ala Leu
                20                  25                  30

Val Ile Leu His Ser Asn Gln Ile Gly Ile Ser Phe Pro Glu Val Asn
            35                  40                  45

Val Lys Leu Gly Arg Leu Phe Arg Leu His Gly Glu Ala Ser Phe Leu
        50                  55                  60

His Asp Leu Gln Gly Leu Asn Trp Leu Gly Pro Leu Ser Gly Tyr Cys
 65                  70                  75                  80

Gln Val Ser Glu Ile Leu Ala Ile Pro Glu Gln Val Gln Tyr Arg Val
                85                  90                  95

Ile Ser Val Lys Arg Ser Asn Leu Ser Gln Ala Lys Leu Arg Arg Leu
                100                 105                 110

Ile Ala Arg Gly Ser Ile Asp Lys Glu Gly Glu Lys Arg Tyr Lys Val
                115                 120                 125

Lys Met Leu Ser Gln Gly Phe Asp Asn Pro Tyr Leu Asp Leu Phe Ser
130                 135                 140

Ser Ser Thr Lys Gln Val His Arg Lys Phe Phe Glu Phe Gly Glu Ile
145                 150                 155                 160

Gln Pro Leu Pro Val Ser Gly Lys Phe Asp Ser Tyr Gly Leu Ser His
                165                 170                 175

Thr Thr Thr Val Pro Trp Phe
                180
```

<210> SEQ ID NO 37
<211> LENGTH: 102
<212> TYPE: PRT
<213> ORGANISM: Citrobacter koseri

<400> SEQUENCE: 37

```
Met Ala Ile Thr Pro Val Pro Ala Val Lys Gly Trp Arg Thr Val Ser
```

```
1               5                   10                  15
Arg Val Gln Val Lys Ser Ser Pro Gln Arg Leu Leu Arg Arg Ser Val
                20                  25                  30

Arg Lys Gly Trp Leu Thr Glu Glu Gln Ala Gln Leu Arg Leu Val Glu
            35                  40                  45

Ser Thr Glu Gln His Ser Asp Leu Pro Tyr Leu Asn Val Lys Ser Leu
50                  55                  60

Ser Asn Gln Gln Gln Phe Arg Val Phe Ile Arg His Ser Glu Leu Arg
65                  70                  75                  80

Ser Glu Pro Val Ser Gly Thr Phe Thr Ser Tyr Gly Leu Ser Ser Thr
                85                  90                  95

Ala Thr Ile Pro Trp Phe
                100
```

<210> SEQ ID NO 38
<211> LENGTH: 183
<212> TYPE: PRT
<213> ORGANISM: Unknown
<220> FEATURE:
<223> OTHER INFORMATION: Vibrio sp. RC586

<400> SEQUENCE: 38

```
Met Asp Ala Tyr Ile Asp Ile Arg Leu Met Pro Asp Ala Glu Met Arg
1               5                   10                  15

Glu Ala Glu Leu Ser Ser Lys Val Phe Ile Lys Phe His Lys Ala Leu
                20                  25                  30

Val Lys Leu Arg Ser Asn Lys Ile Gly Ile Ser Phe Pro Glu Ala Asn
            35                  40                  45

Ile Lys Leu Gly Arg Leu Phe Arg Leu His Gly Glu Met Ser Ala Leu
50                  55                  60

His Asp Leu Gln Gly Leu Asn Trp Leu Gly Pro Leu Ala Gly Tyr Cys
65                  70                  75                  80

Lys Ile Thr Thr Val Thr His Val Pro Asp Gln Val Gln Tyr Arg Ile
                85                  90                  95

Ile Ser Val Lys Arg Ser Asn Leu Ser Lys Ala Lys Leu Thr Arg Leu
                100                 105                 110

Ile Ala Arg Gly Ser Ile Asp Lys Asp Gly Glu Lys Arg Tyr Lys Val
            115                 120                 125

Lys Met Leu Ser Gln Gly Phe Asp Asn Pro Tyr Leu Asp Leu Ser Ser
130                 135                 140

Ser Ser Thr Gly Gln Val Tyr Arg Lys Phe Phe Glu Phe Ser Asp Ile
145                 150                 155                 160

Gln Ala Asp Pro Val Asp Gly Glu Phe Asp Ser Tyr Gly Leu Ser Lys
                165                 170                 175

Thr Ala Thr Val Pro Trp Phe
                180
```

<210> SEQ ID NO 39
<211> LENGTH: 184
<212> TYPE: PRT
<213> ORGANISM: Vibrio cholerae

<400> SEQUENCE: 39

```
Met Met Asp Ala Tyr Ile Asp Ile Arg Leu Met Pro Asp Ala Glu Met
1               5                   10                  15

Arg Glu Ala Glu Leu Ser Ser Lys Val Phe Ile Lys Phe His Lys Ala
                20                  25                  30
```

```
Leu Val Lys Leu Gln Ser Asn Lys Ile Gly Ile Ser Phe Pro Glu Ala
            35                  40                  45

Asn Ile Lys Leu Gly Arg Leu Phe Arg Leu His Gly Glu Val Ser Ala
 50                  55                  60

Leu His Asp Leu Gln Gly Leu Asn Trp Leu Gly Pro Leu Ala Gly Tyr
 65                  70                  75                  80

Cys Lys Ile Thr Thr Val Thr His Val Pro Asp Gln Val Glu Tyr Arg
                 85                  90                  95

Ile Ile Ser Val Lys Arg Ser Asn Leu Ser Lys Ala Lys Leu Ala Arg
                100                 105                 110

Leu Ile Ala Arg Gly Ser Ile Asp Lys Asp Gly Glu Lys Arg Tyr Lys
            115                 120                 125

Val Lys Met Leu Arg Gln Gly Phe Asp Asn Pro Tyr Leu Asp Leu Ser
        130                 135                 140

Ser Ser Ser Thr Gly Gln Val Tyr Arg Lys Phe Phe Glu Phe Ser Asp
145                 150                 155                 160

Ile Gln Ala Glu Pro Val Asp Gly Glu Phe Asp Ser Tyr Gly Leu Ser
                165                 170                 175

Lys Thr Ala Thr Val Pro Trp Phe
            180

<210> SEQ ID NO 40
<211> LENGTH: 197
<212> TYPE: PRT
<213> ORGANISM: Oxalobacter formigenes

<400> SEQUENCE: 40

Met Lys His Tyr Ile Glu Ile Thr Leu Thr Gly Ser Pro Asp Phe Pro
 1               5                  10                  15

Leu Tyr His Leu Trp Ser Lys Leu Tyr Thr Gln Leu His Leu Ala Leu
                20                  25                  30

Val Glu Asn Arg Asp Ala Ser Asp Gln Val Asn Ile Gly Val Ser Phe
            35                  40                  45

Pro Glu Tyr Tyr Phe Asn Glu Glu Lys Gly Met Gly Phe Leu Gly Thr
 50                  55                  60

Lys Leu Arg Leu Phe Ala Glu Asp Glu Thr Ser Leu Gln Lys Ile Asp
 65                  70                  75                  80

Ile Gln Lys Trp Phe Val Arg Leu Asn Asp Cys Ile His Ile Thr Pro
                85                  90                  95

Val Cys Arg Val Pro Leu Asn Gly Ile Thr Gly Tyr Ala Thr Phe Ser
                100                 105                 110

Arg Lys His Ile Lys Ser Asn Ala Glu Arg Leu Ala Arg Arg Gln Met
            115                 120                 125

Lys Arg His Lys Asp Leu Ser Phe His Glu Thr Val Gln Arg Tyr Gln
        130                 135                 140

Lys Asn Leu Ala Lys Ser Pro Leu Pro Phe Ile Gln Leu Glu Ser Leu
145                 150                 155                 160

Thr Asn Ser His Pro Phe Lys Leu Phe Ile Glu Lys Lys Pro Ala Ile
                165                 170                 175

Asn Ala Ser Leu Lys Val Phe Thr Thr Tyr Gly Leu Ser Ala Glu Ser
                180                 185                 190

Thr Ile Pro Glu Phe
            195
```

```
<210> SEQ ID NO 41
<211> LENGTH: 193
<212> TYPE: PRT
<213> ORGANISM: Psychromonas ingrahamii

<400> SEQUENCE: 41

Met Lys Tyr Tyr Leu Asp Ile Thr Leu Leu Pro Asp Ile Glu Ile Pro
1               5                   10                  15

Leu Gly Phe Ile Trp Gln Lys Val Phe Gln Gln Val His Ile Ala Leu
            20                  25                  30

Ala Asp Asn Lys Val Gly Glu Asn Glu Ser Asp Ile Ala Leu Ser Leu
        35                  40                  45

Pro Asn Tyr Gly Asp Lys Ala Phe Pro Leu Gly Asn Lys Leu Arg Leu
    50                  55                  60

Phe Ser Val Ser Glu Gln Ala Leu Glu Arg Leu Ala Ile Thr Lys Trp
65                  70                  75                  80

Leu Lys Arg Phe Thr Asp His Thr His Ile Thr Ser Val Lys Ala Val
                85                  90                  95

Pro Glu Ser Ala Asn Glu Tyr Ala Cys Phe Thr Arg Lys Gln Phe Asn
            100                 105                 110

Thr Asn Ile Ser Arg Leu Ala Arg Arg Ala Lys Arg His Met Glu
        115                 120                 125

Thr Phe Glu Lys Ala Leu Gln Tyr Tyr Asp Asn Phe Ala Glu Glu Gln
    130                 135                 140

Thr Lys Leu Pro Phe Met Asn Ile Lys Ser Leu Thr Asn Asn Ala Gln
145                 150                 155                 160

Phe Arg Ile Phe Ile Glu Arg Ser Ile Thr Lys Ile Pro Lys Gln Gly
                165                 170                 175

Thr Phe Asn Cys Tyr Gly Leu Ser Gln Ala Ile Ala Thr Val Pro Trp
            180                 185                 190

Phe

<210> SEQ ID NO 42
<211> LENGTH: 202
<212> TYPE: PRT
<213> ORGANISM: Dichelobacter nodosus

<400> SEQUENCE: 42

Met Asn Phe Tyr Gln Glu Ile Thr Leu Leu Pro Asp Ala Glu Val Ser
1               5                   10                  15

Leu Tyr Phe Leu Trp Ser Lys Val Tyr Gly Gln Leu His Ile Ala Leu
            20                  25                  30

Ala Asp Val Arg Asn Arg Tyr Gly Ile Asp Thr Ile Gly Val Asn Phe
        35                  40                  45

Pro His Tyr Val Tyr Glu Glu Gln Asn His Lys Val Val Ala Ala Arg
    50                  55                  60

Leu Gly Asp Gln Leu Arg Ile Phe Ala Leu Ala Glu Asn Asp Leu Glu
65                  70                  75                  80

Lys Leu Gln Ile Asn Gln Trp Leu Glu Arg Leu Ser Asp Tyr Val His
                85                  90                  95

Ile Lys Arg Ile Ser Lys Ile Glu Pro Asn Lys Val Thr Gly Tyr Val
            100                 105                 110

Val Val Lys Arg Tyr Arg Tyr Pro Ser Leu Asp Lys Val Ala Leu Arg
        115                 120                 125

Phe Ala Gln Phe Arg Lys Ile Asn Phe Glu Glu Ala Arg Lys His Cys
    130                 135                 140
```

Thr Lys Tyr Lys His Gln Ala Lys Asn Tyr Pro Phe Ile Met Leu Lys
145                 150                 155                 160

Ser Gln Ser Asn Gln Glu Tyr Tyr Lys Leu Ser Ile Arg Gln Glu Asn
            165                 170                 175

Ala Gln Glu Ser Val Ser Gly Arg Phe Asn Val Tyr Gly Ile Asn Ser
        180                 185                 190

Ala Thr Gly Ile Val Thr Val Pro Asn Trp
        195                 200

<210> SEQ ID NO 43
<211> LENGTH: 194
<212> TYPE: PRT
<213> ORGANISM: Shewanella baltica

<400> SEQUENCE: 43

Met Asn His Tyr Leu Asp Ile Thr Leu Leu Pro Asn Glu Glu Val Gly
1               5                   10                  15

His Tyr Phe Leu Trp Glu Lys Leu Tyr His Gln Val His Leu Ala Leu
            20                  25                  30

Val Glu His Lys Asn Arg Val Gly Gln Phe Glu Ile Ala Ala Ala Phe
        35                  40                  45

Pro Gln Phe Asn Glu Met Asp Asn Ser Leu Gly Ser Lys Leu Arg Leu
    50                  55                  60

Leu Ala Thr Gln Pro Gln His Leu Glu Asp Leu Lys Val Ser Asn Trp
65                  70                  75                  80

Leu Arg His Phe Thr Asp Tyr Leu His Ile Ser Ser Ile Arg Pro Val
                85                  90                  95

Pro Glu Lys Ile Glu Val Tyr Val Ala Tyr Ser Arg Pro Ala Ile Arg
            100                 105                 110

Ala Asn Lys Ala Arg Glu Ile Ala Arg Arg Met Lys Arg His Asn Glu
        115                 120                 125

Thr Leu Glu Gln Ala Thr Ala His Phe Glu Gly Phe Lys Pro Lys Lys
    130                 135                 140

Thr Lys Ala Pro Phe Val Tyr Met Gln Ser Tyr Thr Lys Asp Ser Arg
145                 150                 155                 160

Phe Pro Leu Phe Ile Gln Gln Thr His Ser Ala Val Val Lys Glu Gly
                165                 170                 175

Ser Val Ser Phe Asp Ser Tyr Gly Leu Ser Ser Arg Gly Tyr Leu Pro
            180                 185                 190

Lys Phe

<210> SEQ ID NO 44
<211> LENGTH: 194
<212> TYPE: PRT
<213> ORGANISM: Shewanella baltica

<400> SEQUENCE: 44

Met Asn His Tyr Leu Asp Ile Thr Leu Leu Pro Asn Glu Glu Val Gly
1               5                   10                  15

His Tyr Phe Leu Trp Glu Lys Leu Tyr His Gln Met His Leu Ala Leu
            20                  25                  30

Val Glu His Lys Asn Arg Val Gly Gln Phe Glu Ile Ala Ala Ala Phe
        35                  40                  45

Pro Gln Phe Asn Glu Met Asp Asn Asn Leu Gly Ser Lys Leu Arg Leu
    50                  55                  60

Leu Ala Thr Gln Pro Gln His Leu Glu Asp Leu Lys Val Ser Asn Trp
65                  70                  75                  80

Leu Arg His Phe Thr Asp Tyr Leu His Ile Ser Ser Ile Arg Pro Val
            85                  90                  95

Pro Asp Lys Ile Glu Val Tyr Val Ala Tyr Ser Arg Pro Ala Ile Arg
        100                 105                 110

Ala Asn Lys Ala Arg Glu Ile Ala Arg Arg Met Lys Arg His Asn Glu
    115                 120                 125

Thr Leu Val Gln Ala Thr Ala His Phe Glu Gly Phe Lys Pro Lys Lys
130                 135                 140

Thr Lys Ala Pro Phe Val Tyr Met Gln Ser Tyr Thr Lys Asp Ser Arg
145                 150                 155                 160

Phe Pro Leu Phe Ile Gln Gln Thr His Ser Ala Val Val Lys Glu Gly
                165                 170                 175

Asn Val Ser Phe Asp Ser Tyr Gly Leu Ser Ser Arg Gly Tyr Leu Pro
            180                 185                 190

Lys Phe

<210> SEQ ID NO 45
<211> LENGTH: 204
<212> TYPE: PRT
<213> ORGANISM: Acinetobacter baumannii

<400> SEQUENCE: 45

Met Met Asn Trp Tyr Gln Glu Ile Thr Leu Ile Asp Gln Asp Glu Ile
1               5                   10                  15

Ser Leu Tyr Phe Ile Trp Ser Lys Val Tyr Thr Gln Leu His Ile Ala
            20                  25                  30

Phe Ala Glu His Ser Asn Glu Gln Gly Arg Ile Ser Phe Gly Val Ser
        35                  40                  45

Phe Pro Gln Tyr Arg Ile Asn Glu Gln Lys Lys Ile Gly Phe Leu Gly
    50                  55                  60

Thr Lys Ile Arg Val Phe Ala Ser Ser Glu Asn Asp Leu Gln Gln Leu
65                  70                  75                  80

Asn Leu Gly Lys Trp Leu Glu Arg Phe Ile Asp Tyr Val His Ile Thr
                85                  90                  95

Gln Pro Arg Glu Val Pro Arg Ala Lys Ile Thr Gly Tyr Ala His Tyr
            100                 105                 110

Tyr Arg Val Asn His Arg Met Ser Val Glu Glu Arg Ile Val His Gln
        115                 120                 125

Ala Gln Arg Arg Asn Ile Ser Leu Asp Gln Ala Arg Gln His Phe Lys
    130                 135                 140

Gln Tyr Val Glu Gln Pro Val Val Glu Pro Tyr Val Ser Leu Lys Ser
145                 150                 155                 160

Leu Ser Ala Lys Arg Glu Glu Asn Val Asp Arg Pro Tyr Arg Leu Tyr
                165                 170                 175

Ile Gly Lys Ser Leu Val Asp Glu Ala Arg Asp Gly Met Phe Gly Thr
            180                 185                 190

Tyr Gly Leu Ser Arg Met Thr Thr Val Pro Glu Phe
        195                 200

<210> SEQ ID NO 46
<211> LENGTH: 203
<212> TYPE: PRT
<213> ORGANISM: Acinetobacter baumannii

<400> SEQUENCE: 46

```
Met Asn Trp Tyr Gln Glu Ile Thr Leu Ile Asp Gln Asp Glu Ile Ser
1               5                   10                  15

Leu Tyr Phe Ile Trp Ser Lys Val Tyr Thr Gln Leu His Ile Ala Phe
            20                  25                  30

Ala Glu His Ser Asn Glu Gln Gly Arg Ile Ser Phe Gly Val Ser Phe
        35                  40                  45

Pro Gln Tyr Arg Ile Asn Glu Gln Lys Lys Ile Gly Phe Leu Gly Thr
    50                  55                  60

Lys Ile Arg Val Phe Ala Ser Ser Glu Asn Asp Leu Gln Gln Leu Asn
65                  70                  75                  80

Leu Gly Lys Trp Leu Glu Arg Phe Ile Asp Tyr Val His Ile Thr Gln
                85                  90                  95

Pro Arg Glu Val Pro Arg Ala Lys Ile Thr Gly Tyr Ala His Tyr Tyr
            100                 105                 110

Arg Val Asn His Arg Met Ser Val Glu Glu Arg Ile Val His Gln Ala
        115                 120                 125

Gln Arg Arg Asn Ile Ser Leu Asp Gln Ala Arg Gln His Phe Lys Gln
    130                 135                 140

Tyr Val Glu Gln Pro Val Val Glu Pro Tyr Val Ser Leu Lys Ser Leu
145                 150                 155                 160

Ser Ala Lys Arg Glu Glu Asn Val Asp Arg Pro Tyr Arg Leu Tyr Ile
                165                 170                 175

Gly Lys Ser Leu Val Asp Glu Ala Arg Asp Gly Met Phe Gly Thr Tyr
            180                 185                 190

Gly Leu Ser Arg Met Thr Thr Val Pro Glu Phe
        195                 200
```

<210> SEQ ID NO 47
<211> LENGTH: 186
<212> TYPE: PRT
<213> ORGANISM: Pasteurella multocida

<400> SEQUENCE: 47

```
Met Thr Thr His Tyr Ile Glu Leu Lys Ala Ile Pro Gln Met Asp Met
1               5                   10                  15

Leu Gln Ser Glu Val Ile Gly His Cys Met Gln Ile Leu His Gln Phe
            20                  25                  30

Leu Pro His Phe Glu Gly Arg Val Gly Val Ala Phe Pro Ala Tyr Gly
        35                  40                  45

Leu Gly Arg Thr Leu Gly Gly Ile Val Arg Leu Phe Ala Asn Gln Glu
    50                  55                  60

Asp Cys Asn Gln Leu His Gln Gln Leu Leu Arg Ser Gly Leu Ser Asp
65                  70                  75                  80

Tyr Ala Leu Ile Ser Glu Val Ser Lys Thr Pro Leu Pro Thr Glu His
                85                  90                  95

Arg Ser Tyr Ser Arg Val His Arg Lys Gly Gln Ser Ala Ile Arg Arg
            100                 105                 110

Thr Glu Lys Arg Leu Lys Ser Gln Gly Arg Trp Asp Glu Ser Ile Arg
        115                 120                 125

Ala Asp Met Gln Gln Arg Gln Gln Asn Val Ala Phe Phe Pro His Cys
    130                 135                 140

His Leu Lys Ser Ala Ser Thr Gly Gln Arg Phe Ile Leu Ala Val Lys
145                 150                 155                 160
```

Glu Asn Arg Met Pro Gln Ser Cys Val Gly Val Phe Asn Ala Tyr Gly
              165                 170                 175

Leu Ser Asn Ser Ala Thr Val Pro His Phe
            180                 185

<210> SEQ ID NO 48
<211> LENGTH: 187
<212> TYPE: PRT
<213> ORGANISM: Aggregatibacter actinomycetemcomitans

<400> SEQUENCE: 48

Met Thr Val Gln Thr His Tyr Ile Glu Ile Lys Ala Ile Pro Gln Val
1               5                   10                  15

Asp Met Leu Gln Thr Glu Val Ile Gly Phe Cys Leu Gln Lys Leu His
            20                  25                  30

Gln Ile Leu Pro His Phe Glu Gly Arg Ile Gly Leu Ala Phe Pro Ala
        35                  40                  45

Tyr Gly Asn Asp Lys Thr Leu Gly Gly Ile Ile Arg Leu Phe Gly Thr
    50                  55                  60

Glu Asn Asp Cys Gly Phe Ile His Phe Lys Leu Gln Ser Leu Arg Asp
65                  70                  75                  80

Tyr Ala Leu Ile Ser Glu Val Met Pro Ile Pro Glu Lys Val Arg Ser
                85                  90                  95

Tyr Arg Ile Tyr Gln Arg Ile Gln Pro Lys Gly Gln Ser Ser Ile Arg
            100                 105                 110

Arg Ala Glu Lys Arg Leu Thr Ala Gln Gly Lys Trp Asn Glu Glu Val
        115                 120                 125

Leu Gln Asn Met Leu Gln Lys Gln Ala Thr Gln Arg Ile Tyr Pro His
    130                 135                 140

Ala His Leu Lys Ser Ser Ser Thr Lys Gln Gln Phe Ile Leu Ala Ile
145                 150                 155                 160

Lys Ser Val His Gln Thr Lys Ala Val Glu Gly Val Phe Ser Ala Tyr
                165                 170                 175

Gly Leu Ser Gln Thr Thr Thr Val Pro His Phe
            180                 185

<210> SEQ ID NO 49
<211> LENGTH: 199
<212> TYPE: PRT
<213> ORGANISM: Unknown
<220> FEATURE:
<223> OTHER INFORMATION: Marinomonas sp. MWYL1

<400> SEQUENCE: 49

Met Lys His Tyr Ile Asp Ile Thr Leu Leu Pro Ser Asp Asp Ile Gly
1               5                   10                  15

Val His Phe Leu Trp Ser Lys Leu Met Met Gln Val His Leu Ala Leu
            20                  25                  30

Val Glu Ile Gln Asn Glu Gln Lys Gln Val Pro Val Ala Val Ser Phe
        35                  40                  45

Pro Lys Tyr Gln Pro Arg Glu Asn Glu Lys Leu Gly Phe Val Gly Asn
    50                  55                  60

Lys Leu Arg Leu Phe Ala Asn Asp Lys Thr Asp Leu Glu Arg Leu Asn
65                  70                  75                  80

Phe Gly Lys Trp Leu His Arg Leu Glu Asp Tyr Val His Ile Lys Ser
                85                  90                  95

Ile Ala Asp Val Pro Asn Asp Val Ile Ser Tyr Glu Ser Phe Asn Arg

Arg Ser Lys Ser Gly Ser Pro Asp Lys His Ile Lys Arg Arg Met Gln
            100                 105                 110

Arg His Asn Glu Thr Trp Glu Gln Ala Ala Ala Phe Phe Lys Gly Tyr
        115                 120                 125

Ser Met Glu Lys Ala Asp Lys Asp Leu Pro Phe Ile Arg Met Lys Ser
145                 150                 155                 160

Leu His Ser Asp Asn Glu Phe Cys Met Ser Ile Ile Arg Lys Glu Ala
                165                 170                 175

Ala Pro Ser Asn Lys His Ile Met Phe Asn Thr Tyr Gly Leu Ser Ala
            180                 185                 190

Glu Gly Val Leu Pro Lys Phe
        195

<210> SEQ ID NO 50
<211> LENGTH: 190
<212> TYPE: PRT
<213> ORGANISM: Dialister invisus

<400> SEQUENCE: 50

Met Glu Tyr Tyr Gln Glu Ile Thr Leu Leu Pro Cys Ala Glu Val Ser
1               5                   10                  15

Leu Ala Phe Leu Trp Thr Lys Val Phe Thr Gln Leu His Ile Ala Phe
            20                  25                  30

Ala Asp Glu Lys Asn Lys Ser Gly His Asn Leu Tyr Ala Val Ser Phe
        35                  40                  45

Pro Glu Tyr Arg Glu Thr Gly Leu Gly Lys Ile Arg Val Phe Ala
    50                  55                  60

Glu Ala Gln Glu Leu Glu Arg Leu Asn Leu Ser Lys Val Leu Gly Arg
65                  70                  75                  80

Leu Leu Asp Tyr Val His Cys Thr Ser Ile Arg Lys Val Pro Glu Arg
                85                  90                  95

Lys Leu Arg Gly Tyr Ala Val Tyr Ser Arg Tyr Gln Pro Glu Gly Ser
            100                 105                 110

Ile Trp Val Lys Ala Arg Arg Tyr Ala Lys Arg His Pro Gly Val Thr
        115                 120                 125

Ile Glu Glu Ala Ala Arg Leu Leu Gln Gly Lys Arg Lys Ser Val Arg
130                 135                 140

Leu Pro Tyr Ile Gln Met Lys Ser Leu Ser Arg Gly Gly Thr Phe Ser
145                 150                 155                 160

Leu Phe Ile Lys Lys Arg Val Glu Lys Glu Ser Ala Leu Thr Glu Cys
                165                 170                 175

Gly Thr Tyr Gly Leu Ser Asn Asn Arg Thr Val Pro Glu Phe
            180                 185                 190

<210> SEQ ID NO 51
<211> LENGTH: 189
<212> TYPE: PRT
<213> ORGANISM: Actinobacillus pleuropneumoniae

<400> SEQUENCE: 51

Met Ser Glu Leu Thr His Tyr Ile Glu Leu Lys Ala Ile Pro Gln Val
1               5                   10                  15

Asp Ile Leu Gln Thr Asp Val Ile Ala His Gly Leu Gln Ile Leu His
            20                  25                  30

Lys Phe Leu Pro Leu Tyr Gln Gly Glu Ile Gly Leu Ser Phe Pro Ala

```
                35                  40                  45
Tyr Gly Leu Gly Arg Thr Leu Gly Gly Ile Ile Arg Val Phe Gly Asn
 50                  55                  60

Glu Gln His Cys Thr Gln Ile Lys Thr Gln Leu Ile Gly Glu Gly Leu
65                  70                  75                  80

Gln Asp Tyr Val Leu Ile Thr Ser Val Thr Pro Val Pro Glu Glu Ile
                85                  90                  95

Val Glu Tyr His Arg Tyr Gln Arg Val His Arg Lys Gly Gln Ser Ala
                100                 105                 110

Ile Arg Arg Thr Glu Gln Phe Leu Val Gln Gln Gly Lys Trp Thr Glu
                115                 120                 125

Glu Ile Arg Gln Glu Met Leu Ile His Gln Gln Asn Gln Lys Val Phe
            130                 135                 140

Pro Tyr Val Lys Leu Lys Ser Gly Ser Thr Lys Gln His Phe Val Leu
145                 150                 155                 160

Ala Ile Arg Gln Leu Arg Leu Ala Glu Pro Ala Ser Gly Leu Phe Asn
                165                 170                 175

Ala Tyr Gly Leu Ser Gln Ala Ala Thr Val Pro His Phe
            180                 185

<210> SEQ ID NO 52
<211> LENGTH: 189
<212> TYPE: PRT
<213> ORGANISM: Actinobacillus pleuropneumoniae

<400> SEQUENCE: 52

Met Ser Glu Leu Thr His Tyr Ile Glu Leu Lys Ala Ile Pro Gln Val
1               5                   10                  15

Asp Ile Leu Gln Thr Asp Val Ile Ala His Gly Leu Gln Ile Leu His
                20                  25                  30

Lys Phe Leu Pro Leu Tyr Gln Gly Glu Ile Gly Leu Ser Phe Pro Ala
            35                  40                  45

Tyr Gly Leu Gly Arg Thr Leu Gly Gly Ile Ile Arg Val Phe Gly Asn
 50                  55                  60

Glu Gln His Cys Thr Gln Ile Lys Thr Gln Leu Ile Gly Glu Gly Leu
65                  70                  75                  80

Gln Asp Tyr Val Leu Ile Thr Ser Val Thr Pro Val Pro Glu Glu Ile
                85                  90                  95

Val Glu Tyr His Arg Tyr Gln Arg Val His Arg Lys Gly Gln Ser Ala
                100                 105                 110

Ile Arg Arg Thr Glu Gln Phe Leu Val Gln Gln Gly Lys Trp Thr Glu
                115                 120                 125

Glu Ile Arg Gln Glu Met Leu Ile His Gln Gln Asn Gln Lys Val Phe
            130                 135                 140

Pro Tyr Val Lys Leu Lys Ser Gly Ser Thr Lys Gln His Phe Val Leu
145                 150                 155                 160

Ala Ile Arg Gln Leu Arg Leu Ala Glu Pro Val Ser Gly Leu Phe Asn
                165                 170                 175

Ala Tyr Gly Leu Ser Lys Ile Ala Thr Val Pro His Phe
            180                 185

<210> SEQ ID NO 53
<211> LENGTH: 189
<212> TYPE: PRT
<213> ORGANISM: Actinobacillus pleuropneumoniae
```

-continued

<400> SEQUENCE: 53

Met Ser Glu Leu Thr His Tyr Ile Glu Leu Lys Ala Ile Pro Gln Val
1               5                   10                  15

Asp Ile Leu Gln Thr Asp Val Ile Ala His Gly Leu Gln Ile Leu His
            20                  25                  30

Lys Phe Leu Pro Leu Tyr Gln Gly Glu Ile Gly Leu Ser Phe Pro Ala
        35                  40                  45

Tyr Gly Leu Gly Arg Thr Leu Gly Gly Ile Ile Arg Val Phe Gly Asn
    50                  55                  60

Glu Gln His Cys Thr Gln Ile Lys Thr Gln Leu Ile Gly Glu Gly Leu
65                  70                  75                  80

Gln Asp Tyr Val Leu Ile Thr Ser Val Thr Pro Val Pro Glu Glu Ile
                85                  90                  95

Val Glu Tyr His Arg Tyr Gln Arg Val His Arg Lys Gly Gln Ser Ala
            100                 105                 110

Ile Arg Arg Thr Glu Gln Phe Leu Val Gln Gln Gly Lys Trp Thr Glu
        115                 120                 125

Glu Ile Arg Gln Glu Met Leu Ile His Gln Gln Asn Gln Lys Val Phe
    130                 135                 140

Pro His Val Lys Leu Lys Ser Gly Ser Thr Lys Gln His Phe Val Leu
145                 150                 155                 160

Ala Ile Arg Gln Leu Arg Leu Ala Glu Pro Ser Phe Gly Leu Phe Asn
                165                 170                 175

Thr Tyr Gly Leu Ser Lys Ile Ala Thr Val Pro His Phe
            180                 185

<210> SEQ ID NO 54
<211> LENGTH: 189
<212> TYPE: PRT
<213> ORGANISM: Actinobacillus pleuropneumoniae

<400> SEQUENCE: 54

Met Ser Glu Leu Thr His Tyr Ile Glu Leu Lys Ala Ile Pro Gln Val
1               5                   10                  15

Asp Ile Leu Gln Thr Asp Val Ile Ala His Gly Leu Gln Ile Leu His
            20                  25                  30

Lys Phe Leu Pro Leu Tyr Gln Gly Glu Ile Gly Leu Ser Phe Pro Ala
        35                  40                  45

Tyr Gly Leu Gly Arg Thr Leu Gly Gly Ile Ile Arg Val Leu Gly Asn
    50                  55                  60

Glu Gln His Cys Thr Gln Ile Lys Thr Gln Leu Ile Gly Glu Gly Leu
65                  70                  75                  80

Gln Asp Tyr Val Leu Ile Thr Ser Val Thr Pro Val Pro Glu Glu Ile
                85                  90                  95

Val Glu Tyr His Arg Tyr Gln Arg Val His Arg Lys Gly Gln Ser Ala
            100                 105                 110

Ile Arg Arg Thr Glu Gln Phe Leu Val Gln Gln Gly Lys Trp Thr Glu
        115                 120                 125

Glu Ile Arg Gln Glu Met Leu Ile His Gln Gln Asn Gln Lys Val Phe
    130                 135                 140

Pro His Val Lys Leu Lys Ser Gly Ser Thr Lys Gln His Phe Val Leu
145                 150                 155                 160

Ala Ile Arg Gln Leu Arg Leu Ala Glu Pro Ser Phe Gly Leu Phe Asn
                165                 170                 175

Thr Tyr Gly Leu Ser Lys Ile Ala Thr Val Pro His Phe
          180                 185

<210> SEQ ID NO 55
<211> LENGTH: 201
<212> TYPE: PRT
<213> ORGANISM: Streptococcus thermophilus

<400> SEQUENCE: 55

Met Ser Lys Thr Met Ile Ile Gly Leu Thr Gly Gly Ile Ala Ser Gly
1               5                   10                  15

Lys Ser Thr Val Val Glu Ile Ile Lys Asp Ala Gly Tyr Lys Val Ile
            20                  25                  30

Asp Ala Asp Gln Leu Val His Asp Met Gln Val Lys Gly Gly Arg Leu
        35                  40                  45

Tyr Gln Ala Leu Leu Asp Trp Leu Gly Asp Gly Ile Leu Leu Pro Asn
    50                  55                  60

Gly Glu Leu Asn Arg Pro Lys Leu Gly Gln Leu Ile Phe Ser Ser Glu
65                  70                  75                  80

Glu Met Arg Tyr Gln Ser Ala Glu Ile Gln Gly Lys Ile Ile Arg Glu
                85                  90                  95

Glu Leu Ala Ala Lys Arg Asp Cys Leu Ala Lys Glu Glu Asp Val Phe
            100                 105                 110

Phe Met Asp Ile Pro Leu Leu Phe Glu Asn Asp Tyr Gln Asp Trp Phe
        115                 120                 125

Asp Gln Ile Trp Leu Val Ala Val Ser Pro Gln Val Gln Gly Gln Arg
    130                 135                 140

Leu Met Lys Arg Asn His Leu Ser Ala Glu Glu Ala Gly Met Arg Ile
145                 150                 155                 160

Ala Ser Gln Met Pro Leu Ala Glu Lys Leu Pro Tyr Ala Ser Leu Val
                165                 170                 175

Ile Asp Asn Asn Gly Asn Ile Asp Asp Leu Lys Lys Lys Val Lys Gly
            180                 185                 190

Ala Ile Lys Asp Leu Ala Asn Leu Val
        195                 200

<210> SEQ ID NO 56
<211> LENGTH: 28
<212> TYPE: RNA
<213> ORGANISM: Pseudomonas aeruginosa

<400> SEQUENCE: 56
guucacugcc guauaggcag cuaagaaa                                              28

<210> SEQ ID NO 57
<211> LENGTH: 28
<212> TYPE: RNA
<213> ORGANISM: Pseudomonas aeruginosa

<400> SEQUENCE: 57
guucacugcc guguaggcag cuaagaaa                                              28

<210> SEQ ID NO 58
<211> LENGTH: 28
<212> TYPE: RNA
<213> ORGANISM: Pseudomonas aeruginosa

<400> SEQUENCE: 58
guucacugcc guauaggcag cuaagaaa                                              28

-continued

```
<210> SEQ ID NO 59
<211> LENGTH: 28
<212> TYPE: RNA
<213> ORGANISM: Pseudomonas aeruginosa

<400> SEQUENCE: 59
guucacugcc guguaggcag cuaagaaa                                            28

<210> SEQ ID NO 60
<211> LENGTH: 28
<212> TYPE: RNA
<213> ORGANISM: Pseudomonas aeruginosa

<400> SEQUENCE: 60
guucacugcc guauaggcag cuaagaaa                                            28

<210> SEQ ID NO 61
<211> LENGTH: 28
<212> TYPE: RNA
<213> ORGANISM: Pseudomonas aeruginosa

<400> SEQUENCE: 61
guucacugcc guguaggcag cuaagaaa                                            28

<210> SEQ ID NO 62
<211> LENGTH: 28
<212> TYPE: RNA
<213> ORGANISM: Pseudomonas aeruginosa

<400> SEQUENCE: 62
guucacugcc guauaggcag cuaagaaa                                            28

<210> SEQ ID NO 63
<211> LENGTH: 28
<212> TYPE: RNA
<213> ORGANISM: Dickeya dadantii

<400> SEQUENCE: 63
guucacugcc gcguaggcag cuuagaaa                                            28

<210> SEQ ID NO 64
<211> LENGTH: 28
<212> TYPE: RNA
<213> ORGANISM: Dickeya dadantii

<400> SEQUENCE: 64
guucacugcc gaguaggcag cuuagaaa                                            28

<210> SEQ ID NO 65
<211> LENGTH: 28
<212> TYPE: RNA
<213> ORGANISM: Pectobacterium wasabiae

<400> SEQUENCE: 65
guucacugcc guauaggcag cuuagaaa                                            28

<210> SEQ ID NO 66
<211> LENGTH: 29
<212> TYPE: RNA
<213> ORGANISM: Photorhabdus asymbiotica

<400> SEQUENCE: 66
```

-continued guucacuguc guacaggcag cuuagaaaa                                      29

<210> SEQ ID NO 67
<211> LENGTH: 28
<212> TYPE: RNA
<213> ORGANISM: Photorhabdus asymbiotica

<400> SEQUENCE: 67
gugcacugcc guacaggcag cuuagaaa                                       28

<210> SEQ ID NO 68
<211> LENGTH: 24
<212> TYPE: RNA
<213> ORGANISM: Photorhabdus asymbiotica

<400> SEQUENCE: 68
acugccguac aggcaguuua gaaa                                           24

<210> SEQ ID NO 69
<211> LENGTH: 28
<212> TYPE: RNA
<213> ORGANISM: Photorhabdus asymbiotica

<400> SEQUENCE: 69
guucacugcc gcacaggcag cuuagaaa                                       28

<210> SEQ ID NO 70
<211> LENGTH: 28
<212> TYPE: RNA
<213> ORGANISM: Photorhabdus asymbiotica

<400> SEQUENCE: 70
guguacugcc guacaggcag cuuagaaa                                       28

<210> SEQ ID NO 71
<211> LENGTH: 28
<212> TYPE: RNA
<213> ORGANISM: Photorhabdus asymbiotica

<400> SEQUENCE: 71
guucacugcc guacaggcag cuuagaaa                                       28

<210> SEQ ID NO 72
<211> LENGTH: 28
<212> TYPE: RNA
<213> ORGANISM: Dickeya dadantii

<400> SEQUENCE: 72
guucacugcc guguaggcag cuuagaaa                                       28

<210> SEQ ID NO 73
<211> LENGTH: 28
<212> TYPE: RNA
<213> ORGANISM: Dickeya dadantii

<400> SEQUENCE: 73
guucacugcc gaguaggcag cuuagaaa                                       28

<210> SEQ ID NO 74
<211> LENGTH: 28
<212> TYPE: RNA
<213> ORGANISM: Xanthomonas albilineans

<400> SEQUENCE: 74

-continued guucacugcc guguaggcag cucagaaa    28

<210> SEQ ID NO 75
<211> LENGTH: 27
<212> TYPE: RNA
<213> ORGANISM: Xanthomonas albilineans

<400> SEQUENCE: 75
uucacugccg uguaggcagc ucagaaa    27

<210> SEQ ID NO 76
<211> LENGTH: 28
<212> TYPE: RNA
<213> ORGANISM: Xanthomonas albilineans

<400> SEQUENCE: 76
guucacugcc guauaggcag cucagaaa    28

<210> SEQ ID NO 77
<211> LENGTH: 28
<212> TYPE: RNA
<213> ORGANISM: Pectobacterium atrosepticum

<400> SEQUENCE: 77
guucacugcc guacaggcag cuuagaaa    28

<210> SEQ ID NO 78
<211> LENGTH: 28
<212> TYPE: RNA
<213> ORGANISM: Photorhabdus luminescens

<400> SEQUENCE: 78
gugcacugcc guacaggcag cuuagaaa    28

<210> SEQ ID NO 79
<211> LENGTH: 28
<212> TYPE: RNA
<213> ORGANISM: Photorhabdus luminescens

<400> SEQUENCE: 79
guucacugcc guacaggcag cuuagaaa    28

<210> SEQ ID NO 80
<211> LENGTH: 28
<212> TYPE: RNA
<213> ORGANISM: Desulfurivibrio alkaliphilus

<400> SEQUENCE: 80
guucacugcc gcacaggcag cucagaaa    28

<210> SEQ ID NO 81
<211> LENGTH: 28
<212> TYPE: RNA
<213> ORGANISM: Dickeya zeae

<400> SEQUENCE: 81
guucacugcc guguaggcag cuuagaaa    28

<210> SEQ ID NO 82
<211> LENGTH: 28
<212> TYPE: RNA
<213> ORGANISM: Dickeya zeae

<400> SEQUENCE: 82
gugcacugcc guauaggcag cuuagaaa 28

<210> SEQ ID NO 83
<211> LENGTH: 28
<212> TYPE: RNA
<213> ORGANISM: Yersinia pestis

<400> SEQUENCE: 83
guucacugcc gcacaggcag cuuagaaa 28

<210> SEQ ID NO 84
<211> LENGTH: 30
<212> TYPE: RNA
<213> ORGANISM: Yersinia pestis

<400> SEQUENCE: 84
uguucacugc cgcacaggca gcuuagaaaa 30

<210> SEQ ID NO 85
<211> LENGTH: 28
<212> TYPE: RNA
<213> ORGANISM: Dickeya dadantii

<400> SEQUENCE: 85
gugaacugcc gcauaggcag cuuagaaa 28

<210> SEQ ID NO 86
<211> LENGTH: 28
<212> TYPE: RNA
<213> ORGANISM: Dickeya dadantii

<400> SEQUENCE: 86
guucacugcc gaguaggcag cuuagaaa 28

<210> SEQ ID NO 87
<211> LENGTH: 28
<212> TYPE: RNA
<213> ORGANISM: Escherichia coli

<400> SEQUENCE: 87
guucacugcc guacaggcag cuuagaaa 28

<210> SEQ ID NO 88
<211> LENGTH: 28
<212> TYPE: RNA
<213> ORGANISM: Escherichia coli

<400> SEQUENCE: 88
guucacugcc guacaggcag cuuagaaa 28

<210> SEQ ID NO 89
<211> LENGTH: 28
<212> TYPE: RNA
<213> ORGANISM: Tolumonas auensis

<400> SEQUENCE: 89
cuucacugcc gcacaggcag cuuagaaa 28

<210> SEQ ID NO 90
<211> LENGTH: 28
<212> TYPE: RNA
<213> ORGANISM: Erwinia pyrifoliae -continued

<400> SEQUENCE: 90
guucacugcc gcacaggcag cuuagaaa                                            28

<210> SEQ ID NO 91
<211> LENGTH: 28
<212> TYPE: RNA
<213> ORGANISM: Erwinia pyrifoliae

<400> SEQUENCE: 91
uucacugccg uacaggcagc uuagaaaa                                            28

<210> SEQ ID NO 92
<211> LENGTH: 28
<212> TYPE: RNA
<213> ORGANISM: Escherichia coli

<400> SEQUENCE: 92
guucacugcc guacaggcag cuuagaaa                                            28

<210> SEQ ID NO 93
<211> LENGTH: 28
<212> TYPE: RNA
<213> ORGANISM: Verminephrobacter eiseniae

<400> SEQUENCE: 93
guucacugcc ggauaggcag cucagaaa                                            28

<210> SEQ ID NO 94
<211> LENGTH: 28
<212> TYPE: RNA
<213> ORGANISM: Chromobacterium violaceum

<400> SEQUENCE: 94
guucacugcc ggauaggcag cuuagaaa                                            28

<210> SEQ ID NO 95
<211> LENGTH: 28
<212> TYPE: RNA
<213> ORGANISM: Erwinia tasmaniensis

<400> SEQUENCE: 95
guucacugcc gcacaggcag cuuagaaa                                            28

<210> SEQ ID NO 96
<211> LENGTH: 28
<212> TYPE: RNA
<213> ORGANISM: Erwinia tasmaniensis

<400> SEQUENCE: 96
guucacugcc guacaggcag cuuagaag                                            28

<210> SEQ ID NO 97
<211> LENGTH: 28
<212> TYPE: RNA
<213> ORGANISM: Delftia acidovorans

<400> SEQUENCE: 97
guucgcugcc gcguaggcag cucagaaa                                            28

<210> SEQ ID NO 98
<211> LENGTH: 28
<212> TYPE: RNA

```
<213> ORGANISM: Unknown
<220> FEATURE:
<223> OTHER INFORMATION: Enterobacter sp. 638

<400> SEQUENCE: 98
guucacugcc guacaggcag cuuagaaa                                            28

<210> SEQ ID NO 99
<211> LENGTH: 28
<212> TYPE: RNA
<213> ORGANISM: Thioalkalivibrio sp. K90mix

<400> SEQUENCE: 99
guuagcugcc gcacaggcag cucagaaa                                            28

<210> SEQ ID NO 100
<211> LENGTH: 28
<212> TYPE: RNA
<213> ORGANISM: Zymomonas mobilis

<400> SEQUENCE: 100
guucacugcc gcacaggcag cuuagaaa                                            28

<210> SEQ ID NO 101
<211> LENGTH: 28
<212> TYPE: RNA
<213> ORGANISM: Zymomonas mobilis

<400> SEQUENCE: 101
guucacugcc gcacaggcag cuuagaaa                                            28

<210> SEQ ID NO 102
<211> LENGTH: 28
<212> TYPE: RNA
<213> ORGANISM: unknown
<220> FEATURE:
<223> OTHER INFORMATION: Acidovorax sp. JS42

<400> SEQUENCE: 102
guucacugcc gcauaggcag cucagaaa                                            28

<210> SEQ ID NO 103
<211> LENGTH: 28
<212> TYPE: RNA
<213> ORGANISM: Desulfurispirillum indicum

<400> SEQUENCE: 103
guucacugcc gcauaggcag cucagaaa                                            28

<210> SEQ ID NO 104
<211> LENGTH: 28
<212> TYPE: RNA
<213> ORGANISM: Photobacterium profundum

<400> SEQUENCE: 104
guucacugcc gcacaggcag cuuagaaa                                            28

<210> SEQ ID NO 105
<211> LENGTH: 28
<212> TYPE: RNA
<213> ORGANISM: Legionella pneumophila

<400> SEQUENCE: 105
guucacugcc guacaggcag cuuagaaa                                            28
```

<210> SEQ ID NO 106
<211> LENGTH: 28
<212> TYPE: RNA
<213> ORGANISM: Legionella pneumophila

<400> SEQUENCE: 106
guucacugcc gcacaggcag cuuagaaa 28

<210> SEQ ID NO 107
<211> LENGTH: 28
<212> TYPE: RNA
<213> ORGANISM: Legionella pneumophila

<400> SEQUENCE: 107
guucacugcc guacaggcag cuuagaaa 28

<210> SEQ ID NO 108
<211> LENGTH: 28
<212> TYPE: RNA
<213> ORGANISM: Legionella pneumophila

<400> SEQUENCE: 108
guucacugcc gcacaggcag cuuagaaa 28

<210> SEQ ID NO 109
<211> LENGTH: 28
<212> TYPE: RNA
<213> ORGANISM: Shewanella putrefaciens

<400> SEQUENCE: 109
guucaccgcc gcacaggcgg cuuagaaa 28

<210> SEQ ID NO 110
<211> LENGTH: 28
<212> TYPE: RNA
<213> ORGANISM: Legionella pneumophila

<400> SEQUENCE: 110
guuaacugcc gcacaggcag cuuagaag 28

<210> SEQ ID NO 111
<211> LENGTH: 28
<212> TYPE: RNA
<213> ORGANISM: Vibrio metschnikovii

<400> SEQUENCE: 111
guucacugcc gcacaggcag cuuagaaa 28

<210> SEQ ID NO 112
<211> LENGTH: 28
<212> TYPE: RNA
<213> ORGANISM: Vibrio metschnikovii

<400> SEQUENCE: 112
guucacugcc gcauaggcag cuuagaaa 28

<210> SEQ ID NO 113
<211> LENGTH: 29
<212> TYPE: RNA
<213> ORGANISM: Citrobacter koseri

<400> SEQUENCE: 113

-continued uguucacugc cguacaggca gcuuagaaa	29

<210> SEQ ID NO 114
<211> LENGTH: 28
<212> TYPE: RNA
<213> ORGANISM: Unknown
<220> FEATURE:
<223> OTHER INFORMATION: Vibrio sp. RC586

<400> SEQUENCE: 114
guucacugcc gcacaggcag cuuagaaa	28

<210> SEQ ID NO 115
<211> LENGTH: 28
<212> TYPE: RNA
<213> ORGANISM: Unknown
<220> FEATURE:
<223> OTHER INFORMATION: Vibrio sp. RC586

<400> SEQUENCE: 115
aguguucugc cgaauaggca gcuaagaa	28

<210> SEQ ID NO 116
<211> LENGTH: 29
<212> TYPE: RNA
<213> ORGANISM: Vibrio cholerae

<400> SEQUENCE: 116
guucacugcc gcacaggcag cuuagaaau	29

<210> SEQ ID NO 117
<211> LENGTH: 28
<212> TYPE: RNA
<213> ORGANISM: Oxalobacter formigenes

<400> SEQUENCE: 117
guucacugcc guauaggcag cuuagaag	28

<210> SEQ ID NO 118
<211> LENGTH: 29
<212> TYPE: RNA
<213> ORGANISM: Psychromonas ingrahamii

<400> SEQUENCE: 118 guguucccg ugcccacggg gaugaaccg	29

<210> SEQ ID NO 119
<211> LENGTH: 28
<212> TYPE: RNA
<213> ORGANISM: Dichelobacter nodosus

<400> SEQUENCE: 119
guucaccgcc gcacaggcgg cuuagaaa	28

<210> SEQ ID NO 120
<211> LENGTH: 28
<212> TYPE: RNA
<213> ORGANISM: Shewanella baltica

<400> SEQUENCE: 120
guucaccgcc gcacaggcgg cuuagaaa	28

<210> SEQ ID NO 121
<211> LENGTH: 28

<212> TYPE: RNA
<213> ORGANISM: Shewanella baltica

<400> SEQUENCE: 121
guucaccgcc gcacaggcgg cuuagaaa					28

<210> SEQ ID NO 122
<211> LENGTH: 28
<212> TYPE: RNA
<213> ORGANISM: Acinetobacter baumannii

<400> SEQUENCE: 122
guucauggcg gcauacgcca uuuagaaa					28

<210> SEQ ID NO 123
<211> LENGTH: 28
<212> TYPE: RNA
<213> ORGANISM: Acinetobacter baumannii

<400> SEQUENCE: 123
guucauggcg gcauacgcca uuuagaaa					28

<210> SEQ ID NO 124
<211> LENGTH: 28
<212> TYPE: RNA
<213> ORGANISM: Pasteurella multocida

<400> SEQUENCE: 124
guucaccauc guguagaugg cuuagaaa					28

<210> SEQ ID NO 125
<211> LENGTH: 28
<212> TYPE: RNA
<213> ORGANISM: Pasteurella multocida

<400> SEQUENCE: 125
guuaacugcc guauaggcag cuuagaaa					28

<210> SEQ ID NO 126
<211> LENGTH: 28
<212> TYPE: RNA
<213> ORGANISM: Aggregatibacter actinomycetemcomitans

<400> SEQUENCE: 126
cuucacugcc gaauaggcag cuuagaaa					28

<210> SEQ ID NO 127
<211> LENGTH: 28
<212> TYPE: RNA
<213> ORGANISM: Unknown
<220> FEATURE:
<223> OTHER INFORMATION: Marinomonas sp. MWYL1

<400> SEQUENCE: 127
guucgccgcc gagcacgcgg cuuagaaa					28

<210> SEQ ID NO 128
<211> LENGTH: 28
<212> TYPE: RNA
<213> ORGANISM: Dialister invisus

<400> SEQUENCE: 128
guuaacugcc gcauaggu ag uuuagaaa					28

```
<210> SEQ ID NO 129
<211> LENGTH: 28
<212> TYPE: RNA
<213> ORGANISM: Dialister invisus

<400> SEQUENCE: 129
guuaucugcc guauaggcag cuuagaaa                                              28

<210> SEQ ID NO 130
<211> LENGTH: 28
<212> TYPE: RNA
<213> ORGANISM: Actinobacillus pleuropneumoniae

<400> SEQUENCE: 130
cuucacugcc guauaggcag cuuagaaa                                              28

<210> SEQ ID NO 131
<211> LENGTH: 28
<212> TYPE: RNA
<213> ORGANISM: Actinobacillus pleuropneumoniae

<400> SEQUENCE: 131
cuucacugcc guauaggcag cuuagaaa                                              28

<210> SEQ ID NO 132
<211> LENGTH: 187
<212> TYPE: PRT
<213> ORGANISM: Artificial sequence
<220> FEATURE:
<223> OTHER INFORMATION: Synthetic amino acid sequence

<400> SEQUENCE: 132
```

Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu Ala Gln Ala Leu
            20                  25                  30

Val Ala Gln Gly Gly Asp Arg Ile Gly Val Ser Phe Pro Asp Leu Asp
        35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Val Lys Ser Asn Pro Glu Arg Leu
            100                 105                 110

Arg Arg Arg Leu Met Arg Arg His Asp Leu Ser Glu Glu Glu Ala Arg
        115                 120                 125

Lys Arg Ile Pro Asp Thr Val Ala Arg Ala Leu Asp Leu Pro Phe Val
    130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Gly Phe Thr Cys Tyr
                165                 170                 175

Gly Leu Ser Lys Gly Gly Phe Val Pro Trp Phe
            180                 185

```
<210> SEQ ID NO 133
<211> LENGTH: 187
```

```
<212> TYPE: PRT
<213> ORGANISM: Artificial sequence
<220> FEATURE:
<223> OTHER INFORMATION: Synthetic amino acid sequence

<400> SEQUENCE: 133

Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu Ala Gln Ala Leu
            20                  25                  30

Val Ala Gln Gly Gly Asp Arg Ile Gly Val Ser Phe Pro Asp Leu Asp
        35                  40                  45

Glu Cys Arg Ser Arg Leu Gly Glu Arg Leu Arg Ile His Ala Ser Ala
50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Val Lys Ser Asn Pro Glu Arg Leu
            100                 105                 110

Arg Arg Arg Leu Met Arg Arg His Asp Leu Ser Glu Glu Glu Ala Arg
        115                 120                 125

Lys Arg Ile Pro Asp Thr Val Ala Arg Ala Leu Asp Leu Pro Phe Val
130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Gly Phe Thr Cys Tyr
                165                 170                 175

Gly Leu Ser Lys Gly Gly Phe Val Pro Trp Phe
            180                 185

<210> SEQ ID NO 134
<211> LENGTH: 199
<212> TYPE: PRT
<213> ORGANISM: Escherichia coli

<400> SEQUENCE: 134

Met Tyr Leu Ser Lys Val Ile Ile Ala Arg Ala Trp Ser Arg Asp Leu
1               5                   10                  15

Tyr Gln Leu His Gln Gly Leu Trp His Leu Phe Pro Asn Arg Pro Asp
            20                  25                  30

Ala Ala Arg Asp Phe Leu Phe His Val Glu Lys Arg Asn Thr Pro Glu
        35                  40                  45

Gly Cys His Val Leu Leu Gln Ser Ala Gln Met Pro Val Ser Thr Ala
50                  55                  60

Val Ala Thr Val Ile Lys Thr Lys Gln Val Glu Phe Gln Leu Gln Val
65                  70                  75                  80

Gly Val Pro Leu Tyr Phe Arg Leu Arg Ala Asn Pro Ile Lys Thr Ile
                85                  90                  95

Leu Asp Asn Gln Lys Arg Leu Asp Ser Lys Gly Asn Ile Lys Arg Cys
            100                 105                 110

Arg Val Pro Leu Ile Lys Glu Ala Glu Gln Ile Ala Trp Leu Gln Arg
        115                 120                 125

Lys Leu Gly Asn Ala Ala Arg Val Glu Asp Val His Pro Ile Ser Glu
130                 135                 140

Arg Pro Gln Tyr Phe Ser Gly Asp Gly Lys Ser Gly Lys Ile Gln Thr
```

-continued

```
            145                 150                 155                 160
Val Cys Phe Glu Gly Val Leu Thr Ile Asn Asp Ala Pro Ala Leu Ile
                165                 170                 175
Asp Leu Val Gln Gln Gly Ile Gly Pro Ala Lys Ser Met Gly Cys Gly
                180                 185                 190
Leu Leu Ser Leu Ala Pro Leu
            195

<210> SEQ ID NO 135
<211> LENGTH: 199
<212> TYPE: PRT
<213> ORGANISM: Shigella dysenteriae

<400> SEQUENCE: 135

Met Tyr Leu Ser Lys Val Ile Ile Ala Arg Ala Trp Ser Arg Asp Leu
1               5                   10                  15
Tyr Gln Leu His Gln Gly Leu Trp His Leu Phe Pro Asn Arg Pro Asp
                20                  25                  30
Ala Ala Arg Asp Phe Leu Phe His Val Glu Lys Arg Asn Thr Pro Glu
            35                  40                  45
Gly Cys His Val Leu Leu Gln Ser Ala Gln Met Pro Val Ser Thr Ala
        50                  55                  60
Val Ala Thr Val Ile Lys Thr Lys Gln Val Glu Phe Gln Leu Gln Val
65                  70                  75                  80
Gly Val Pro Leu Tyr Phe Arg Leu Arg Ala Asn Pro Ile Lys Thr Ile
                85                  90                  95
Leu Asp Asn Gln Lys Arg Leu Asp Ser Lys Gly Asn Ile Lys Arg Cys
                100                 105                 110
Arg Val Pro Leu Ile Lys Glu Ala Glu Gln Ile Ala Trp Leu Gln Arg
            115                 120                 125
Lys Leu Gly Asn Ala Ala Arg Val Glu Asp Val His Pro Ile Ser Glu
        130                 135                 140
Arg Pro Gln Tyr Phe Ser Gly Glu Gly Lys Asn Gly Lys Ile Gln Thr
145                 150                 155                 160
Val Cys Phe Glu Gly Val Leu Thr Ile Asn Asp Ala Pro Ala Leu Ile
                165                 170                 175
Asp Leu Leu Gln Gln Gly Ile Gly Pro Ala Lys Ser Met Gly Cys Gly
                180                 185                 190
Leu Leu Ser Leu Ala Pro Leu
            195

<210> SEQ ID NO 136
<211> LENGTH: 199
<212> TYPE: PRT
<213> ORGANISM: Escherichia coli

<400> SEQUENCE: 136

Met Tyr Leu Ser Lys Ile Ile Ile Ala Arg Ala Trp Ser Arg Asp Leu
1               5                   10                  15
Tyr Gln Leu His Gln Glu Leu Trp His Leu Phe Pro Asn Arg Pro Asp
                20                  25                  30
Ala Ala Arg Asp Phe Leu Phe His Val Glu Lys Arg Asn Thr Pro Glu
            35                  40                  45
Gly Cys His Val Leu Leu Gln Ser Ala Gln Met Pro Val Ser Thr Ala
        50                  55                  60
Val Ala Thr Val Ile Lys Thr Lys Gln Val Glu Phe Gln Leu Gln Val
```

-continued

```
                65                  70                  75                  80
Gly Val Pro Leu Tyr Phe Arg Leu Arg Ala Asn Pro Ile Lys Thr Ile
                    85                  90                  95

Leu Asp Asn Gln Lys Arg Leu Asp Ser Lys Gly Asn Ile Lys Arg Cys
                100                 105                 110

Arg Val Pro Leu Ile Lys Glu Ala Glu Gln Ile Ala Trp Leu Gln Arg
                115                 120                 125

Lys Leu Gly Asn Ala Ala Arg Val Glu Asp Val His Pro Ile Ser Glu
            130                 135                 140

Arg Pro Gln Tyr Phe Ser Gly Glu Gly Lys Asn Gly Lys Ile Gln Thr
145                 150                 155                 160

Val Cys Phe Glu Gly Val Leu Thr Ile Asn Asp Ala Pro Ala Leu Ile
                    165                 170                 175

Asp Leu Leu Gln Gln Gly Ile Gly Pro Ala Lys Ser Met Gly Cys Gly
                180                 185                 190

Leu Leu Ser Leu Ala Pro Leu
            195

<210> SEQ ID NO 137
<211> LENGTH: 200
<212> TYPE: PRT
<213> ORGANISM: Erwinia amylovora

<400> SEQUENCE: 137

Met Ile Tyr Leu Ser Gln Ile Ala Val Pro Trp Ser Trp Ala Lys Asp
1               5                   10                  15

Pro Tyr Gln Leu His Arg Ala Leu Trp Gln Leu Phe Pro Asp Arg Pro
                20                  25                  30

Ser Asp Arg Arg Asp Phe Leu Phe Arg Val Glu Thr Arg His Ala Arg
            35                  40                  45

Ala Gly Gln Val Val Leu Leu Gln Ser Leu Gln Ala Pro Gln Asn Cys
        50                  55                  60

Ala Ala Ala Gln Val Leu Ala Ser Lys Val Thr Gln Phe Ala Leu Ser
65                  70                  75                  80

Pro Gly Gln Arg Leu His Phe Arg Leu Arg Ala Asn Pro Val Lys Asn
                    85                  90                  95

Ile Lys Asp Asn Arg Gly Arg Val Asn Ser Arg Gly Glu Val Lys Ser
                100                 105                 110

Cys Arg Val Pro Leu Ile Asp Asp Asn Gln Leu Met Gln Trp Leu Val
                115                 120                 125

Arg Lys Leu Gln Asp Ala Ala Val Leu His Ser Ala Ser Val Ser Lys
            130                 135                 140

Glu Pro Ala Leu Cys Phe Asn Lys Gln Ala Val Ala Gly Lys Ile Gln
145                 150                 155                 160

Pro Val Cys Phe Glu Gly Ile Leu Gln Val Thr Ser Glu Thr His Phe
                    165                 170                 175

Tyr Gln Cys Leu Val Asn Gly Ile Gly Pro Ala Lys Ser Met Gly Cys
                180                 185                 190

Gly Met Leu Ser Ile Ala Arg Ala
            195                 200

<210> SEQ ID NO 138
<211> LENGTH: 202
<212> TYPE: PRT
<213> ORGANISM: Geobacter sulfurreducens
```

```
<400> SEQUENCE: 138

Met Tyr Leu Ser Lys Val Leu Ile Asn Gly Thr Ala Cys Arg Asn Pro
1               5                   10                  15

Tyr Glu Ile His Arg Val Leu Trp Lys Leu Phe Pro Glu Asp Ala Asp
            20                  25                  30

Ala Glu Arg Asp Phe Leu Phe Arg Val Glu Arg Ser Gly Gln Gln Ser
        35                  40                  45

Val Glu Val Leu Leu Gln Ser Arg Arg Glu Pro Thr Met Ala Ala Ser
50                  55                  60

Arg Glu Val Leu Leu Met Gly Ser Lys Pro Tyr Leu Leu Ser Leu Gln
65                  70                  75                  80

Gln Asp Gln Gln Leu Arg Phe Met Leu Val Ala Asn Pro Ile Lys Thr
                85                  90                  95

Ile Asn Asp Glu Ser Ala Arg Leu Asn Ser Ala Asn Glu Ile Lys Lys
            100                 105                 110

Cys Arg Val Pro Leu Ile Arg Glu Glu Asp Leu Arg Ala Trp Leu Lys
        115                 120                 125

Arg Lys Leu Glu Gly Val Ala Val Ile Glu Ala Val Glu Val Glu Lys
130                 135                 140

Arg Pro Ala Met Asn Phe Arg Lys Ala Arg Glu Lys Arg Val Gly Lys
145                 150                 155                 160

Val Gln Ala Val Ser Phe His Gly Val Leu Ser Val Thr Asp Pro Val
                165                 170                 175

Gly Leu Ile Ser Leu Ile Asn Thr Gly Ile Gly Pro Ala Lys Ala Phe
            180                 185                 190

Gly Cys Gly Leu Leu Ser Leu Ala Arg Thr
        195                 200

<210> SEQ ID NO 139
<211> LENGTH: 216
<212> TYPE: PRT
<213> ORGANISM: Salmonella enterica

<400> SEQUENCE: 139

Met Tyr Leu Ser Arg Ile Thr Leu His Thr Ser Glu Leu Ser Pro Ala
1               5                   10                  15

Gln Leu Leu His Leu Val Glu Arg Gly Glu Tyr Val Met His Gln Trp
            20                  25                  30

Leu Trp Asp Leu Phe Pro Gly Gly Lys Glu Arg Gln Phe Leu Tyr Arg
        35                  40                  45

Arg Glu Glu Leu Gln Gly Ala Phe Arg Phe Val Leu Ser Gln Glu
50                  55                  60

Gln Pro Ala Ala Ser Thr Ile Phe Asp Val Gln Thr Arg Pro Phe Ala
65                  70                  75                  80

Pro Met Leu Ser Ala Gly Gln Thr Leu Arg Phe Asn Leu Arg Ala Asn
                85                  90                  95

Pro Thr Ile Cys Lys Asn Gly Lys Arg His Asp Leu Leu Met Glu Ala
            100                 105                 110

Lys Arg Gln Arg Lys Thr Gln Gly Asp Ser Gln Asp Ile Trp Ser Tyr
        115                 120                 125

Gln Gln Gln Ala Ala Leu Glu Trp Leu Ala Arg Gly Glu Gln Asn
130                 135                 140

Gly Phe Thr Leu Arg Glu Ala Ser Val Asp Ala Tyr Arg Gln Gln Gln
145                 150                 155                 160
```

Ile Arg Arg Glu Lys Ser Arg Gln Met Ile Gln Phe Ser Ser Val Asp
              165                 170                 175

Tyr Thr Gly Val Leu Val Ile Asn Glu Pro Ala Leu Phe Leu Gln Arg
          180                 185                 190

Leu Ala Gln Gly Tyr Gly Lys Ser Arg Ala Phe Gly Cys Gly Met Met
          195                 200                 205

Met Ile Lys Pro Gly Asp Asp Ala
      210                 215

<210> SEQ ID NO 140
<211> LENGTH: 264
<212> TYPE: PRT
<213> ORGANISM: Pyrococcus furiosus

<400> SEQUENCE: 140

Met Arg Phe Leu Ile Arg Leu Val Pro Glu Asp Lys Asp Arg Ala Phe
1               5                   10                  15

Lys Val Pro Tyr Asn His Gln Tyr Tyr Leu Gln Gly Leu Ile Tyr Asn
            20                  25                  30

Ala Ile Lys Ser Ser Asn Pro Lys Leu Ala Thr Tyr Leu His Glu Val
        35                  40                  45

Lys Gly Pro Lys Leu Phe Thr Tyr Ser Leu Phe Met Ala Glu Lys Arg
    50                  55                  60

Glu His Pro Lys Gly Leu Pro Tyr Phe Leu Gly Tyr Lys Lys Gly Phe
65                  70                  75                  80

Phe Tyr Phe Ser Thr Cys Val Pro Glu Ile Ala Glu Ala Leu Val Asn
                85                  90                  95

Gly Leu Leu Met Asn Pro Glu Val Arg Leu Trp Asp Glu Arg Phe Tyr
            100                 105                 110

Leu His Glu Ile Lys Val Leu Arg Glu Pro Lys Lys Phe Asn Gly Ser
        115                 120                 125

Thr Phe Val Thr Leu Ser Pro Ile Ala Val Thr Val Val Arg Lys Gly
    130                 135                 140

Lys Ser Tyr Asp Val Pro Pro Met Glu Lys Glu Phe Tyr Ser Ile Ile
145                 150                 155                 160

Lys Asp Asp Leu Gln Asp Lys Tyr Val Met Ala Tyr Gly Asp Lys Pro
                165                 170                 175

Pro Ser Glu Phe Glu Met Glu Val Leu Ile Ala Lys Pro Lys Arg Phe
            180                 185                 190

Arg Ile Lys Pro Gly Ile Tyr Gln Thr Ala Trp His Leu Val Phe Arg
        195                 200                 205

Ala Tyr Gly Asn Asp Asp Leu Leu Lys Val Gly Tyr Glu Val Gly Phe
    210                 215                 220

Gly Glu Lys Asn Ser Leu Gly Phe Gly Met Val Lys Val Glu Gly Asn
225                 230                 235                 240

Lys Thr Thr Lys Glu Ala Glu Glu Gln Glu Lys Ile Thr Phe Asn Ser
                245                 250                 255

Arg Glu Glu Leu Lys Thr Gly Val
            260

<210> SEQ ID NO 141
<211> LENGTH: 262
<212> TYPE: PRT
<213> ORGANISM: Pyrococcus abyssi

<400> SEQUENCE: 141

```
Met Arg Phe Leu Ile Arg Val Arg Pro Glu Arg Lys Phe Lys Val
1               5                   10                  15

Pro Tyr Asn His Gln Tyr Tyr Leu Gln Gly Leu Ile Tyr Asn Arg Ile
                20                  25                  30

Lys Met Val Asn Pro Arg Leu Ser Thr Phe Leu His Glu Thr Arg Gly
            35                  40                  45

Pro Lys Met Phe Thr Tyr Ser Leu Phe Met Thr Glu Lys Arg Lys His
    50                  55                  60

Pro Lys Gly Leu Pro Tyr Phe Leu Gly Phe Lys Arg Gly Phe Phe Tyr
65                  70                  75                  80

Phe Ser Thr Cys Ile Pro Glu Ile Ala Glu Ala Phe Ile Thr Gly Leu
                85                  90                  95

Phe Arg Glu Pro Glu Ile Val Leu Trp Gly Glu Arg Phe Tyr Leu Glu
                100                 105                 110

Glu Val Lys Thr Leu Arg Glu Pro Thr Lys Phe Ser Gly Ser Thr Phe
            115                 120                 125

Ile Thr Leu Ser Pro Val Ala Val Thr Met Val Lys Glu Gly Lys Arg
            130                 135                 140

Tyr Asp Val Ser Pro Leu Glu Glu Phe Tyr Thr Leu Ile Lys Glu
145                 150                 155                 160

Asn Leu Lys Asp Lys Tyr Val Met Ile Lys Gly Glu Lys Pro Pro Asp
                165                 170                 175

Asp Phe Glu Met Glu Val Ile Val Ala Lys Pro Lys Arg Phe Glu Val
                180                 185                 190

Lys Pro Gly Ile Tyr Gln Met Ala Trp His Leu Val Phe Lys Ala Tyr
            195                 200                 205

Gly Asp Asp Glu Leu Ile Lys Val Gly Tyr Val Val Gly Phe Gly Glu
    210                 215                 220

Lys Asn Ser Leu Gly Phe Gly Met Val Lys Val Glu Asn Asn Arg Glu
225                 230                 235                 240

Glu Lys Gly Met Gly Val Gln Glu Arg Met Leu Phe Lys Asn Glu Asp
            245                 250                 255

Gly Leu Lys Thr Gly Pro
            260

<210> SEQ ID NO 142
<211> LENGTH: 242
<212> TYPE: PRT
<213> ORGANISM: Thermococcus barophilus

<400> SEQUENCE: 142

Met Arg Phe Leu Ile Arg Leu Arg Asn Glu Asn Leu Glu Phe Lys Val
1               5                   10                  15

Pro Tyr Asn His Leu Tyr Tyr Leu Gln Gly Leu Val Tyr Arg Arg Ile
                20                  25                  30

Gln Arg Val Asn Pro Glu Leu Ser Leu Ser Leu His Arg Pro Lys Val
            35                  40                  45

Pro Lys Leu Phe Thr Phe Ser Leu Phe Met Thr Lys Glu Arg His Arg
    50                  55                  60

Met Ser Gly Asn Asn Lys Tyr Phe Ile Gly Arg Lys Leu Ala Phe Phe
65                  70                  75                  80

Tyr Phe Ser Thr Ala Val Pro Glu Ile Ala Glu Ala Phe Ile Gly Gly
            85                  90                  95

Leu Leu Gln Glu Pro Glu Val Lys Leu Trp Gly Glu Arg Phe Tyr Val
                100                 105                 110
```

```
Glu Thr Val Lys Ala Leu Pro Glu Pro Ile Ser Phe Ser Gly Lys Ile
            115                 120                 125

Tyr Ser Thr Leu Ser Pro Ile Ala Val Thr Thr Val Lys Met Gln Phe
        130                 135                 140

Gly Lys Pro Arg His Tyr Asp Leu Gly Pro Asp Glu Pro Glu Phe Tyr
145                 150                 155                 160

Glu Asn Leu Lys Glu Asn Leu Lys Gln Lys Tyr Leu Leu Ile Tyr Gly
                165                 170                 175

Lys Lys Pro Pro Glu Asp Phe Glu Ile Glu Val Leu Ser Ala Lys Pro
            180                 185                 190

Lys Arg Phe Glu Val Lys Pro Gly Ile Phe Gln Arg Ala Trp His Leu
        195                 200                 205

Ile Phe Arg Ala Tyr Gly Asp Asp Glu Leu Ile Arg Ala Gly Tyr Leu
    210                 215                 220

Ala Gly Phe Gly Glu Lys Asn Ser Leu Gly Phe Gly Met Val Lys Val
225                 230                 235                 240

Asp Glu

<210> SEQ ID NO 143
<211> LENGTH: 250
<212> TYPE: PRT
<213> ORGANISM: Methanococcus voltae

<400> SEQUENCE: 143

Met Arg Ile Ser Ile Asn Leu Lys Cys Glu Lys Asn Thr Thr Ile Pro
1               5                   10                  15

Phe Asn Tyr Gln Tyr Gln Leu Ser Thr Ala Leu Tyr Asn Cys Met Tyr
            20                  25                  30

Asp Asn Asn Lys Glu Phe Ala Glu Asn Leu His Lys Ser Lys Asp Phe
        35                  40                  45

Lys Phe Phe Thr His Ser Trp Leu Phe Met Pro Asn Ser Lys Val Gly
    50                  55                  60

Lys Asn Gly Ile Ile Cys Lys Asp Gly Asn Ala Phe Phe Lys Val Ser
65                  70                  75                  80

Ser Pro Asn Asp Glu Leu Met Thr His Leu Leu Gln Gly Leu Phe Lys
                85                  90                  95

Val Gly Tyr Met Gln Ile Asn Asn Thr Lys Leu Asp Val Val Gly Val
            100                 105                 110

Leu Asn Glu Lys Gly Tyr Asn Ser Asn Ile Lys Lys Met Lys Thr Ile
        115                 120                 125

Ser Pro Val Leu Leu Arg Thr Lys Lys Glu Arg Asn Gly Ile Asp Asn
    130                 135                 140

Thr Glu Gly Leu Lys Ile Tyr Asp Ile Leu Pro Gln Glu Asn Ser Glu
145                 150                 155                 160

Lys Phe His Glu Asn Leu Lys Asn Asn Leu Lys Arg Lys Tyr Ser Leu
                165                 170                 175

Phe Tyr Asp Lys Asp Tyr Glu Asn Cys Asp Leu Asp Phe Asp Ile Asn
            180                 185                 190

Ile Ser Glu Ala Lys Ser Lys Arg Val Lys Ile Lys Asp Ser Phe Gln
        195                 200                 205

Arg Cys Ser Asn Leu Lys Phe Glu Ile Ser Gly Asp Glu Asp Leu Ile
    210                 215                 220

Lys Phe Ala Tyr Glu Cys Gly Leu Gly Glu Leu Asn Ser Met Gly Phe
225                 230                 235                 240
```

```
Gly Met Ile Asp Lys Tyr Ser Tyr Lys Cys
            245                 250

<210> SEQ ID NO 144
<211> LENGTH: 254
<212> TYPE: PRT
<213> ORGANISM: Clostridium difficile

<400> SEQUENCE: 144

Met His Leu Val Arg Arg His Leu Ile Leu Thr Val Asp Asn Glu Val
1               5                   10                  15

Val Leu Asp Tyr Asn Tyr Gln Tyr Glu Leu Met Lys Arg Ile Tyr Glu
            20                  25                  30

Ala Ile Glu Ile Asn Asp Lys Arg Lys Ala Leu Ser Leu His Asn Glu
        35                  40                  45

Gly Tyr Lys Val Asp Lys Lys Val Phe Lys Leu Phe Asn Tyr Thr Ile
    50                  55                  60

Met Phe Glu Asn Ala Lys Tyr Leu Lys Glu Gly Ile His Leu Asn Pro
65                  70                  75                  80

Gln Thr Lys Ile Lys Leu Ile Leu Ser Gly Tyr Asp Asp Ile Leu Asn
                85                  90                  95

Asn Ile Ile Lys Gly Phe Ile Lys Cys Lys Val Phe Lys Leu Asn Asn
            100                 105                 110

Ile Glu Phe Lys Val Ser Asp Ile Glu Glu Asp Ser Lys Lys Asn Phe
        115                 120                 125

Asn Asn Ile Thr Leu Tyr Lys Val Arg Ser Pro Ile Val Ala Ser Leu
    130                 135                 140

Tyr Asp Leu Lys Ser Arg Lys Gln Val Tyr Leu Asn Pro Met Gln Glu
145                 150                 155                 160

Glu Phe Tyr Lys Ala Leu His Asp Asn Leu Gly Asn Lys Tyr Lys Leu
                165                 170                 175

Ile His Asn Lys Glu Tyr Thr Gly Glu Leu Tyr Phe Asp Ile Glu Asp
            180                 185                 190

Val Leu Ala Val Lys Lys Lys Tyr Ile Thr Asn Ile Lys Gly Lys Gly
        195                 200                 205

Phe Ile Ile Gly Tyr Thr Asp Phe Glu Ile Phe Val Gln Ala Asn Lys
    210                 215                 220

Asp Met Gln Glu Val Ile Tyr Tyr Cys Gly Leu Gly Glu Lys Asn Ser
225                 230                 235                 240

Ile Gly Met Gly Leu Leu Thr Tyr Ile Thr Ser Arg Arg Ala
                245                 250

<210> SEQ ID NO 145
<211> LENGTH: 119
<212> TYPE: PRT
<213> ORGANISM: Escherichia coli

<400> SEQUENCE: 145

Met Val Lys Leu Ala Phe Pro Arg Glu Leu Arg Leu Leu Thr Pro Ser
1               5                   10                  15

Gln Phe Thr Phe Val Phe Gln Gln Pro Gln Arg Ala Gly Thr Pro Gln
            20                  25                  30

Ile Thr Ile Leu Gly Arg Leu Asn Ser Leu Gly His Pro Arg Ile Gly
        35                  40                  45

Leu Thr Val Ala Lys Lys Asn Val Arg Arg Ala His Glu Arg Asn Arg
    50                  55                  60
```

```
Ile Lys Arg Leu Thr Arg Glu Ser Phe Arg Leu Arg Gln His Glu Leu
 65                  70                  75                  80

Pro Ala Met Asp Phe Val Val Ala Lys Gly Val Ala Asp Leu
                 85                  90                  95

Asp Asn Arg Ala Leu Ser Glu Ala Leu Glu Lys Leu Trp Arg Arg His
            100                 105                 110

Cys Arg Leu Ala Arg Gly Ser
            115

<210> SEQ ID NO 146
<211> LENGTH: 20
<212> TYPE: RNA
<213> ORGANISM: Artificial sequence
<220> FEATURE:
<223> OTHER INFORMATION: Synthetic nucleic acid sequence

<400> SEQUENCE: 146
guucacugcc guauaggcag                                              20

<210> SEQ ID NO 147
<211> LENGTH: 205
<212> TYPE: PRT
<213> ORGANISM: Unknown
<220> FEATURE:
<223> OTHER INFORMATION: Moritella sp.

<400> SEQUENCE: 147

Met Leu Asn Arg Phe Tyr Phe Tyr Ile Lys Phe Ile Pro Gln His Thr
  1               5                  10                  15

Asp Asn Ala Phe Leu Ile Gly Arg Cys Ile Lys Val Ser His Ala Phe
             20                  25                  30

Phe Ala Lys Gly Ser Ile Thr Gly Val Gly Val Ser Phe Pro Cys Trp
         35                  40                  45

Ser Glu Gln Asp Ile Gly Asn Ala Leu Ala Phe Val Ser Thr Asp Met
 50                  55                  60

Glu Ala Leu Glu Gln Leu Lys Ala Gln Pro Leu Phe Ser Val Met Ala
 65                  70                  75                  80

Asp Glu Leu Ile Phe Glu Ile Ser Asp Val Leu Ser Ile Pro Asp Lys
                 85                  90                  95

Leu Glu Glu Glu Arg Phe Thr Leu Asn Tyr Ala Ile Arg Lys Ser Phe
            100                 105                 110

Ala Gly Asp Lys Lys Arg Arg Leu Lys Arg Lys Lys Arg Ala Glu
            115                 120                 125

Ala Arg Gly Glu Thr Tyr Lys Pro Val Leu His Ile Asn Thr Glu Lys
130                 135                 140

Arg Val Phe Asn His Tyr His Thr Ile Pro Met Asn Ser Lys Glu Lys
145                 150                 155                 160

Pro Asp Gly Phe Thr Leu His Val Gln Lys Asn Pro Cys Val Glu Gln
                165                 170                 175

Tyr Ala Ala Asp Phe Leu Asp Tyr Gly Phe Ala Thr Asn Glu Gln His
            180                 185                 190

Arg Gly Thr Val Pro Lys Leu Ser Ser Ile Leu Met Lys
            195                 200                 205

<210> SEQ ID NO 148
<211> LENGTH: 192
<212> TYPE: PRT
<213> ORGANISM: Unknown
<220> FEATURE:
```

-continued

<223> OTHER INFORMATION: Moritella sp. PE36

<400> SEQUENCE: 148

Met Asp Val Phe Leu Leu Ser Gly Arg Cys Ala Lys Ala Leu His Asn
1               5                   10                  15

Phe Glu Phe Lys Lys Arg Lys His Asn Ile Gly Ile Ala Leu Pro Cys
            20                  25                  30

Trp Ser Glu Asn Ser Val Gly Asp Met Ile Ala Phe Val Ser Glu Asp
        35                  40                  45

Lys Asn Gln Leu Leu Lys Phe His Gln Asp Ser Tyr Phe Gln Met Met
    50                  55                  60

Ala Ser Asp Glu Ile Phe Ile Ser Asp Ile Thr Ala Val Asn Ser
65                  70                  75                  80

Glu Leu Pro Glu Val Gln Phe Cys Arg Asn Asn Thr Ile Ser Lys Met
                85                  90                  95

Phe Ile Lys Asp Thr Gln Lys Arg Leu Arg Arg Thr Gln Lys Arg Ala
            100                 105                 110

Glu Ala Arg Gly Asp Ala Phe Lys Pro Ala Leu His Glu Asn Ser Lys
        115                 120                 125

Lys Arg Val Phe Glu Asn Phe His Ser Leu Pro Ile Asp Ser Tyr Gly
    130                 135                 140

Thr Glu Glu Asp Phe Met Leu His Ile Gln Lys His Asn Asp Val Ala
145                 150                 155                 160

Leu Ser Asp Cys Tyr Thr Ser Tyr Gly Phe Ala Thr Asn Asn Asp Asn
                165                 170                 175

Arg Gly Thr Val Pro Asp Met Ser Ile Leu Phe Asn Gln Met Thr Lys
            180                 185                 190

<210> SEQ ID NO 149
<211> LENGTH: 223
<212> TYPE: PRT
<213> ORGANISM: Unknown
<220> FEATURE:
<223> OTHER INFORMATION: Shewanella sp.

<400> SEQUENCE: 149

Met Lys Tyr Tyr Leu Asp Ile Thr Leu Leu Pro Ala Glu Ala Asn Leu
1               5                   10                  15

Gly Phe Leu Trp His Lys Val Tyr Gln Gln Ile His Leu Met Leu Val
            20                  25                  30

Glu His Lys Val Ser Val Glu Asn Ser Ala Ile Gly Leu Ser Phe Pro
        35                  40                  45

Lys Tyr Asp Ala Lys Ser Phe Ser Asp Asn Thr Lys Phe Pro Leu Gly
    50                  55                  60

Asp Lys Leu Arg Leu Phe Ala Gly Thr Glu Gln Leu Ala Asp Leu
65                  70                  75                  80

Lys Val Ala Gln Trp Leu Ala Arg Leu Ala Asp Tyr Val His Ile Lys
                85                  90                  95

Ala Ile Lys Ala Val Pro Asp Asn Val Ser Glu Tyr Ala Tyr Phe Lys
            100                 105                 110

Arg Arg His Phe Lys Ser Pro Asp Lys Leu Arg Asn Ile Asp Ala
        115                 120                 125

Arg Ala Ile Val Ile Ala Gln Lys Asn Gly Phe Ala Ile Asn Glu Val
    130                 135                 140

Lys Thr Arg Leu Leu Ala Ser Ile Asp Asn Leu Asp Thr Lys Ser Lys
145                 150                 155                 160

```
Leu Pro Phe Ile Asn Leu Arg Ser Leu Ser Thr Glu Lys Asp Val Ser
            165                 170                 175

Pro Ala Asp Arg Arg Lys Phe Leu Leu Phe Ile Glu Cys Glu Lys Val
        180                 185                 190

Thr Lys Pro Ser Gln Asn Asn Gly Leu Phe Asn Cys Tyr Gly Leu Ser
    195                 200                 205

Arg Arg Ala Gln Thr Glu Gln Ala Ala Val Pro Trp Phe Glu Gly
210                 215                 220
```

<210> SEQ ID NO 150
<211> LENGTH: 60
<212> TYPE: DNA
<213> ORGANISM: Artificial sequence
<220> FEATURE:
<223> OTHER INFORMATION: Synthetic nucleic acid sequence

<400> SEQUENCE: 150
ttcaaaagat ctaaagagga gaaaggatct atggaccact acctcgacat tcgcttgcga    60

<210> SEQ ID NO 151
<211> LENGTH: 39
<212> TYPE: DNA
<213> ORGANISM: Artificial sequence
<220> FEATURE:
<223> OTHER INFORMATION: Synthetic nucleic acid sequence

<400> SEQUENCE: 151
tccttactcg agttatcaga accagggaac gaaacctcc    39

<210> SEQ ID NO 152
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 152
gttcactgcc gtataggcag ctaagaaa    28

<210> SEQ ID NO 153
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 153
cttcagcacg cgtcttgtag gtcccgtcat c    31

<210> SEQ ID NO 154
<211> LENGTH: 43
<212> TYPE: DNA
<213> ORGANISM: Artificial sequence
<220> FEATURE:
<223> OTHER INFORMATION: Synthetic nucleic acid sequence

<400> SEQUENCE: 154
cgtcaatgag caaaggtatt aactttactc ccttcctccc cgc    43

<210> SEQ ID NO 155
<211> LENGTH: 27
<212> TYPE: DNA
<213> ORGANISM: Artificial sequence
<220> FEATURE:

<223> OTHER INFORMATION: Synthetic nucleic acid sequence

<400> SEQUENCE: 155
gaattcatta aagaggagaa aggtacc    27

<210> SEQ ID NO 156
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 156
tttaagaagg agatatacat    20

<210> SEQ ID NO 157
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 157
attaaagagg agaaattaag c    21

<210> SEQ ID NO 158
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 158
tctagagaaa gagggacaa actagt    26

<210> SEQ ID NO 159
<211> LENGTH: 41
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (1)..(10)
<223> OTHER INFORMATION: n is a, c, g, or t

<400> SEQUENCE: 159
nnnnnnnnnn agatctatta tacctaggac tgagctagct g    41

<210> SEQ ID NO 160
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 160
ttgacagcta gctcagtcct aggtataata gatct    35

<210> SEQ ID NO 161
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 161
tttacagcta gctcagtcct aggtattata gatct    35

<210> SEQ ID NO 162
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 162
tttacggcta gctcagtcct aggtactata gatct    35

<210> SEQ ID NO 163
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 163
tttacggcta gctcagtcct aggtacaata gatct    35

<210> SEQ ID NO 164
<211> LENGTH: 102
<212> TYPE: DNA
<213> ORGANISM: Artificial sequence
<220> FEATURE:
<223> OTHER INFORMATION: Synthetic nucleic acid sequence

<400> SEQUENCE: 164
cgaggccaac ttaaagagac ttaaaagatt aatttaaaat ttatcaaaaa gagtattgac    60
ttaaagtcta acctatagga tacttacagc catcgagagg ga    102

<210> SEQ ID NO 165
<211> LENGTH: 75
<212> TYPE: DNA
<213> ORGANISM: Artificial sequence
<220> FEATURE:
<223> OTHER INFORMATION: Synthetic nucleic acid sequence

<400> SEQUENCE: 165
ataaatgtga gcggataaca ttgacattgt gagcggataa caagatactg agcacatcag    60
caggacgcac tgacc    75

<210> SEQ ID NO 166
<211> LENGTH: 84
<212> TYPE: DNA
<213> ORGANISM: Artificial sequence
<220> FEATURE:
<223> OTHER INFORMATION: Synthetic nucleic acid sequence

<400> SEQUENCE: 166
aaaatttatc aaaagagtg ttgacttgtg agcggataac aatgatactt agattcaatt    60
gtgagcggat aacaatttca caca    84

<210> SEQ ID NO 167
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 167

```
gcgaaaaatc aataaggaga caacaag                                        27
```

<210> SEQ ID NO 168
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 168

```
ggcttaaatc aataaggaga caacaag                                        27
```

<210> SEQ ID NO 169
<211> LENGTH: 115
<212> TYPE: DNA
<213> ORGANISM: Artificial sequence
<220> FEATURE:
<223> OTHER INFORMATION: Synthetic nucleic acid sequence

<400> SEQUENCE: 169

```
tcgcacatct tgttgtctga ttattgattt ttcgcgaaac catttgatca tatgacaaga    60
tgtgtatcca ccttaactta atgattttta ccaaaatcat tagggattc atcag         115
```

<210> SEQ ID NO 170
<211> LENGTH: 115
<212> TYPE: DNA
<213> ORGANISM: Artificial sequence
<220> FEATURE:
<223> OTHER INFORMATION: Synthetic nucleic acid sequence

<400> SEQUENCE: 170

```
tcgcacatct tgttgtctga ttattgattt aagccgaaac catttgatca tatgacaaga    60
tgtgtatcca ccttaactta atgattttta ccaaaatcat tagggattc atcag         115
```

<210> SEQ ID NO 171
<211> LENGTH: 287
<212> TYPE: DNA
<213> ORGANISM: Artificial sequence
<220> FEATURE:
<223> OTHER INFORMATION: Synthetic nucleic acid sequence

<400> SEQUENCE: 171

```
aacaaaataa aaggagtcg ctcacgccct gaccaaagtt tgtgaacgac atcattcaaa     60 gaaaaaaca ctgagttgtt tttataatct tgtatattta gatattaaac gatatttaaa   120
tatacataaa gatatatatt tgggtgagcg attccttaaa cgaaattgag attaaggagt   180
cgctcttttt tatgtataaa aacaatcatg caaatcattc aaatcatttg gaaaatcacg   240
atttagacaa tttttctaaa accggctact ctaatagccg gttgtaa                287
```

<210> SEQ ID NO 172
<211> LENGTH: 91
<212> TYPE: DNA
<213> ORGANISM: Artificial sequence
<220> FEATURE:
<223> OTHER INFORMATION: Synthetic nucleic acid sequence

<400> SEQUENCE: 172

```
atacaagatt ataaaaacaa ctcagtgttt ttttctttga atgatgtcgt tcacaaactt    60
tggtcagggc gtgagcgact ccttttttatt t                                  91
```

<210> SEQ ID NO 173
<211> LENGTH: 30

-continued

```
<212> TYPE: DNA
<213> ORGANISM: Artificial sequence
<220> FEATURE:
<223> OTHER INFORMATION: Synthetic nucleic acid sequence

<400> SEQUENCE: 173
agttcactgc cgtataggca gctaagaaat                                     30

<210> SEQ ID NO 174
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 174
ggatctaagg aggaaggatc t                                              21

<210> SEQ ID NO 175
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 175
ggcaagggag agccccgaag gggagcgac                                      29

<210> SEQ ID NO 176
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 176
ggcaaacccg agcccgagag gagaaac                                        27

<210> SEQ ID NO 177
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 177
ggacgaaccc accccgaaga aaagggacg agaac                                35

<210> SEQ ID NO 178
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 178
gcgcagaccc aaaaccccga gaggggacgg aaac                                34

<210> SEQ ID NO 179
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 179
```
gaaaaaccaa acccgagagg ggacggaaac					30

<210> SEQ ID NO 180
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 180
ccccagcacc cgggagggga cggaaac					27

<210> SEQ ID NO 181
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 181
gccaaaacaa acccaaggga gaaac					25

<210> SEQ ID NO 182
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 182
ggcaagggag agccccgaag gggagcgac					29

<210> SEQ ID NO 183
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 183
ggcaaacccg agcccgagag gagaaac					27

<210> SEQ ID NO 184
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 184
ggacgaaccc accccgaaga aaagggacg agaac					35

<210> SEQ ID NO 185
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 185
gcgcagaccc aaaacccccga gaggggacgg aaac					34

<210> SEQ ID NO 186
<211> LENGTH: 30
<212> TYPE: DNA
<213> ORGANISM: Artificial sequence

```
<220> FEATURE:
<223> OTHER INFORMATION: Synthetic nucleic acid sequence

<400> SEQUENCE: 186
gaaaaaccaa acccgagagg ggacggaaac                                        30

<210> SEQ ID NO 187
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 187
ccccagcacc cgggaggga cggaaac                                            27

<210> SEQ ID NO 188
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 188
gccaaaacaa acccaaggga gaaac                                             25

<210> SEQ ID NO 189
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 189 gcgccccca cgcggggcg ggagaaac                                            28

<210> SEQ ID NO 190
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 190
ccagccgccc gggcggcggg gaaac                                             25

<210> SEQ ID NO 191
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 191
gcgcaccaca gaggcgggag aaa                                               23

<210> SEQ ID NO 192
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 192
gcgcaccaaa gggcgggaga aa                                                22
```

```
<210> SEQ ID NO 193
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 193
gcgcgccccg cagggggcgcg ggagaaa                                        27
```

METHODS AND COMPOSITIONS FOR CONTROLLING GENE EXPRESSION BY RNA PROCESSING

CROSS-REFERENCE

This application is a continuation of PCT/US13/53287, filed Aug. 1, 2013, and claims the benefit of U.S. Provisional Patent Application No. 61/679,397, filed Aug. 3, 2012, which applications are incorporated herein by reference in their entirety.

STATEMENT REGARDING FEDERALLY SPONSORED RESEARCH

This invention was made with government support under Grant Nos. EEC-0540879 and MCB-0950971 awarded by the National Science Foundation, and Grant No. DE-AC02-05CH11231 awarded by the U.S. Department of Energy. The government has certain rights in the invention.

INCORPORATION BY REFERENCE OF SEQUENCE LISTING PROVIDED AS A TEXT FILE

A Sequence Listing is provided herewith as a text file, "BERK-179CON SeqList.v2_ST25.txt" created on Jun. 13, 2014 and having a size of 144 KB. The contents of the text file are incorporated by reference herein in their entirety.

INTRODUCTION

Genetic systems often behave unpredictably due to structural interactions between DNA, RNA and protein components as well as functional interactions with host factors and metabolites. Due to these complexities, the ability to program gene expression quantitatively based on the characteristics of individual components is very limited. In nature, the control of the activity of an RNA transcript is crucial to its function. For example, the transcription, translation, and degradation of an mRNA is crucial to any gene expression event, and all three processes are controlled by a combination of elements including promoters, ribosome binding sites (RBSs), and cis-regulatory signals encoded in untranslated regions (UTRs).

Methods and/or tools to facilitate the combination of various regulatory elements originating from various different sources to predictably control the activity of any desired RNA would be beneficial for numerous biotechnology applications. However, regulatory elements can unpredictably interact with each other through the formation of RNA structures and the recruitment of factors that affect global transcript accessibility and stability. Thus, the identification of appropriate combinations of regulatory elements is a difficult and time-consuming task. There is need in the field for a technology that allows the combination of multiple regulatory elements in a fashion that predictably affects RNA activity. The present disclosure addresses this need.

SUMMARY

The present disclosure provides nucleic acids encoding an RNA recognition sequence positioned proximal to an insertion site for the insertion of a sequence of interest; and host cells genetically modified with the nucleic acids. The present disclosure also provides methods of modifying the activity of a target RNA, and kits and compositions for carrying out the methods.

In one aspect, the disclosure provides for a recombinant expression vector comprising a recognition nucleotide sequence that encodes an RNA recognition sequence recognized by an RNA-cleaving enzyme, wherein the recognition nucleotide sequence is positioned proximal to an insertion site for the insertion of a sequence of interest. In some embodiments, less than about 50 nucleotides are disposed between the recognition nucleotide sequence and the insertion site. In some embodiments, the recombinant expression vector further comprises a promoter 5' of the recognition nucleotide sequence, wherein the promoter is operably linked to the recognition nucleotide sequence and to the insertion site. In some embodiments, the recognition nucleotide sequence is positioned within a coding region, proximal to a regulatory element, or proximal to a coding region. In some embodiments, the recombinant expression vector further comprises a nucleotide sequence encoding the RNA-cleaving enzyme. In some embodiments, the RNA-cleaving enzyme is selected from the group consisting of a ribozyme, an RNase III enzyme, or a CRISPR related endonuclease. In some embodiments, the RNA-cleaving enzyme is a CRISPR related endonuclease. In some embodiments, the CRISPR related endonuclease is a Csy4 endoribonuclease. In some embodiments, the Csy4 endoribonuclease comprises an amino acid sequence having at least about 75% amino acid sequence identity to any one of the amino acid sequences depicted in FIGS. 10-12 (identity to the amino acid sequence set forth in one of SEQ ID NOs: 1-55, 132-133, and 147-149). In some embodiments, the Csy4 endoribonuclease is a conditionally active variant Csy4 endoribonuclease that is enzymatically inactive in the absence of imidazole, and is enzymatically active in the presence of imidazole. In some embodiments, the RNA recognition sequence is at least about 90% identical to any one of the RNA recognition sequences listed in FIG. 10 (% identical to the RNA recognition sequence set forth in one of SEQ ID NOs: 56-131). In some embodiments, the RNA-cleaving enzyme is a ribozyme. In some embodiments, the RNA-cleaving enzyme is an RNase III.

In one aspect, the disclosure provides for a recombinant expression vector comprising a recognition nucleotide sequence that encodes an RNA recognition sequence recognized by an RNA-cleaving enzyme, wherein the recognition nucleotide sequence is positioned between a regulatory element and a coding region, between a first regulatory element and a second regulatory element, between a first coding region and a second coding region, or within a coding region.

In one aspect, the disclosure provides for a recombinant expression vector comprising a nucleotide sequence encoding a self-cleaving regulatory element, wherein the nucleotide sequence encoding a self-cleaving regulatory element is positioned proximal to an insertion site for the insertion of a sequence of interest. In some embodiments, less than about 50 nucleotides are disposed between the insertion site and the nucleotide sequence encoding a self-cleaving regulatory element. In some embodiments, the recombinant expression vector further comprises a promoter 5' of the nucleotide sequence encoding a self-cleaving regulatory element, wherein the promoter is operably linked to the insertion site and to the nucleotide sequence encoding a self-cleaving regulatory element.

In one aspect, the disclosure provides for a genetically modified cell comprising the recombinant expression vector comprising a recognition nucleotide sequence that encodes an RNA recognition sequence recognized by an RNA-cleaving enzyme, wherein the recognition nucleotide sequence is positioned proximal to an insertion site for the insertion of a sequence of interest. In some embodiments, the recombinant expression vector further comprises a second recombinant expression vector encoding the RNA-cleaving enzyme. In some embodiments, the cell is selected from a group consisting of an archaeal cell, a bacterial cell, and a eukaryotic cell. In some embodiments, the cell is a eukaryotic cell. In some embodiments, the cell is a mammalian cell. In some embodiments, the cell is selected from a group consisting of a eukaryotic single-cell organism, a somatic cell, a germ cell, and a stem cell. In some embodiments, the cell is in vitro. In some embodiments, the cell is in vivo.

In one aspect, the disclosure provides for a composition for modifying the activity of a target RNA, the composition comprising a target RNA comprising an RNA recognition sequence that is recognized by an RNA-cleaving enzyme and is positioned between a regulatory element and a coding region, between a first regulatory element and a second regulatory element, between a first coding region and a second coding region, or within a coding region, and an RNA-cleaving enzyme. In some embodiments, the RNA-cleaving enzyme is selected from the group consisting of a ribozyme, an RNase III enzyme, or a CRISPR related endonuclease. In some embodiments, the RNA-cleaving enzyme is a CRISPR related endonuclease. In some embodiments, the CRISPR related endonuclease is a Csy4 endoribonuclease. In some embodiments, the Csy4 endoribonuclease comprises an amino acid sequence having at least about 75% amino acid sequence identity to any of the amino acid sequences depicted in FIG. 10 (identity to the amino acid sequence set forth in one of SEQ ID NOs: 1-55, 132-133, and 147-149). In some embodiments, the Csy4 endoribonuclease is a conditionally active variant Csy4 endoribonuclease that is enzymatically inactive in the absence of imidazole, and is enzymatically active in the presence of imidazole. In some embodiments, the RNA recognition sequence is at least about 90% identical to any one of the RNA recognition sequences listed in FIG. 10 (% identical to the RNA recognition sequence set forth in one of SEQ ID NOs: 56-131). In some embodiments, the RNA-cleaving enzyme is a ribozyme. In some embodiments, the RNA-cleaving enzyme is an RNase III.

In one aspect, the disclosure provides for a method of modifying the activity of a target RNA, the method comprising contacting the target RNA with an RNA-cleaving enzyme, wherein the target RNA comprises an RNA recognition sequence that is recognized by the RNA-cleaving enzyme and is positioned between a regulatory element and a coding region, between a first regulatory element and a second regulatory element, between a first coding region and a second coding region, or within a coding region, and wherein the RNA-cleaving enzyme cleaves the target RNA, thereby modifying the activity of the target RNA. In some embodiments, the RNA-cleaving enzyme is selected from the group consisting of a ribozyme, an RNase III enzyme, or a CRISPR related endonuclease. In some embodiments, the RNA-cleaving enzyme is a CRISPR related endonuclease. In some embodiments, the CRISPR related endonuclease is a Csy4 endoribonuclease. In some embodiments, the Csy4 endoribonuclease comprises an amino acid sequence having at least about 75% amino acid sequence identity to any of the amino acid sequences depicted in FIG. 10 (identity to the amino acid sequence set forth in one of SEQ ID NOs: 1-55, 132-133, and 147-149). In some embodiments, the Csy4 endoribonuclease is a conditionally active variant Csy4 endoribonuclease that is enzymatically inactive in the absence of imidazole, and is enzymatically active in the presence of imidazole. In some embodiments, the RNA recognition sequence is at least about 90% identical to any one of the RNA recognition sequences listed in FIG. 10 (% identical to the RNA recognition sequence set forth in one of SEQ ID NOs: 56-131). In some embodiments, the RNA-cleaving enzyme is a ribozyme. In some embodiments, the RNA-cleaving enzyme is an RNase III.

In one aspect the disclosure provides for a method of modifying the activity of a target RNA in a cell, the method comprising introducing into the cell a target RNA, wherein the target RNA comprises an RNA recognition sequence that is recognized by an RNA-cleaving enzyme and is positioned between a regulatory element and a coding region, between a first regulatory element and a second regulatory element, between a first coding region and a second coding region, or within a coding region, and wherein the cell comprises the RNA-cleaving enzyme and the RNA-cleaving enzyme cleaves the target RNA, thereby modifying the activity of the target RNA. In some embodiments, the cell is selected from a group consisting of an archaeal cell, a bacterial cell, and a eukaryotic cell. In some embodiments, the cell is a eukaryotic cell. In some embodiments, the cell is a mammalian cell. In some embodiments, the cell is selected from a group consisting of a eukaryotic single-cell organism, a somatic cell, a germ cell, and a stem cell. In some embodiments, the cell is in vitro. In some embodiments, the cell is in vivo.

In one aspect, the disclosure provides for a method of modifying the activity of a target RNA, the method comprising inducing the expression of the target RNA, wherein the target RNA comprises a self-cleaving regulatory element that is positioned between a regulatory element and a coding region, between a first regulatory element and a second regulatory element, between a first coding region and a second coding region, or within a coding region, and wherein the self-cleaving regulatory element cleaves the target RNA, thereby modifying the activity of the target RNA.

In one aspect the disclosure provides for a kit for modifying the activity of a target RNA, the kit comprising a first recombinant expression vector comprising a recognition nucleotide sequence encoding an RNA recognition sequence that is recognized by an RNA-cleaving enzyme, wherein the recognition nucleotide sequence is positioned proximal to an insertion site for the insertion of a sequence of interest, and a second recombinant expression vector comprising a nucleotide sequence that encodes the RNA-cleaving enzyme. In some embodiments, less than about 50 nucleotides are disposed between the recognition nucleotide sequence and the insertion site. In some embodiments, the first recombinant expression vector further comprises a promoter 5' of the recognition nucleotide sequence, wherein the promoter is operably linked to the recognition nucleotide sequence and to the insertion site. In some embodiments, the RNA-cleaving enzyme is selected from the group consisting of a ribozyme, an RNase III enzyme, or a CRISPR related endonuclease. In some embodiments, the RNA-cleaving enzyme is a CRISPR related endonuclease. In some embodiments, the CRISPR related endonuclease is a Csy4 endoribonuclease. In some embodiments, the Csy4 endoribonuclease comprises an amino acid sequence having at least about 75% amino acid sequence identity to any of the amino acid sequences depicted in FIG. 10 (identity to the amino acid sequence set forth in one of SEQ ID NOs: 1-55, 132-133, and 147-149). In some embodiments, the Csy4 endoribonuclease is a conditionally active variant Csy4 endoribonuclease that is enzymatically inactive in the absence of imidazole, and is enzymatically active in the presence of imidazole. In some embodiments, the RNA recognition sequence is at least about 90% identical to any of the RNA recognition sequences listed in FIG. 10 (% identical to the RNA recognition sequence set forth in one of SEQ ID NOs: 56-131). In some embodiments, the RNA-cleaving enzyme is a ribozyme. In some embodiments, the RNA-cleaving enzyme is an RNase III.

In one aspect, the disclosure provides for a kit for modifying the activity of a target RNA, the kit comprising a recombinant expression vector comprising a recognition nucleotide sequence encoding an RNA recognition sequence that is recognized by an RNA-cleaving enzyme, wherein the recognition nucleotide sequence is positioned proximal to an insertion site for the insertion of a sequence of interest, and a nucleotide sequence encoding the RNA-cleaving enzyme, and a reagent for reconstitution and/or dilution.

In one aspect, the disclosure provides for a kit for modifying the activity of a target RNA, the kit comprising a recombinant expression vector comprising a nucleotide sequence encoding a self-cleaving regulatory element, wherein the nucleotide sequence encoding a self-cleaving regulatory element is positioned proximal to an insertion site for the insertion of a sequence of interest, and a reagent for reconstitution and/or dilution.

In one aspect, the disclosure provides for a kit for modifying the activity of a target RNA, the kit comprising a recombinant expression vector comprising a recognition nucleotide sequence encoding an RNA recognition sequence that is recognized by an RNA-cleaving enzyme, wherein the recognition nucleotide sequence is positioned proximal to an insertion site for the insertion of a sequence of interest, and a genetically modified that can produce the RNA-cleaving enzyme. In some embodiments, the kit further comprising a positive control recombinant expression vector.

BRIEF DESCRIPTION OF THE DRAWINGS

FIGS. 10A-10BC present the amino acid sequences of various Csy4 polypeptides (Seq ID NOs: 1-55), as well as the nucleotide sequences of RNAs recognized by the Csy4 polypeptides (Seq ID NOs: 56-131).

FIG. 12 depicts examples of amino acid sequences of enzymatically inactive, sequence-specific endoribonucleases (His29Ala, SEQ ID NO: 132; His29Ala/Ser50Cys, SEQ ID NO: 133).

FIGS. 13A-13F present the amino acid sequences of various CRISPR-related CasE polypeptides (SEQ ID NOs: 134-139).

FIGS. 14A-14E present the amino acid sequences of various CRISPR-related Cas6 polypeptides (SEQ ID NOs: 140-144).

FIG. 15 presents the amino acid sequence of the *E. coli* protein C5 component of RNase P (SEQ ID NO: 145).

DEFINITIONS

Figure 1:
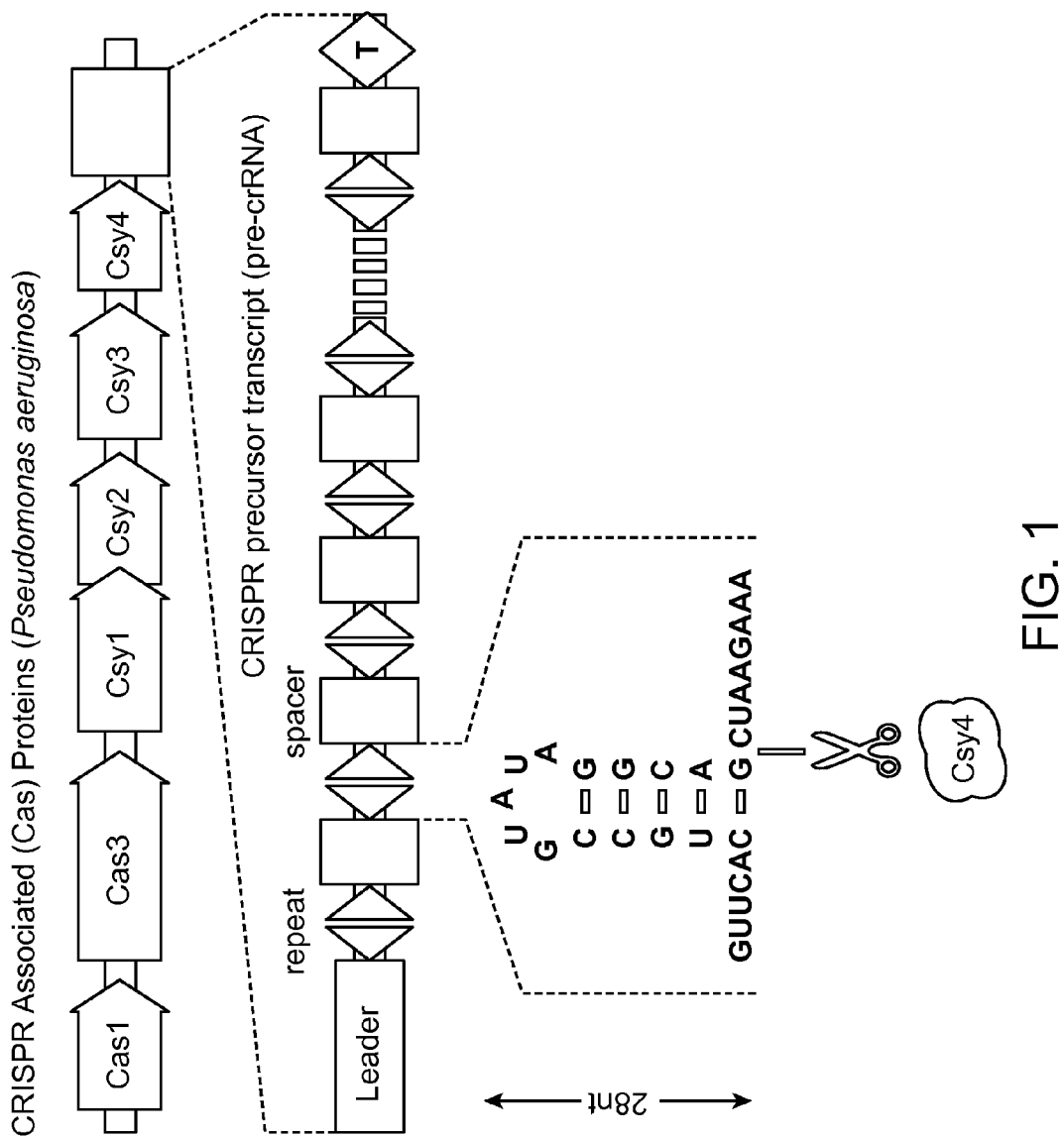
FIG. 1 schematizes the CRISPR/Cas system in *Pseudomonas aeruginosa* strain UCBPP-PA14. The CRISPR locus consists of a cluster of invader-derived spacer sequences (boxes) separated by 28-nt repetitive elements (diamonds). After transcription, the Csy4 protein specifically cleaves the repetitive elements at G20 (scissors). (SEQ ID NO: 56).

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (also called "non-coding" RNA or "ncRNA"; e.g. tRNA, rRNA, a ribozyme, etc.).

A "protein coding sequence" or "coding region" is a sequence that encodes a particular protein or polypeptide. A "protein coding sequence" or "coding region" is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic, viral, or eukaryotic mRNA, genomic DNA sequences from prokaryotic, viral, or eukaryotic DNA, and synthetic nucleic acids. A transcription termination sequence will usually be located 3' to the coding region.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

The term "binding", as used herein refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

As used herein, the terms "specific binding," "specifically binds," "recognizes" and the like, refer to the preferential binding to a molecule relative to other molecules or moieties in a solution or reaction mixture (e.g., an RNA-cleaving enzyme recognizes, or specifically binds, to an RNA recognition sequence of an RNA molecule). Specific binding interactions between a protein and a nucleic acid can either be non-sequence specific (e.g., a protein can specifically bind to DNA or RNA, preferably over other types of molecules, in a sequence independent manner) or sequence specific (e.g., a protein can specifically bind to, or recognize, a specific sequence within a DNA or RNA molecule).

As used herein, a "promoter sequence" is a DNA regulatory region capable of binding RNA polymerase and initiating transcription of a downstream (3' direction) coding or non-coding sequence. For purposes of defining the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various prokaryotic and eukaryotic promoters, including inducible promoters, may be used in the various recombinant expression vectors of the present disclosure. The promoter may be a constitutively active promoter, i.e. a promoter is active in the absence externally applied agents, or it may be an inducible promoter (e.g., T7 RNA polymerase promoter, T3 RNA polymerase promoter, Isopropyl-beta-D-thiogalactopyranoside (IPTG)-regulated promoter, heat shock promoter, Tetracycline-regulated promoter, Steroid-regulated promoter, Metal-regulated promoter, methionine-inducible promoter; a galactose-inducible promoter, and the like). As used herein, an inducible promoter is a promoter whose activity is regulated upon the application of an agent to the cell, (e.g. doxycycline) or the induced presence of a particular RNA polymerase (e.g., T7 RNA polymerase).

Agents that induce any given inducible promoter are known in art. For example, tetracycline-regulatable promoters can be regulated by tetracycline or doxycycline; carbohydrates can be used to induce a carbohydrate-inducible promoter (e.g., galactose for a galactose-inducible promoter); methionine can be used to induce a methionine-inducible promoter; metals can be used to induce a metallothionein promoter, etc.).

The terms "control element," and "regulatory element," used interchangeably herein, refer to transcriptional, translational, and degradation control sequences that are transcribed as part of the RNA molecule whose activity that they regulate. Such regulatory elements can control a wide variety of processes (activities) including but not limited to transcription (e.g., initiation, elongation, and/or termination), translation (initiation, elongation, and/or termination), RNA stability, etc. Regulatory elements include but are not limited to recognition sequences for antisense RNAs, leader sequences, riboswitches, a 5' methyl cap, a 3' poly-A tail, sequences recognized by ribozymes, sequences recognized by ribosomes (e.g., a ribosomome binding site (RBS), e.g., Shine-Delgarno Sequence), self-cleaving ribozymes, leader-sequences, sequences bound by RNA binding proteins, sequences targeted by a guide-strand-bound RISC complex, etc.

For example, some regulatory elements (e.g., PT181wt) are operably linked (defined below) to a promoter, but reciprocally regulate transcription (e.g., via early termination of RNA polymerase elongation) such that the promoter affects transcription of the regulatory element and the regulatory element also affects transcription of its own transcript. Some regulatory elements (e.g., IS10wt, IS10-9, and others known in the art: the RNA-IN/OUT translation control system) can function as part of an antisense RNA-mediated translation control system (Mutalik et al. Nature Chem. Biol. 2012 (8) May: 447-454; Kittle et al. J Mol. Biol. 1989 Dec. 5; 210 (3):561-72: Insertion sequence IS10 anti-sense pairing initiates by an interaction between the 5' end of the target RNA and a loop in the anti-sense RNA). Other exemplary regulatory elements that find use in the expression vectors, compositions, methods, and kits of this disclosure include but are not limited to PT181 wt and its orthologs, IS10wt and its orthologs, Bujard RBS, B0030 RBS, Weiss RBS, Anderson RBS, lacZp1 UTR, serB UTR, chiA UTR, lacY UTR, sodA UTR, ompRp3UTR, trpR UTR, glpA UTR, rhoL UTR, CRISPRI UTR, fixA UTR, lldP UTR, and the like.

The term "naturally-occurring" or "unmodified" as used herein as applied to a nucleic acid, a polypeptide, a cell, or an organism that is found in nature. For example, a polypeptide or polynucleotide sequence that is present in an organism (including viruses) that can be isolated from a source in nature and which has not been intentionally modified by a human in the laboratory is naturally occurring. The term "variant" refers to a form of a nucleic acid (e.g., containing at least one mutation), a polypeptide (e.g., containing at least one amino acid change), a cell (e.g., containing at least one mutation in its chromosomal DNA), or an organism that is not normally found in nature. For example, one variant of the Csy4 endoribonuclease has a His29 to Ala29 amino acid substitution, which renders the endonuclease enzymatically inactive in the absence of imidazole, but active in the presence of imidazole (see WO2011143124, incorporated here in full by reference). As such, the His29 to Ala29 (His29Ala, depicted in FIG. 12, SEQ ID NO: 132) variant of the sequence-specific Csy4 endoribonuclease is "conditionally" enzymatically inactive (e.g., a subject enzymatically inactive, sequence-specific endoribonuclease, e.g., a subject variant Csy4 endoribonuclease, is enzymatically inactive in the absence of imidazole), and the enzymatically inactive sequence-specific endoribonuclease is activatable by imidazole. As such, the His29Ala variant of the Csy4 endoribonuclease is activatable.

A conditionally enzymatically inactive endoribonuclease can bind to a polynucleotide in a nucleic acid in a sequence-specific manner. A conditionally enzymatically inactive sequence-specific endoribonuclease can bind a polynucleotide in a nucleic acid in a sequence-specific manner, but cannot cleave the polyribonucleotide.

A variant sequence specific endoribonuclease can be a conditionally enzymatically inactive endoribonuclease (e.g., Csy4). For example, the variant sequence-specific enzymatically inactive endoribonuclease can have 90% or less, 80% or less, 70% or less, 60% or less, 50% or less, 40% or less, 30% or less, 20% or less, 10% or less, 5% or less, or 1% or less of the nucleic acid-cleaving activity of the wild-type sequence-specific endoribonuclease. The variant sequence-specific endoribonuclease can have no substantial nucleic acid-cleaving activity.

Imidazole can be added to activate an enzymatically inactive sequence-specific endoribonuclease (e.g., Csy4) to a final concentration of from about 100 mM to about 500 mM (e.g., from about 100 mM to about 150 mM, from about 150 mM to about 200 mM, from about 200 mM to about 250 mM, from about 250 mM to about 300 mM, from about 300 mM to about 350 mM, from about 350 mM to about 400 mM, from about 400 mM to about 450 mM, or from about 450 mM to about 500 mM). Imidazole can reactivate the enzymatically inactive endoribonuclease such that the endoribonuclease becomes enzymatically active and cleaves the target nucleic acid from the RNA recognition sequence, thereby releasing the target nucleic acid.

Figure 11:
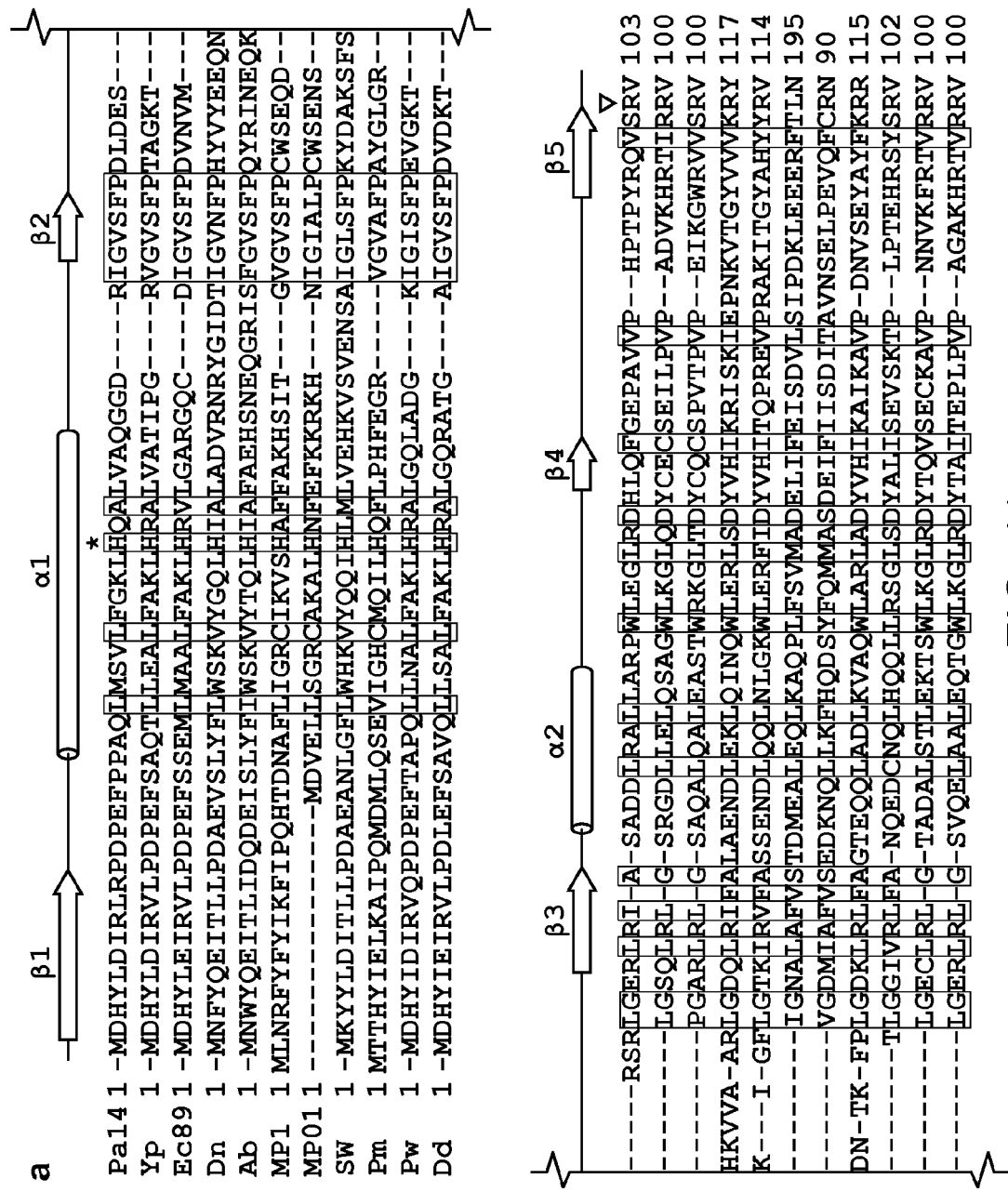
FIGS. 11A-B depicts invariant amino acids among 12 Csy4 sequences. Pa14 (SEQ ID NO: 1); Yp (SEQ ID NO: 14); Ec89 (SEQ ID NO: 17); Dn (SEQ ID NO: 42); Ab (SEQ ID NO: 45); MP1 (SEQ ID NO: 147); MP01 (SEQ ID NO: 148); SW (SEQ ID NO: 149); Pm (SEQ ID NO: 47); Pw (SEQ ID NO: 6); and Dd (SEQ ID NO: 5).
Figure 11:
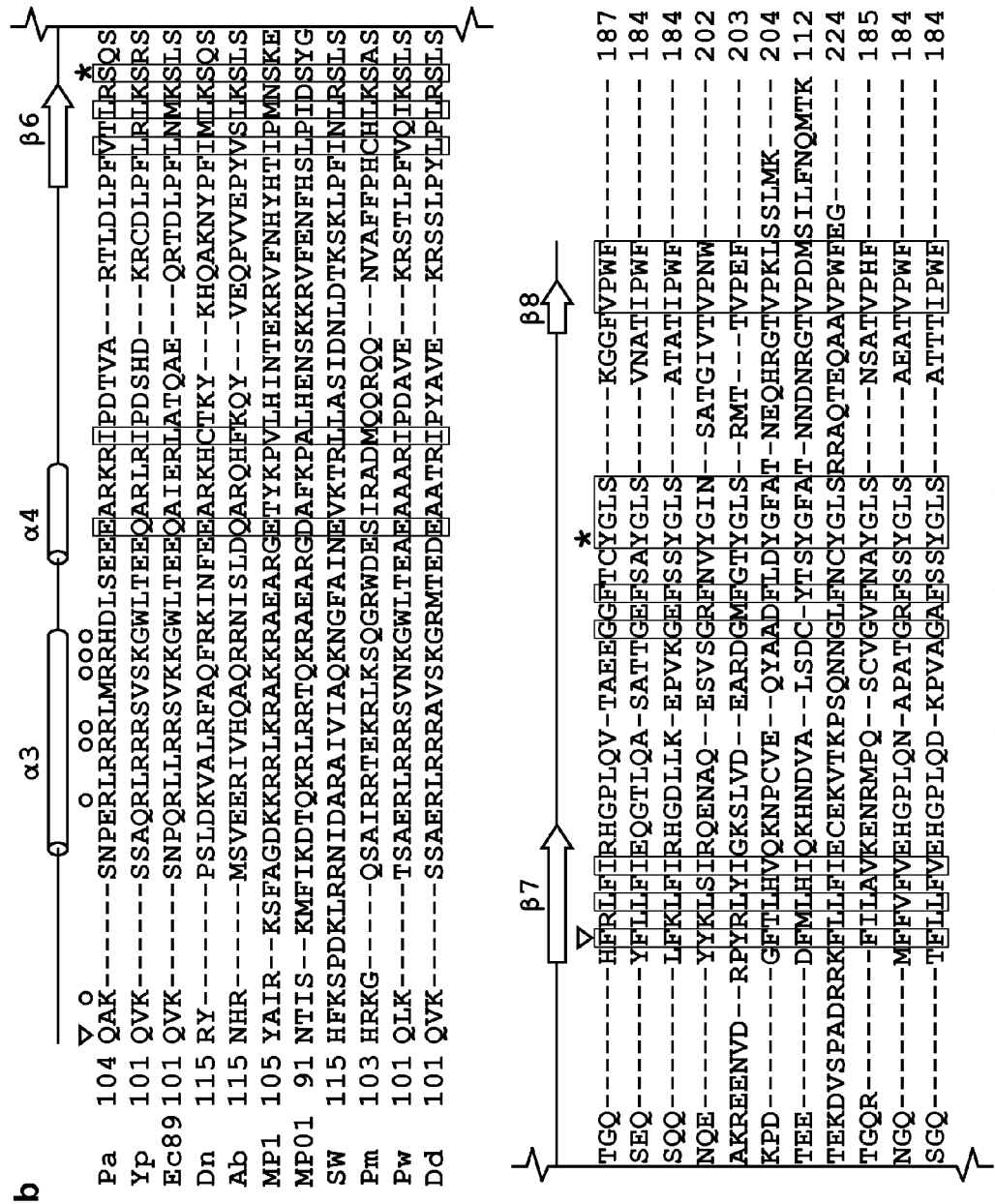

The presence of imidazole (e.g., in a concentration range of from about 100 mM to about 500 mM) reactivates the sequence-specific enzymatically inactive endoribonuclease such that the endoribonuclease becomes enzymatically active, e.g., the endoribonuclease exhibits at least about 50%, at least about 60%, at least about 70%, at least about 80%, at least about 90%, at least about 95%, or more than 95%, of a wild-type sequence-specific endoribonuclease (FIG. 10 and/or FIG. 11; SEQ ID NOs: 1-55 and 147-149).

The term "chimeric" as used herein as applied to a nucleic acid or polypeptide refers to two components that are defined by structures derived from different sources. For example, where "chimeric" is used in the context of a chimeric polypeptide, the chimeric polypeptide includes amino acid sequences that are derived from different polypeptides. A chimeric polypeptide may comprise either modified or naturally-occurring polypeptide sequences. Similarly, "chimeric" in the context of a polynucleotide encoding a chimeric polypeptide includes nucleotide sequences derived from different coding regions.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame and may indeed act to modulate production of a desired product by various mechanisms (see "regulatory element", above). Alternatively, DNA sequences encoding RNA that is not translated may also be considered recombinant. Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a chimeric amino acid sequence is a recombinant polypeptide.

A "vector" or "expression vector" is a replicon, such as plasmid, phage, virus, or cosmid, to which another DNA segment, i.e. an "insert", may be attached so as to bring about the replication of the attached segment in a cell. An "expression cassette" comprises a DNA coding sequence operably linked to a promoter. The term "operably linked" refers to a juxtaposition wherein the components so described are in a relationship permitting them to function in their intended manner. For instance, a coding sequence is operably linked to a promoter (or the promoter can be said to be operably linked to the coding sequence) if the promoter affects the transcription or expression of the coding sequence. If a regulatory element is operably linked to a promoter, the regulatory element is transcribed and the promoter affects the transcription of the regulatory element. Some regulatory elements (e.g., PT181 wt) are operably linked to a promoter, but reciprocally regulate transcription such that the promoter affects transcription of the regulatory element and the regulatory element also affects transcription of its own transcript.

The terms "recombinant expression vector," or "DNA construct" are used interchangeably herein to refer to a DNA molecule comprising a vector and at least one insert (e.g., a recognition nucleotide sequence that encodes an RNA recognition sequence). Recombinant expression vectors are usually generated for the purpose of expressing and/or propagating the insert(s), or for the construction of other recombinant nucleotide sequences. The insert(s) may or may not be operably linked to a promoter sequence.

A recombinant expression vector may also contain an insertion site for the insertion of a sequence of interest. An "insertion site" is any nucleotide sequence intentionally positioned within the vector that allows for convenient insertion and/or excision of additional nucleic acid sequences. The term "insertion site" encompasses sequences that facilitate any convenient cloning methodology (e.g., standard restriction enzyme/ligation based methods, integrase based methods, T4 DNA Polymerase based methods, BioBrick cloning, Circular Polymerase Extension Cloning (CPEC) cloning, etc.) (Quan, J. & Tian, J. Nat. Protoc. 6, 242-251 (2011); Shetty et al. J. Biol. Eng. 2, 5 (2008)). An example of one possible type of standard insertion site is a multiple cloning site (or polylinker), which is a stretch of sequences that contains multiple restriction enzyme sites that together facilitate convenient restriction enzyme/ligation based cloning methods.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include viral infection, transfection, conjugation, protoplast fusion, electroporation, particle gun technology, calcium phosphate precipitation, direct micro injection, and the like. The choice of method is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a site-specific endoribonuclease" includes a plurality of such site-specific endoribonucleases and reference to "the target polyribonucleotide" includes reference to one or more target polyribonucleotides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides nucleic acids encoding an RNA recognition sequence positioned proximal to an insertion site for the insertion of a sequence of interest; and host cells genetically modified with the nucleic acids. The present disclosure also provides methods of modifying the activity of a target RNA, and kits and compositions for carrying out the methods.

CRISPR Systems

A CRISPR (Clustered Regularly Interspaced Short Palindromic Repeats) can be a genomic locus found in the genomes of many prokaryotes (e.g., bacteria and archaea). CRISPR loci can provide resistance to foreign invaders (e.g., virus, phage) in prokaryotes. In this way, the CRISPR system can be thought to function as a type of immune system to help defend prokaryotes against foreign invaders. There can be three stages of CRISPR locus function: integration of new sequences into the locus, biogenesis of CRISPR RNA (crRNA), and silencing of foreign invader nucleic acid. There can be four types of CRISPR systems (e.g., Type I, Type II, Type III, TypeU).

A CRISPR locus can include a number of short repeating sequences referred to as "repeats." Repeats can form hairpin structures and/or repeats can be unstructured single-stranded sequences. The repeats can occur in clusters. Repeats sequences can frequently diverge between species. Repeats can be regularly interspaced with unique intervening sequences referred to as "protospacers," resulting in a repeat-spacer-repeat locus architecture. Protospacers can be identical to or have high homology with known foreign invader sequences. A protospacer-repeat unit can encode a crisprRNA (crRNA). A crRNA can refer to the mature form of the protospacer-repeat unit. A crRNA can comprise a "seed" sequence that can be involved in targeting a target nucleic acid (e.g., possibly as a surveillance mechanism against foreign nucleic acid). A seed sequence can be located at the 5' or 3' end of the crRNA.

A CRISPR locus can comprise polynucleotide sequences encoding for Crispr Associated Genes (Cas) genes. Cas genes can be involved in the biogenesis and/or the interference stages of crRNA function. Cas genes can display extreme sequence (e.g., primary sequence) divergence between species and homologues. For example, Cas1 homologues can comprise less than 15% primary sequence identity between homologues. Some Cas genes can comprise homologous secondary and/or tertiary structures. For example, despite extreme sequence divergence, many members of the Cas6 family of CRISPR proteins comprise a N-terminal ferredoxin-like fold. Cas genes can be named according to the organism from which they are derived. For example, Cas genes in *Staphylococcus epidermidis* can be referred to as Csm-type, Cas genes in *Streptococcus thermophilus* can be referred to as Csn-type, and Cas genes in *Pyrococcus furiosus* can be referred to as Cmr-type.

Integration

The integration stage of CRISPR system can refer to the ability of the CRISPR locus to integrate new protospacers into the crRNA array upon being infected by a foreign invader. Acquisition of the foreign invader protospacers can help confer immunity to subsequent attacks by the same foreign invader. Integration can occur at the leader end of the CRISPR locus. Cas proteins (e.g., Cas1 and Cas2) can be involved in integration of new protospacer sequences. Integration can proceed similarly for some types of CRISPR systems (e.g., Type I-III).

Biogenesis

Mature crRNAs can be processed from a longer polycistronic CRISPR locus transcript (i.e., pre-crRNA array). A pre-crRNA array can comprise a plurality of crRNAs. The repeats in the pre-crRNA array can be recognized by Cas genes. Cas proteins comprising ribonuclease activity can bind to the repeats and cleave the repeats. This action can liberate the plurality of crRNAs. In some instances, crRNAs can be subjected to further events to produce the mature crRNA form such as trimming (e.g., with an exonuclease). A crRNA may comprise all, some, or none of the CRISPR repeat sequence.

Interference

Interference can refer to the stage in the CRISPR system that is functionally responsible for combating infection by a foreign invader. CRISPR interference can follow a similar mechanism to RNA interference (RNAi), wherein a target RNA is targeted, resulting in target RNA degradation and/or destabilization. CRISPR systems can perform interference of a target nucleic acid by coupling crRNAs and Cas genes, thereby forming CRISPR ribonucleoproteins (crRNPs). crRNA of the crRNP can guide the crRNP to foreign invader nucleic acid, by recognizing the foreign invader nucleic acid through hybridization. Hybridized target foreign invader nucleic acid-crRNA units can be subjected to cleavage by Cas proteins.

Types of CRISPR Systems

There can be four types of CRISPR systems: Type I, Type II, Type III, and Type U. More than one CRISPR type system can be found in an organism. CRISPR systems can be complementary to each other, and/or can lend functional units in trans to facilitate CRISPR locus processing.

Type I CRISPR Systems crRNA biogenesis in Type I CRISPR systems can comprise endoribonuclease cleavage of repeats in the pre-crRNA array, which can result in a plurality of crRNAs. crRNAs of Type I systems may not be subjected to crRNA trimming. A crRNA can be processed from a pre-crRNA array by a multi-protein complex called Cascade (originating from CRISPR-associated complex for antiviral defense). Cascade can comprise protein subunits (e.g., CasA-CasE). Some of the subunits can be members of the Repeat Associated Mysterious Protein (RAMP) superfamily (e.g., Cas5 and Cas6 families). The Cascade-crRNA complex (i.e., interference complex) can recognize target nucleic acid through hybridization of the crRNA with the target nucleic acid. The Cascade interference complex can recruit the Cas3 helicase/nuclease which can act in trans to facilitate cleavage of target nucleic acid. The Cas3 nuclease can cleave target nucleic acid with its HD nuclease domain. Target nucleic acid in a Type I CRISPR system can be DNA.

Type I systems can be further subdivided by their species of origin. Type I systems can comprise Types IA (*Aeropyrum pernix* or CASS5), IB (*Thermotoga neapolitana-Haloarcula marismortui* or CASS7), IC (*Desulfovibrio vulgaris* or CASS1), ID, IE (*Escherichia coli* or CASS2), and IF (*Yersinia pestis* or CASS3) subfamilies.

Type II CRISPR Systems crRNA biogenesis in a Type II CRISPR system can involve a trans-activating CRISPR RNA (tracrRNA). A tracrRNA can be generated by endogenous RNaseIII. A tracrRNA can interact with a site-directed polypeptide (e.g., Cas9), thereby forming a complex. The tracrRNA of the complex can hybridize to a crRNA repeat in the pre-crRNA array. Endogenous RnaseIII can be recruited to cleave the pre-crRNA. Cleaved crRNAs can be subjected to exoribonuclease trimming to produce the mature crRNA form (e.g., 5' trimming). The crRNA of the liberated crRNA-tracrRNA-Cas9 complex can guide the complex to a target nucleic acid to which the crRNA can hybridize. Hybridization of the crRNA to the target nucleic acid can activate Cas9 for target nucleic acid cleavage.

Type II systems can be further subdivided into II-A (Nmeni or CASS4) and II-B (Nmeni or CASS4a).

Type III CRISPR Systems crRNA biogenesis in Type III CRISPR systems can comprise a step of endoribonuclease cleavage of repeats in the pre-crRNA array, which can result in a plurality of crRNAs. Repeats in the Type III CRISPR system can be unstructured single-stranded regions. Repeats can be recognized and cleaved by a member of the RAMP superfamily of endoribonucleases (e.g., Cas6). crRNAs of Type III (e.g., Type III-B) systems may be subjected to crRNA trimming (e.g., 3' trimming). Type III systems can comprise a polymerase-like protein (e.g., Cas10). Cas10 can comprise a domain homologous to a palm domain.

Type III systems can process pre-crRNA with a complex comprising a plurality of RAMP superfamily member proteins and one or more CRISPR polymerase-like proteins. Type III systems can be divided into III-A and III-B. An interference complex of the Type III-A system (i.e., Csm complex) can target plasmid nucleic acid. Cleavage of the plasmid nucleic acid can occur with the HD nuclease domain of a polymerase-like protein the complex. An interference complex of the Type III-B system (i.e., Cmr complex) can target RNA.

Type U CRISPR Systems

Type U CRISPR systems may not comprise the signature genes of either of the Type I-III CRISPR systems (e.g., Cas3, Cas9, Cas6, Cas1, Cas2). Examples of Type U CRISPR Cas genes can include, but are not limited to, Csf1, Csf2, Csf3, Csf4. Type U Cas genes may be very distant homologues of Type I-III Cas genes. For example, Csf3 may be highly diverged but functionally similar to Cas5 family members. A Type U system may function complementarily in trans with a Type I-III system. In some instances, Type U systems may not be associated with processing CRISPR arrays. In some instances, Type U systems may represent an alternative foreign invader defense system.

RAMP Superfamily

Repeat Associated Mysterious Proteins (RAMP proteins) can be characterized by a protein fold comprising a $\beta\alpha\beta\beta\alpha\beta$ motif of β-strands (β) and α-helices (α). A RAMP protein can comprise an RNA recognition motif (RRM) (which can comprise a ferredoxin or ferredoxin-like fold). RAMP proteins can comprise an N-terminal RRM. The C-terminal domain of RAMP proteins can vary, but can also comprise an RRM. RAMP family members can recognize structured and/or unstructured nucleic acid. RAMP family members can recognize single-stranded and/or double-stranded nucleic acid. RAMP proteins can be involved in the biogenesis and/or the interference stage of CRISPR Type I and Type III systems. RAMP superfamily members can comprise members of the Cas7, Cas6, and Cas5 families.

RRM domains in the RAMP superfamily can be extremely divergent. RRM domains can comprise about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or 100% sequence or structural homology to an RRM domain Cas7 Family Cas7 family members can be a subclass of RAMP family proteins. Cas7 family proteins can be categorized in Type I CRISPR systems. Cas7 family members may not comprise a glycine rich loop that is familiar to some RAMP family members. Cas7 family members can comprise one RRM domain. Cas7 family members can include, but are not limited to, Cas7 (COG1857), Cas7 (COG3649), Cas7 (CT1975), Csy3, Csm3, Cmr6, Csm5, Cmr4, Cmr1, Csf2, Csc2.

Cas6 Family

The Cas6 family can be a RAMP subfamily. Cas6 family members can comprise two RNA recognition motif (RRM)-like domains. In some instances, a Cas6 family member (e.g., Cas6f) can comprise a N-terminal RRM domain and a distinct C-terminal domain that may show weak sequence similarity or structural homology to an RRM domain. Cas6 family members can comprise a catalytic histidine that may be involved in endoribonuclease activity. A comparable motif can be found in Cas5 and Cas7 RAMP families. Cas6 family members can include, but are not limited to, Cas6, Cas6e, Cas6f (e.g., Csy4).

Cas5 Family

The Cas5 family can be a RAMP subfamily. The Cas5 family can be divided into two subgroups: one subgroup that can comprise two RRM domains, and one subgroup that can comprise one RRM domain. Cas5 family members can include, but are not limited to, Csm4, Csx10, Cmr3, Cas5, Cas5(BH0337), Csy2, Csc1, Csf3.

Cas Genes

Exemplary CRISPR Cas genes can include Cas1, Cas2, Cas3', Cas3", Cas4, Cas5, Cas6, Cas6e (formerly referred to as CasE, Cse3), Cas6f (i.e., Csy4), Cas7, Cas8a1, Cas8a2, Cas8b, Cas8c, Cas9, Cas10, Cas10d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4. Table 1 provides an exemplary categorization of CRISPR Cas genes by CRISPR system Type.

The CRISPR-Cas gene naming system has undergone extensive rewriting since the Cas genes were discovered. For the purposes of this disclosure, Cas gene names are described herein are based on the naming system outlined in Makarova et al. Evolution and classification of the CRISPR-Cas systems. Nature Reviews Microbiology. 2011 June; 9 (6): 467-477. Doi:10.1038/nrmicro2577. Table 1 provides an exemplary classification of CRISPR Cas genes by CRISPR type.

TABLE 1

Exemplary classification of CRISPR Cas genes by CRISPR type

| System type or subtype | Gene Name |
|---|---|
| Type I | cas1, cas2, cas3' |
| Type II | cas1, cas2, cas9 |
| Type III | cas1, cas2, cas10 |
| Subtype I-A | cas3", cas4, cas5, cas6, cas7, cas8a1, cas8a2, csa5 |
| Subtype I-B | cas3", cas4, cas5, cas6, cas7, cas8b |
| Subtype I-C | cas4, cas5, cas7, cas8c |
| Subtype I-D | cas4, cas6, cas10d, csc1, csc2 |
| Subtype I-E | cas5, cas6e, cas7, cse1, cse2 |
| Subtype I-F | cas6f, csy1, csy2, csy3 |
| Subtype II-A | csn2 |
| Subtype II-B | cas4 |
| Subtype III-A | cas6, csm2, csm3, csm4, csm5, csm6 |
| Subtype III-B | cas6, cmr1, cmr3, cmr4, cmr5, cmr6 |
| Subtype I-U | csb1, csb2, csb3, csx17, csx14, csx10 |
| Subtype III-U | csx16, csaX, csx3, csx1 |
| Unknown | csx15 |
| Type U | csf1, csf2, csf3, csf4 |

Nucleic Acids and Host Cells

The present disclosure provides recombinant expression vectors comprising a recognition nucleotide sequence that encodes an RNA recognition sequence recognized by an RNA-cleaving enzyme. As used herein, "recognition nucleotide sequence" is a nucleotide sequence encoding an RNA sequence (i.e., an "RNA recognition sequence") that is recognized (i.e., specifically bound) by an RNA-cleaving enzyme in a sequence-specific manner. If the RNA-cleaving enzyme is active/functional, the RNA molecule containing the RNA recognition sequence is hydrolyzed (i.e. cleaved), thus dividing the RNA molecule in two.

RNA Recognition Sequence

A subject recombinant expression vector can contain any recognition nucleotide sequence that is known to be recognized and cleaved by a sequence-specific RNA-cleaving enzyme. Suitable recognition nucleotide sequences include the RNA recognition sequences depicted in FIGS. 10A-10AZ, which are each recognized by a corresponding (i.e., "cognate") Csy4 related endonuclease. In some embodiments, a subject RNA recognition sequence is at least about 90% identical (e.g., at least about 95% identical, at least about 96% identical, at least about 97% identical, at least about 98% identical, at least about 99% identical, at least about 99.5% identical, or 100% identical) to any of the RNA recognition sequences set forth in FIG. 10 (% identical to the amino acid sequence set forth in one of SEQ ID NOs: 56-131). In some instances, RNA recognition sequences can comprise a sequence that can be bound by a member of Type I, Type II, and/or Type III CRISPR systems. The RNA sequence can be bound by a RAMP family member protein. The RNA sequence can be bound by a Cas6 family member protein (e.g. Cas6). The RNA sequence can be bound by a Cas5 family member protein (e.g., Cas5). The RNA sequence can be bound by a Csy4 family member protein. For example, Csy4 can bind to a specific RNA hairpin sequence with high affinity (Kd~50 pM) and can cleave RNA at a site 3' to the hairpin. In some instances, the, Csy4, Cas5, or Cas6 family member protein can bind an RNA sequence that comprises at least 70%, at least 75%, at least 80%, at least 85%, at least 90%, at least 95%, or 100% identity to the nucleotide sequence set forth in one of SEQ ID Nos: 56-131 and/or the following nucleotide sequences:

5'-GUUCACUGCCGUAUAGGCAGCUAAGAAA-3'; (SEQ ID NO: 56)

5'-GUUGCAAGGGAUUGAGCCCCGUAAGGGGAUUGCGAC-3'; (SEQ ID NO: 175)

5'-GUUGCAAACCUCGUUAGCCUCGUAGAGGAUUGAAAC-3'; (SEQ ID NO: 176)

5'-GGAUCGAUACCCACCCCGAAGAAAAGGGGACGAGAAC-3'; (SEQ ID NO: 177)

5'-GUCGUCAGACCCAAAACCCCGAGAGGGGACGGAAAC-3'; (SEQ ID NO: 178)

5'-GAUAUAAACCUAAUUACCUCGAGAGGGGACGGAAAC-3'; (SEQ ID NO: 179)

5'-CCCCAGUCACCUCGGGAGGGGACGGAAAC-3'; (SEQ ID NO: 180)

5'-GUUCCAAUUAAUCUUAAACCCUAUUAGGGAUUGAAAC-3'; (SEQ ID NO: 181)

5'-GUUGCAAGGGAUUGAGCCCCGUAAGGGGAUUGCGAC-3'; (SEQ ID NO: 182)

5'-GUUGCAAACCUCGUUAGCCUCGUAGAGGAUUGAAAC-3'; (SEQ ID NO: 183)

5'-GGAUCGAUACCCACCCCGAAGAAAAGGGGACGAGAAC-3'; (SEQ ID NO: 184)

5'-GUCGUCAGACCCAAAACCCCGAGAGGGGACGGAAAC-3'; (SEQ ID NO: 185)

5'-GAUAUAAACCUAAUUACCUCGAGAGGGGACGGAAAC-3'; (SEQ ID NO: 186)

5'-CCCCAGUCACCUCGGGAGGGGACGGAAAC-3'; (SEQ ID NO: 187)

5'-GUUCCAAUUAAUCUUAAACCCUAUUAGGGAUUGAAAC-3'; (SEQ ID NO: 188)

5'-GUCGCCCCCACGCGGGGCGU GGAUUGAAAC-3'; (SEQ ID NO: 189)

5'-CCAGCCGCCUUCGGGCGGCUGUGUGUUGAAAC-3'; (SEQ ID NO: 190)

5'-GUCGCACUCUACAUGAGUGCGUGGAUUGAAAU-3'; (SEQ ID NO: 191)

5'-UGUCGCACCUUAUAUAGGUGCGUGGAUUGAAAU-3'; (SEQ ID NO: 192)
and

5'-GUCGCGCCCCGCAUGGGGCGCGUGGAUUGAAA-3'. (SEQ ID NO: 193)

Figure 9:
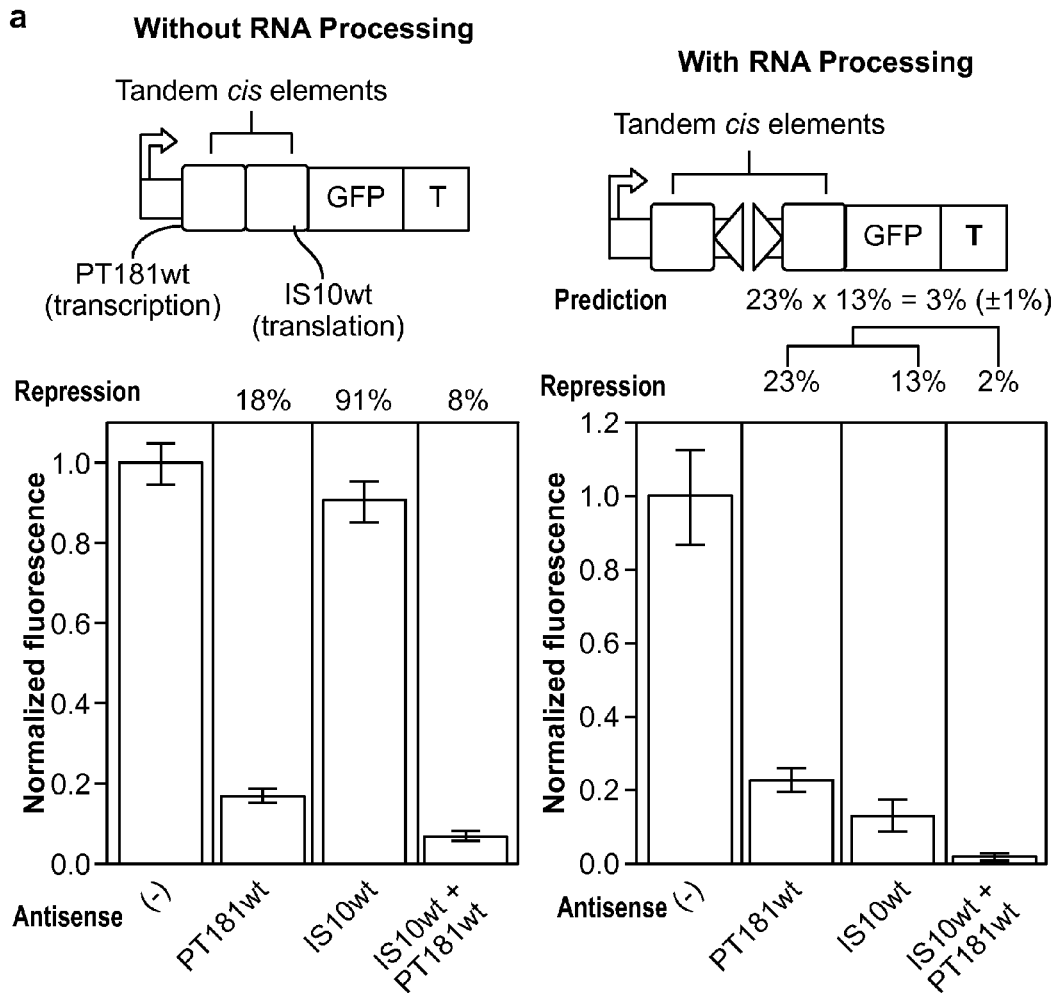
FIG. 9a displays data collected for a complex cis-regulatory system without (left) or with (right) RNA processing. All data are normalized to gene expression without any antisense RNA.
FIG. 9b displays a comparison of the efficacy of different RNA cleavage elements. RNA cleavage elements are inserted between the tandem cis regulators (PT181wt and IS10wt). sTRSV, small Tobacco RingSpot Virus hammerhead ribozyme; ASBV, Avacado SunBlotch Virus ribozyme, T7 R1.1, the RNase III binding site from T7 phage; tRNA$^{Arg5}$, tRNA sequence for Arg5.
FIG. 9c demonstrates that Csy4 recognizes and cleaves its RNA target in different organisms (both prokaryotes and eukaryotes). The 30-nt Csy4 cleavage site was inserted in frame into a reporter system between the ATG start codon and downstream protein coding sequence. The reporter systems were tested (relative PPR was determined) in three organisms without and with Csy4 co-expression: gram-negative *Escherichia coli* K12, gram-positive *Bacillus subtilis* sp. 168, and yeast *Saccharomyces cerevisiae* BY4741. In all cases, co-expression of Csy4 protein effectively knocked down gene expression with more than 10-fold ON/OFF dynamic range.
FIG. 9d shows the *E. coli* cells, *B. subtilis* cells, and *S. cerevisiae* cells of FIG. 9c without and with Csy4 expression.

RNA recognition sequences are also those sequences recognized and cleaved by RNA-cleaving enzymes other than Csy4 related endonucleases. For example, suitable recognition nucleotides sequences also include those recognized by self-cleaving ribozymes, which can be placed in tandem to increase efficiency (e.g., small Tobacco RingSpot Virus hammerhead ribozyme (sTRSV); Avacado SunBlotch Virus ribozyme (ASBV); beta-globin co-transcriptional ribozyme; bacterial group II introns; glucosamine-6-phosphate ribozyme; group I/II/III introns; hepatitis delta virus ribozyme; CPEB3 ribozyme; VS ribozyme; the group of hairpin ribozymes such as chicory yellow mottle virus ribozyme and arabis mosaic virus ribozyme; the group of hammerhead ribozymes such as eggplant viroid ribozyme, velvet tobacco mottle virus ribozyme, and cherry small circular viroid-like ribozyme; etc.) and those (e.g., T7 R1.1, T7 R0.3, T7 R0.5, T7 R1.3, T7 R4.7, T7 R6.5, T7 R18.5, Phage SP82 cleavage site, phage T3 cleavage site, and the like) recognized by sequence-specific RNase III enzymes (e.g., RNase III from T7 phage) (FIG. 9b).

Position of the RNA Recognition Sequence

The position of the RNA recognition sequence within a transcript determines the position of RNA cleavage and therefore the nature of the resulting cleavage products. A recognition nucleotide sequence (encoding an RNA recognition sequence) can be positioned anywhere within a recombinant expression vector. For example, a recognition nucleotide sequence can be positioned within a protein coding region, between a regulatory element and a coding region, between a first regulatory element and a second regulatory element, between a first coding region and a second coding region, etc.

Figure 3:
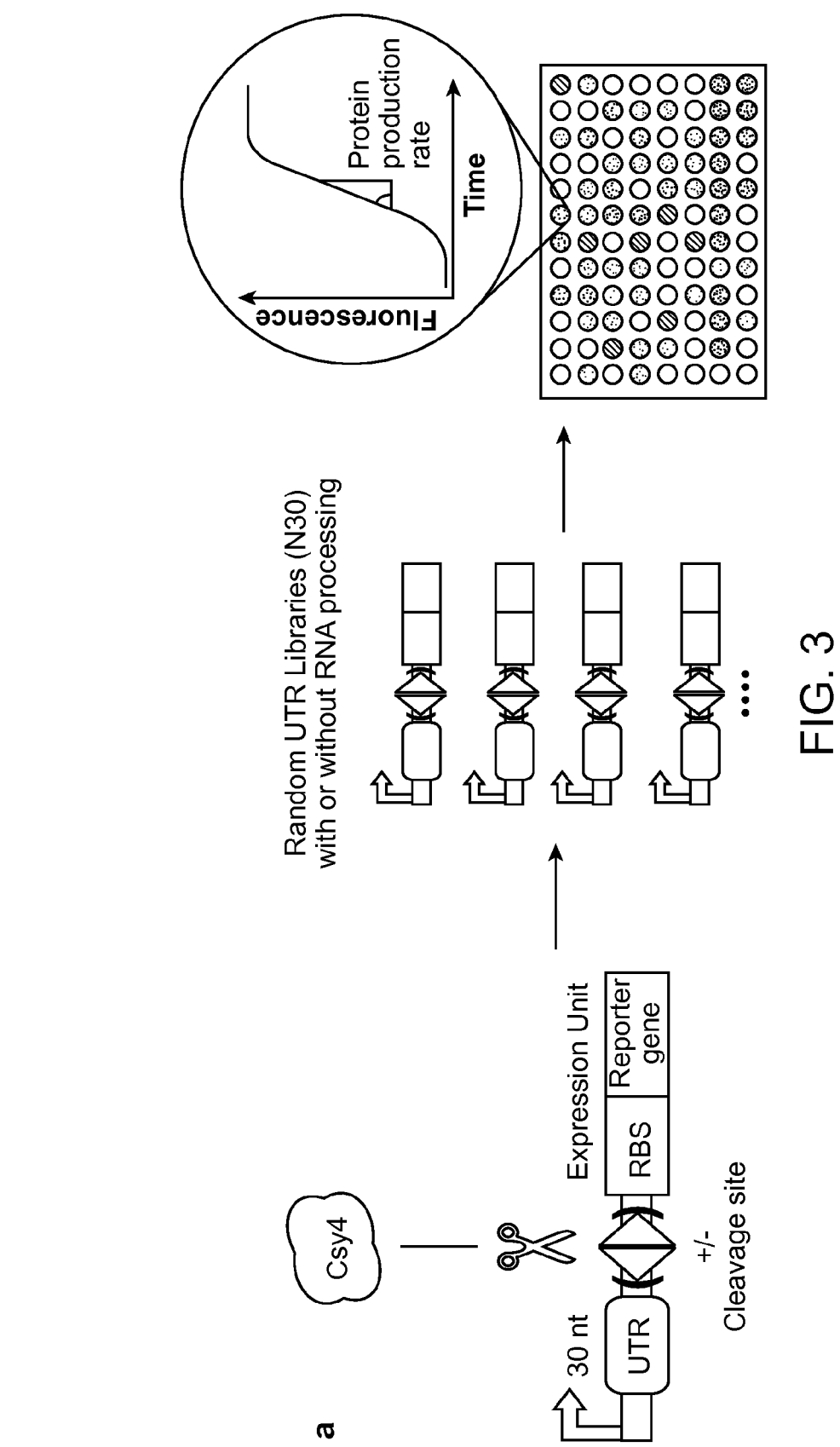
FIG. 3a depicts the experimental procedure for measuring the effects of random UTRs on gene expression with and without the CRISPR cleavage element (diamond).
FIGS. 3b-d depict statistical analysis of measure (protein production rates) PPRs. The expression of baseline constructs without 30-nt UTR insertions are plotted as shaded lines, with the width representing the standard deviation of biological triplicates.
FIG. 3e presents a 2D plot of the mean PPRs for 12 genomic UTR insertions with and without RNA processing. The gray lines show the PPR values of the baseline constructs.
FIGS. 3f-g illustrate experimental data for twenty-eight combinatory circuits composed of seven promoters, two RBSs and two reporter genes with the cleavage element inserted between promoters and RBSs. The heatmaps show measured relative promoter units (RPUs) values, with each column normalized to a reference promoter J23105. The RSD values for each row and Spearman's rank correlation coefficients between adjacent columns are labeled. The data of FIG. 3f were measured without RNA processing while the data of FIG. 3g were measured with RNA processing. In all cases, P<0.0001 for the differences in RSD and BB using two-tailed Student's t-test.
Figure 4:
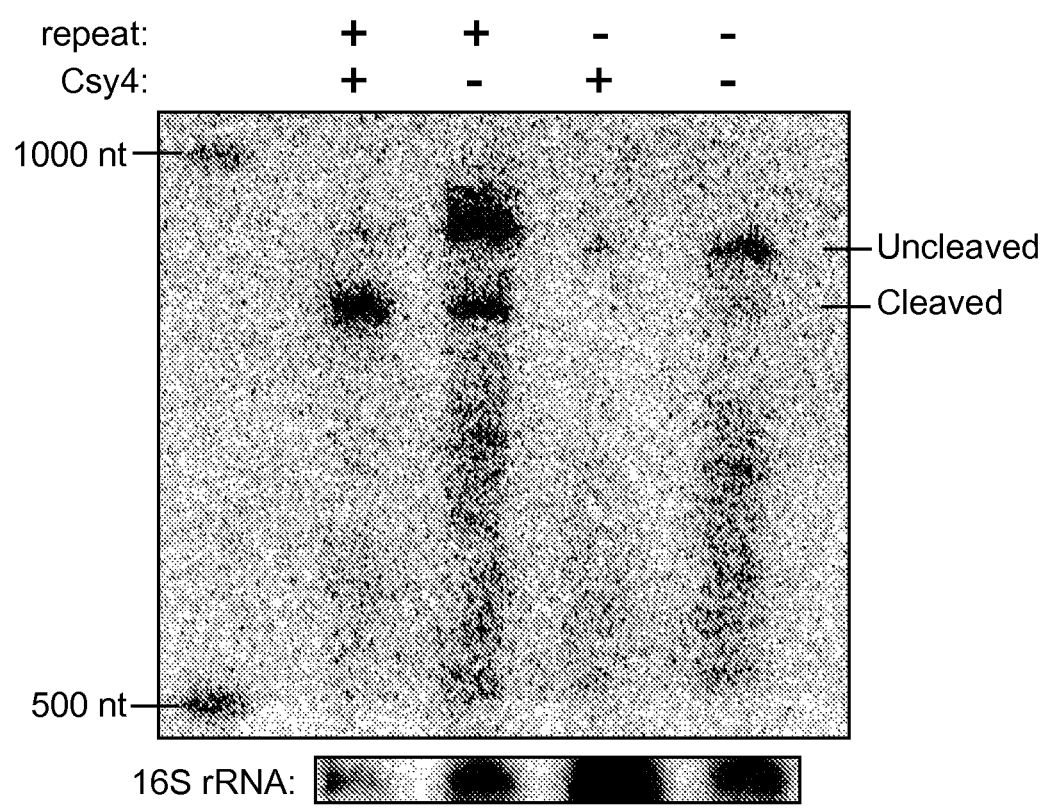
FIG. 4 shows a Northern analysis of total RNA of *E. coli* cells to verify in vivo Csy4 cleavage. The cells in all columns contained an expression cassette that transcribed a segment of genomic lldP UTR (90 nt) and GFP-coding gene (744 nt). The first two columns further contained a 28-nt CRISPR cleavage hairpin inserted between the lldP UTR and GFP. When the Csy4 protein is co-expressed, cleavage should reduce the transcript size to 752 nt, which was observed in the first column (more than 70% cleaved). Whereas without Csy4, uncleaved transcript is 864 nt as shown in the second column (more than 65% remained uncleaved). In the absent of CRISPR repeat hairpin, no cleavage was observed as shown in columns 3 & 4. The leaky cleavage (~35%) in the second column in the absence of Csy4 protein is probably due to an intrinsic transcriptional start site inside the lldP UTR sequence, which will be further investigated.
Figure 5:
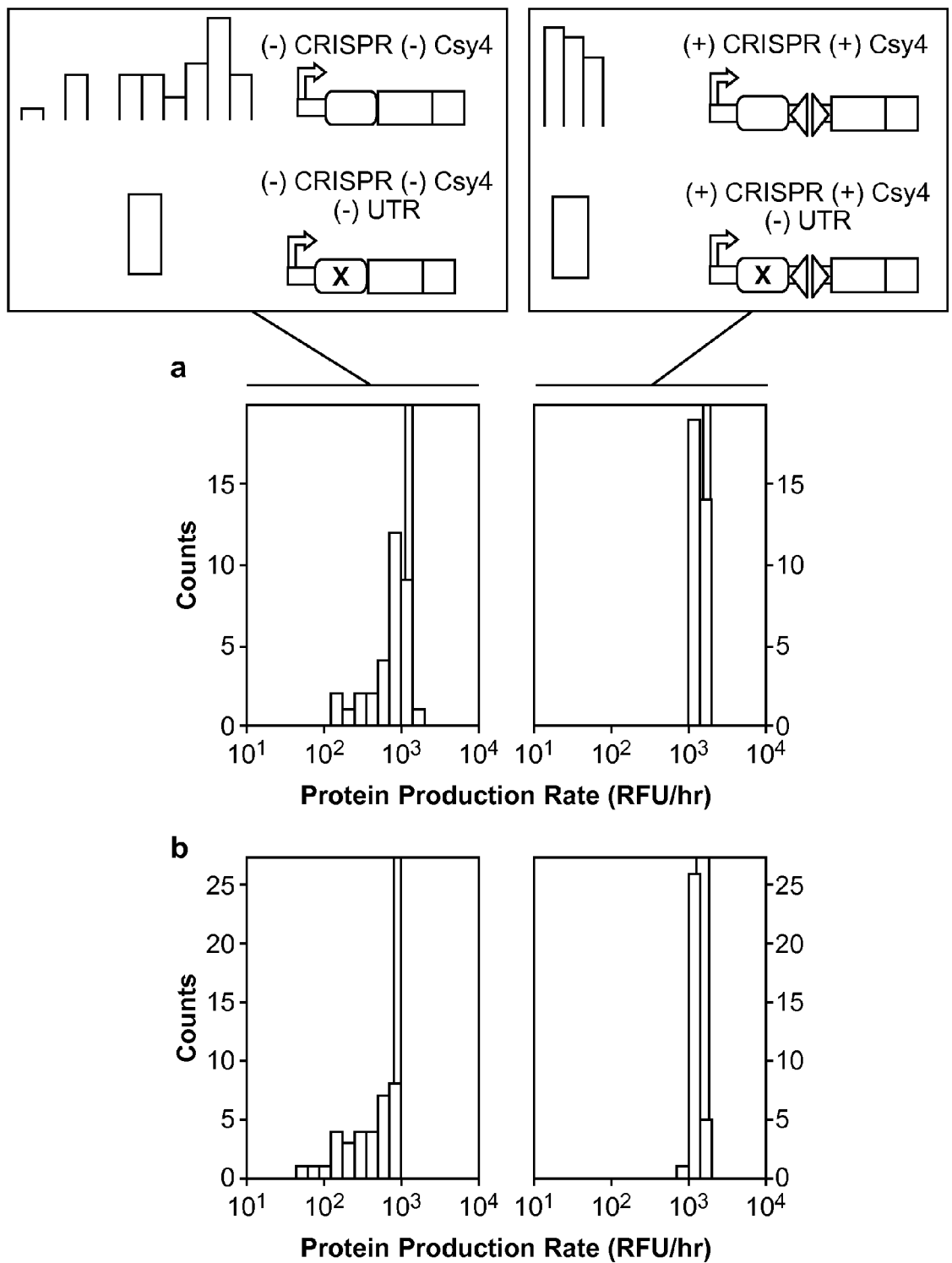
FIGS. 5a-h illustrate the data collected for eight translation units composed of four RBS sequences and two reporter genes that were tested with randomized 30-nt UTR sequences with or without the Csy4 hairpin. The histograms on the left show the constructs without RNA processing, and the histograms on the right show those with processing. The mean value of the control construct without a 30-nt UTR sequence is shown as a shaded bar without an outline. The width of each shaded bar (without an outline) represents the standard deviation of biological triplicates.
FIG. 5i displays the statistical summary of FIGS. 5a-h.

In some embodiments, a recognition nucleotide sequence is positioned within a protein coding region. Thus, after cleavage by the RNA-cleaving enzyme, translation of the resulting cleavage products will be severely affected and may be completely eliminated (e.g., when the RNA recognition sequence is positioned 3' of, and adjacent to, the start codon, e.g., ATG) (FIG. 9c). In some embodiments, a recognition nucleotide sequence is positioned between a regulatory element and a coding region. Thus, after cleavage by the RNA-cleaving enzyme, the regulatory element no longer affects or regulates the activity (e.g., transcription, translation, degradation, etc.) of the RNA cleavage products. For example, the presence of a 5' untranslated region (UTR) can have an unpredictable impact on the level of translation of an mRNA (FIGS. 3-5). However, when an RNA recognition sequence is positioned between the 5' UTR and the protein coding region, the translation of the protein coding region is consistent and predictable (FIGS. 3-5) after cleavage of the mRNA (by and RNA-cleaving enzyme that recognized the RNA recognition sequence).

In some embodiments, a recognition nucleotide sequence is positioned between a first regulatory element and a second regulatory element. Thus, after cleavage by the RNA-cleaving enzyme, the regulatory elements are separated onto two separate RNA molecules and each regulatory therefore only exerts an influence on those sequences remaining on the same molecule. For example, some regulatory elements interfere with the function of other regulatory elements in an unpredictable manner (FIG. 9a). If one regulatory element regulates transcription (e.g., PT181 wt) and the other regulatory element regulates translation (e.g., IS10wt), and both regulatory elements are 5' of a protein coding sequence, the transcription-regulating element can be experimentally regulated in a predictable manner, without affecting the translation-regulating element, because the transcription-regulating element is transcribed first. However, once a transcript is complete, the transcribed transcription-regulating element can interfere with the function of the translation-regulating element. Thus, the positioning of a recognition nucleotide sequence between a first regulatory element (e.g., the transcription-regulating element) and a second regulatory element (e.g., the translation-regulating element) allows cleavage of the transcript by an RNA-cleaving enzyme that recognizes the RNA recognition sequence, generating an RNA without a first regulatory element, but retaining both the second regulatory element (e.g., the translation-regulating element) and the protein coding sequence. The translation-regulating element therefore modulates RNA activity (e.g., translation) without the influence of the first regulatory element (FIG. 9a.)

Figure 6:
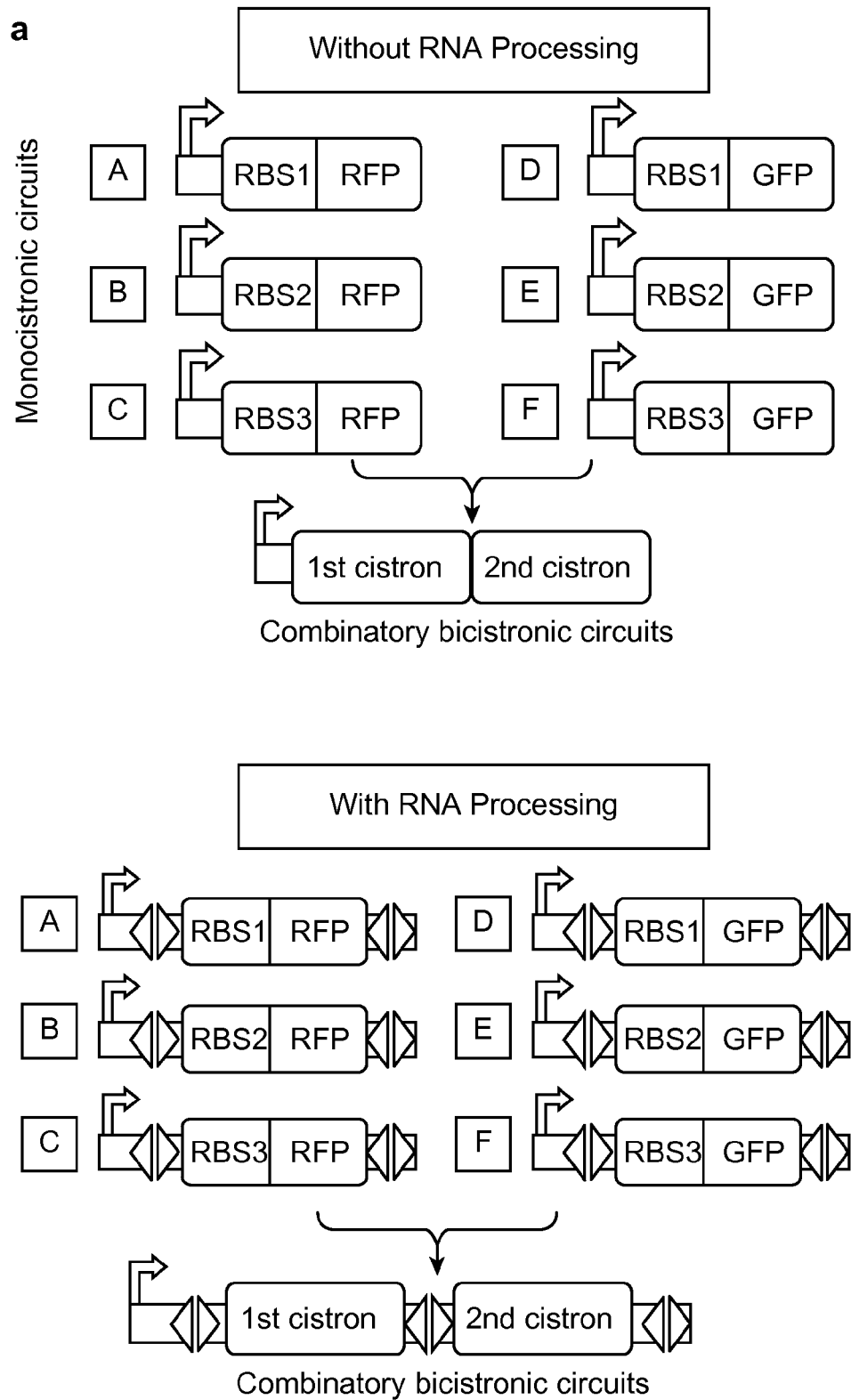
FIG. 6a schematizes six monocistrons that are combined in pairs to generate eighteen bicistrons without (top) and with (bottom) cleavage elements.
FIG. 6b shows measured PPRs (for RFP) for the monocistrons and bicistrons without RNA processing.
FIG. 6c shows measured PPRs (for RFP) with RNA processing.
FIG. 6d shows measured PPRs (for GFP) for the monocistrons and bicistrons without RNA processing.
FIG. 6e shows measured PPRs (for GFP) with RNA processing.

In some embodiments, a recognition nucleotide sequence is positioned between a first coding region and a second coding region (e.g., mRNA, viral RNA). Thus, after cleavage by an RNA-cleaving enzyme, each cleavage product contains one of the two protein coding regions. For example, polycistronic mRNAs contain multiple protein coding regions, each of which is preceded by a Ribosomal Binding Site (RBS) to allow for the simultaneous translation of each gene. However, the position and identity of genes within a polycistronic mRNA, as well at the position and identity of RBS sequences within a polycistronic mRNA can interact in unpredictable ways to modulate the translation of each gene in an unpredictable manner. When a recognition nucleotide sequence is positioned between a first coding region and a second coding region of a polycistronic mRNA, cleavage by an RNA-cleaving enzyme that recognizes the RNA recognition sequence separates the two protein coding regions into two different mRNA molecules therefore allowing for the translation of each gene in an independent manner (FIG. 6). In some instances, a recognition nucleotide sequence is positioned between a plurality of coding regions.

In some instances, a recognition nucleotide sequence is positioned between a first non-coding region and a second non-coding region. In some instances, a recognition nucleotide sequence is positioned between a plurality of non-coding regions. Suitable types of non-coding regions can include, but are not limited to, short-hairpin RNAs (shRNAs), microRNAs (miRNAs), small interfering RNAs (siRNA), long non-coding RNA (lncRNA), endogenous siRNAs (endo-siRNAs), transfer RNA (tRNA), small nucleolar RNA (snoRNA), ribosomal RNA (rRNA), piwi-interacting RNA (piRNA), small nuclear RNA (snRNA), trans-acting small interfering RNA (tasiRNA), repeat associated small interfering RNA (rasiRNA), and vault RNA (vRNA).

In some embodiments, the recognition nucleotide sequence encoding an RNA recognition sequence is positioned proximal to an insertion site (defined above) for the insertion of a sequence of interest. A sequence of interest can be any nucleotide sequence. In some embodiments, the sequence of interest is a regulatory element (defined above). In some embodiments, the sequence of interest is a promoter (defined above). In some embodiments, the sequence of interest is a coding region that encodes a reporter protein such as a fluorescent protein (e.g., a green fluorescent protein, a yellow fluorescent protein, a red fluorescent protein, a blue fluorescent protein, a far-red fluorescent protein, and the like), an enzyme (luciferase, β-galactosidase, β-glucuronidase, peroxidase, and the like), and the like. In some instances, the sequence of interest is an RNA sequence.

In some embodiments, a subject recombinant expression vector has two or more recognition nucleotide sequences encoding an RNA recognition sequence. In such a case, the multiple RNA recognition sequences can be the same such that they are cleaved by the same RNA-cleaving enzyme or they can be different such that they are cleaved by different RNA-cleaving enzymes. In some embodiments, the recombinant expression vector has two or more insertion sites for the insertion of a sequence of interest. As such the same or different sequences of interest can be inserted into each insertion site.

As used herein, when one sequence is proximal to another, it is meant that less than about 500 nucleotides are disposed between the two sequences. For example, a first sequence is proximal to a second sequence if less than about 500 nucleotides (e.g., less than about 400 nucleotides, less than about 300 nucleotides, less than about 200 nucleotides, less than about 150 nucleotides, less than about 100, less than about 80, less than about 50, less than about 40, less than about 30, less than about 20, less than about 15, less than about 10, less than about 5, or zero nucleotides) are disposed between the 3' end of the first sequence and the 5' end of the second sequence.

In some embodiments, a recognition nucleotide sequence is positioned proximal to an insertion site. As such, less than about 500 nucleotides are disposed between the recognition nucleotide sequence and the insertion site. For example, less than about 500 nucleotides, less than about 400, less than about 300, less than about 200, less than about 150, less than about 100, less than about 80, less than about 50, less than about 40, less than about 30, less than about 20, less than about 15, less than about 10, less than about 5, or zero nucleotides are disposed either: (i) between the 3' end of the recognition nucleotide sequence and the 5' end of the insertion site or (ii) between the 3' end of the insertion site and the 5' end of the recognition nucleotide sequence.

In some embodiments, a recognition nucleotide sequence is positioned proximal to a regulatory element. As such, less than about 500 nucleotides are disposed between the recognition nucleotide sequence and the regulatory element. For example, less than about 500 nucleotides, less than about 400, less than about 300, less than about 200, less than about 150, less than about 100, less than about 80, less than about 50, less than about 40, less than about 30, less than about 20, less than about 15, less than about 10, less than about 5, or zero nucleotides are disposed either: (i) between the 3' end of the recognition nucleotide sequence and the 5' end of the regulatory element or (ii) between the 3' end of the regulatory element and the 5' end of the recognition nucleotide sequence.

In some embodiments, a recognition nucleotide sequence is positioned proximal to a coding region. As such, less than about 500 nucleotides are disposed between the recognition nucleotide sequence and the coding region. For example, less than about 500 nucleotides, less than about 400, less than about 300, less than about 200, less than about 150, less than about 100, less than about 80, less than about 50, less than about 40, less than about 30, less than about 20, less than about 15, less than about 10, less than about 5, or zero nucleotides are disposed either: (i) between the 3' end of the recognition nucleotide sequence and the 5' end of the coding region or (ii) between the 3' end of the coding region and the 5' end of the recognition nucleotide sequence.

A nucleotide sequence that encodes a transcript containing a subject RNA recognition sequence, or encoding a subject RNA-cleaving enzyme (e.g., a subject sequence-specific, enzymatically active endonuclease; a subject sequence-specific, enzymatically inactive endonuclease, etc.) can be operably linked to a transcription control element (e.g., a promoter, an enhancer, etc.). In some embodiments, a subject recombinant expression vector has a promoter that is positioned 5' of the recognition nucleotide sequence, wherein the promoter is operably linked to the recognition nucleotide sequence. An insertion site for the insertion of a sequence of interest can also be operably linked to a promoter such that the promoter will affect the transcription of the inserted sequence as well the recognition nucleotide sequence.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter, a pagC promoter, and the like; a sigma70 promoter, e.g., a consensus sigma70 promoter; a stationary phase promoter, e.g., a dps promoter, an spy promoter, and the like; a promoter derived from the pathogenicity island SPI-2; an actA promoter; an rpsM promoter; a tet promoter; an SP6 promoter; and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator.

Nucleotides Encoding RNA-Cleaving Enzymes

As used herein the term "endonuclease" means a protein enzyme that cleaves (or hydrolyzes) phosphodiester bonds within a polynucleotide chain. Endonuclease is an inclusive term that refers both to enzymes that catalyze the endonucleolytic cleavage of DNA and to enzymes that catalyze the endonucleolytic cleavage of RNA. An "endoribonuclease" or an "RNA-cleaving enzyme" is an enzyme that cleaves (or hydrolyzes) phosphodiester bonds within an RNA molecule. Thus, for example, an enzyme that catalyzes the endonucleolytic cleavage of RNA can be referred to as an endonuclease, an endoribonuclease, or an RNA-cleaving enzyme (e.g., Csy4 endonuclease, Csy4 endoribonuclease, Csy4 RNA-cleaving enzyme).

The term "RNA-cleaving enzyme" is an inclusive term that refers to any molecule (e.g., nucleic acid, polypeptide, etc.) that catalyzes the cleavage/hydrolysis of a phosphodiester bond of an RNA molecule. As such, the term RNA-cleaving enzyme encompasses both RNA-cleaving proteins (e.g., Csy4, Cas5 family members, Cas6 family members) as well as self-cleaving nucleotide sequences (e.g., tRNA sequences, ribozymes, etc.). A "sequence specific" RNA-cleaving enzyme (e.g., Csy4 endoribonuclease, Cas6 family endoribonuclease, Cas5 family endoribonuclease, T7 RNAse III, self-cleaving ribozyme, etc.) is a selective RNA-cleaving enzyme that selectively cleaves only RNA molecules containing a specific RNA recognition sequence. The term "endoribonuclease" is used to refer specifically to an RNA-cleaving protein enzyme and a sequence specific endoribonuclease is an RNA-cleaving protein enzyme that selectively cleaves only RNA molecules containing an appropriate RNA recognition sequence.

Suitable RNA-cleaving enzymes include but are not limited to self-cleaving ribozymes, which can be placed in tandem to increase efficiency (e.g., small Tobacco RingSpot Virus hammerhead ribozyme (sTRSV); Avacado SunBlotch Virus ribozyme (ASBV); beta-globin co-transcriptional ribozyme; bacterial group II introns; glucosamine-6-phosphate ribozyme; group I/II/III introns; hepatitis delta virus ribozyme; CPEB3 ribozyme; VS ribozyme; the group of hairpin ribozymes such as chicory yellow mottle virus ribozyme and arabis mosaic virus ribozyme; the group of hammerhead ribozymes such as eggplant viroid ribozyme, velvet tobacco mottle virus ribozyme, and cherry small circular viroid-like ribozyme; etc.), sequence-specific RNase III enzymes (e.g., RNase III from T7 phage), sequence specific CRISPR-related endoribonucleases (e.g., the Csy4 endoribonuclease and its homologs as set forth in FIG. 10 and/or FIG. 11 (the amino acid sequences set forth in SEQ ID NOs: 1-55 and 147-149), the CRISPR-related CasE enzyme and its homologs as set forth in FIG. 13 (the amino acid sequences set forth in SEQ ID NOs: 134-139), the CRISPR-related Cas6 enzyme and its homologs as set forth in FIG. 14 (the amino acid sequences set forth in SEQ ID NOs: 140-144), Type I CRISPR system endoribonucleases, Type II CRISPR system endoribonucleases, Type III CRISPR system endoribonucleases, Cas5 family members, Cas6 family members, etc.), other RNases that do not cause RNA degradation (e.g., RNase P and its homologs as set forth in FIG. 15 (the amino acid sequence set forth in SEQ ID NO: 145)), etc.

Examples of suitable RNA-cleaving enzymes are set forth in FIGS. 10-14 (SEQ ID NOs: 1-55, 147-149, 132-133, 134-139, and 140-144). In some embodiments, a subject RNA-cleaving enzyme is a Csy4 endoribonuclease, wherein the Csy4 endoribonuclease comprises an amino acid sequence having at least about 75% amino acid sequence identity to any one of the amino acid sequences depicted in FIG. 10 and/or FIG. 11 (identity to the amino acid sequence set forth in one of SEQ ID NOs: 1-55 and 147-149). In some embodiments, a subject nucleic acid comprises a nucleotide sequence encoding a polypeptide having at least about 75%, at least about 80%, at least about 85%, at least about 90%, at least about 95%, at least about 98%, at least about 99%, at least about 99.5%, or 100%, with an amino acid sequence set forth in FIG. 10, FIG. 11, and/or FIG. 12 (identity to the amino acid sequence set forth in one of SEQ ID NOs: 1-55, 147-149, and 132-133). In some embodiments, a subject nucleic acid comprises a nucleotide sequence encoding a polypeptide having at least about 75%, at least about 80%, at least about 85%, at least about 90%, at least about 95%, at least about 98%, at least about 99%, at least about 99.5%, or 100%, with an amino acid sequence set forth in FIG. 10, FIG. 11, FIG. 12, FIG. 13, and/or FIG. 14 (identity to the amino acid sequence set forth in one of SEQ ID NOs: 1-55, 147-149, 132-133, 134-139, and 140-144).

In some instances, a subject RNA-cleaving enzyme (e.g., Csy4, Cas6, Cas5, CasE) comprises about 10, 15, 20, 25, 30, 35, 40, 45, 50, 55, 60, 65, 70, 75, 80, 85, 90, 95, or 100% sequence identity to a RNA-cleaving enzyme (Csy4, Cas6, Cas5, CasE).

In some embodiments, a subject nucleic acid comprises a nucleotide sequence encoding a variant Csy4 polypeptide (e.g., see SEQ ID NOs: 132-133). As described above, one suitable variant of the Csy4 endoribonuclease has a His29 to Ala29 amino acid substitution, which renders the endonuclease enzymatically inactive in the absence of imidazole, but enzymatically active in the presence of imidazole (see WO2011143124, incorporated here in full by reference). As such, the His29 to Ala29 variant of the Csy4 endoribonuclease is activatable (e.g., by contacting the variant Csy4 endoribonuclease with imidazole).

A suitable RNA-cleaving enzyme can comprise a heterologous polypeptide and such an RNA-cleaving enzyme can therefore be considered a fusion protein (also referred to herein as a chimeric RNA-cleaving enzyme). In some embodiments, a chimeric RNA-cleaving enzyme is generated by fusing an RNA-cleaving enzyme polypeptide (e.g., a Csy4, Cas6, CasE, etc., or a variant thereof), or a nucleic acid encoding an RNA-cleaving enzyme polypeptide, with a heterologous sequence that provides for subcellular localization (e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag for ease of tracking or purification (e.g., a fluorescent protein, e.g., green fluorescent protein (GFP), YFP, RFP, CFP, mCherry, tdTomato, and the like; a HIS tag, e.g., a 6×His tag; a hemagglutinin (HA) tag; a FLAG tag; a V5 tag; a Myc tag; and the like). In some embodiments, the heterologous sequence can provide for increased or decreased stability Vectors An expression vector can include a selectable marker, an origin of replication, and other features that provide for replication and/or maintenance of the vector. Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus; adeno-associated virus; SV40; herpes simplex virus; human immunodeficiency virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Cells

The present disclosure provides isolated genetically modified host cells (e.g., in vitro cells) that are genetically modified with a subject nucleic acid. In some embodiments, a subject isolated genetically modified host cell can produce a subject sequence-specific endoribonuclease (e.g., a subject sequence-specific, enzymatically active endoribonuclease; a subject sequence-specific, enzymatically inactive endoribonuclease).

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. Examples of *Salmonella* strains which can be employed in the present disclosure include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Compositions

The present disclosure provides compositions comprising a target RNA comprising an RNA recognition sequence that is recognized by an RNA-cleaving enzyme; and an RNA-cleaving enzyme. A subject composition can comprise, in addition to a subject target RNA comprising an RNA recognition sequence that is recognized by an RNA-cleaving enzyme and an RNA-cleaving enzyme, a one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; a nuclease inhibitor; and the like.

Methods

The present disclosure provides a method of modifying the activity of a target RNA. As used herein, the "activity" (e.g., the activity of a target RNA) is used as in inclusive term to refer to all biological activities associated with the RNA molecule. As such, the term "activity" can refer to the function (e.g. message-encoding information carrier, mRNA; message translator, tRNA; antisense regulator, microRNA or siRNA; ribosomal component, rRNA; etc.) of any type of RNA (tRNA, rRNA, non-coding RNA, mRNA, etc) as well as to the production, use, or stability of the RNA (e.g., transcription, translation, degradation). The methods disclosed herein involve contacting the target RNA with an RNA-cleaving enzyme, where the target RNA comprises an RNA recognition sequence that is recognized by the RNA-cleaving enzyme and is positioned between a regulatory element and a coding region, between a first regulatory element and a second regulatory element, between a first coding region and a second coding region, or within a coding region. As such, the RNA-cleaving enzyme cleaves the target RNA, thereby modifying the activity of the target RNA.

FIG. 2, FIG. 3a, FIG. 6a, FIG. 8a, FIG. 9a, FIG. 9b, and FIG. 9c provide schematic depictions of exemplary methods of modifying the activity of a target RNA. In some embodiments the target RNA is an mRNA and modifying the activity of the target RNA refers to modifying the translation of the target RNA. In such cases, the disclosed methods can increase RNA activity (e.g., protein production rate) up to 100-fold. For example, the cleavage of a target RNA using methods disclosed herein can modify the activity of the target RNA (e.g., increase protein production rate) up to about 80-fold, up to about 60-fold, up to about 40-fold, up to about 20-fold, up to about 10-fold, up to about 5-fold, up to about 4-fold, up to about 3-fold, up to about 2-fold, or up to about 1.5-fold, compared to the activity of the uncleaved target RNA. In some cases, the cleavage of a target RNA using methods disclosed herein can increase the activity of the target RNA (e.g., increase protein production rate) by at least 2-fold, at least 5-fold, at least 10-fold, at least 25-fold, at least 50-fold, at least 80-fold, at least 100-fold, or more than 100-fold, compared to the activity of the uncleaved target RNA. Likewise, the disclosed methods can decrease RNA activity (e.g., protein production rate) by about 100-fold. For example, the cleavage of a target RNA using methods disclosed herein can modify the activity of the target RNA (e.g., decrease protein production rate) by about 80-fold, by about 60-fold, by about 40-fold, by about 20-fold, by about 10-fold, by about 5-fold, by about 4-fold, by about 3-fold, by about 2-fold, or by about 1.5-fold as compared to the activity of the uncleaved target RNA.

Figure 2:
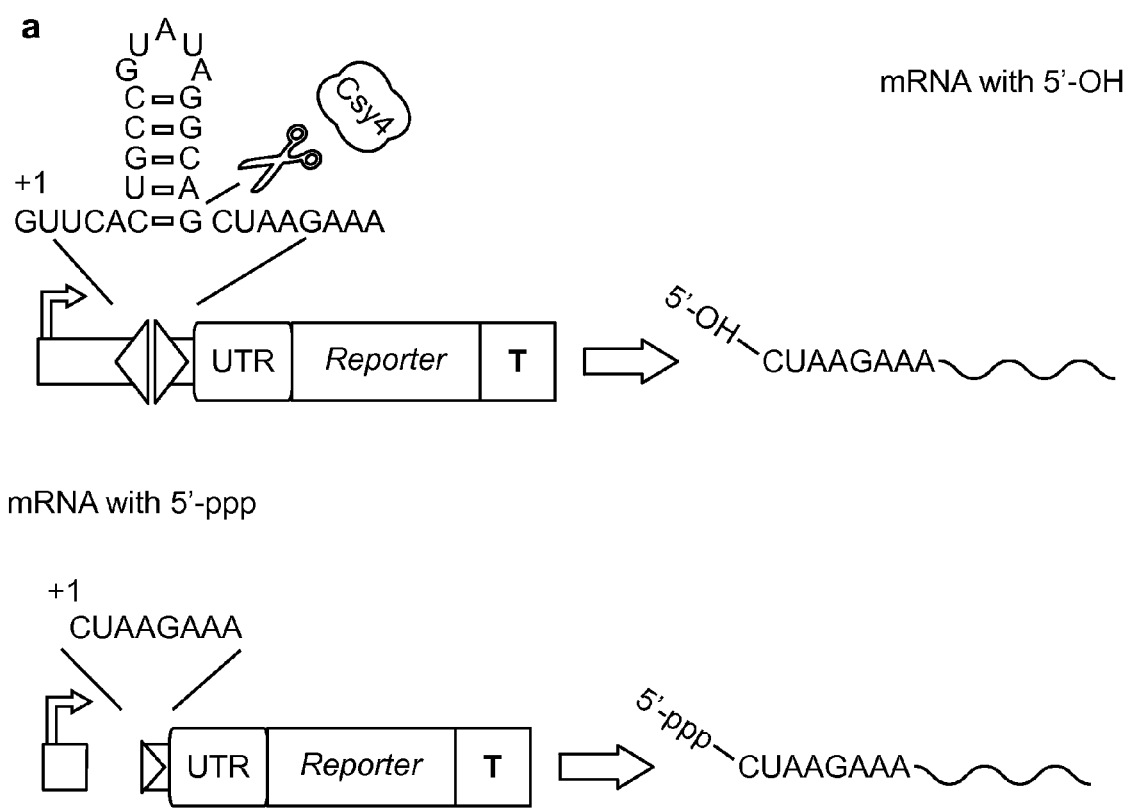
FIG. 2a depicts two libraries of mRNAs that were constructed. One consists of six reporters combined from three RBSs and two fluorescent proteins (Methods) with an intact 28-nt cleavage site inserted between the promoter +1 site and the RBSs. The other consists of same six reporters with 8-nt residual sequence inserted between the promoter +1 site and the RBSs. After cleavage, the two libraries generate mRNAs with the same composition but different 5' modifications, 5'-OH (hydroxyl) in the first library and 5'-PPP (triple phosphate) in the second library. (SEQ ID NO: 56).
FIG. 2b displays a comparison of the two libraries for corresponding reporter gene expression. In all cases, 5' OH-mRNAs exhibited higher gene expression as assessed by fluorescence.
Figure 2:
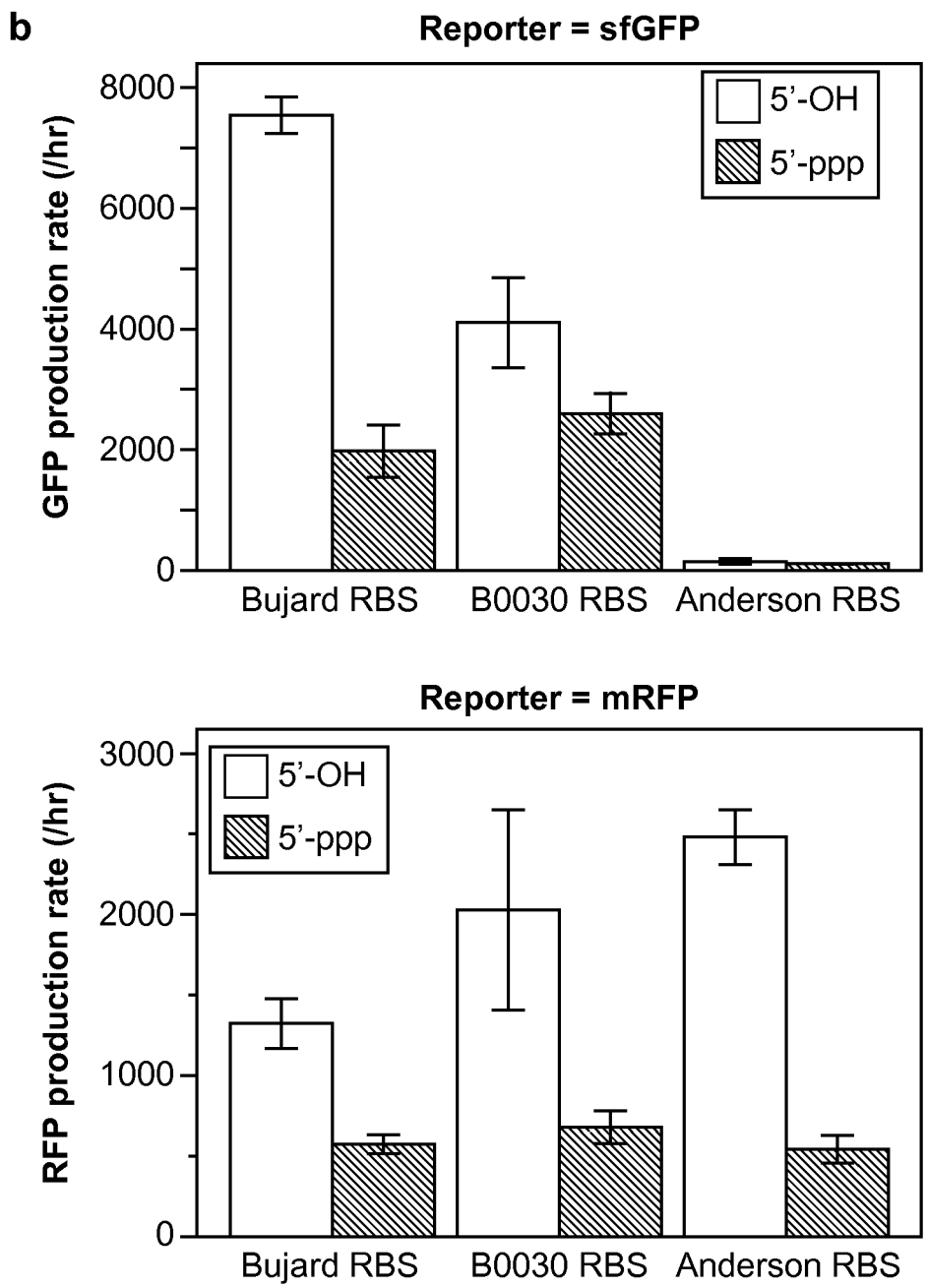

In FIG. 2, a target RNA is modified to include an exemplary Csy4 RNA recognition sequence (e.g., GUUCA-CUGCCGUAUAGGCAG (SEQ ID NO: 146); or SEQ ID NO: 56) in the 5' untranslated region (5' UTR) upstream of other 5' UTR sequence. Cys4 expression in the host cell leads to binding and cleavage of the RNA substrate (i.e., the target RNA). The cleaved RNA now lacks the sequences that were position 5' of the RNA recognition sequence.

In FIG. 3a, a target RNA is modified to include an RNA recognition sequence positioned in the 5' UTR disposed between other 5' UTR sequences and a Ribosomal Binding Site (RBS). Expression of an RNA-cleaving enzyme (e.g., Csy4) that recognizes the RNA recognition sequence in the host cell leads to binding and cleavage of the RNA substrate (i.e., the target RNA). The cleaved RNA now lacks the sequences that were position 5' of the RNA recognition sequence and translation of the depicted reporter gene is independent of the 5' UTR sequences that were removed (FIGS. 3b-3g and FIGS. 5a-5i).

In FIG. 6a a target RNA is modified to include multiple RNA recognition sequences positioned in a polycistronic mRNA to border (on the 5' end and the 3' end) each gene (e.g., reporter gene such as Red Fluorescent Protein, Green Fluorescent Protein, etc.) and its associated RBS. Expression of an RNA-cleaving enzyme (e.g., Csy4) that recognizes the RNA recognition sequence in the host cell leads to binding and cleavage of the RNA substrate (i.e., the target RNA). The cleaved RNA molecules will contain an RBS associated with a gene and translation of each depicted reporter gene is independent of other sequences present on the polycistron (FIGS. 6b-6e).

In FIG. 8a a target RNA is modified to include multiple RNA recognition sequences positioned in a polycistronic mRNA to border (on the 5' end and the 3' end) each gene (e.g., reporter gene such as Red Fluorescent Protein, Green Fluorescent Protein, etc.) and its associated regulatory element. Expression of an RNA-cleaving enzyme (e.g., Csy4) that recognizes the RNA recognition sequence in the host cell leads to binding and cleavage of the RNA substrate (i.e., the target RNA). The cleaved RNA molecules will contain a regulatory element associated with a gene. The translation of each depicted reporter gene is regulated by the associated regulatory element and is independent of other sequences present on the polycistron (FIGS. 8a-8d).

In FIG. 9a a target RNA is modified to include an RNA recognition sequence positioned between two different regulatory elements (a transcription-regulating element and a translation-regulating element). Expression of an RNA-cleaving enzyme (e.g., Csy4) that recognizes the RNA recognition sequence in the host cell leads to binding and cleavage of the RNA substrate (i.e., the target RNA) and one of the cleaved RNA molecules will contain a single translation-regulating regulatory element associated with the reporter gene. Translation of the reporter gene is then regulated by the associated regulatory element and is independent of other sequences present on the uncleaved RNA transcript (FIG. 9a).

In FIG. 9b, a target RNA is modified to include one of various different RNA recognition sequences positioned 5' of a reporter gene and an associated translation-regulating regulatory element. The present of the appropriate RNA-cleaving enzyme in the host cell leads to binding and cleavage of the RNA substrate (i.e., the target RNA). One of the cleaved RNA molecules will contain a single translation-regulating regulatory element associated with the reporter gene. Translation of the reporter gene is then regulated by the associated regulatory element (e.g., translation can be inhibited by the addition of a translation-blocking antisense RNA) and is independent of other sequences present on the uncleaved RNA transcript. The method depicted is successful for self-cleaving ribozyme sequences when present in tandem, for RNase III from phage T7 when the appropriate RNA recognition sequence is used, and for Csy4 endoribonuclease when the appropriate RNA recognition sequence is used (FIG. 9b).

In FIG. 9c, a target RNA is modified to include an RNA recognition sequence positioned within a coding region (e.g., within the protein coding region of a reporter gene). Expression of an RNA-cleaving enzyme (e.g., Csy4) that recognizes the RNA recognition sequence in the host cell leads to binding and cleavage of the RNA substrate (i.e., the target RNA). Neither of the cleaved RNA molecules will contain sequences appropriate for translation of the reporter gene; gene expression is therefore inhibited when a functional/active RNA-cleaving enzyme (e.g., Csy4) is present (FIG. 9c).

For example, in some embodiments, the present disclosure provides a method of modifying the activity of a target RNA in a cell, where the method involves introducing into the cell a target RNA, where the target RNA comprises an RNA recognition sequence that is recognized by an RNA-cleaving enzyme and is positioned between a regulatory element and a coding region, between a first regulatory element and a second regulatory element, between a first coding region and a second coding region, or within a coding region; and where the cell comprises the RNA-cleaving enzyme and the RNA-cleaving enzyme cleaves the target RNA.

In such embodiments, the host cell is genetically modified with a recombinant expression vector comprising a nucleotide sequence encoding an enzymatically active sequence-specific RNA-cleaving enzyme (e.g., Csy4 endoribonuclease) that catalyzes cleavage at a RNA recognition site in a substrate (i.e., target) RNA. In some embodiments, the enzyme-encoding nucleotide sequence is operably linked to an inducible promoter and upon activation of the inducible promoter, the enzyme is produced in the cell and cleaves said target RNA from a precursor RNA. In some cases, the target RNA species is a regulatory RNA. In some cases, cleavage of said target RNA from a precursor RNA inactivates the precursor RNA.

A suitable sequence-specific RNA-cleaving enzyme is a sequence-specific endoribonuclease. Endoribonucleases that are suitable for use in a subject method of regulating production of a target RNA include endoribonucleases that bind to and cleave a substrate polyribonucleotide in a sequence-specific manner include enzymatically active polypeptides (e.g., active and/or conditionally active) that have at least about 85%, at least about 90%, at least about 95%, at least about 98%, at least about 99%, or 100%, amino acid sequence identity to an amino acid sequence set forth in FIG. 10, 11, or 12 (Csy4 amino acid sequences) (identity to the amino acid sequence set forth in one of 1-55, 147-149, and 132-133).

Endoribonucleases that are suitable for use in a subject method of regulating production of a target RNA include endoribonucleases that bind to and cleave a substrate polyribonucleotide in a sequence-specific manner include enzymatically active polypeptides and that differ from an amino acid sequence set forth in FIG. 10, 11, or 12 by from 1 to 20 (e.g., 1, 2, 3, 4, 5, 6, 7, 8, 9, 10, 11, 12, 13, 14, 15, 16, 17, 18, 19, or 20) amino acid substitutions and/or insertions and/or deletions.

Exemplary suitable inducible promoters and agents that can induce them are described above. The target RNA can be a regulatory RNA. Regulator RNAs are well known in the art and include, e.g., micro-RNAs, short hairpin RNAs (shRNAs), and the like. The cell (e.g., genetically modified host cell) of the method can be an in vitro cell, e.g., a prokaryotic cell, or a eukaryotic cell (e.g., a mammalian cell, including primary cells, transformed cell lines, and the like). The genetically modified host cell can be an in vivo cell. In some embodiments, the in vivo cell is a non-human cell.

The cell (e.g., genetically modified host cell) can be a cell of a multicellular organism (or can be obtained from a cell of a multicellular organism). The cell (e.g., genetically modified host cell) can be a cell obtained from or present in an organism of any of the six kingdoms, e.g., Bacteria (e.g., Eubacteria); Archaebacteria; Protista; Fungi; Plantae; and Animalia. Suitable organisms include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e.g, Apicomplexa, Myxozoa, Microsporidia), and ciliates (e.g., Paramecium). Suitable organisms include members of the kingdom Fungi, including, but not limited to, members of any of the phyla: Basidiomycota (club fungi; e.g., members of *Agaricus, Amanita, Boletus, Cantherellus*, etc.); Ascomycota (sac fungi, including, e.g., *Saccharomyces*); Mycophycophyta (lichens); Zygomycota (conjugation fungi); and Deuteromycota. Suitable organisms include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable organisms include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms); Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Thus, e.g., a suitable cell (e.g., genetically modified host cell) can be a cell obtained from or present in a protozoan, a plant, a fungus, an algal cell, a yeast, a reptile, an amphibian, a mammal, a marine microorganism, a marine invertebrate, an arthropod, an isopod, an insect, an arachnid, an archaebacterium, and a *eubacterium*.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

The cell (e.g., genetically modified host cell) can be a cell obtained from or present in a non-human embryo, e.g., a *Drosophila* embryo; a zebrafish embryo; a mouse embryo; etc. The cell (e.g., genetically modified host cell) can be a stem cell, e.g., an in vitro stem cell; a non-human stem cell; etc. Suitable stem cells include embryonic stem cells, adult stem cells, and induced pluripotent stem (iPS) cells. The cell (e.g., genetically modified host cell) can be a eukaryotic single-cell organism, a somatic cell, a germ cell, etc.

Kits

The present disclosure provides kits for carrying out a subject method. A subject kit can include a recombinant expression vector comprising a recognition nucleotide sequence encoding an RNA recognition sequence that is recognized by an RNA-cleaving enzyme and/or a recombinant expression vector comprising a nucleotide sequence that encodes an RNA-cleaving enzyme. A recombinant expression vector comprising a recognition nucleotide sequence encoding an RNA recognition sequence that is recognized by an RNA-cleaving enzyme, and a recombinant expression vector comprising a nucleotide sequence that encodes an RNA-cleaving enzyme are described in detail above. In some embodiments, a subject kit comprises a recombinant expression vector comprising both (i) a recognition nucleotide sequence encoding an RNA recognition sequence that is recognized by an RNA-cleaving enzyme and (ii) a nucleotide sequence that encodes an RNA-cleaving enzyme.

A subject kit comprising a recombinant expression vector that comprises a recognition nucleotide sequence encoding an RNA recognition sequence that is recognized by an RNA-cleaving enzyme, can further include one or more additional reagents, where such additional reagents can be selected from: a recombinant expression vector comprising a nucleotide sequence that encodes an RNA-cleaving enzyme, a buffer for introducing expression vector into a cell; a wash buffer; a control reagent; a control expression vector or RNA recognition sequence-containing RNA transcript; a reagent for in vitro production of the target RNA, and the like. In some cases, a recombinant expression vector comprising a nucleotide sequence that encodes the RNA-cleaving enzyme encodes a variant RNA-cleaving enzyme that is enzymatically inactive in the absence of imidazole, and is enzymatically active in the presence of imidazole.

In some embodiments, a subject kit comprises: (i) a first recombinant expression vector comprising a recognition nucleotide sequence encoding an RNA recognition sequence that is recognized by an RNA-cleaving enzyme, wherein the recognition nucleotide sequence is positioned proximal to an insertion site for the insertion of a sequence of interest; and (ii) a second recombinant expression vector comprising a nucleotide sequence that encodes the RNA-cleaving enzyme. In some cases, the kit comprises: (i) a recombinant expression vector comprising: (a) a recognition nucleotide sequence encoding an RNA recognition sequence that is recognized by an RNA-cleaving enzyme, wherein the recognition nucleotide sequence is positioned proximal to an insertion site for the insertion of a sequence of interest, and (b) a nucleotide sequence encoding the RNA-cleaving enzyme; and (ii) a reagent for reconstitution and/or dilution. In some cases, the kit comprises a recombinant expression vector comprising a nucleotide sequence encoding a self-cleaving regulatory element positioned proximal to an insertion site for the insertion of a sequence of interest.

In some embodiments, a subject kit comprises: (i) a recombinant expression vector comprising a recognition nucleotide sequence encoding an RNA recognition sequence that is recognized by an RNA-cleaving enzyme, wherein the recognition nucleotide sequence is positioned proximal to an insertion site for the insertion of a sequence of interest; and (ii) a genetically modified cell that can produce an RNA-cleaving enzyme (e.g., a subject sequence-specific, enzymatically active endoribonuclease, e.g., a Csy4 endoribonuclease or at least one of its homologs as set forth in FIG. 10 and/or FIG. 11 (SEQ ID NOs: 1-55 and 147-149), a CRISPR-related CasE enzyme or at least one of its homologs as set forth in FIG. 13 (SEQ ID NOs: 134-139), a CRISPR-related Cas6 enzyme or at least one of its homologs as set forth in FIG. 14 (SEQ ID NOs: 140-144), etc.; a subject sequence-specific, enzymatically inactive endoribonuclease, e.g., a variant Csy4 polypeptide that is enzymatically inactive in the absence of imidazole, but enzymatically active in the presence of imidazole; a Cas5 family member, a Cas6 family member, a Type I CRISPR system endoribonuclease, a Type II CRISPR system endoribonuclease, a Type III CRISPR system endoribonuclease etc.).

A kit can comprise vector comprising a recognition nucleotide sequence encoding an RNA recognition sequence that is recognized by an RNA-cleaving enzyme, wherein the recognition nucleotide sequence is positioned proximal to sequence encoding a coding region (e.g., mRNA, viral RNA). In some instances, a kit can comprise vector comprising a recognition nucleotide sequence encoding an RNA recognition sequence that is recognized by an RNA-cleaving enzyme, wherein the recognition nucleotide sequence is positioned proximal to sequence encoding a coding region and/or non-coding region (e.g., miRNA, siRNA, shRNA, etc).

In some instances, a kit comprises a plurality of vectors each comprising a nucleotide sequence encoding an RNA recognition sequence that is recognized by an RNA-cleaving enzyme, wherein the RNA recognition sequence is positioned proximal to a sequence encoding a coding region and/or a non-coding region, wherein each coding region and/or non-coding region differs by at least 1 nucleotide. In such cases, the kit can be referred to as a library.

A library can comprise from about 10 individual members to about $10^{12}$ individual members; e.g., a library can comprise from about 10 individual members to about $10^2$ individual members, from about $10^2$ individual members to about $10^3$ individual members, from about $10^3$ individual members to about $10^5$ individual members, from about $10^5$ individual members to about $10^7$ individual members, from about $10^7$ individual members to about $10^9$ individual members, or from about $10^9$ individual members to about $10^{12}$ individual members. An "individual member" of a library differs from other members of the library in the nucleotide sequence of the coding region and/or non-coding region of the vector.

A subject kit can include one or more positive and/or negative controls. A positive control can be any component that provides a positive result when used in the subject methods. A negative control can be any component that provides a negative result when used in the subject methods. An example of a positive control includes but is not limited to a positive control recombinant expression vector. A subject positive control recombinant expression vector can contain, for example, a recognition nucleotide sequence encoding an RNA recognition sequence that is recognized by an RNA-cleaving enzyme, wherein the recognition nucleotide sequence is positioned (a) between a regulatory element and a coding region, (b) between a first regulatory element and a second regulatory element, (c) between a first coding region and a second coding region, or (d) within a coding region. The coding region of a subject positive control can be, for example, a reporter protein (e.g., a fluorescent protein, an enzyme, etc.).

An example of a negative control includes but is not limited to a negative control recombinant expression vector. A subject negative control recombinant expression vector can contain, for example, a modified recognition nucleotide sequence encoding a modified RNA recognition sequence that is not recognized by an RNA-cleaving enzyme, wherein the modified recognition nucleotide sequence is positioned (a) between a regulatory element and a coding region, (b) between a first regulatory element and a second regulatory element, (c) between a first coding region and a second coding region, or (d) within a coding region. The coding region of a subject negative control can be a reporter protein (e.g., a fluorescent protein, an enzyme, etc.).

Components of a subject kit can be in separate containers; or can be combined in a single container. Any of the above-described kits can further include one or more additional reagents, where such additional reagents can be selected from: a dilution buffer; a reconstitution solution; a wash buffer; a control reagent; a control expression vector or RNA polynucleotide; a reagent for in vitro production of the site-directed modifying polypeptide from DNA, and the like.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The vectors, compositions, methods, and kits disclosed herein facilitate the predictable activity (in new, previously untested contexts) of untested combinations and assemblies of RNA regulatory elements. Previous methods to identify combinations of promoters and regulatory elements to control gene expression in a new context have relied upon library-based screening techniques. To do so, one or more regulatory elements and/or promoters are combined and/or mutated to generate a library of combinations of various elements. However, the selection process to identify combinations that perform as desired in the new context is time-consuming, cost-inefficient, and the whole process often needs to be repeated for each new context.

The vectors, compositions, methods, and kits disclosed herein can be used to efficiently build new combinations and assemblies of RNA expression elements (e.g., promoters, regulatory elements, and translation units, etc.) in a way that avoids the unpredictability usually inherent in such combinations. The activity of the engineered systems follows predictable quantitative relationships. Because each element (together with the target molecule) is isolated after transcription, the methods, vectors, compositions, and kits disclosed herein allow the rational and predictable design of combinations of regulatory elements without the need for library-screening techniques. Thus, the methods, vectors, compositions, and kits disclosed herein find uses in the predictable control of gene expression in a variety of biological contexts.

For example, the vectors, compositions, methods, and kits disclosed herein find use in the field of protein engineering. As such, protein expression systems can be quickly and reliably constructed using previously characterized genetic parts. Because the methods described herein remove the unpredictability of combining elements that were characterized independently of each other, the process of trial and error is precipitously reduced, adding reliability and predictability in constructing a new expression system. Thus, the vectors, compositions, methods, and kits disclosed herein can be used for quantitatively altering the level of protein expression of a gene of interest in any expression system. (e.g., to increase or decrease protein production in order to crystallize the protein of interest for structure determination, e.g., X-ray crystallography, antigen production, etc.).

The vectors, compositions, methods, and kits disclosed herein find use in the field of metabolic engineering. Because protein levels can be efficiently and predictably altered by modifying RNA activity, as disclosed herein, the activity of metabolic pathways can be precisely controlled and tuned by controlling the level of specific enzymes within a metabolic pathway of interest. Metabolic pathways of interest include those used for chemical (fine chemicals, fuel, antibiotics, toxins, agonists, antagonists, etc.) and/or drug production. Because the vectors, compositions, methods, and kits disclosed herein provide an efficient way to construct predictable expression systems by reusing characterized genetic parts, they reduce the need to perform large scale library selection to optimize expression of various enzymes within a given pathway of interest.

Biosynthetic pathways of interest include but are not limited to (1) the mevalonate pathway (i.e., HMG-CoA reductase pathway) (converts acetyl-CoA to dimethylallyl pyrophosphate (DMAPP) and isopentenyl pyrophosphate (IPP), which are used for the biosynthesis of a wide variety of biomolecules including terpenoids/isoprenoids), (2) the non-mevalonate pathway (i.e., the "2-C-methyl-D-erythritol 4-phosphate/1-deoxy-D-xylulose 5-phosphate pathway" or "MEP/DOXP pathway" or "DXP pathway") (also produces DMAPP and IPP, instead by converting pyruvate and glyceraldehyde 3-phosphate into DMAPP and IPP via an alternative pathway to the mevalonate pathway), (3) the polyketide synthesis pathway (produces a variety of polyketides via a variety of polyketide synthase enzymes. Polyketides include naturally occurring small molecules used for chemotherapy (e.g., tetracyclin, and macrolides) and industrially important polyketides include rapamycin (immunosuppressant), erythromycin (antibiotic), lovastatin (anticholesterol drug), and epothilone B (anticancer drug)), (4) fatty acid synthesis pathways, (5) the DAHP (3-deoxy-D-arabino-heptulosonate 7-phosphate) synthesis pathway, (6) pathways that produce potential biofuels (such as short-chain alcohols and alkane, fatty acid methyl esters and fatty alcohols, isoprenoids, etc.), etc.

The vectors, compositions, methods, and kits disclosed herein further find use in the investigation of polycistronic regulation, which is important and ubiquitous in prokaryotes. Many critical pathways, including those that can either produce valuable chemicals or produce toxins, involve polycistronic regulation. The strategies disclosed herein to refactor the wildtype polycistronic pathway and conditionally alter the activity of each individual cistron facilitates approaches to understand the biological underpinnings of polycistronic regulation. As such, by separating each cistron with an RNA recognition sequence, one can construct synthetic polycistronic regulatory systems by direct composition of multiple cistrons.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Materials and Methods

Strains and Media.

The *Escherichia coli* strain Top10 (Invitrogen) was used in all experiments. EZ rich defined media (EZ-RDM, Teknoka) was used as the growth media for in vivo fluorescence assays. The antibiotics used were 100 μg ml$^{-1}$ carbenicillin (Fisher) and 34 μg ml$^{-1}$ chloramphenicol (Acros). Culturing, genetic transformation and verification of transformation were done as previously described (Lucks et al. Proc. Natl. Acad. Sci. USA 108, 8617-8622 (2011)), using either AmpR or CmR as selectable markers. Low-salt (5 g/L) Luria Broth media (Sigma) was used for in vivo fluorescence assay of *B. subtilis* cells, with chloramphenicol as the selectable marker. Drop-out Mix Synthetic Complete Media (US Biological) was used for in vivo fluorescence assay of *Saccharomyces cerevisiae* cells, with uracil and methionine as auxotrophic selectable markers.

Plasmids Construction.

The Csy4 gene was cloned from the previous described vector pHMGWA-Csy4 vector (Haurwitz et al. *Science* 329, 1355-1358 (2010)) using primers 5'-TTCAAAAGATCTAAAGAGGAGAAAGGATCTATG-GACCACTACCTCGACATTCGCTT GCGA-3' (SEQ ID NO: 150) and 5'-TCCTTACTCGAGTTATCAGAACCA-GGGAACGAAACCTCC-3' (SEQ ID NO: 151), and inserted into a vector containing a tetracycline-inducible promoter P$_L$tetO-1 (Lutz et al. *Nucleic Acids Res.* 25, 1203-1210 (1997)), an ampicillin selectable marker and a ColE1 replication origin (pCsy4). A second vector containing a chloramphenicol selectable marker and a pSC101 replication origin (low copy) was used for cloning reporter constructs with or without the 28-nt Csy4 recognition site (5' GTTCACTGCCGTATAGGCAGCTAAGAAA 3' (SEQ ID NO: 152)) following standard cloning techniques (pControl library and pCRISPR library). In the case of complex cis-regulatory circuits, the vector containing a chloramphenicol selectable marker and a p15A replication origin was used. Detailed cloning procedures are described below.

Time Course Measurements.

The *E. coli* strain expressing the Csy4 protein, Top10-Csy4, was derived by transforming *E. coli* Top10 cells with pCsy4. Reporter plasmids were then transformed into the Top10-Csy4 cells, and plated on Difco LB+Agar plates containing 100 μg ml$^{-1}$ carbenicillin and 34 μg ml$^{-1}$ chloramphenicol, followed by incubation at 37° C. overnight. For the strains with random 30-nt UTRs, one single colony with a unique 30-nt UTR insertion (sequencing verified) was picked. In all other experiments, three single colonies of each construct were picked. The picked colonies were grown in 300 μL of EZ-RDM containing 100 μg ml$^{-1}$ carbenicillin and 34 μg ml$^{-1}$ chloramphenicol in 2 mL 96-well deep well plates (Costar 3960) overnight at 37° C. and 1000 r.p.m. in a high-speed Multitron shaker (ATR Inc.). One-μL of this overnight culture was then added to 149 μL of fresh EZ-RDM with the same antibiotic concentrations with or without 2 μM anhydrotetracycline (Fluka) supplemented. The temporal fluorescence expression from the lag growth phase to the stationary phase was monitored using a high-throughput fluorescence plate reader (Tecan M1000) for 24 hours. The excitation and emission wavelengths used for sfGFP were 485 nm and 510 nm; they were 587 nm and 610 nm for mRFP; the optical densities was measured at 600 nm (OD$_{600}$); the shaking period between consecutive measurements is 900 seconds with the shaking diameter of 2.5 mm.

Flow Cytometry and Analysis.

Flow cytometry measurements were carried out as previously described (Lucks et al. Proc. Natl. Acad. Sci. USA 108, 8617-8622 (2011)). The 300 μl cell cultures were grown for 8 hr to an OD600 of 0.3 in a Multitron shaker before measurement. Cells were sampled with a medium flow rate until 80,000 cells had been collected. Data were analyzed using FCS Express (De Novo Software) by gating on a polygonal region containing 75% cell population in the forward scatter-side scatter plot.

Northern Blotting.

Single colonies containing indicated genomic UTR-GFP reporter construct with or without Csy4 co-expression were grown in 5 ml EZ-RDM containing 100 μg ml$^{-1}$ carbenicillin, 34 μg ml$^{-1}$ chloramphenicol, and 2 μM anhydrotetracycline. Samples were pelleted by centrifugation at OD$_{600}$ of 0.6~0.7. Total RNA was extracted using the mirVana miRNA Isolation Kit (Ambion) as per the manufacturer's instructions. 5 μg of each total RNA sample were separated by electrophoresis on a 9% urea polyacrylamide gel. Samples were subsequently transferred to a nylon membrane (Hybond-N+, GE Healthcare) using a semi-dry transfer cell (Bio-Rad). The membrane was pretreated with ULTRAHyb-Oligo Hybridization Buffer (Ambion) and probed overnight with a 5'-[$^{32}$P]-radiolabeled DNA oligonucleotide complementary to the GFP open reading frame (5'-CTTCAG-CACGCGTCTTGTAGGTCCCGTCATC-3') (SEQ ID NO: 153). The membrane was washed twice with 2× saline-sodium citrate (SSC) buffer containing 0.5% sodium dodecyl sulfate (SDS) and visualized by phosphorimaging. The probe was stripped from the membrane by rocking the membrane in 200 ml pre-boiled 0.1% SDS at 66 C for 20 min. The membrane was pretreated with hybridization buffer again and then probed with a 5'-[$^{32}$P]-radiolabeled DNA oligonucleotide complementary to 16S ribosomal RNA (5'-CGTCAATGAGCAAAGGTATTAACTTTACTCCCTTC-CTCCCCGC-3') (SEQ ID NO: 154). After washing with 2×SSC as before, the membrane was visualized by phosphorimaging.

Construction of Random 30-Nucleotide UTR Libraries.

The last six nucleotides in the $\theta^{70}$ promoter J23119 (http://partsregistry.org/Part:BBa_J23119) was modified to be a BglII restriction enzyme site to enable BioBrick cloning (Shetty et al. J. Biol. Eng. 2, 5 (2008)). Inverse polymerase chain reaction (iPCR) was performed to insert various RBS sequences and the 28-nt cleavage elements (gttcactgccg-tataggcagctaagaaa) upstream of the sfGFP or mRFP genes (Huang, S. H. Mol. Biotechnol. 2, 15-22 (1994); Pédelacq et al. Nat. Biotechnol. 24, 79-88 (2006); Campbell et al. Proc. Natl. Acad. Sci. USA 99, 7877-7882 (2002)). The RBS sequences used are (with SD sequences in bold) listed in Table 2.

TABLE 2

| RBS | Sequences |
|---|---|
| Bujard RBS (Lutz et al. *Nucleic Acids Res.* 25, 1203-1210 (1997)) | gaattcattaaagaggagaaaggtacc (SEQ ID NO: 155) |
| B0030 RBS (partsregistry.org/Part: BBa_B0030) | tttaagaaggagatatacat (SEQ ID NO: 156) |
| Weiss RBS | attaaagaggagaaattaagc (SEQ ID NO: 157) |
| Anderson RBS (partsregistry.org/Part: BBa_J61100) | tctagagaaagagggacaaactagt (SEQ ID NO: 158) | iPCR-based saturation mutagenesis was performed to insert random 30-nt sequence either between the promoter and the RBS sequences, or between the promoter and the cleavage element. A common reverse primer 5'-NNNNNNNNNNAGATCTATTATACCTAGGACT-GAGCTAGCTG-3' (SEQ ID NO: 159) with different forward primers 5'-NNNNNNNNNNNNNNNNNNNN-overlap sequences-3' were used together for iPCRs, where N represents a random nucleotide. All primers were polyacrylamide gel electrophoresis (PAGE) purified. Random colonies were picked and sequence verified to make sure each colony contained a circuit with a unique 30-nt UTR insertion. All UTR insertions were computed to not contain explicit SD sequences using the RBS calculator with low efficient of translation initiation (Salis, H. M., Mirsky, E. A. & Voigt, C. A. Nat. Biotechnol. 27, 946-950 (2009)).

Cloning Genomic UTR Sequences into Reporter Plasmids.

The 5' UTR sequences of 12 genes from the *E. coli* MG1655 strain were obtained from the website ("ecocyc" followed by ".org"). The genes were randomly chosen from a list of genes with known transcriptional start sites which were labeled as "promoter experimentally verified". For all 12 UTRs except for lldP, iPCR was performed to insert the sequences into the plasmid containing the Bujard RBS and sfGFP gene with and without the cleavage element. For the lldP UTR, the CPEC cloning method was applied to insert its sequence into the circuits (Quan, J. & Tian, J. Nat. Protoc. 6, 242-251 (2011)). The information of the 12 UTRs is summarized in Table 3.

TABLE 3

| Gene | Length (nt) | Strand | Description |
|---|---|---|---|
| lacZp1 | 18 | −1 | β-D-galactosidase; The first gene in lacZYA operon; The first one of four promoters |
| serB | 19 | +1 | Phosphoserine phosphatase; SerB-RadA operon |
| chiA | 23 | −1 | Endochitinase |
| lacY | 31 | −1 | Lactose MFS transporter; The second gene in lacZYA operon |
| sodA | 31 | +1 | Superoxide dismutases |
| ompRp3 | 35 | −1 | OmpR response regulator; ompR-envZ operon; The third of multiple promoters |
| trpR | 36 | +1 | Tryptophan transcriptional repressor |
| glpA | 44 | +1 | The large unit of the glycerol-3-phosphate dehydrogenase; glpABC operon |
| rhoL | 45 | +1 | Rho operon leader peptide |
| CRISPRI | 53 | +1 | The leader sequence between the promoter P$_{CRISPRI}$ and the first repeat hairpin |
| fixA | 58 | +1 | Hypothetical flavoprotein subunit required for anaerobic carnitine metabolism; fixABCX operon |
| lldP | 90 | +1 | Lactate transporter; lldPRD operon |

Construction of the Twenty-Eight Combinatory Circuits.

These circuits were constructed by modifying the promoter sequences using either iPCR (for J23101, J23105, and J23110, "partsregistry" followed by ".org/Part: BBa_J23119") or CPEC cloning (for P$_{T7A1}$, P$_L$lacO-1 and P$_{A1}$lacO-1) (Higuchi et al. Nucleic Acids Res. 16, 7351-7367 (1988); Lutz et al. Nucleic Acids Res. 25, 1203-1210 (1997)). The promoter sequences are summarized in Table 4.

TABLE 4

| Promoter | Constitutive or Inducible | Sequence (bold underline - transcriptional start site; bold italic - operator sites) |
|---|---|---|
| J23119 | Constitutive | ttgacagctagctcagtcctaggtataata gat<u>c</u>t (SEQ ID NO: 160) |
| J23101 | Constitutive | tttacagctagctcagtcctaggtattata gat<u>c</u>t (SEQ ID NO: 161) |

TABLE 4-continued

| Promoter | Constitutive or Inducible | Sequence (bold underdline - transcriptional start site; bold italic - operator sites) |
|---|---|---|
| J23105 | Constitutive | tttacggctagctcagtcctaggtactata gatct (SEQ ID NO: 162) |
| J23110 | Constitutive | tttacggctagctcagtcctaggtacaata gatct (SEQ ID NO: 163) |
| P$_{T7A1}$ | Constitutive | cgaggccaacttaaagagacttaaaagatta atttaaaatttatcaaaaagagtattgactt aaagtctaacctataggatacttacagccat cgagaggga (SEQ ID NO: 164) |
| P$_L$lacO-1 | Inducible* | *ataaatgtgagcggataaca*ttgaca *ttgtgagcggataacaa*gatactgag cacatcagcaggacgcactgacc (SEQ ID NO: 165) |
| P$_{A1}$lacO-1 | Inducible* | aaaatttatcaaaaagagtgttgact *tgtgagcggataacaa*tgatacttagat tca*attgtgagcggataacaatttcacaca* (SEQ ID NO: 166) |

* Induced by 500 μM Isopropyl β-D-1-thiogalactopyranoside (IPTG)

Construction of Synthetic Operons.

Multiple-step BioBrick cloning was used to clone all operon circuits (Shetty et al. J. Biol. Eng. 2, 5 (2008)). As the first step, BioBrick cloning sites (BglII/BamHI with AatII) were introduced into the monocistronic plasmids using iPCR. As the second step, double digestions of the monocistronic plasmids were performed using either combination of AatII & BglII or combination of AatII & BamHI, and ligated the digestion production following standard protocols. As the third step, double digestions were performed again to assemble multiple cistrons onto a single plasmid. The same procedure was used to clone the bicistronic circuits with orthogonal IS10 cis-regulatory elements. The orthogonal IS10wt and IS10-9 sequences and their antisense RNAs are described in Table 5.

TABLE 5

| Description | Sequence (bold - Shine-Dalgarno sequences; bold italic - specificitysites) |
|---|---|
| IS10 wt UTR | *gcgaaaaa*tcaataaggagacaacaag (SEQ ID NO: 167) |
| IS10-9 UTR | *ggcttaaa*tcaataaggagacaacaag (SEQ ID NO: 168) |
| IS10 wt antisense RNA | tcgcacatcttgttgtctgattattga ttttt*cgc*gaaaccatttgat catatgacaagatgtgtatccaccttaa cttaatgattttaccaaaatcattagg ggattcatcag (SEQ ID NO: 169) |
| IS10-9 antisense RNA | tcgcacatcttgttgtctgattattga ttt*aagcc*gaaaccatttgatcatat gacaagatgtgtatccaccttaacttaa tgattttaccaaaatcattaggggatt catcag (SEQ ID NO: 170) |

Construction of Synthetic Circuits with Composite UTR Functions.

BioBrick cloning was used to assemble the PT181 with the IS10wt cis-regulatory elements onto a single sfGFP reporter plasmid. The antisense plasmids were constructed by inserting the cassette that expressed the PT181 antisense RNA under the promoter J23119 into pCsy4. This cassette was also inserted into the ColE1 vector harboring both csy4 gene and the IS10wt antisense RNA expression cassette to obtain a plasmid that expresses both antisense RNAs. The sequences of PT181 wt system are given in Table 6.

TABLE 6

| Description | Sequence |
|---|---|
| PT181 UTR | aacaaaataaaaggagtcgctcacgccctgaccaaagt ttgtgaacgacatcattcaaagaaaaaaacactgagttg tttttataatcttgtatatttagatattaaacgatattt aaatatacataaagatatatatttgggtgagcgattcct taaacgaaattgagattaaggagtcgctattttatgta taaaaacaatcatgcaaatcattcaaatcatttggaaaa tcacgatttagacaatttttctaaaaccggctactctaa tagccggttgtaa (SEQ ID NO: 171) |
| PT181 antisense RNA | atacaagattataaaaacaactcagtgtttifttattga atgatgtcgttcacaaactttggtcagggcgtgagcgac tccttttattt (SEQ ID NO: 172) |

Calculation of Protein Production Rates (PPRs)

The PPRs are calculated following the mathematical equation:

$$\frac{\partial P}{\partial t}\bigg|_{production,ss} = \frac{\partial F}{\partial OD}\bigg|_{ss} \cdot \mu \cdot \left(1 + \frac{\mu}{\nu}\right),$$

where P is the PPR, F is fluorescence, ν is protein maturation rate (per hour), and μ is growth rate (per hour). For each construct, the temporal curves of F and OD$_{600}$ (Leveau et al. J. Bacteriol. 183, 6752-6762 (2001)) were measured. The plot of the measured fluorescence F as a function of OD$_{600}$ showed a linear curve for all circuits tested during the exponential growth phase, which allowed us to calculate the slopes of this linear curve $$\left(\frac{\partial F}{\partial OD}\bigg|_{ss}\right).$$

The growth rate (μ) was during the exponential phase was calculated for each construct by plotting Log(OD$_{600}$) over time. The maturation constants for sfGFP and mRFP are $m_{sfGFP}$=7 h$^{-16}$ and $m_{mRFP}$=3.5 h$^{-17}$. The data was then analyzed using Mathematica 7 (Wolfram). The statistics were performed using Prism 5 (GraphPad Software), and the Spearman's rank correlation coefficients were calculated using Microsoft Excel.

Comparison of Efficacy of RNA Cleavage Elements

Different types of RNA cleavage elements were inserted between the tandem cis regulators (PT181 wt and IS10wt) as shown in FIG. 9b. The native IS10wt that is not fuse in tandem to PT181 wt was used as the control, which exhibits more than 10-fold ON/OFF range. Repression effects of the IS10wt antisense RNA on the tandem cis-regulatory systems was measured with each RNA cleavage element inserted (FIG. 9b). sTRSV, small Tabacco RingSpot Virus hammerhead ribozyme; ASBV, Avacado SunBlotch Virus ribozyme, T7 R1.1, the RNase III binding site from T7 phage; tRNA$^{Arg5}$, tRNA sequence for Arg5 (Hampel et al. Biochemistry 28, 4929-4933 (1989); Daròs et al. Proc. Natl. Acad. Sci. USA 91, 12813-12817 (1994); Dunn et al. Proc. Natl. Acåad. Sci. USA 70, 3296-3300 (1973); Espéli et al. J. Mol. Biol. 314, 375-386 (2001)). CRISPR allowed maximal repression and exhibited the highest efficacy of restoring riboregulator-UTR function.

Measurement of RNA Polymerase Dropoff Rate and Discussion.

Transcriptional polarity describes that operonic genes that are distant from the promoter are expressed at lower levels than proximal genes (Wek et al. J. Biol. Chem. 262, 15256-15261 (1987)). In the synthetic operon circuits described herein, with RNA processing (FIG. 6c), similar transcriptional polarity effects are expected because distant genes have lower frequencies of RNA polymerases readthrough compared to proximal genes. To verify this hypothesis, a mathematical model was developed that assumes that there is a simple linear relationship between the length of the first cistron and the expression of the second cistron. The average dropoff rate of RNA polymerase is postulated to be a constant (by ignoring detailed sequence, AT-content, and secondary structures, etc), and the assumed rate is $\lambda$ (per nucleotide, $0<\lambda<1$). Then the quantity $(1-\lambda)^L$ is proportional to expression of the second gene, where L is the length of the first gene. Taking logarithm on this quantity obtains a linear relationship $Log(RFP)=Log(1-\lambda)\cdot L$. The length of the first cistron (L) from the 3' end was shortened to 690, 594, 495, 393, 294, 198, 150, and 0 (bp), and measured the RFP expression from the second cistron (FIG. 6d-e). The experimental data were used for linear regression between RFP and L. Our results showed a linear correlation between these two quantities, whose slope equals to $Log(1-\lambda)$. The calculated 95% confidence interval (CI) of the average RNA polymerase dropoff rate was $\lambda=8.3\times10^{-4}\sim1.04\times10^{-3}$ (per nucleotide). Previous studies mostly focused on translational polarity (due to ribosome dropoff) and Rho-dependent transcriptional polarity (due to interaction between the Rho factor and the RNA polymerase) (Janssen et al. J. Mol. Biol. 394, 251-267 (2009); de Smit et al. J. Mol. Biol. 385, 733-747 (2009)). Our results are consistent with those reported either in E. coli or other organisms (Lim et al. Proc. Natl. Acad. Sci. USA 108, 10626-10631 (2011); Klumpp et al. Proc. Natl. Acad. Sci. USA 105, 18159-18164 (2008); Laing et al. Genome Biol. 7, R46 (2006)). While more experiments are required to determine the mechanistic causes of transcriptional polarity on the genome-wide scale, our results imply that control of RNA polymerase processivity could be used as one layer of gene regulation in bacteria genomes for coordinated and fine-tuned expression of multiple genes. Minimizing RNA polymerase dropoff could be one way of optimizing gene expression in addition to codon optimization.

Comparison of Gene Expression from 5' OH-mRNAs and 5' PPP-mRNAs.

The first 20 nucleotides of the cleavage site were removed by inverse PCR in the constructs containing Bujard RBS, B0030 RBS, and Anderson RBS with either sfGFP or mRFP, generating a library of six 5' PPP-mRNAs. This library was compared to a library of six 5' OH-mRNAs, which contain 28-nt intact cleavage site in the presence of Csy4 co-expression. For each construct, three colonies were picked and their protein production rates were assayed. These two libraries contain the same transcript composition but different 5' modifications. Our results showed that 5' OH-mRNA exhibited higher levels (1.5-3 fold) of protein production than the corresponding 5' PPP-mRNA, implying 5' OH-mRNA is more stable than 5' PPP-mRNA with the same sequence (FIG. 2).

Testing Csy4 Cleavage in Different Organisms.

The gram-negative model bacterium Escherichia coli K12 strain Top10, the gram-positive model bacterium Bacillus subtilis sp. 168, and the eukaryotic model organism Saccharomyces cerevisiae strain BY4741 were used. Three reporter systems with similar architecture were constructed by inserting a 30-nt Csy4 cleavage site (aGTTCACTGC-CGTATAGGCAGCTAAGAAAt) (SEQ ID NO: 173) in-frame between the ATG start codon and downstream reporter protein-coding sequence. The E. coli reporter system consisted of a J23119 promoter, a Bujard RBS, and the sfGFP coding gene. The B. subtilis reporter system consisted of a Hyperspank promoter ("partsregistry" followed by ".org/Part:BBa_K143054"), a consensus B. subtilis RBS (GGATCTAAGGAGGAAGGATCT; SEQ ID NO: 174), and a GFP coding gene (GFPmut3) (Andersen, J. B. et al. Appl. Environ. Microbiol. 64, 2240-2246 (1998)). The yeast reporter system consisted of a strong pTDH3 promoter and a Venus coding gene (one mutant of yellow fluorescent protein) (Nagai, T. et al. Nat. Biotechnol. 20, 87-90 (2002)). Time-course fluorescence of these reporter systems was assayed in their host cells with and without Csy4 co-expression as described. Protein production rates of three colonies were measured. The cells were further visualized with microscope (Zeiss, Axio Observer D1). In all cases, Csy4 cleavage led to almost complete reporter gene silencing due to removal of the SD sequence and ATG start codon for E. coli and B. subtilis, or due to removal of the 5' m7G capping and ATG start codon for Saccharomyces cerevisiae (FIG. 9c-d).

Results

To test whether physically separating genetic elements at the transcript level allows modular programming of predictable genetic systems, a synthetic RNA processing platform was developed. The synthetic platform was derived from the clustered regularly interspaced short palindromic repeats (CRISPR) system. CRISPRs are wide-spread in bacteria and archaea and confer resistance to invasive genetic elements (Wiedenheft et al. Nature 482, 331-338 (2012); Barrangou et al. Science 315, 1709-1712 (2007)). The CRISPR locus is transcribed into a long precursor RNA (pre-crRNA) that contains a series of repetitive sequence elements (Gesner et al. Nat. Struct. Mol. Biol. 18, 688-692 (2011)). A dedicated CRISPR-associated (Cas) endoribonuclease usually cleaves the pre-crRNA within each repetitive element, generating short crRNAs necessary for protection against invaders (Lintner et al. J. Biol. Chem. 286, 21643-21656 (2011); Brouns et al. Science 321, 960-964 (2008)). For example, in Pseudomonas aeruginosa strain UCBPP-PA14, the endoribonuclease Csy4 recognizes and cleaves a 28-nucleotide (nt) repetitive sequence to produce stable transcripts with a 5' hydroxyl group (FIGS. 1-2; Haurwitz et al. Science 329, 1355-1358 (2010); Deana et al. Nature 451, 355-358 (2008)).

The synthetic cleavage platform described herein is modularly comprised of the csy4 gene and its cleavage element (i.e., RNA recognition sequence). The cleavage element is inserted between components (e.g., regulatory elements, protein coding regions, etc.) of a transcript, and the Csy4 protein is induced to cleave at designed loci and generate well-defined RNA segments. Csy4 is highly specific for only its cognate RNA target and does not recognize other types of CRISPR repeat sites such as those in the

*Escherichia coli* K12 strain (Haurwitz et al. *Science* 329, 1355-1358 (2010)), and is therefore well-suited for use as a synthetic platform.

Two reporter libraries were constructed in *Escherichia coli* to test whether RNA cleavage could eliminate unwanted interactions between UTRs and translational elements such as RBSs. In the control library, random 30-nt UTR sequences were placed between a constitutive promoter and a characterized RBS region fused to a green fluorescent protein-coding gene. In the CRISPR library, the 28-nt CRISPR hairpin was inserted between the random UTRs and the RBS. The protein production rates (PPRs) in clones randomly sampled from each library (N=45) were calculated during exponential cell growth (FIG. 3a). The control library demonstrated an almost three-fold wider distribution of PPRs (RSD=46%, FIG. 3b) than the CRISPR library (RSD=19%, FIG. 3c) measured by the relative standard deviation (RSD). Moreover, the difference in mean expression between the control library and a baseline construct (the baseline bias, BB) lacking the 30-nt UTR insertion (BB=0.44) was larger than that of the CRISPR library (BB=0.19). Both RSD and BB increased in the absence of Csy4 expression (FIG. 3d). Co-expression of Csy4 with the cleavage element led to a reduction in size of the transcript as detected by Northern blotting, consistent with cleavage of mRNA at the CRISPR hairpin (FIG. 4). Similar experiments by inserting random 30-nt UTRs between different RBSs and genes with the cleavage element showed a consistent reduction of expression variability and BB compared to those without (FIG. 5). Since genomic 5' UTRs exist in varying lengths and encode a variety of structures that might not be captured in the above random library, 12 different UTR sequences ranging from 18- to 90-nt in length from the *E. coli* MG1665 genome were tested in the reporter system. As expected, a much lower variance of the PPR was observed with RNA cleavage compared to that without (FIG. 3e), implying that RNA processing enabled predictable gene expression regardless of UTR contexts.

Most promoters used in genetic engineering are derived from natural DNA sequences, usually with poorly annotated operator sequences and transcriptional start sites (Cases et al. Nat. Rev. Microbiol. 3, 105-118 (2005)). As a consequence, direct assembly of promoters with UTR, RBS and coding sequence (CDS) elements often modifies transcript compositions, which changes translational efficiency and transcript stability and alters the putative activity of the promoter in different contexts. To determine if RNA processing could eliminate this interference, two expression libraries were compared with and without RNA cleavage. Both libraries consisted of twenty-eight parallel constructs generated via combinatorial assembly of seven promoters with two RBSs and two reporter genes. The cleavage element was inserted between the promoters and RBSs in the CRISPR library and assayed the relative promoter unit (RPU) of each promoter by normalizing its protein production rate to that of a reference promoter. The measured RPU values in the control library varied widely across different RBSs and genes (RSD=67%~129%, FIG. 3f). In contrast, the RPU of each promoter in the CRISPR library was almost constant and the rank orders were completely conserved across different contexts (FIG. 3g). This implies that cleavage of the mRNA between promoters and downstream elements allowed precise characterization of the standard RPUs of promoters, which could be used predictably in complex genetic systems in a plug-and-play manner.

Figure 7:
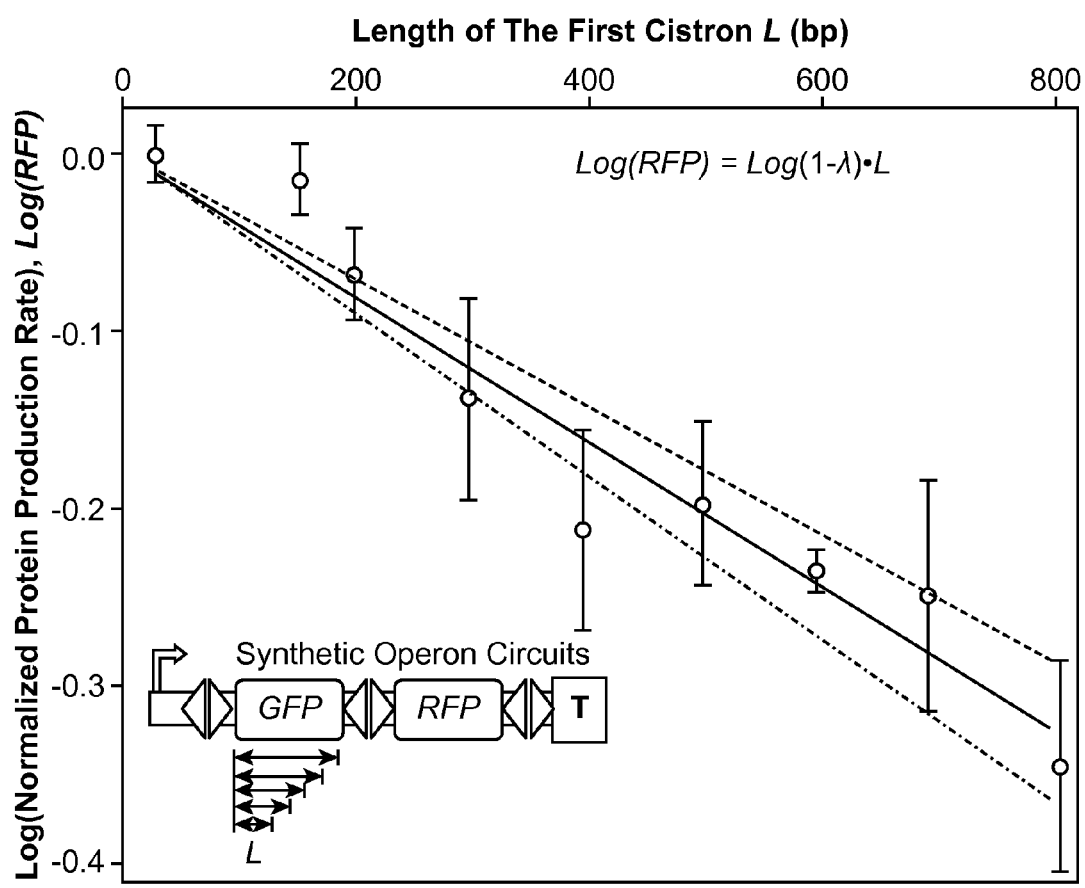
FIG. 7 displays a plot of measurement of transcriptional polarity using the synthetic operon. The length of the first cistron was systematically shortened from the 3' end, and the expression of RFP was measured in the second cistron. The plot of the normalized RFP expression data versus the length of the first cistron shows a linear correlation, whose slope is used to calculate the average dropoff rate of RNA polymerase. The dotted lines show the 95% confidence interval of the fitness.

RNA processing was applied to the rational design of multi-cistronic operons. In both prokaryotes and eukaryotes, multi-gene operons are ubiquitous and present significant advantages due to their compactness, coordinated regulation, and improved dynamics of transcription and growth (Rocha et al. Annu. Rev. Genet. 42, 211-233 (2008); Zaslaver et al. Cell 145, 981-992 (2011)). As such, engineering operons with predictable behaviors has been the focus in metabolic engineering applications (Pfleger et al. Nat. Biotechnol. 24, 1027-1032 (2006); Martin et al. Nat. Biotechnol. 21, 796-802 (2003)). However, multiple cistrons encoded on the same transcript may interfere with one another through RNA structures and translational coupling, which affects both transcript stability and translation efficiency. Here, expression of a set of genes in monocistronic format was compared to different arrangements in bicistronic operons, when these cistrons were or were not bounded by the cleavage elements at both 5' and 3' ends to remove context interference from either side. Six monocistrons were first constructed by combining three RBSs with two fluorescent proteins, and the bicistrons were constructed by pairing every RFP monocistron with all GFP monocistrons such that both serve as the first and second gene in the operon. This provided two parallel sets of eighteen bicistrons in permutation: one without RNA processing and one with (FIG. 6a). In the control library, expression of the first cistron was linearly correlated to the monocistronic format, but expression of the second cistron was highly variable (FIG. 6b). The results from the CRISPR library were strikingly different. If a gene appeared as the first cistron in a bicistronic operon, its production was almost the same as the corresponding monocistron; if a gene appeared as the second cistron, there was a strong linear correlation between its expression and the corresponding monocistron (FIG. 6c-e). The consistent difference in the second cistron expression reflects transcriptional polarity, an effect that results in lower expression levels of operonic genes distal to the promoter compared to proximal genes (Wek et al. J. Biol. Chem. 262, 15256-15261 (1987)). Notably, our synthetic cleavage system allows precise measurement of the RNA polymerase dropoff rate during elongation, which was estimated as $8 \times 10^{-4}$ per nucleotide in our constructs (Methods & FIG. 7).

Figure 8:
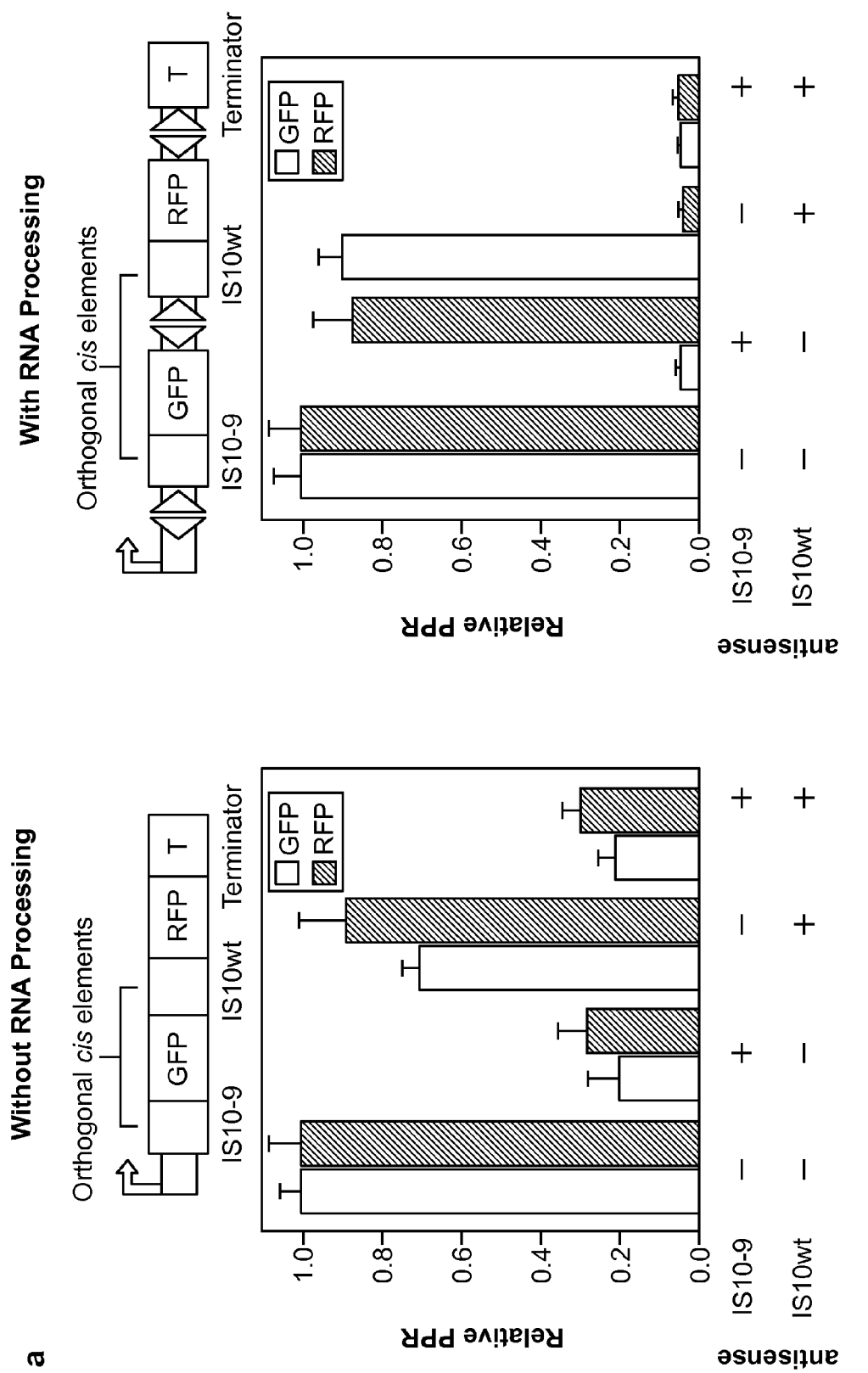
FIG. 8a depicts a method whereby orthogonally-acting IS10 antisense RNA-mediated cis elements are used to control translation of individual genes in a synthetic operon without (left) or with (right) RNA processing.
FIG. 8b-e depict flow cytometry data of the synthetic operon controlled by orthogonal IS10 cis-regulatory systems with no antisense RNA, IS10-9 antisense RNA only, IS10wt antisense RNA only, and both antisense RNAs. The first column shows the forward scatter-side scatter 2D plots with the polygon gating 75% of cell populations. The second and third columns show histograms of RFP and GFP, respectively.

Next, the RNA processing platform was applied to design complex regulatory systems. Two families of antisense RNA-mediated cis elements were used to achieve multi-input regulation: two orthogonal pairs of translational repressors (IS10wt and IS10-9) and one transcriptional attenuator (PT181 wt) (Mutalik et al. Nat. Chem. Biol. 8, 447-454 (2012); Lucks et al. Proc. Natl. Acad. Sci. USA 108, 8617-8622 (2011)). Attempts to use orthogonal IS10 elements to differentially control translation of individual genes inside an operon failed likely due to coupled transcript stability and structural interactions between the two cistrons. However, when the precursor transcript was cleaved at designed loci to free the 5'- and 3'-ends, each antisense RNA individually repressed the cognate gene without affecting the other (FIG. 8). This suggests that RNA processing could effectively decouple transcript stability and remove structural interactions between elements on the same transcript. Complex RNA-level regulations were further designed by combining two cis-regulatory systems, PT181 wt and IS100 wt, in tandem to control a monocistron. Ideally, such tandem multi-input control would result in a multiplicative function of the two elements (Lucks et al. Proc. Natl. Acad. Sci. USA 108, 8617-8622 (2011)). Without RNA cleavage, this function was not obtained. In contrast, cleavage allowed ideal multiplicative regulation, indicating that complex cis regulations could only be achieved using RNA processing, which is crucial to the design of sophisticated and quantitatively predictable RNA-level genetic circuits (FIG. 9a). The efficacy of CRISPR-based cleavage was further compared to other RNA cleavage elements by inserting different cleavage elements into the complex cis-regulatory system (FIG. 9b). For example, a self-cleaving tRNA, (tRNA$^{lg5}$), self-cleaving ribozymes (small Tobacco RingSpot Virus hammerhead ribozyme—sTRSV and Avacado SunBlotch Virus ribozyme—ASBV), and RNase III (with its cognate cleavage site derived from T7 phage) were tested. None of these elements behaved as effectively as CRISPR, suggesting that the CRISPR system may be more robust to different genetic contexts, which could be a unique feature of CRISPR, since Csy4 naturally cleaves its RNA target in a variety of context sequences derived from phage genomes (Wiedenheft et al. Nature 482, 331-338 (2012)).

Csy4 functions in a wide spectrum of prokaryotes and eukaryotes. Using a reporter system wherein the cleavage site was inserted in-frame between the translation start codon and downstream protein coding sequence, Csy4 cleavage led to effective gene silencing in the gram-negative bacterium *Escherichia coli*, the gram-positive bacterium *Bacillus subtilis*, and the eukaryote *Saccharomyces cerevisiae* (FIG. 9c-d and Methods). This suggests that the RNA processing platform based on Csy4 can be readily expanded to different organisms to build predictable genetic systems with dynamic controls.

Our results demonstrate that RNA processing enforces high levels of modularity between physically linked and functionally coupled elements within the precursor transcript, leading to predictable genetic programming. Our choice of the Csy4 cleavage platform recapitulates the highly specific and efficient ribonuclease activity of this natural CRISPR system. Existence of numerous Csy4 homologs from other independent CRISPR/Cas systems potentially enables us to cleave distinct RNA targets specifically, which opens the possibility of controlling RNA processing in a parallel and sophisticated manner (Wiedenheft et al. Nature 482, 331-338 (2012)). In addition, Csy4 cleavage is fully functional in different organisms ranging from prokaryotes to eukaryotes, suggesting the universality of our platform across the life kingdom. Our study provides a proof of principle that RNA processing allows for the creation of standard, context-free genetic elements such as promoters and RBSs that are quantitatively predictable in different contexts, which is crucial to the design of modular and reliable complex genetic and cellular systems. Together with technologies for genome-scale modification (Wang et al. Nature 460, 894-898 (2009)), our work establishes a foundation for applications including creation of standardized promoters and UTR elements, engineering of differentially-regulated metabolic pathways and design of predictable complex genetic programs for cell therapies, chemical production and cellular computation.

Example 2: Expression of Csy4 in Mammalian Cells

Figure 16:
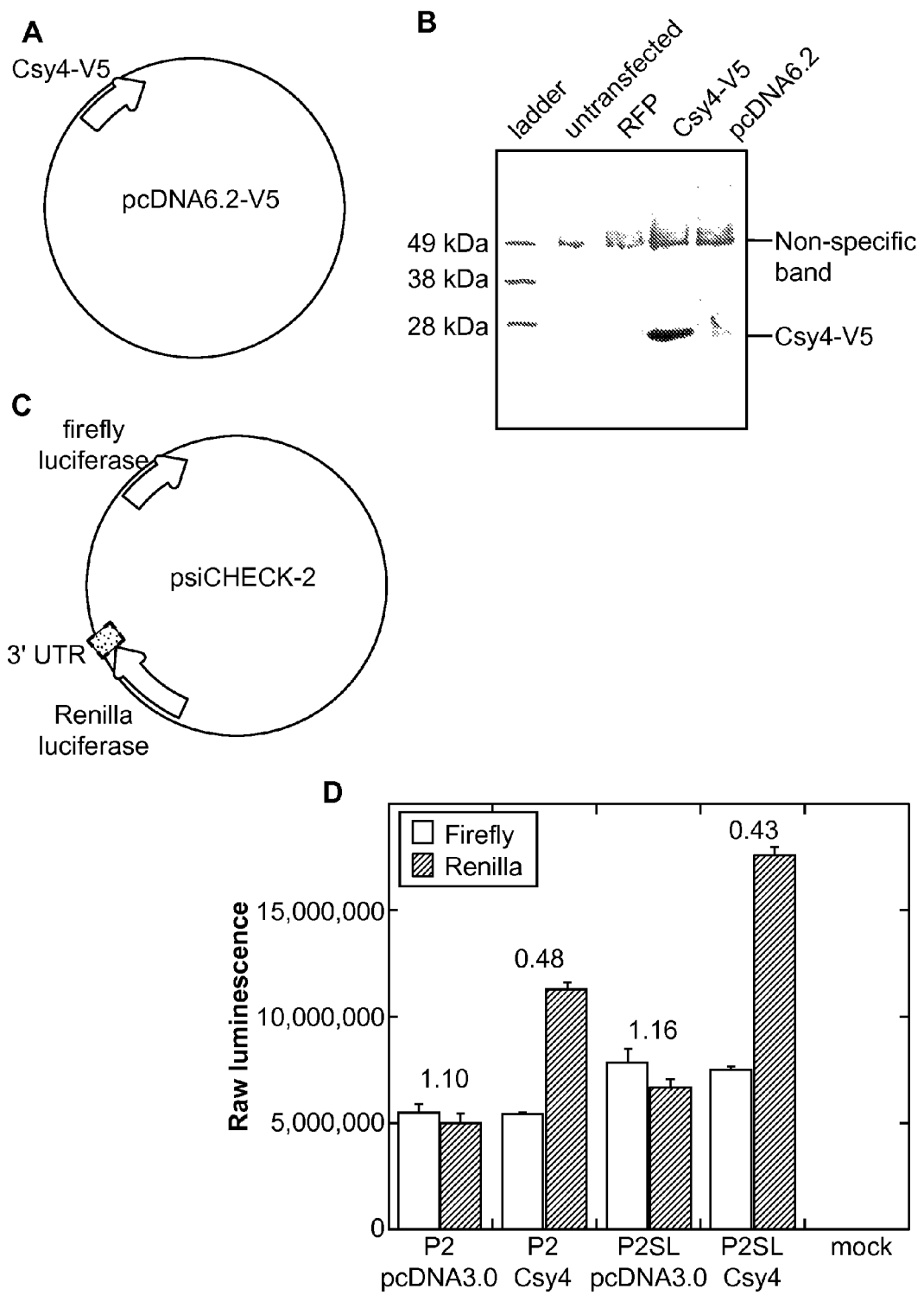
FIGS. 16A-B demonstrate expression of Csy4 in mammalian cells.
FIGS. 16C-D depict psiCHECK-2 and luminescence from various constructs.

FIG. 16 demonstrates expression of Csy4 in mammalian cells. (A) Csy4 was cloned into pcDNA6.2-V5, a mammalian expression vector. (B) Csy4 expression was measured in mammalian cells. The pcDNA6.2-V5-Csy4 vector was transfected in HEK293T cells. Cells were harvested and lysed 48 hours post-transfection. Clarified cell lysate was separated on a 12% SDS PAGE gel and probed with an anti-V5 antibody. Csy-4-V5 (expected size ~22 kDa) was readily detected.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant expression vector comprising:
a first recognition nucleotide sequence that encodes an RNA recognition sequence recognized by a Csy4 endoribonuclease, wherein the first recognition nucleotide sequence is positioned between a first coding region and a first regulatory element positioned 5' of the coding region; and
a second recognition nucleotide sequence that encodes an RNA recognition sequence recognized by the Csy4 endoribonuclease, wherein the second recognition nucleotide sequence is positioned between the first coding region and a second coding region positioned 3' of the first coding region,
wherein the Csy4 endoribonuclease is enzymatically active and comprises an amino acid sequence having at least about 75% amino acid sequence identity to the amino acid sequence set forth in one of SEQ ID NOs: 1-55, 132-133, and 147-149.

2. The recombinant expression vector of claim 1, wherein less than 50 nucleotides are disposed between the recognition nucleotide sequence and the insertion site.

3. The recombinant expression vector of claim 1, further comprising a promoter 5' of the recognition nucleotide sequence, wherein the promoter is operably linked to the recognition nucleotide sequence and to the insertion site.

4. The recombinant expression vector of claim 1, further comprising a nucleotide sequence encoding the Csy4 endoribonuclease.

5. The recombinant expression vector of claim 1, wherein the Csy4 endoribonuclease comprises an amino acid sequence having at least about 95% amino acid sequence identity to the amino acid sequence set forth in one of SEQ ID NOs: 1-55, 132-133, and 147-149.

6. The recombinant expression vector of claim 1, wherein the RNA recognition sequence is at least about 90% identical to the RNA recognition sequence set forth in one of SEQ ID NOs: 56-131.

7. A genetically modified cell comprising the recombinant expression vector of claim 1.

8. The genetically modified cell of claim 7, further comprising a second recombinant expression vector encoding the Csy4 endoribonuclease.

9. The genetically modified cell of claim 7, wherein the cell is selected from a group consisting of an archaeal cell, a bacterial cell, and a eukaryotic cell.

10. The genetically modified cell of claim 7, wherein the cell is a mammalian cell.

11. The genetically modified cell of claim 7, wherein the cell is selected from a group consisting of a eukaryotic single-cell organism, a somatic cell, a germ cell, and a stem cell.

12. A composition for modifying the activity of a target RNA, the composition comprising:
(i) a recombinant target RNA comprising:
a first RNA recognition sequence that is recognized by a Csy4 endoribonuclease and is positioned between a first coding region and a first regulatory element 5' of the coding region; and,
a second RNA recognition sequence that is recognized by the Csy4 endoribonuclease and is positioned between the first coding region and a second coding region positioned 3' of the first coding region; and
(ii) an enzymatically active Csy4 endoribonuclease.

13. The composition of claim 12, wherein the Csy4 endoribonuclease comprises an amino acid sequence having at least about 75% amino acid sequence identity to the amino acid sequence set forth in one of SEQ ID NOs: 1-55, 132-133, and 147-149.

14. The composition of claim 12, wherein the RNA recognition sequence is at least about 90% identical to the RNA recognition sequence set forth in one of SEQ ID NOs: 56-131.

15. The composition of claim 12, wherein the Csy4 endoribonuclease comprises an amino acid sequence having at least about 95% amino acid sequence identity to the amino acid sequence set forth in one of SEQ ID NOs: 1-55, 132-133, and 147-149.

16. The recombinant expression vector of claim 1, further comprising a third recognition nucleotide sequence that encodes an RNA recognition sequence recognized by the Csy4 endoribonuclease, wherein the third recognition nucleotide sequence is positioned between the second coding region and a second regulatory sequence positioned 3' of the second coding region.

17. The composition of claim 12, further comprising a third RNA recognition sequence that is recognized by the Csy4 endoribonuclease and is positioned (c) between the second coding region and a second regulatory sequence positioned 3' of the second coding region.

18. The composition of claim 12, wherein the Csy4 endoribonuclease comprises an amino acid sequence having at least about 85% amino acid sequence identity to the amino acid sequence set forth in one of SEQ ID NOs: 1-55, 132-133, and 147-149.

* * * * *